(12) United States Patent
Iwamura et al.

(10) Patent No.: US 8,648,097 B2
(45) Date of Patent: Feb. 11, 2014

(54) PYRIDYLAMINOACETIC ACID COMPOUND

(75) Inventors: Ryo Iwamura, Ube (JP); Masayuki Tanaka, Ube (JP); Tetsushi Katsube, Ube (JP); Manabu Shigetomi, Ube (JP); Eiji Okanari, Ube (JP); Yasunori Tokunaga, Ube (JP); Hiroshi Fujiwara, Ube (JP)

(73) Assignee: Ube Industries, Ltd., Ube-Shi (JP)

( * ) Notice: Subject to any disclaimer, the term of this patent is extended or adjusted under 35 U.S.C. 154(b) by 118 days.

(21) Appl. No.: 12/922,028

(22) PCT Filed: Mar. 12, 2009

(86) PCT No.: PCT/JP2009/054713
§ 371 (c)(1),
(2), (4) Date: Sep. 10, 2010

(87) PCT Pub. No.: WO2009/113600
PCT Pub. Date: Sep. 17, 2009

(65) Prior Publication Data
US 2011/0054172 A1    Mar. 3, 2011

(30) Foreign Application Priority Data
Mar. 12, 2008 (JP) ................. 2008-062926

(51) Int. Cl.
*A61K 31/4439* (2006.01)
*C07D 401/14* (2006.01)

(52) U.S. Cl.
USPC ........................... 514/337; 546/256

(58) Field of Classification Search
USPC ........................... 546/256; 514/337
See application file for complete search history.

(56) References Cited

U.S. PATENT DOCUMENTS

| | | | |
|---|---|---|---|
| 6,448,290 B1 | 9/2002 | Ohuchida et al. |
| 6,498,172 B1 | 12/2002 | Cameron et al. |
| 7,491,748 B2 | 2/2009 | Tani et al. |
| 2003/0216445 A1 | 11/2003 | Cameron et al. |
| 2006/0258728 A1 | 11/2006 | Tani et al. |
| 2007/0049625 A1 | 3/2007 | Woodward et al. |
| 2008/0045545 A1 | 2/2008 | Prasanna et al. |
| 2008/0114002 A1 | 5/2008 | Bonnert et al. |
| 2010/0113388 A1 | 5/2010 | Tani et al. |
| 2011/0054172 A1 | 3/2011 | Iwamura et al. |

FOREIGN PATENT DOCUMENTS

| | | |
|---|---|---|
| EP | 2 264 009 A1 | 12/2010 |
| EP | 2415763 A1 | 2/2012 |
| JP | 2001-519414 A | 10/2001 |
| JP | 2005-521668 A | 7/2005 |
| JP | 2006-519250 A | 8/2006 |
| JP | 2007-515467 A | 6/2007 |
| JP | 2007-186424 A | 7/2007 |
| JP | 2008-503490 A | 2/2008 |
| JP | 2008-505874 A | 2/2008 |
| JP | 2009-502982 A | 1/2009 |
| WO | WO 98/27053 A1 | 6/1998 |
| WO | WO 98/28264 A1 | 7/1998 |
| WO | WO 91/19300 A1 | 4/1999 |
| WO | WO 02/24647 A1 | 3/2002 |
| WO | WO 03/016254 A1 | 2/2003 |
| WO | 03/037433 A1 | 5/2003 |
| WO | 03/074483 A1 | 9/2003 |
| WO | WO 2004/078169 A1 | 9/2004 |
| WO | WO 2005/061449 A1 | 7/2005 |
| WO | WO 2005/072743 A1 | 8/2005 |
| WO | 2006/009876 A1 | 1/2006 |
| WO | WO 2006/005909 A1 | 1/2006 |
| WO | WO 2007/014462 A1 | 2/2007 |
| WO | WO 2007/017687 A2 | 2/2007 |
| WO | 2007/027468 A1 | 3/2007 |
| WO | WO 2008/015517 A2 | 2/2008 |
| WO | WO 2009/113600 A1 | 9/2009 |
| WO | WO 2010/113957 A1 | 10/2010 |

OTHER PUBLICATIONS

International Search Report, dated Apr. 28, 2009, for Application No. PCT/JP2009/054713.
Supplementary European Search Report for European Patent Application No. 10758726.9, dated Jul. 17, 2012.
Biswas et al., "Prostaglandin E2 receptor subtypes, EP1, EP2, EP3 and EP4 in human and mouse ocular tissues—a comparative immunohistochemical study," Prostaglandins, Leukotrienes and Essential Fatty Acids, vol. 71, 2004, pp. 277-288.
Bito et al., "Long-term Maintenance of Reduced Intraocular Pressure by Daily or Twice Daily Topical Application of Prostaglandins to Cat or Rhesus Monkey Eyes," Investigative Ophthalmology & Visual Science, vol. 24, No. 3, Mar. 1983, pp. 312-319.
Holmes et al., "PTP1B inhibitors: Synthesis and evaluation of difluoro-methylenephosphonate bioisosteres on a sulfonamide scaffold," Bioorganic & Medicinal Chemistry Letters, vol. 18, 2008, pp. 2719-2724.
International Search Report dated Jun. 8, 2010 for International Application No. PCT/JP2010/055719.
Schlotzer-Schrehardt et al., "Expression and Localization of FP and EP Prostanoid Receptor Subtypes in Human Ocular Tissues," Investigative Ophthalmology & Visual Science, vol. 43, No. 5, May 2002, pp. 1475-1487.
Supplementary European Search Report for corresponding European Patent Application No. 09 72 1163, dated Jun. 22, 2012.

(Continued)

*Primary Examiner* — Patricia L Morris
(74) *Attorney, Agent, or Firm* — Birch, Stewart, Kolasch & Birch, LLP

(57) ABSTRACT

The present invention provides a novel pyridylaminoacetic acid compound represented by the following formula (1):

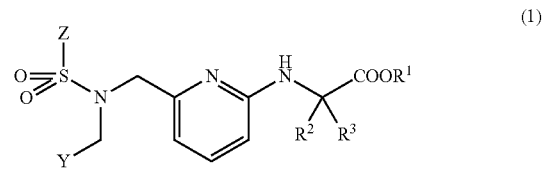

(1)

(wherein $R^1$, $R^2$, $R^3$, Y and Z are as defined in the description and claims), or a pharmacologically acceptable salt thereof. The pyridylaminoacetic acid compound has EP2 agonistic action and is therefore useful as a therapeutic and/or prophylactic agent for respiratory diseases such as asthma or chronic obstructive pulmonary disease.

15 Claims, No Drawings

(56) References Cited

OTHER PUBLICATIONS

US Office Action for U.S. Appl. No. 13/260,946 dated Mar. 19, 2013.
Cameron et al., "Discovery of CP-533536: An EP2 receptor selective prostaglandin E2 (PGE2) agonist that induces local bone formation", Bioorganic & Medicinal Chemistry Letters, vol. 19, 2009 (available online Jan. 23, 2009), pp. 2075-2078.
Carey, "Organic Chemistry," 6th Edition, Chapter 1, 2006, pp. 9-10 (9 pages total).
Cornelison, "Human papillomavirus genotype 16 vaccines for cervical cancer prophylaxis and treatment," Current Opinion in Oncology, vol. 12, 2000, pp. 466-473.
Dermer, "Another Anniversary for the War on Cancer," BiolTechnology, vol. 12, Mar. 1994, p. 320.
Extended European Search Report dated Dec. 18, 2012 for European Patent Application No. 10815458.4.
Extended European Search Report dated Jan. 17, 2013 for European Patent Application No. 10815462.6.
Extended European Search Report dated Jun. 18, 2013 for European Application No. 10839533.6.
Freshney, "Culture of Animal Cells: A Manual of Basic Technique and Specialized Applications," Fifth Edition, 2005, pp. 7-9.
Gauvreau et al., "Protective Effects of Inhaled PGE2 on Allergen-induced Airway Responses and Airway Inflammation", American Journal of Respiratory and Critical Care Medicine, vol. 159, 1999, pp. 31-36.
International Preliminary Report on Patentability, and Translation of Written Opinion of the International Searching Authority, dated Apr. 19, 2012, for International Application No. PCT/JP2010/065649 (Forms PCT/IB/338, PCT/IB/373 and PCT/ISA/237).
International Preliminary Report on Patentability, and Translation of Written Opinion of the International Searching Authority, dated Apr. 19, 2012, for International Application No. PCT/JP2010/065654 (Forms PCT/IB/338, PCT/IB/373 and PCT/ISA/237).
International Preliminary Report on Patentability, and Translation of Written Opinion of the International Searching Authority, dated Aug. 23, 2012, for International Application No. PCT/JP2010/073274 (Forms PCT/IB/338, PCT/IB/373 and PCT/ISA/237).
International Search Report dated Mar. 15, 2011 for International Application No. PCT/JP2010/073274.
International Search Report dated Oct. 26, 2010 for International Application No. PCT/JP2010/065649.
International Search Report dated Oct. 5, 2010 for International Application No. PCT/JP2010/065654.
Linden et al., "Prostaglandin Analogues in the Treatment of Glaucoma," Drugs and Aging, May 1999, vol. 14, No. 5, pp. 387-398, XP009014535.
Paralkar et al., "An EP2 receptor-selective prostaglandin E2 agonist induces bone healing", PNAS, vol. 100, No. 11, May 27, 2003, pp. 6736-6740.
Tilley et al., "Receptors and pathways mediating the effects of prostaglandin E2 on airway tone", American Journal of Physiology—Lung Cellular and Molecular Physiology, vol. 284, 2003, L599-L606.
Tsuji et al., "A systemically administered EP2 receptor agonist stimulates pulmonary angiogenesis in a murine model of emphysema," Prostaglandins & Other Lipid Mediators, vol. 90, 2009 (available online Sep. 16, 2009), pp. 85-88.
U.S. Office Action dated Mar. 14, 2013 for U.S. Appl. No. 13/518,824.
U.S. Office Action dated May 13, 2013 for U.S. Appl. No. 13/395,303.
U.S. Office Action dated May 28, 2013 for U.S. Appl. No. 13/395,370.

PYRIDYLAMINOACETIC ACID COMPOUND

TECHNICAL FIELD

The present invention relates to a novel pyridylaminoacetic acid compound, or pharmacologically acceptable salt thereof, that is useful as a pharmaceutical. More particularly, the pyridylamino acetic acid compound as related to the present invention has EP2 agonistic action and is therefore useful as a therapeutic and/or prophylactic agent for respiratory diseases such as asthma or chronic obstructive pulmonary disease (abbreviated as COPD).

BACKGROUND ART

Prostaglandin $E_2$ (abbreviated as $PGE_2$), which is administered by inhalation, has been reported to inhibit immediate-type and late-type asthmatic responses in asthma patients (see Non-Patent Document 1). In addition, $PGE_2$ is known to act as an agonist against receptors such as EP1, EP2, EP3 and EP4, and its agonistic action against EP2 receptor in particular has been suggested to be intimately involved with bronchodilatory action (see Non-Patent Document 2).

Sulfonamide compounds, which have a structure that resembles the compound of the present invention, have been previously found to have EP2 agonistic action (see Patent Documents 1 to 4). In particular, the compound described as Example 14e in Patent Document 2 has been reported to increase concentration of cyclic adenosine monophosphate (abbreviated as cAMP) due to its EP2 agonistic action, and have an action that accelerates healing of fractures (see Non-Patent Document 3). However, there are no specific descriptions regarding bronchodilatory action based on EP2 agonistic action of these compounds described in Patent Documents 1 to 4, and there are no specific disclosures in any of these publications regarding a sulfonamide compound related to the present invention having the pyridylaminoacetic acid or ester thereof as a partial structure.

Patent Document 1: WO 98/28264A
Patent Document 2: WO 99/19300A
Patent Document 3: WO 2004/078169A
Patent Document 4: WO 2008/015517A
Non-Patent Document 1: American Journal of Respiratory and Critical Care Medicine, 159, 31 (1999)
Non-Patent Document 2: American Journal of Physiology-Lung Cellular and Molecular Physiology, 284, L599 (2003)
Non-Patent Document 3: Proceedings of the National Academy of Sciences of the United States of America, 100, 6736 (2003)

DISCLOSURE OF THE INVENTION

Problems to be Solved by the Invention

As a result of conducting extensive research on various sulfonamide compounds with the aim of developing a superior therapeutic agent or prophylactic agent for respiratory diseases, the inventors of the present invention found that a novel pyridyl-aminoacetic acid compound having a specific structure has superior bronchodilatory action based on potent EP2 agonistic action, while also having superior properties in terms of tissue distribution, bioavailability (BA), fast-acting pharmacological effect, sustained pharmacological effect, solubility, physical stability, drug interaction, toxicity and the like, and is particularly useful as a therapeutic and/or prophylactic agent (and preferably a therapeutic agent) for respiratory diseases such as asthma or COPD, thereby leading to completion of the present invention.

An object of the present invention is to provide a novel pyridylaminoacetic acid compound, or a pharmacologically acceptable salt thereof, that has superior bronchodilatory action based on potent EP2 agonistic action, and is particularly useful as a therapeutic and/or prophylactic agent (and preferably a therapeutic agent) for respiratory diseases such as asthma or COPD.

Means for Solving the Problems

The pyridylaminoacetic acid compound in the present invention refers to a compound represented by the following formula (1):

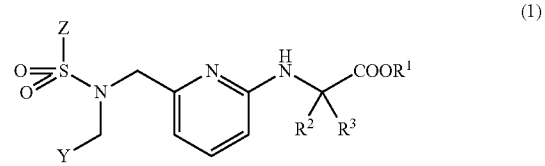

(1)

[wherein,
$R^1$, $R^2$ and $R^3$ respectively and independently represent a hydrogen atom or a $C_1$-$C_6$ alkyl group,
Y represents a bicyclic heteroaromatic group, which may be substituted with a group(s) selected from the group consisting of a halogen atom, a $C_1$-$C_6$ alkyl group, a halogeno-$C_1$-$C_6$ alkyl group, a $C_1$-$C_6$ alkoxy group, a halogeno-$C_1$-$C_6$ alkoxy group and a $C_1$-$C_6$ alkylthio group, or a -$Q^1$-$Q^2$ group (wherein $Q^1$ represents an arylene group or a 5- to 6-membered heteroarylene group, and $Q^2$ represents an aromatic group or a 5- to 6-membered heterocyclic group, each of which may be substituted with a group(s) selected from the group consisting of a halogen atom, a hydroxy group, a $C_1$-$C_6$ alkyl group, a halogeno-$C_1$-$C_6$ alkyl group, a $C_1$-$C_6$ alkoxy group and a halogeno-$C_1$-$C_6$ alkoxy group), and
Z represents an aromatic group or a 5- to 6-membered heteroaromatic group, each of which may be substituted with a group(s) selected from the group consisting of a halogen atom, a $C_1$-$C_6$ alkyl group, a halogeno-$C_1$-$C_6$ alkyl group, a $C_1$-$C_6$ alkoxy group and a halogeno-$C_1$-$C_6$ alkoxy group].
or a pharmacologically acceptable salt thereof.

Effects of the Invention

The pyridylaminoacetic acid compound represented by the formula (1) or a pharmacologically acceptable salt thereof of the present invention demonstrates superior bronchodilatory action based on potent EP2 agonistic action, and also has superior properties in terms of tissue distribution, bio availability (BA), fast-acting pharmacological effect, sustained pharmacological effect, solubility, physical stability, drug interaction, toxicity and the like. Thus, the present invention is able to provide a novel compound having superior properties as a therapeutic and/or prophylactic agent for respiratory diseases (such as asthma, COPD, bronchitis, emphysema, pulmonary fibrosis, acute respiratory distress syndrome (ARDS), cystic fibrosis and pulmonary hypertension). Moreover, a compound represented by the formula (1) of the present invention is also useful as a therapeutic and/or prophylactic agent for diseases for which EP2 agonistic action is thought to be useful (such as dysmenorrhea, premature labor, ischemic organ diseases (including arteriosclerosis obliterans, Berger's disease, Raynaud's disease, myocardial infarction, angina pectoris, cerebral infarction and diabetic neuropathy), bone diseases, gastric ulcer, hypertension and glaucoma).

BEST MODE FOR CARRYING OUT THE INVENTION

In the above-mentioned compound represented by the formula (1), "$C_1$-$C_6$ alkyl group" represented by $R^1$ means a linear or branched $C_1$-$C_6$ alkyl group such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-methylbutyl group, a 2-methylbutyl group, a 1-ethylpropyl group, a 1,2-dimethylpropyl group, a hexyl group, a 1-methylpentyl group, a 2-methylpentyl group, a 3-methylpentyl group, a 4-methylpentyl group, a 1-ethylbutyl group, a 2-ethylbutyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1-ethyl-1-methylpropyl group, a 1-ethyl-2-methylpropyl group, a 1,1,2-trimethylpropyl group and a 1,2,2-trimethylpropyl group. Preferably, it is a methyl group, an ethyl group, a propyl group, an isopropyl group, a butyl group, an isobutyl group, a sec-butyl group, a tert-butyl group, a pentyl group or a hexyl group, more preferably a methyl group, an ethyl group, a propyl group, an isopropyl group, a tert-butyl group or a hexyl group, and particularly preferably a methyl group, an ethyl group, an isopropyl group or a hexyl group.

$R^1$ is, preferably, a hydrogen atom, a methyl group, an ethyl group, a propyl group, an isopropyl group, a butyl group, an isobutyl group, a sec-butyl group, a tert-butyl group, a pentyl group or a hexyl group, more preferably a hydrogen atom, a methyl group, an ethyl group, a propyl group, an isopropyl group, a tert-butyl group or a hexyl group, and particularly preferably a hydrogen atom, a methyl group, an ethyl group, an isopropyl group or a hexyl group.

In the above-mentioned compound represented by the formula (1), any of "$C_1$-$C_6$ alkyl group" represented by $R^2$; "$C_1$-$C_6$ alkyl group" represented by $R^3$; "$C_1$-$C_6$ alkyl group", "$C_1$-$C_6$ alkyl group moiety" of a halogen-$C_1$-$C_6$ alkyl group, "$C_1$-$C_6$ alkyl group moiety" of a $C_1$-$C_6$ alkylthio group as a substituent of a bicyclic heteroaromatic group represented by Y; "$C_1$-$C_6$ alkyl group", "$C_1$-$C_6$ alkyl group moiety" of a halogeno-$C_1$-$C_6$ alkyl group as a substituent of an aromatic group or a 5- to 6-membered heterocyclic group represented by $Q^2$ in a -$Q^1$-$Q^2$ group represented by Y; and "$C_1$-$C_6$ alkyl group", "$C_1$-$C_6$ alkyl group moiety" of a halogeno-$C_1$-$C_6$ alkyl group as a substituent of an aromatic group or a 5- to 6-membered heteroaromatic group represented by Z has the same meaning and examples as those of the above-mentioned "$C_1$-$C_6$ alkyl group" represented by $R^1$. Preferably, it is a $C_1$-$C_4$ alkyl group, more preferably a methyl group, an ethyl group, a propyl group, an isopropyl group or a tert-butyl group, and particularly preferably a methyl group or an ethyl group.

$R^2$ is preferably a hydrogen atom, a methyl group, an ethyl group, a propyl group or an isopropyl group, more preferably a hydrogen atom or a methyl group, and particularly preferably a hydrogen atom.

$R^3$ is preferably a hydrogen atom, a methyl group, an ethyl group, a propyl group or an isopropyl group, more preferably a hydrogen atom or a methyl group, and particularly preferably a hydrogen atom.

In the above-mentioned compound represented by the formula (1), "halogen atom" means a fluorine atom, a chlorine atom, a bromine atom or an iodine atom, preferably a fluorine atom, a chlorine atom or a bromine atom, and particularly preferably a fluorine atom or a chlorine atom. Any of "halogen atom", "halogen moiety" of a halogeno-$C_1$-$C_6$ alkyl group, "halogen moiety" of a halogeno-$C_1$-$C_6$ alkoxy group as a substituent of a bicyclic heteroaromatic group represented by Y; "halogen atom", "halogen moiety" of a halogeno-$C_1$-$C_6$ alkyl group, "halogeno moiety" of a halogeno-$C_1$-$C_6$ alkoxy group as a substituent of an aromatic group or a 5- to 6-membered heterocyclic group represented by $Q^2$ in a -$Q^1$-$Q^2$ group represented by Y; and "halogen atom", "halogen moiety" of a halogeno-$C_1$-$C_6$ alkyl group, "halogeno moiety" of a halogeno-$C_1$-$C_6$ alkoxy group as a substituent of an aromatic group or a 5- to 6-membered heteroaromatic group represented by Z has the same meaning and examples of those of the above-mentioned "halogen atom".

In the above-mentioned compound represented by the formula (1), "halogeno-$C_1$-$C_6$ alkyl group" means the above-mentioned "$C_1$-$C_6$ alkyl group" substituted with the above-mentioned at least one "halogen atom" which may be the same or different. Any of "halogeno-$C_1$-$C_6$ alkyl group" as a substituent of a bicyclic heteroaromatic group represented by Y; "halogeno-$C_1$-$C_6$ alkyl group" as a substituent of an aromatic group or a 5- to 6-membered heterocyclic group represented by $Q^2$ in a -$Q^1$-$Q^2$ group represented by Y; "halogeno-$C_1$-$C_6$ alkyl group" as a substituent of an aromatic group or a 5- to 6-membered heteroaromatic group represented by Z has the same meaning as that of the above-mentioned "halogeno-$C_1$-$C_6$ alkyl group". Examples of such "halogeno-$C_1$-$C_6$ alkyl group" include a linear or branched halogeno-$C_1$-$C_6$ alkyl group such as a trifluoromethyl group, a difluoromethyl group, a fluoromethyl group, a trichloromethyl group, a dichloromethyl group, a chloromethyl group, a pentafluoroethyl group, a 2,2,2-trifluoroethyl group, a 2-fluoroethyl group, a 2,2,2-trichloroethyl group, a 2-chloroethyl group, a 2-bromoethyl group, a heptafluoropropyl group, a 3,3,3-trifluoropropyl group, a 3-fluoropropyl group, a 3-chloropropyl group, a 1,2,2,2-tetrafluoro-1-trifluoromethylethyl group, a 2,2,2-trifluoro-1-methylethyl group, a 2-fluoro-1-methylethyl group, a 2-chloro-1-methylethyl group, a perfluorobutyl group, a 4,4,4-trifluorobutyl group, a 4-fluorobutyl group, a 4-chlorobutyl group, a perfluoro-tert-butyl group, a 2,2,2-trifluoro-1,1-dimethylethyl group, a 2-fluoro-1,1-dimethylethyl group, a 2-chloro-1,1-dimethylethyl group, a perfluoropentyl group or a perfluorohexyl group, preferably a fluoro $C_1$-$C_4$ alkyl group or a chloro $C_1$-$C_4$ alkyl group, more preferably a trifluoromethyl group, a difluoromethyl group, a trichloromethyl group, a dichloromethyl group, a 2,2,2-trifluoroethyl group or a 2,2,2-trichloroethyl group, and particularly preferably a trifluoromethyl group.

In the above-mentioned compound represented by the formula (1), "$C_1$-$C_6$ alkoxy group" means the above-mentioned "$C_1$-$C_6$ alkyl group" bonded via oxygen (i.e., —O—($C_1$-$C_6$ alkyl) group). Any of "$C_1$-$C_6$ alkoxy group", "$C_1$-$C_6$ alkoxy group moiety" of a halogeno-$C_1$-$C_6$ alkoxy group as a substituent of a bicyclic heteroaromatic group represented by Y; "$C_1$-$C_6$ alkoxy group", "$C_1$-$C_6$ alkoxy group moiety" of a halogeno-$C_1$-$C_6$ alkoxy group as a substituent of an aromatic group or a 5- to 6-membered heterocyclic group represented by $Q^2$ in a -$Q^1$-$Q^2$ group represented by Y; "$C_1$-$C_6$ alkoxy group", "$C_1$-$C_6$ alkoxy group moiety" of a halogeno-$C_1$-$C_6$ alkoxy group as a substituent of an aromatic group or a 5- to 6-membered hetero aromatic group represented by Z has the meaning as that of the above-mentioned "$C_1$-$C_6$ alkoxy group". Examples of such "$C_1$-$C_6$ alkoxy group" include a linear or branched $C_1$-$C_6$ alkoxy group such as a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a 1-methylbutoxy group, a 2-methylbutoxy group, a 1-ethylpropoxy group, a 1,2-dimethylpropoxy group, a hexyloxy group, a 1-methylpentyloxy group, a 2-methylpentyloxy group, a 3-methylpentyloxy group, a 4-methylpentyloxy group, a 1-ethylbutoxy group, a 2-ethylbutoxy group, a 1,1-dimethylbutoxy group, a 1,2-dimethylbutoxy group, a 1,3-dimethylbutoxy group, a 2,2-dimethylbutoxy group, a 2,3-dimethylbutoxy group, a 3,3-dimethylbutoxy group, a 1-ethyl-1-methylpropoxy group, a 1-ethyl-2-methylpropoxy group, a 1,1,2-trimethylpropoxy group or a 1,2,2-trimethylpropoxy group, preferably a $C_1$-$C_4$ alkoxy group, more preferably a methoxy group, an ethoxy group, a propoxy group, an isopropoxy group or a tert-butoxy group, and particularly preferably a methoxy group.

In the above-mentioned compound represented by the formula (1), "halogeno-$C_1$-$C_6$ alkoxy group" means the above-mentioned "$C_1$-$C_6$ alkoxy group" substituted with the above-mentioned at least one "halogen atom" which may be the same or different. Any of "halogen-$C_1$-$C_6$ alkoxy group" as a substituent of a bicyclic heteroaromatic group represented by Y; "halogeno-$C_1$-$C_6$ alkoxy group" as a substituent of an aromatic group or a 5- to 6-membered heterocyclic group represented by $Q^2$ in a -$Q^1$-$Q^2$ group represented by Y; "halogeno-$C_1$-$C_6$ alkoxy group" as a substituent of an aromatic group or a 5- to 6-membered heteroaromatic group represented by Z has the same meaning as that of the above-mentioned "halogeno-$C_1$-$C_6$ alkoxy group". Examples of such "halogeno-$C_1$-$C_6$ alkoxy group" include a linear or branched halogeno-$C_1$-$C_6$ alkoxy group such as a trifluoromethoxy group, a difluoromethoxy group, a trichloromethoxy group, a dichloromethoxy group, a pentafluoroethoxy group, a 2,2,2-trifluoroethoxy group, a 2-fluoroethoxy group, a 2,2,2-trichloroethoxy group, a 2-chloroethoxy group, a 2-bromoethoxy group, a heptafluoropropoxy group, a 3,3,3-trifluoropropoxy group, a 3-fluoropropoxy group, a 3-chloropropoxy group, a 1,2,2,2-tetrafluoro-1-trifluoromethylethoxy group, a 2,2,2-trifluoro-1-methylethoxy group, a 2-fluoro-1-methylethoxy group, a 2-chloro-1-methylethoxy group, a perfluorobutoxy group, a 4,4,4-trifluorobutoxy group, a 4-fluorobutoxy group, a 4-chlorobutoxy group, a perfluoro-tert-butoxy group, a 2,2,2-trifluoro-1,1-dimethylethoxy group, a 2-fluoro-1,1-dimethylethoxy group, a 2-chloro-1,1-dimethylethoxy group, a perfluoropentyloxy group or a perfluorohexyloxy group, preferably a fluoro $C_1$-$C_4$ alkoxy group or a chloro $C_1$-$C_4$ alkoxy group, more preferably a trifluoromethoxy group, a difluoromethoxy group, a trichloromethoxy group or a dichloromethoxy group, and particularly preferably a difluoromethoxy group.

In the above-mentioned compound represented by the formula (1), "$C_1$-$C_6$ alkylthio group" as a substituent of a bicyclic hetero aromatic group represented by Y means the above-mentioned "$C_1$-$C_6$ alkyl group" bonded via sulfur (i.e., —S—($C_1$-$C_6$ alkyl) group), and examples thereof include a linear or branched $C_1$-$C_6$ alkylthio group such as a methylthio group, an ethylthio group, a propylthio group, an isopropylthio group, a butylthio group, an isobutylthio group, a sec-butylthio group, a tert-butylthio group, a pentylthio group, an isopentylthio group, a neopentylthio group, a tert-pentylthio group, a 1-methylbutylthio group, a 2-methylbutylthio group, a 1-ethylpropylthio group, a 1,2-dimethylpropylthio group, a hexylthio group, a 1-methylpentylthio group, a 2-methylpentylthio group, a 3-methylpentylthio group, a 4-methylpentylthio group, a 1-ethylbutylthio group, a 2-ethylbutylthio group, a 1,1-dimethylbutylthio group, a 1,2-dimethylbutylthio group, a 1,3-dimethylbutylthio group, a 2,2-dimethylbutylthio group, a 2,3-dimethylbutylthio group, a 3,3-dimethylbutylthio group, a 1-ethyl-1-methylpropylthio group, a 1-ethyl-2-methylpropylthio group, a 1,1,2-trimethylpropylthio group and a 1,2,2-trimethylpropylthio group, preferably a $C_1$-$C_4$ alkylthio group, more preferably a methylthio group, an ethylthio group, a propylthio group, an isopropylthio group or a tert-butylthio group, and particularly preferably a methylthio group.

Examples of a substituent(s) of a bicyclic hetero aromatic group represented by Y preferably include a halogen atom, a $C_1$-$C_4$ alkyl group, a halogeno-$C_1$-$C_4$ alkyl group, a $C_1$-$C_4$ alkoxy group, a halogeno-$C_1$-$C_4$ alkoxy group or a $C_1$-$C_4$ alkylthio group, for example, a fluorine atom, a chlorine atom, a bromine atom, a methyl group, an ethyl group, a propyl group, an isopropyl group, a tert-butyl group, a trifluoromethyl group, a difluoromethyl group, a trichloromethyl group, a dichloromethyl group, a 2,2,2-trifluoroethyl group, a 2,2,2-trichloroethyl group, a methoxy group, an ethoxy group, a propoxy group, an isopropoxy group, a tert-butoxy group, a trifluoromethoxy group, a difluoromethoxy group, a trichloromethoxy group, a dichloromethoxy group, a methylthio group, an ethylthio group, a propylthio group, an isopropylthio group or a tert-butylthio group, particularly a fluorine atom, a chlorine atom, a methyl group, an ethyl group, a trifluoromethyl group, a methoxy group, a difluoromethoxy group or a methylthio group. Examples thereof particularly preferably include a halogen atom or a $C_1$-$C_4$ alkoxy group, for example, a fluorine atom, a chlorine atom or a methoxy group.

The number of substituent(s) on a bicyclic heteroaromatic group represented by Y is, for example, 1 to 5, preferably 1 to 3, particularly preferably 1 to 2, and in the case of a plural number, these substituents may be the same or different from each other.

The "bicyclic heteroaromatic group" represented by Y means a fully unsaturated 9- to 10-membered bicyclic group containing, as a constitutional element(s) of a ring, 1 to 4 hetero atom(s) (in the case of a plural number, each independently represents) selected from the group consisting of an oxygen atom, a nitrogen atom and a sulfur atom, and examples thereof may include a benzofuryl group, a benzothienyl group, a benzoxazolyl group, a benzothiazolyl group, an isoindolyl group, an indolyl group, an indazolyl group, a benzimidazolyl group, an isoquinolyl group or a quinolyl group, preferably benzofuryl group, a benzothienyl group, a benzoxazolyl group or a benzothiazolyl group, and particularly preferably a benzofuryl group or a benzothienyl group.

Examples of "bicyclic heteroaromatic group, which may be substituted with a group(s) selected from the group consisting of a halogen atom, a $C_1$-$C_6$ alkyl group, a halogeno-$C_1$-$C_6$ alkyl group, a $C_1$-$C_6$ alkoxy group, a halogeno-$C_1$-$C_6$ alkoxy group and a $C_1$-$C_6$ alkylthio group" represented by Y include, for example, a benzofuran-2-yl group, a 5-fluorobenzofuran-2-yl group, a 6-fluorobenzofuran-2-yl group, a 7-fluorobenzofuran-2-yl group, a 5,6-difluorobenzofuran-2-yl group, a 5-chlorobenzofuran-2-yl group, a 6-chlorobenzofuran-2-yl group, a 7-chlorobenzofuran-2-yl group, a 6-chloro-5-fluorobenzofuran-2-yl group, a 6-bromobenzofuran-2-yl group, a 5-methylbenzofuran-2-yl group, a 6-methylbenzofuran-2-yl group, a 5-fluoro-6-methylbenzofuran-2-yl group, a 5-ethylbenzofuran-2-yl group, a 6-ethylbenzofuran-2-yl group, a 6-ethyl-5-fluorobenzofuran-2-yl group, a 6-propylbenzofuran-2-yl group, a 6-isopropylbenzofuran-2-yl group, a 6-tert-butylbenzofuran-2-yl group, a 5-trifluoromethylbenzofuran-2-yl group, a 6-trifluoromethylbenzofuran-2-yl group, a 5-fluoro-6-trifluoromethylbenzofuran-2-yl group, a 6-difluoromethylbenzofuran-2-yl group, a 6-trichloromethylbenzofuran-2-yl group, a 6-dichloromethylbenzofuran-2-yl group, a 6-(2,2,2-trifluoroethyl)benzofuran-2-yl group, a 6-(2,2,2-trichloroethyl)benzofuran-2-yl group, a 5-methoxybenzofuran-2-yl group, a 6-methoxybenzofuran-2-yl group, a 7-methoxybenzofuran-2-yl group, a 5-fluoro-6-methoxybenzo furan-2-yl group, a 6-ethoxybenzofuran-2-yl group, a 6-propoxybenzofuran-2-yl group, a 6-isopropoxybenzofuran-2-yl group, a 6-tert-butoxybenzofuran-2-yl group, a 6-trifluoromethoxybenzofuran-2-yl group, a 5-difluoromethoxybenzofuran-2-yl group, a 6-difluoromethoxybenzo furan-2-yl group, a 6-difluoromethoxy-5-fluorobenzofuran-2-yl group, a 6-trichloromethoxybenzofuran-2-yl group, a 6-dichloromethoxybenzofuran-2-yl group, a 5-methylthiobenzofuran-2-yl group, a 6-methylthiobenzofuran-2-yl group, a 5-fluoro-6-methylthiobenzofuran-2-yl group, a 6-ethylthiobenzofuran-2-yl group, a 6-propylthiobenzofuran-2-yl group, a 6-isopropylthiobenzofuran-2-yl group, a 6-tert-butylthiobenzofuran-2-yl group, a benzo[b]thiophen-2-yl group, a 5-fluorobenzo[b]thiophen-2-yl group, a 6-fluorobenzo[b]thiophen-2-yl group, a 7-fluorobenzo[b]thiophen-2-yl group, a 5,6-difluorobenzo[b]thiophen-2-yl group, a 5-chlorobenzo[b]thiophen-2-yl group, a 6-chlorobenzo[b]thiophen-2-yl group, a 7-chlorobenzo[b]thiophen-2-yl group, a 6-chloro-5-fluorobenzo[b]thiophen-2-yl group, a 6-bromobenzo[b]thiophen-2-yl group, a 5-methylbenzo[b]thiophen-2-yl group, a 6-methylbenzo[b]thiophen-2-yl group, a 5-fluoro-6-methylbenzo[b]thiophen-2-yl group, a 5-ethylbenzo[b]thiophen-2-yl group, a 6-ethylbenzo[b]thiophen-2-yl group, a 6-ethyl-5-fluorobenzo[b]thiophen-2-yl group, a 6-propylbenzo[b]thiophen-2-yl group, a 6-isopropylbenzo[b]thiophen-2-yl group, a 6-butylbenzo[b]thiophen-2-yl group, a 6-isobutylbenzo[b]thiophen-2-yl group, a 6-sec-butylbenzo[b]thiophen-2-yl group, a 6-tert-butylbenzo[b]thiophen-2-yl group, a 6-pentylbenzo[b]thiophen-2-yl group, a 6-hexylbenzo[b]thiophen-2-yl group, a 5-trifluoromethylbenzo[b]thiophen-2-yl group, a 6-trifluoromethylbenzo[b]thiophen-2-yl group, a 5-fluoro-6-trifluoromethylbenzo[b]thiophen-2-yl group, a 6-difluoromethylbenzo[b]thiophen-2-yl group, a 6-trichloromethylbenzo[b]thiophen-2-yl group, a 6-dichloromethylbenzo[b]thiophen-2-yl group, a 6-(2,2,2-trifluoroethyl)benzo[b]thiophen-2-yl group, a 6-(2,2,2-trichloroethyl)benzo[b]thiophen-2-yl group, a 5-methoxybenzo[b]thiophen-2-yl group, a 6-methoxybenzo[b]thiophen-2-yl group, a 7-methoxybenzo[b]thiophen-2-yl group, a 5-fluoro-6-methoxybenzo[b]thiophen-2-yl group, a 6-ethoxybenzo[b]thiophen-2-yl group, a 6-propoxybenzo[b]thiophen-2-yl group, a 6-isopropoxybenzo[b]thiophen-2-yl group, a 6-butoxybenzo[b]thiophen-2-yl group, a 6-isobutoxybenzo[b]thiophen-2-yl group, a 6-sec-butoxybenzo[b]thiophen-2-yl group, a 6-tert-butoxybenzo[b]thiophen-2-yl group, a 6-pentyloxybenzo[b]thiophen-2-yl group, a 6-hexyloxybenzo[b]thiophen-2-yl group, a 6-trifluoromethoxybenzo[b]thiophen-2-yl group, a 5-difluoromethoxybenzo[b]thiophen-2-yl group, a 6-difluoromethoxybenzo-[b]thiophen-2-yl group, a 6-difluoromethoxy-5-fluorobenzo[b]thiophen-2-yl group, a 6-trichloromethoxybenzo[b]thiophen-2-yl group, a 6-dichloromethoxybenzo[b]thiophen-2-yl group, a 5-methylthiobenzo[b]thiophen-2-yl group, a 6-methylthiobenzo[b]thiophen-2-yl group, a 5-fluoro-6-methylthiobenzo[b]thiophen-2-yl group, a 6-ethylthiobenzo[b]thiophen-2-yl group, a 6-propylthiobenzo[b]thiophen-2-yl group, a 6-isopropylthiobenzo[b]thiophen-2-yl group, a 6-tert-butylthiobenzo[b]thiophen-2-yl group, a benzoxazol-2-yl group, a 6-fluorobenzoxazol-2-yl group, a 6-chlorobenzoxazol-2-yl group, a 6-methoxybenzoxazol-2-yl group, a benzothiazol-2-yl group, a 6-fluorobenzothiazol-2-yl group, a 6-chlorobenzothiazol-2-yl group, a 6-methoxybenzothiazol-2-yl group, an isoindol-2-yl group, a 1H-indol-2-yl group, a 6-fluoro-1H-indol-2-yl group, a 6-chloro-1H-indol-2-yl group, a 6-methoxy-1H-indol-2-yl group, an indazol-2-yl group, a 1H-benzimidazol-2-yl group, an isoquinolin-3-yl group, a 7-fluoroisoquinolin-3-yl group, a 7-chloroisoquinolin-3-yl group, a 7-methoxyisoquinolin-3-yl group, a quinolin-2-yl group, a 6-fluoroquinolin-2-yl group, a 6-chloroquinolin-2-yl group or a 6-methoxyquinolin-2-yl group.

Examples thereof preferably include a benzofuran-2-yl group, a 6-fluorobenzofuran-2-yl group, a 5,6-difluorobenzofuran-2-yl group, a 6-chlorobenzofuran-2-yl group, a 6-chloro-5-fluorobenzofuran-2-yl group, a 6-methylbenzofuran-2-yl group, a 5-fluoro-6-methylbenzofuran-2-yl group, a 6-ethylbenzofuran-2-yl group, a 6-ethyl-5-fluorobenzofuran-2-yl group, a 6-trifluoromethylbenzofuran-2-yl group, a 5-fluoro-6-trifluoromethylbenzofuran-2-yl group, a 6-methoxybenzofuran-2-yl group, a 5-fluoro-6-methoxybenzofuran-2-yl group, a 6-difluoromethoxybenzofuran-2-yl group, a 6-difluoromethoxy-5-fluorobenzofuran-2-yl group, a 6-methylthiobenzofuran-2-yl group, a 5-fluoro-6-methylthiobenzofuran-2-yl group, a benzo[b]thiophen-2-yl group, a 6-fluorobenzo[b]thiophen-2-yl group, a 5,6-difluorobenzo[b]thiophen-2-yl group, a 6-chlorobenzo[b]thiophen-2-yl group, a 6-chloro-5-fluorobenzo[b]thiophen-2-yl group, a 6-bromobenzo[b]thiophen-2-yl group, a 6-methylbenzo[b]thiophen-2-yl group, a 5-fluoro-6-methylbenzo[b]thiophen-2-yl group, a 6-ethylbenzo[b]thiophen-2-yl group, a 6-ethyl-5-fluorobenzo[b]thiophen-2-yl group, a 6-propylbenzo[b]thiophen-2-yl group, a 6-isopropylbenzo[b]thiophen-2-yl group, a 6-tert-butylbenzo[b]thiophen-2-yl group, a 6-trifluoromethylbenzo[b]thiophen-2-yl group, a 5-fluoro-6-trifluoromethylbenzo[b]-thiophen-2-yl group, a 6-difluoromethylbenzo[b]thiophen-2-yl group, a 6-trichloromethylbenzo[b]thiophen-2-yl group, a 6-dichloromethylbenzo[b]thiophen-2-yl group, a 6-(2,2,2-trifluoroethyl)benzo[b]thiophen-2-yl group, a 6-(2,2,2-trichloroethyl)benzo[b]-thiophen-2-yl group, a 6-methoxybenzo[b]thiophen-2-yl group, a 5-fluoro-6-methoxybenzo[b]thiophen-2-yl group, a 6-ethoxybenzo[b]thiophen-2-yl group, a 6-propoxybenzo[b]thiophen-2-yl group, a 6-isopropoxybenzo[b]thiophen-2-yl group, a 6-tert-butoxybenzo[b]thiophen-2-yl group, a 6-trifluoromethoxybenzo[b]thiophen-2-yl group, a 6-difluoromethoxybenzo[b]thiophen-2-yl group, a 6-difluoromethoxy-5-fluorobenzo-[b]thiophen-2-yl group, a 6-trichloromethoxybenzo[b]thiophen-2-yl group, a 6-dichloromethoxybenzo[b]thiophen-2-yl group, a 6-methylthiobenzo[b]thiophen-2-yl group, a 5-fluoro-6-methylthiobenzo[b]thiophen-2-yl group, a 6-ethylthiobenzo[b]thiophen-2-yl group, a 6-propylthiobenzo[b]thiophen-2-yl group, a 6-isopropylthiobenzo-[b]thiophen-2-yl group, a 6-tert-butylthiobenzo[b]thiophen-2-yl group, a benzoxazol-2-yl group, a 6-chlorobenzoxazol-2-yl group, a 6-methoxybenzoxazol-2-yl group, a benzothiazol-2-yl group, a 6-chlorobenzothiazol-2-yl group or a 6-methoxybenzothiazol-2-yl group.

Examples thereof more preferably include a benzofuran-2-yl group, a 6-fluorobenzofuran-2-yl group, a 6-chlorobenzofuran-2-yl group, a 6-methoxybenzofuran-2-yl group, a benzo[b]thiophen-2-yl group, a 6-fluorobenzo[b]thiophen-2-yl group, a 5,6-difluorobenzo[b]thiophen-2-yl group, a 6-chlorobenzo[b]thiophen-2-yl group, a 6-chloro-5-fluorobenzo[b]thiophen-2-yl group, a 6-methylbenzo[b] thiophen-2-yl group, a 5-fluoro-6-methylbenzo[b]thiophen-2-yl group, a 6-ethylbenzo[b]thiophen-2-yl group, a 6-ethyl-5-fluorobenzo[b]thiophen-2-yl group, a 6-trifluoromethylbenzo-[b]thiophen-2-yl group, a 5-fluoro-6-trifluoromethylbenzo[b]thiophen-2-yl group, a 6-methoxybenzo[b]thiophen-2-yl group, a 5-fluoro-6-methoxybenzo[b]thiophen-2-yl group, a 6-difluoromethoxybenzo[b]thiophen-2-yl group, a 6-difluoromethoxy-5-fluorobenzo[b]thiophen-2-yl group, a 6-methylthiobenzo[b]thiophen-2-yl group or a 5-fluoro-6-methylthiobenzo[b]thiophen-2-yl group, and particularly preferably a benzofuran-2-yl group, a benzo[b]thiophen-2-yl group, a 6-chlorobenzo[b]thiophen-2-yl group or a 6-methoxybenzo[b]thiophen-2-yl group.

In a $-Q^1-Q^2$ group represented by Y, "arylene group" represented by $Q^1$ means a divalent group of aromatic hydrocarbon of a 6- to 10-membered ring, and examples thereof may include a phenylene group or a naphthylene group, and preferably a phenylene group.

In a $-Q^1-Q^2$ group represented by Y, "5- to 6-membered heteroarylene group" represented by $Q^1$ means a fully unsaturated 5- to 6-membered cyclic divalent group containing, as a constitutional element(s) of a ring, 1 to 4 hetero atom(s) (in the case of a plural number, each independently represents) selected from the group consisting of an oxygen atom, a nitrogen atom and a sulfur atom, and examples thereof may include a furylene group, a thienylene group, a thiazolylene group, a pyridylene group, a pyridazinylene group or a pyrimidinylene group, preferably a thienylene group, a pyridazineylene group or a pyrimidinylene group, and particularly preferably a pyridazinylene group.

In Y, "$Q^1$" is preferably a phenylene group, a thienylene group, a pyridazinylene group or a pyrimidinylene group, more preferably a phenylene group or a pyridazinylene group, and particularly preferably a 1,4-phenylene group or a 3,6-pyridazinylene group.

In a $-Q^1-Q^2$ group represented by Y, any of "aromatic group" represented by $Q^2$; and "aromatic group" represented by Z means a 6- to 10-membered aromatic hydrocarbon group, and examples of such "aromatic group" include a phenyl group or a naphthyl group, and preferably a phenyl group.

In a $-Q^1-Q^2$ group represented by Y, "5- to 6-membered heterocyclic group" represented by $Q^2$ means a fully unsaturated, a partially unsaturated or a fully saturated 5- to 6-membered cyclic group containing, as a constitutional element(s) of a ring, 1 to 4 hetero atom(s) (in the case of a plural number, each independently represents) selected from the group consisting of an oxygen atom, a nitrogen atom and a sulfur atom, and examples of the fully unsaturated 5- to 6-membered heterocyclic group include, for example, a pyrrolyl group, a furyl group, a thienyl group, a pyrazolyl group, an imidazolyl group, an oxazolyl group, a thiazolyl group, a 1,2,4-triazolyl group, a pyridyl group, a pyridazinyl group, a pyrimidinyl group or a pyrazinyl group, examples of the partially unsaturated 5- to 6-membered heterocyclic group include, for example, a 4,5-dihydro-1H-imidazolyl group, a 4,5-dihydroxazolyl group, a 4,5-dihydrothiazolyl group, a 1,4,5,6-tetrahydropyrimidinyl group, a 5,6-dihydro-4H-1,3-oxazinyl group or a 5,6-dihydro-4H-1,3-thiazinyl group, and examples of the fully saturated 5- to 6-membered heterocyclic group include, for example, a pyrrolidinyl group, a tetrahydrofuryl group, a 1,3-dioxolanyl group, a piperidinyl group, a tetrahydropyranyl group, a piperadinyl group, a morpholinyl group, a thiomorpholinyl group, a 1,3-dioxanyl group or a 1,4-dioxanyl group. Examples of "5- to 6-membered heterocyclic group" represented by $Q^2$ preferably include a thienyl group, a pyrazolyl group, an oxazolyl group, a thiazolyl group, a 1,2,4-triazolyl group, a pyridyl group, a pyridazinyl group, a pyrimidinyl group, a 4,5-dihydrothiazolyl group, a pyrrolidinyl group or a piperidinyl group, more preferably a thienyl group, a pyrazolyl group, an oxazolyl group, a thiazolyl group, a 1,2,4-triazolyl group, a pyridyl group, a pyridazinyl group, a pyrimidinyl group or a 4,5-dihydrothiazolyl group, and particularly preferably a pyrazolyl group, a thiazolyl group, a 1,2,4-triazolyl group, a pyridyl group, a pyridazinyl group, a pyrimidinyl group or a 4,5-dihydrothiazolyl group.

In a $-Q^1-Q^2$ group represented by Y, a substituent(s) of an aromatic group and a 5- to 6-membered heterocyclic group represented by $Q^2$ is preferably a halogen atom, a hydroxy group, a $C_1$-$C_4$ alkyl group, a halogeno-$C_1$-$C_4$ alkyl group, a $C_1$-$C_4$ alkoxy group or a halogeno-$C_1$-$C_4$ alkoxy group, for example, a fluorine atom, a chlorine atom, a bromine atom, a methyl group, an ethyl group, a propyl group, an isopropyl group, a tert-butyl group, a trifluoromethyl group, a difluoromethyl group, a trichloromethyl group, a dichloromethyl group, a 2,2,2-trifluoroethyl group, a 2,2,2-trichloroethyl group, a methoxy group, an ethoxy group, a propoxy group, an isopropoxy group, a tert-butoxy group, a trifluoromethoxy group, a difluoromethoxy group, a trichloromethoxy group or a dichloromethoxy group, and particularly a fluorine atom, a chlorine atom, a hydroxy group, a methyl group, an ethyl group, a trifluoromethyl group, a methoxy group or a difluoromethoxy group. It is particularly preferably a halogen atom, a $C_1$-$C_4$ alkyl group or a halogeno-$C_1$-$C_4$ alkyl group, for example, a fluorine atom, a chlorine atom, a methyl group or a trifluoromethyl group.

In Y, the number of substituent(s) on an aromatic group and a 5- to 6-membered heterocyclic group represented by $Q^2$ is, for example, 1 to 5, preferably 1 to 3, particularly preferably 1 to 2, and in the case of a plural number, these substituents may be the same or different from each other.

In a $-Q^1-Q^2$ group represented by Y, examples of "an aromatic group which may be substituted with a group(s) selected from the group consisting of a halogen atom, a hydroxy group, a $C_1$-$C_6$ alkyl group, a halogeno-$C_1$-$C_6$ alkyl group, a $C_1$-$C_6$ alkoxy group and a halogeno-$C_1$-$C_6$ alkoxy group" represented by $Q^2$ include, for example, a phenyl group, a 1-naphthyl group, a 2-naphthyl group, a 2-fluorophenyl group, a 3-fluorophenyl group, a 4-fluorophenyl group, a 3-fluoro-1-naphthyl group, a 4-fluoro-1-naphthyl group, a 4-fluoro-2-naphthyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,3,4-trifluorophenyl group, a 2,3,5-trifluorophenyl group, a 2,3,6-trifluorophenyl group, a 2,4,5-trifluorophenyl group, a 2,4,6-trifluorophenyl group, a 3,4,5-trifluorophenyl group, a 2,3,4,5,6-penta-fluorophenyl group, a 2-chlorophenyl group, a 3-chlorophenyl group, a 4-chlorophenyl group, a 3-chloro-1-naphthyl group, a 4-chloro-1-naphthyl group, a 4-chloro-2-naphthyl group, a 2,3-dichlorophenyl group, a 2,4-dichlorophenyl group, a 2,5-dichlorophenyl group, a 2,6-dichlorophenyl group, a 3,4-dichlorophenyl group, a 3,5-dichlorophenyl group, a 3-chloro-4-fluorophenyl group, a 3-chloro-5-fluorophenyl group, a 4-chloro-2-fluorophenyl group, a 4-chloro-3-fluorophenyl group, a 3-bromophenyl group, a 4-bromophenyl group, a 3-iodophenyl group, a 2-hydroxyphenyl group, a 3-hydroxyphenyl group, a 4-hydroxyphenyl group, a 2-methylphenyl group, a 3-methylphenyl group, a 4-methylphenyl group, a 2-ethylphenyl group, a 3-ethylphenyl group, a 4-ethylphenyl group, a 3-propylphenyl group, a 4-propylphenyl group, a 3-isopropylphenyl group, a 4-isopropylphenyl group, a 3-butylphenyl group, a 3-isobutylphenyl group, a 3-sec-butylphenyl group, a 3-tert-butylphenyl group, a 4-tert-butylphenyl group, a 3-pentylphenyl group, a 3-hexylphenyl group, a 2-trifluoromethylphenyl group, a 3-trifluoromethylphenyl group, a 4-trifluoromethylphenyl group, a 3-difluoromethylphenyl group, a 4-difluoromethylphenyl group, a 3-trichloromethylphenyl group, a 4-trichloromethylphenyl group, a 3-dichloromethylphenyl group, a 4-dichloromethylphenyl group, a 3-(2,2,2-trifluoroethyl)phenyl group, a 4-(2,2,2-trifluoroethyl)phenyl group, a 3-(2,2,2-trichloroethyl)phenyl group, a 4-(2,2,2-trichloroethyl)phenyl group, a 2-methoxyphenyl group, a 3-methoxyphenyl group, a 4-methoxyphenyl group, a 3-ethoxyphenyl group, a 4-ethoxyphenyl group, a 3-propoxyphenyl group, a 4-propoxyphenyl group, a 3-isopropoxyphenyl group, a 4-isopropoxyphenyl group, a 3-butoxyphenyl group, a 3-isobutoxyphenyl group, a 3-sec-butoxyphenyl group, a 3-tert-butoxyphenyl group, a 4-tert-butoxyphenyl group, a 3-pentyloxyphenyl group, a 3-hexyloxyphenyl group, a 3-trifluoromethoxyphenyl group, a 4-trifluoromethoxyphenyl group, a 2-difluoromethoxyphenyl group, a 3-difluoromethoxyphenyl group, a 4-difluoromethoxyphenyl group, a 3-trichloromethoxyphenyl group, a 4-trichloromethoxyphenyl group, a 3-dichloromethoxyphenyl group or a 4-dichloromethoxyphenyl group, preferably a phenyl group, a 2-fluorophenyl group, a 3-fluorophenyl group, a 4-fluorophenyl group, a 2,4-difluorophenyl group, a 3,4-difluorophenyl group, a 2-chlorophenyl group, a 3-chlorophenyl group, a 4-chlorophenyl group, a 2,4-dichlorophenyl group, a 3,4-dichlorophenyl group, a 4-chloro-2-fluorophenyl group, a 4-chloro-3-fluorophenyl group, a 3-bromophenyl group, a 3-hydroxyphenyl group, a 4-hydroxyphenyl group, a 3-methylphenyl group, a 3-ethylphenyl group, a 3-propylphenyl group, a 3-isopropylphenyl group, a 3-tert-butylphenyl group, a 3-trifluoromethylphenyl group, a 3-difluoromethylphenyl group, a 3-trichloromethylphenyl group, a 3-dichloromethylphenyl group, a 3-(2,2,2-trifluoroethyl)phenyl group, a 3-(2,2,2-trichloroethyl)phenyl group, a 3-methoxyphenyl group, a 3-ethoxyphenyl group, a 3-propoxyphenyl group, a 3-isopropoxyphenyl group, a 3-tert-butoxyphenyl group, a 3-trifluoromethoxyphenyl group, a 3-difluoromethoxyphenyl group, a 3-trichloromethoxyphenyl group or a 3-dichloromethoxyphenyl group, more preferably a phenyl group, a 2-fluorophenyl group, a 3-fluorophenyl group, a 4-fluorophenyl group, a 2,4-difluorophenyl group, a 3,4-difluorophenyl group, a 2-chlorophenyl group, a 3-chlorophenyl group, a 4-chlorophenyl group, a 4-chloro-2-fluorophenyl group, a 4-chloro-3-fluorophenyl group, a 4-hydroxyphenyl group, a 3-methylphenyl group, a 3-ethylphenyl group, a 3-trifluoromethylphenyl group, a 3-methoxyphenyl group or a 3-difluoromethoxyphenyl group, and particularly preferably a phenyl group, a 4-fluorophenyl group or a 4-chlorophenyl group.

In a -$Q^1$-$Q^2$ group represented by Y, examples of "5- to 6-membered heterocyclic group, which may be substituted with a group(s) selected from the group consisting of a halogen atom, a hydroxy group, a $C_1$-$C_6$ alkyl group, a halogeno-$C_1$-$C_6$ alkyl group, a $C_1$-$C_6$ alkoxy group and a halogeno-$C_1$-$C_6$ alkoxy group" represented by $Q^2$ include, for example, a pyrrol-1-yl group, a furan-2-yl group, a furan-3-yl group, a thiophen-2-yl group, a thiophen-3-yl group, a pyrazol-1-yl group, a 4-fluoropyrazol-1-yl group, a 4-chloropyrazol-1-yl group, a 1H-imidazol-2-yl group, an oxazol-2-yl group, an oxazol-4-yl group, a thiazol-2-yl group, a 4-fluorothiazol-2-yl group, a 4-chlorothiazol-2-yl group, a 5-chlorothiazol-2-yl group, a 4-bromothiazol-2-yl group, a 4-methylthiazol-2-yl group, a 5-methylthiazol-2-yl group, a 4,5-dimethylthiazol-2-yl group, a 4-ethylthiazol-2-yl group, a 4-propylthiazol-2-yl group, a 4-isopropylthiazol-2-yl group, a 4-tert-butylthiazol-2-yl group, a 4-trifluoromethylthiazol-2-yl group, a 4-difluoromethylthiazol-2-yl group, a 4-trichloromethylthiazol-2-yl group, a 4-dichloromethylthiazol-2-yl group, a 4-(2,2,2-trifluoroethyl)thiazol-2-yl group, a 4-(2,2,2-trichloroethyl)thiazol-2-yl group, a 4-methoxythiazol-2-yl group, a 4-ethoxythiazol-2-yl group, a 4-propoxythiazol-2-yl group, a 4-isopropoxythiazol-2-yl group, a 4-tert-butoxythiazol-2-yl group, a 4-trifluoromethoxythiazol-2-yl group, a 4-difluoromethoxythiazol-2-yl group, a 4-trichloromethoxythiazol-2-yl group, a 4-dichloromethoxythiazol-2-yl group, a thiazol-4-yl group, a 2-fluorothiazol-4-yl group, a 2-chlorothiazol-4-yl group, a 2-bromothiazol-4-yl group, a 2-methylthiazol-4-yl group, a 2-ethylthiazol-4-yl group, a 2-propylthiazol-4-yl group, a 2-isopropylthiazol-4-yl group, a 2-tert-butylthiazol-4-yl group, a 2-trifluoromethylthiazol-4-yl group, a 2-difluoromethylthiazol-4-yl group, a 2-trichloromethylthiazol-4-yl group, a 2-dichloromethylthiazol-4-yl group, a 2-(2,2,2-trifluoroethyl)thiazol-4-yl group, a 2-(2,2,2-trichloroethyl)thiazol-4-yl group, a 2-methoxythiazol-4-yl group, a 2-ethoxythiazol-4-yl group, a 2-propoxythiazol-4-yl group, a 2-isopropoxythiazol-4-yl group, a 2-tert-butoxythiazol-4-yl group, a 2-trifluoromethoxythiazol-4-yl group, a 2-difluoromethoxythiazol-4-yl group, a 2-trichloromethoxythiazol-4-yl group, a 2-dichloromethoxythiazol-4-yl group, a thiazol-5-yl group, a 1,2,4-triazol-1-yl group, a pyridin-2-yl group, a pyridin-3-yl group, a pyridin-4-yl group, a pyridazin-3-yl group, a pyridazin-4-yl group, a pyrimidin-2-yl group, a 4-fluoropyrimidin-2-yl group, a 5-fluoropyrimidin-2-yl group, a 4-chloropyrimidin-2-yl group, a 5-chloropyrimidin-2-yl group, a 5-hydroxypyrimidin-2-yl group, a 4-methylpyrimidin-2-yl group, a 4-ethylpyrimidin-2-yl group, a 4-trifluoromethylpyrimidin-2-yl group, a 4-methoxypyrimidin-2-yl group, a 4-difluoromethoxypyrimidin-2-yl group, a pyrimidin-4-yl group, a pyrimidin-5-yl group, a pyrazin-2-yl group, a 4,5-dihydro-1H-imidazol-2-yl group, a 4,5-dihydroxazol-2-yl group, a 4,5-dihydrothiazol-2-yl group, a 1,4,5,6-tetrahydropyrimidin-2-yl group, a 5,6-dihydro-4H-1,3-oxazin-2-yl group, a 5,6-dihydro-4H-1,3-thiazin-2-yl group, a pyrrolidin-1-yl group, a tetrahydrofuran-2-yl group, a 1,3-dioxolan-2-yl group, a piperidin-1-yl group, a tetrahydropyran-2-yl group, a piperazin-1-yl group, a morpholin-4-yl group, a thiomorpholin-4-yl group, a 1,3-dioxan-2-yl group or a 1,4-dioxan-2-yl group, preferably a thiophen-2-yl group, a thiophen-3-yl group, a pyrazol-1-yl group, a 4-fluoropyrazol-1-yl group, a 4-chloropyrazol-1-yl group, an oxazol-2-yl group, an oxazol-4-yl group, a thiazol-2-yl group, a 4-fluorothiazol-2-yl group, a 4-chlorothiazol-2-yl group, a 5-chlorothiazol-2-yl group, a 4-methylthiazol-2-yl group, a 5-methylthiazol-2-yl group, a 4,5-dimethylthiazol-2-yl group, a 4-ethylthiazol-2-yl group, a 4-trifluoromethylthiazol-2-yl group, a 4-methoxythiazol-2-yl group, a 4-difluoromethoxythiazol-2-yl group, a thiazol-4-yl group, a 2-fluorothiazol-4-yl group, a 2-chlorothiazol-4-yl group, a 2-methylthiazol-4-yl group, a 2-ethylthiazol-4-yl group, a 2-trifluoromethylthiazol-4-yl group, a 2-methoxythiazol-4-yl group, a 2-difluoromethoxythiazol-4-yl group, a thiazol-5-yl group, a 1,2,4-triazol-1-yl group, a pyridin-2-yl group, a pyridin-3-yl group, a pyridin-4-yl group, a pyridazin-3-yl group, a pyridazin-4-yl group, a pyrimidin-2-yl group, a 5-fluoropyrimidin-2-yl group, a 5-chloropyrimidin-2-yl group, a 5-hydroxypyrimidin-2-yl group, a pyrimidin-4-yl group, a pyrimidin-5-yl group, a 4,5-dihydrothiazol-2-yl group, a pyrrolidin-1-yl group or a piperidin-1-yl group, more preferably a thiophen-2-yl group, a thiophen-3-yl group, a pyrazol-1-yl group, an oxazol-2-yl group, an oxazol-4-yl group, a thiazol-2-yl group, a 4-fluorothiazol-2-yl group, a 4-chlorothiazol-2-yl group, a 5-chlorothiazol-2-yl group, a 5-methylthiazol-2-yl group, a 4,5-dimethylthiazol-2-yl group, a 4-trifluoromethylthiazol-2-yl group, a thiazol-4-yl group, a 2-fluorothiazol-4-yl group, a 2-chlorothiazol-4-yl group, a thiazol-5-yl group, a 1,2,4-triazol-1-yl group, a pyridin-2-yl group, a pyridazin-3-yl group, a pyridazin-4-yl group, a pyrimidin-2-yl group, a 5-hydroxypyrimidin-2-yl group, a pyrimidin-4-yl group, a pyrimidin-5-yl group or a 4,5-dihydrothiazol-2-yl group, and particularly preferably a pyrazol-1-yl group, a thiazol-2-yl group, a 5-chlorothiazol-2-yl group, a 5-methylthiazol-2-yl group, a 4,5-dimethylthiazol-2-yl group, a 4-trifluoromethylthiazol-2-yl group, a thiazol-4-yl group, a 1,2,4-triazol-1-yl group, a pyridin-2-yl group, a pyridazin-4-yl group, a pyrimidin-2-yl group or a 4,5-dihydrothiazol-2-yl group.

In a $-Q^1-Q^2$ group represented by Y, "$Q^2$" is preferably a phenyl group, a thienyl group, a pyrazolyl group, an oxazolyl group, a thiazolyl group, a 1,2,4-triazolyl group, a pyridyl group, a pyridazinyl group, a pyrimidinyl group, a 4,5-dihydrothiazolyl group, a pyrrolidinyl group or a piperidinyl group, each of which may be substituted with a group(s) selected from the group consisting of a halogen atom, a hydroxy group, a $C_1$-$C_4$ alkyl group, a halogeno-$C_1$-$C_4$ alkyl group, a $C_1$-$C_4$ alkoxy group and a halogeno-$C_1$-$C_4$ alkoxy group, for example, a phenyl group, a 2-fluorophenyl group, a 3-fluorophenyl group, a 4-fluorophenyl group, a 2,4-difluorophenyl group, a 3,4-difluorophenyl group, a 2-chlorophenyl group, a 3-chlorophenyl group, a 4-chlorophenyl group, a 2,4-dichlorophenyl group, a 3,4-dichlorophenyl group, a 4-chloro-2-fluorophenyl group, a 4-chloro-3-fluorophenyl group, a 3-bromophenyl group, a 3-hydroxyphenyl group, a 4-hydroxyphenyl group, a 3-methylphenyl group, a 3-ethylphenyl group, a 3-propylphenyl group, a 3-isopropylphenyl group, a 3-tert-butylphenyl group, a 3-trifluoromethylphenyl group, a 3-difluoromethylphenyl group, a 3-trichloromethylphenyl group, a 3-dichloromethylphenyl group, a 3-(2,2,2-trifluoroethyl)phenyl group, a 3-(2,2,2-trichloroethyl)phenyl group, a 3-methoxyphenyl group, a 3-ethoxyphenyl group, a 3-propoxyphenyl group, a 3-isopropoxyphenyl group, a 3-tert-butoxyphenyl group, a 3-trifluoromethoxyphenyl group, a 3-difluoromethoxyphenyl group, a 3-trichloromethoxyphenyl group, a 3-dichloromethoxyphenyl group, a thiophen-2-yl group, a thiophen-3-yl group, a pyrazol-1-yl group, a 4-fluoropyrazol-1-yl group, a 4-chloropyrazol-1-yl group, an oxazol-2-yl group, an oxazol-4-yl group, a thiazol-2-yl group, a 4-fluorothiazol-2-yl group, a 4-chlorothiazol-2-yl group, a 5-chlorothiazol-2-yl group, a 4-methylthiazol-2-yl group, a 5-methylthiazol-2-yl group, a 4,5-dimethylthiazol-2-yl group, a 4-ethylthiazol-2-yl group, a 4-trifluoromethylthiazol-2-yl group, a 4-methoxythiazol-2-yl group, a 4-difluoromethoxythiazol-2-yl group, a thiazol-4-yl group, a 2-fluorothiazol-4-yl group, a 2-chlorothiazol-4-yl group, a 2-methylthiazol-4-yl group, a 2-ethylthiazol-4-yl group, a 2-trifluoromethylthiazol-4-yl group, a 2-methoxythiazol-4-yl group, a 2-difluoromethoxythiazol-4-yl group, a thiazol-5-yl group, a 1,2,4-triazol-1-yl group, a pyridin-2-yl group, a pyridin-3-yl group, a pyridin-4-yl group, a pyridazin-3-yl group, a pyridazin-4-yl group, a pyrimidin-2-yl group, a 5-fluoropyrimidin-2-yl group, a 5-chloropyrimidin-2-yl group, a 5-hydroxypyrimidin-2-yl group, a pyrimidin-4-yl group, a pyrimidin-5-yl group, a 4,5-dihydrothiazol-2-yl group, a pyrrolidin-1-yl group or a piperidin-1-yl group, particularly a phenyl group, a 2-fluorophenyl group, a 3-fluorophenyl group, a 4-fluorophenyl group, a 2,4-difluorophenyl group, a 3,4-difluorophenyl group, a 2-chlorophenyl group, a 3-chlorophenyl group, a 4-chlorophenyl group, a 4-chloro-2-fluorophenyl group, a 4-chloro-3-fluorophenyl group, a 4-hydroxyphenyl group, a 3-methylphenyl group, a 3-ethylphenyl group, a 3-trifluoromethylphenyl group, a 3-methoxyphenyl group, a 3-difluoromethoxyphenyl group, a thiophen-2-yl group, a thiophen-3-yl group, a pyrazol-1-yl group, an oxazol-2-yl group, an oxazol-4-yl group, a thiazol-2-yl group, a 4-fluorothiazol-2-yl group, a 4-chlorothiazol-2-yl group, a 5-chlorothiazol-2-yl group, a 5-methylthiazol-2-yl group, a 4,5-dimethylthiazol-2-yl group, a 4-trifluoromethylthiazol-2-yl group, a thiazol-4-yl group, a 2-fluorothiazol-4-yl group, a 2-chlorothiazol-4-yl group, a thiazol-5-yl group, a 1,2,4-triazol-1-yl group, a pyridin-2-yl group, a pyridazin-3-yl group, a pyridazin-4-yl group, a pyrimidin-2-yl group, a 5-hydroxypyrimidin-2-yl group, a pyrimidin-4-yl group, a pyrimidin-5-yl group or a 4,5-dihydrothiazol-2-yl group. "$Q^2$" is particularly preferably a phenyl group, a pyrazolyl group, a thiazolyl group, a 1,2,4-triazolyl group, a pyridyl group, a pyridazinyl group, a pyrimidinyl group or a 4,5-dihydrothiazolyl group, each of which may be substituted with a group(s) selected from the group consisting of a halogen atom, a $C_1$-$C_4$ alkyl group and a halogeno-$C_1$-$C_4$ alkyl group, for example, a phenyl group, a 4-fluorophenyl group, a 4-chlorophenyl group, a pyrazol-1-yl group, a thiazol-2-yl group, a 5-chlorothiazol-2-yl group, a 5-methylthiazol-2-yl group, a 4,5-dimethylthiazol-2-yl group, a 4-trifluoromethylthiazol-2-yl group, a thiazol-4-yl group, a 1,2,4-triazol-1-yl group, a pyridin-2-yl group, a pyridazin-4-yl group, a pyrimidin-2-yl group or a 4,5-dihydrothiazol-2-yl group.

Examples of "$-Q^1-Q^2$ group" represented by Y include, for example, a biphenyl-3-yl group, a biphenyl-4-yl group, a 4-(naphthalen-1-yl)phenyl group, a 4-(naphthalen-2-yl)phenyl group, a 2'-fluorobiphenyl-4-yl group, a 3'-fluorobiphenyl-4-yl group, a 4'-fluorobiphenyl-4-yl group, a 2',3'-difluorobiphenyl-4-yl group, a 2',4'-difluorobiphenyl-4-yl group, a 2',5'-difluorobiphenyl-4-yl group, a 2',6'-difluorobiphenyl-4-yl group, a 3',4'-difluorobiphenyl-4-yl group, a 3',5'-difluorobiphenyl-4-yl group, a 2'-chlorobiphenyl-4-yl group, a 3'-chlorobiphenyl-4-yl group, a 4'-chlorobiphenyl-4-yl group, a 2',3'-dichlorobiphenyl-4-yl group, a 2',4'-dichlorobiphenyl-4-yl group, a 2',5'-dichlorobiphenyl-4-yl group, a 2',6'-dichlorobiphenyl-4-yl group, a 3',4'-dichlorobiphenyl-4-yl group, a 3',5'-dichlorobiphenyl-4-yl group, a 3'-chloro-4'-fluorobiphenyl-4-yl group, a 3'-chloro-5'-fluorobiphenyl-4-yl group, a 4'-chloro-2'-fluorobiphenyl-4-yl group, a 4'-chloro-3'-fluorobiphenyl-4-yl group, a 3'-bromobiphenyl-4-yl group, a 4'-bromobiphenyl-4-yl group, a 3'-iodobiphenyl-4-yl group, a 2'-hydroxybiphenyl-4-yl group, a 3'-hydroxybiphenyl-4-yl group, a 4'-hydroxybiphenyl-4-yl group, a 2'-methylbiphenyl-4-yl group, a 3'-methylbiphenyl-4-yl group, a 4'-methylbiphenyl-4-yl group, a 2'-ethylbiphenyl-4-yl group, a 3'-ethylbiphenyl-4-yl group, a 4'-ethylbiphenyl-4-yl group, a 3'-propylbiphenyl-4-yl group, a 4'-propylbiphenyl-4-yl group, a 3'-isopropylbiphenyl-4-yl group, a 4'-isopropylbiphenyl-4-yl group, a 3'-tert-butylbiphenyl-4-yl group, a 4'-tert-butylbiphenyl-4-yl group, a 2'-trifluoromethylbiphenyl-4-yl group, a 3'-trifluoromethylbiphenyl-4-yl group, a 4'-trifluoromethylbiphenyl-4-yl group, a 3'-difluoromethylbiphenyl-4-yl group, a 4'-difluoromethylbiphenyl-4-yl group, a 3'-trichloromethylbiphenyl-4-yl group, a 4'-trichloromethylbiphenyl-4-yl group, a 3'-dichloromethylbiphenyl-4-yl group, a 4'-dichloromethylbiphenyl-4-yl group, a 3'-(2,2,2-trifluoroethyl)biphenyl-4-yl group, a 4'-(2,2,2-trifluoroethyl)biphenyl-4-yl group, a 3'-(2,2,2-trichloroethyl)biphenyl-4-yl group, a 4'-(2,2,2-trichloroethyl)biphenyl-4-yl group, a 2'-methoxybiphenyl-4-yl group, a 3'-methoxybiphenyl-4-yl group, a 4'-methoxybiphenyl-4-yl group, a 3'-ethoxybiphenyl-4-yl group, a 4'-ethoxybiphenyl-4-yl group, a 3'-propoxybiphenyl-4-yl group, a 4'-propoxybiphenyl-4-yl group, a 3'-isopropoxybiphenyl-4-yl group, a 4'-isopropoxybiphenyl-4-yl group, a 3'-tert-butoxybiphenyl-4-yl group, a 4'-tert-butoxybiphenyl-4-yl group, a 3'-trifluoromethoxybiphenyl-4-yl group, a 4'-trifluoromethoxybiphenyl-4-yl group, a 2'-difluoromethoxybiphenyl-4-yl group, a 3'-difluoromethoxybiphenyl-4-yl group, a 4'-difluoromethoxybiphenyl-4-yl group, a 3'-trichloromethoxybiphenyl-4-yl group, a 4'-trichloromethoxybiphenyl-4-yl group, a 3'-dichloromethoxybiphenyl-4-yl group, a 4'-dichloromethoxybiphenyl-4-yl group, a 4-(pyrrol-1-yl)phenyl group, a 4-(furan-2-yl)phenyl group, a 4-(furan-3-yl)-phenyl group, a 4-(thiophen-2-yl)phenyl group, a 4-(thiophen-3-yl)phenyl group, a 4-(pyrazol-1-yl)phenyl group, a 4-(4-fluoropyrazol-1-yl)phenyl group, a 4-(4-chloropyrazol-1-yl)phenyl group, a 4-(1H-imidazol-2-yl)phenyl group, a 4-(oxazol-2-yl)-phenyl group, a 4-(oxazol-4-yl)phenyl group, a 3-(thiazol-2-yl)phenyl group, a 4-(thiazol-2-yl)phenyl group, a 4-(4-fluorothiazol-2-yl)phenyl group, a 4-(4-chlorothiazol-2-yl)phenyl group, a 4-(5-chlorothiazol-2-yl)phenyl group, a 4-(4-bromothiazol-2-yl)phenyl group, a 4-(4-methylthiazol-2-yl)phenyl group, a 4-(5-methylthiazol-2-yl)phenyl group, a 4-(4,5-dimethylthiazol-2-yl)phenyl group, a 4-(4-ethylthiazol-2-yl)phenyl group, a 4-(4-propylthiazol-2-yl)phenyl group, a 4-(4-isopropylthiazol-2-yl)phenyl group, a 4-(4-tert-butylthiazol-2-yl)phenyl group, a 4-(4-trifluoromethyl-thiazol-2-yl)-phenyl group, a 4-(4-difluoromethylthiazol-2-yl)phenyl group, a 4-(4-trichloromethylthiazol-2-yl)phenyl group, a 4-(4-dichloromethylthiazol-2-yl)phenyl group, a 4-[4-(2,2,2-trifluoroethyl)thiazol-2-yl]phenyl group, a 4-[4-(2,2,2-trichloroethyl)thiazol-2-yl]phenyl group, a 4-(4-methoxythiazol-2-yl)phenyl group, a 4-(4-ethoxythiazol-2-yl)-phenyl group, a 4-(4-propoxythiazol-2-yl)phenyl group, a 4-(4-isopropoxythiazol-2-yl)-phenyl group, a 4-(4-tert-butoxythiazol-2-yl)phenyl group, a 4-(4-trifluoromethoxythiazol-2-yl)phenyl group, a 4-(4-difluoromethoxythiazol-2-yl)phenyl group, a 4-(4-trichloromethoxythiazol-2-yl)phenyl group, a 4-(4-dichloromethoxythiazol-2-yl)phenyl group, a 3-(thiazol-4-yl)phenyl group, a 4-(thiazol-4-yl)phenyl group, a 4-(2-fluorothiazol-4-yl)phenyl group, a 4-(2-chlorothiazol-4-yl)phenyl group, a 4-(2-bromothiazol-4-yl)phenyl group, a 4-(2-methylthiazol-4-yl)phenyl group, a 4-(2-ethylthiazol-4-yl)-phenyl group, a 4-(2-propylthiazol-4-yl)phenyl group, a 4-(2-isopropylthiazol-4-yl)-phenyl group, a 4-(2-tert-butylthiazol-4-yl)phenyl group, a 4-(2-trifluoromethylthiazol-4-yl)phenyl group, a 4-(2-difluoromethylthiazol-4-yl)phenyl group, a 4-(2-trichloromethylthiazol-4-yl)phenyl group, a 4-(2-dichloromethylthiazol-4-yl)phenyl group, a 4-[2-(2,2,2-trifluoroethyl)thiazol-4-yl]phenyl group, a 4-[2-(2,2,2-trichloroethyl)thiazol-4-yl]phenyl group, a 4-(2-methoxythiazol-4-yl)phenyl group, a 4-(2-ethoxythiazol-4-yl)-phenyl group, a 4-(2-propoxythiazol-4-yl)phenyl group, a 4-(2-isopropoxythiazol-4-yl)-phenyl group, a 4-(2-tert-butoxythiazol-4-yl)phenyl group, a 4-(2-trifluoromethoxythiazol-4-yl)phenyl group, a 4-(2-difluoromethoxythiazol-4-yl)phenyl group, a 4-(2-trichloromethoxythiazol-4-yl)phenyl group, a 4-(2-dichloromethoxythiazol-4-yl)phenyl group, a 4-(thiazol-5-yl)phenyl group, a 4-(1,2,4-triazol-1-yl)phenyl group, a 4-(pyridin-2-yl)phenyl group, a 4-(pyridin-3-yl)phenyl group, a 4-(pyridin-4-yl)phenyl group, a 4-(pyridazin-3-yl)phenyl group, a 4-(pyridazin-4-yl)phenyl group, a 4-(pyrimidin-2-yl)phenyl group, a 4-(4-fluoropyrimidin-2-yl)phenyl group, a 4-(5-fluoropyrimidin-2-yl)phenyl group, a 4-(4-chloropyrimidin-2-yl)phenyl group, a 4-(5-chloropyrimidin-2-yl)phenyl group, a 4-(5-hydroxypyrimidin-2-yl)phenyl group, a 4-(4-methylpyrimidin-2-yl)phenyl group, a 4-(4-ethylpyrimidin-2-yl)phenyl group, a 4-(4-trifluoromethylpyrimidin-2-yl)phenyl group, a 4-(4-methoxypyrimidin-2-yl)phenyl group, a 4-(4-difluoromethoxypyrimidin-2-yl)phenyl group, a 4-(pyrimidin-4-yl)phenyl group, a 4-(pyrimidin-5-yl)phenyl group, a 4-(pyrazin-2-yl)phenyl group, a 4-(4,5-dihydro-1H-imidazol-2-yl)phenyl group, a 4-(4,5-dihydroxazol-2-yl)phenyl group, a 4-(4,5-dihydrothiazol-2-yl)phenyl group, a 4-(1,4,5,6-tetrahydropyrimidin-2-yl)phenyl group, a 4-(5,6-dihydro-4H-1,3-oxazin-2-yl)-phenyl group, a 4-(5,6-dihydro-4H-1,3-thiazin-2-yl)phenyl group, a 4-(pyrrolidin-1-yl)-phenyl group, a 4-(tetrahydrofuran-2-yl)phenyl group, a 4-(1,3-dioxolan-2-yl)phenyl group, a 4-(piperidin-1-yl)phenyl group, a 4-(tetrahydropyran-2-yl)phenyl group, a 4-(piperazin-1-yl)phenyl group, a 4-(morpholin-4-yl)phenyl group, a 4-(thiomorpholin-4-yl)phenyl group, a 4-(1,3-dioxan-2-yl)phenyl group, a 4-(1,4-dioxan-2-yl)phenyl group, a 4-phenylnaphthalen-1-yl group, a 5-phenylfuran-2-yl group, a 5-phenylthiophen-2-yl group, a 5-(thiazol-2-yl)thiophen-2-yl group, a 5-(thiazol-4-yl)thiophen-2-yl group, a 2-phenylthiazol-5-yl group, a 5-phenylpyridin-2-yl group, a 6-phenylpyridin-3-yl group, a 6-phenylpyridazin-3-yl group, a 6-(4-fluorophenyl)pyridazin-3-yl group, a 6-(4-chlorophenyl)pyridazin-3-yl group, a 6-(pyrazol-1-yl)pyridazin-3-yl group, a 6-(thiazol-2-yl)-pyridazin-3-yl group, a 6-(thiazol-4-yl)pyridazin-3-yl group, a 6-(pyrimidin-2-yl)-pyridazin-3-yl group, a 2-phenylpyrimidin-4-yl group, a 2-(thiazol-2-yl)pyrimidin-4-yl group or a 2-(thiazol-4-yl)pyrimidin-4-yl group, preferably a biphenyl-3-yl group, a biphenyl-4-yl group, a 2'-fluorobiphenyl-4-yl group, a 3'-fluorobiphenyl-4-yl group, a 4'-fluorobiphenyl-4-yl group, a 2',4'-difluorobiphenyl-4-yl group, a 3',4'-difluorobiphenyl-4-yl group, a 2'-chlorobiphenyl-4-yl group, a 3'-chlorobiphenyl-4-yl group, a 4'-chlorobiphenyl-4-yl group, a 2',4'-dichlorobiphenyl-4-yl group, a 3',4'-dichlorobiphenyl-4-yl group, a 4'-chloro-2'-fluorobiphenyl-4-yl group, a 4'-chloro-3'-fluorobiphenyl-4-yl group, a 3'-bromobiphenyl-4-yl group, a 3'-hydroxybiphenyl-4-yl group, a 4'-hydroxybiphenyl-4-yl group, a 3'-methylbiphenyl-4-yl group, a 3'-ethylbiphenyl-4-yl group, a 3'-propylbiphenyl-4-yl group, a 3'-isopropylbiphenyl-4-yl group, a 3'-tert-butylbiphenyl-4-yl group, a 3'-trifluoromethylbiphenyl-4-yl group, a 3'-difluoromethylbiphenyl-4-yl group, a 3'-trichloromethylbiphenyl-4-yl group, a 3'-dichloromethylbiphenyl-4-yl group, a 3'-(2,2,2-trifluoroethyl)biphenyl-4-yl group, a 3'-(2,2,2-trichloroethyl)biphenyl-4-yl group, a 3'-methoxybiphenyl-4-yl group, a 3'-ethoxybiphenyl-4-yl group, a 3'-propoxybiphenyl-4-yl group, a 3'-isopropoxybiphenyl-4-yl group, a 3'-tert-butoxybiphenyl-4-yl group, a 3'-trifluoromethoxybiphenyl-4-yl group, a 3'-difluoromethoxybiphenyl-4-yl group, a 3'-trichloromethoxybiphenyl-4-yl group, a 3'-dichloromethoxybiphenyl-4-yl group, a 4-(thiophen-2-yl)phenyl group, a 4-(thiophen-3-yl)phenyl group, a 4-(pyrazol-1-yl)phenyl group, a 4-(4-fluoropyrazol-1-yl)phenyl group, a 4-(4-chloropyrazol-1-yl)phenyl group, a 4-(oxazol-2-yl)phenyl group, a 4-(oxazol-4-yl)phenyl group, a 4-(thiazol-2-yl)phenyl group, a 4-(4-fluorothiazol-2-yl)phenyl group, a 4-(4-chlorothiazol-2-yl)phenyl group, a 4-(5-chlorothiazol-2-yl)phenyl group, a 4-(4-methylthiazol-2-yl)phenyl group, a 4-(5-methylthiazol-2-yl)phenyl group, a 4-(4,5-dimethylthiazol-2-yl)phenyl group, a 4-(4-ethylthiazol-2-yl)phenyl group, a 4-(4-trifluoromethylthiazol-2-yl)phenyl group, a 4-(4-methoxythiazol-2-yl)phenyl group, a 4-(4-difluoromethoxythiazol-2-yl)phenyl group, a 4-(thiazol-4-yl)phenyl group, a 4-(2-fluorothiazol-4-yl)phenyl group, a 4-(2-chlorothiazol-4-yl)phenyl group, a 4-(2-methylthiazol-4-yl)phenyl group, a 4-(2-ethylthiazol-4-yl)phenyl group, a 4-(2-trifluoromethylthiazol-4-yl)phenyl group, a 4-(2-methoxythiazol-4-yl)phenyl group, a 4-(2-difluoromethoxythiazol-4-yl)phenyl group, a 4-(thiazol-5-yl)phenyl group, a 4-(1,2,4-triazol-1-yl)phenyl group, a 4-(pyridin-2-yl)-phenyl group, a 4-(pyridin-3-yl)phenyl group, a 4-(pyridin-4-yl)phenyl group, a 4-(pyridazin-3-yl)phenyl group, a 4-(pyridazin-4-yl)phenyl group, a 4-(pyrimidin-2-yl)-phenyl group, a 4-(5-fluoropyrimidin-2-yl)phenyl group, a 4-(5-chloropyrimidin-2-yl)-phenyl group, a 4-(5-hydroxypyrimidin-2-yl)phenyl group, a 4-(pyrimidin-4-yl)phenyl group, a 4-(pyrimidin-5-yl)phenyl group, a 4-(4,5-dihydrothiazol-2-yl)phenyl group, a 4-(pyrrolidin-1-yl)phenyl group, a 4-(piperidin-1-yl)phenyl group, a 5-phenylthiophen-2-yl group, a 5-(thiazol-2-yl)thiophen-2-yl group, a 5-(thiazol-4-yl)thiophen-2-yl group, a 6-phenylpyridazin-3-yl group, a 6-(thiazol-2-yl)pyridazin-3-yl group, a 6-(thiazol-4-yl)pyridazin-3-yl group, a 2-phenylpyrimidin-4-yl group, a 2-(thiazol-2-yl)pyrimidin-4-yl group or a 2-(thiazol-4-yl)pyrimidin-4-yl group, more preferably a biphenyl-4-yl group, a 2'-fluorobiphenyl-4-yl group, a 3'-fluorobiphenyl-4-yl group, a 4'-fluorobiphenyl-4-yl group, a 2',4'-difluorobiphenyl-4-yl group, a 3',4'-difluorobiphenyl-4-yl group, a 2'-chlorobiphenyl-4-yl group, a 3'-chlorobiphenyl-4-yl group, a 4'-chlorobiphenyl-4-yl group, a 4'-chloro-2'-fluorobiphenyl-4-yl group, a 4'-chloro-3'-fluorobiphenyl-4-yl group, a 4'-hydroxybiphenyl-4-yl group, a 3% methylbiphenyl-4-yl group, a 3'-ethylbiphenyl-4-yl group, a 3'-trifluoromethylbiphenyl-4-yl group, a 3'-methoxybiphenyl-4-yl group, a 3'-difluoromethoxybiphenyl-4-yl group, a 4-(thiophen-2-yl)phenyl group, a 4-(thiophen-3-yl)phenyl group, a 4-(pyrazol-1-yl) phenyl group, a 4-(oxazol-2-yl)phenyl group, a 4-(oxazol-4-yl)phenyl group, a 4-(thiazol-2-yl)phenyl group, a 4-(4-fluorothiazol-2-yl)phenyl group, a 4-(4-chlorothiazol-2-yl) phenyl group, a 4-(5-chlorothiazol-2-yl)phenyl group, a 4-(5-methylthiazol-2-yl)phenyl group, a 4-(4,5-dimethylthiazol-2-yl)phenyl group, a 4-(4-trifluoromethylthiazol-2-yl)phenyl group, a 4-(thiazol-4-yl)phenyl group, a 4-(2-fluorothiazol-4-yl)phenyl group, a 4-(2-chlorothiazol-4-yl)phenyl group, a 4-(thiazol-5-yl)phenyl group, a 4-(1,2,4-triazol-1-yl)phenyl group, a 4-(pyridin-2-yl)phenyl group, a 4-(pyridazin-3-yl) phenyl group, a 4-(pyridazin-4-yl)phenyl group, a 4-(pyrimidin-2-yl)phenyl group, a 4-(5-hydroxypyrimidin-2-yl)phenyl group, a 4-(pyrimidin-4-yl)phenyl group, a 4-(pyrimidin-5-yl)phenyl group, a 4-(4,5-dihydrothiazol-2-yl)phenyl group, a 6-phenylpyridazin-3-yl group, a 6-(thiazol-2-yl)pyridazin-3-yl group or a 6-(thiazol-4-yl)-pyridazin-3-yl group, and particularly preferably a biphenyl-4-yl group, a 4'-fluorobiphenyl-4-yl group, a 4'-chlorobiphenyl-4-yl group, a 4-(pyrazol-1-yl)phenyl group, a 4-(thiazol-2-yl)phenyl group, a 4-(5-chlorothiazol-2-yl)phenyl group, a 4-(5-methylthiazol-2-yl)phenyl group, a 4-(4,5-dimethylthiazol-2-yl)phenyl group, a 4-(4-trifluoromethylthiazol-2-yl)phenyl group, a 4-(thiazol-4-yl)phenyl group, a 4-(1,2,4-triazol-1-yl)phenyl group, a 4-(pyridin-2-yl)phenyl group, a 4-(pyridazin-4-yl) phenyl group, a 4-(pyrimidin-2-yl)phenyl group, a 4-(4,5-dihydrothiazol-2-yl)phenyl group or a 6-phenylpyridazin-3-yl group.

Y is preferably a benzofuryl group, a benzothienyl group, a benzoxazolyl group or a benzothiazolyl group, each of which may be substituted with a group(s) selected from the group consisting of a halogen atom, a $C_1$-$C_4$ alkyl group, a halogeno-$C_1$-$C_4$ alkyl group, a $C_1$-$C_4$ alkoxy group, a halogeno-$C_1$-$C_4$ alkoxy group and a $C_1$-$C_4$ alkylthio group, or, in a -$Q^1$-$Q^2$ group represented by Y, $Q^1$ represents a phenylene group, a thienylene group, a pyridazinylene group or a pyrimidinylene group, and $Q^2$ is a phenyl group, a thienyl group, a pyrazolyl group, an oxazolyl group, a thiazolyl group, a 1,2,4-triazolyl group, a pyridyl group, a pyridazinyl group, a pyrimidinyl group, a 4,5-dihydrothiazolyl group, a pyrrolidinyl group or a piperidinyl group, each of which may be substituted with a group(s) selected from the group consisting of a halogen atom, a hydroxy group, a $C_1$-$C_4$ alkyl group, a halogeno-$C_1$-$C_4$ alkyl group, a $C_1$-$C_4$ alkoxy group and a halogeno-$C_1$-$C_4$ alkoxy group, more preferably a benzofuryl group, a benzothienyl group, a benzoxazolyl group or a benzothiazolyl group, each of which may be substituted with a group(s) selected from the group consisting of a fluorine atom, a chlorine atom, a bromine atom, a methyl group, an ethyl group, a propyl group, an isopropyl group, a tert-butyl group, a trifluoromethyl group, a difluoromethyl group, a trichloromethyl group, a dichloromethyl group, a 2,2,2-trifluoroethyl group, a 2,2,2-trichloroethyl group, a methoxy group, an ethoxy group, a propoxy group, an isopropoxy group, a tert-butoxy group, a trifluoromethoxy group, a difluoromethoxy group, a trichloromethoxy group, a dichloromethoxy group, a methylthio group, an ethylthio group, a propylthio group, an isopropylthio group and a tert-butylthio group, or, in a -$Q^1$-$Q^2$ group represented by Y, $Q^1$ is a phenylene group, a thienylene group, a pyridazinylene group or a pyrimidinylene group, and $Q^2$ is a phenyl group, a thienyl group, a pyrazolyl group, an oxazolyl group, a thiazolyl group, a 1,2,4-triazolyl group, a pyridyl group, a pyridazinyl group, a pyrimidinyl group, a 4,5-dihydrothiazolyl group, a pyrrolidinyl group or a piperidinyl group, each of which may be substituted with a group(s) selected from the group consisting of a fluorine atom, a chlorine atom, a bromine atom, a hydroxy group, a methyl group, an ethyl group, a propyl group, an isopropyl group, a tert-butyl group, a trifluoromethyl group, a difluoromethyl group, a trichloromethyl group, a dichloromethyl group, a 2,2,2-trifluoroethyl group, a 2,2,2-trichloro ethyl group, a methoxy group, an ethoxy group, a propoxy group, an isopropoxy group, a tert-butoxy group, a trifluoromethoxy group, a difluoromethoxy group, a trichloromethoxy group and a dichloromethoxy group.

Examples thereof preferably include a benzofuran-2-yl group, a 6-fluorobenzofuran-2-yl group, a 5,6-difluorobenzofuran-2-yl group, a 6-chlorobenzofuran-2-yl group, a 6-chloro-5-fluorobenzofuran-2-yl group, a 6-methylbenzofuran-2-yl group, a 5-fluoro-6-methylbenzofuran-2-yl group, a 6-ethylbenzofuran-2-yl group, a 6-ethyl-5-fluorobenzofuran-2-yl group, a 6-trifluoromethylbenzofuran-2-yl group, a 5-fluoro-6-trifluoromethylbenzofuran-2-yl group, a 6-methoxybenzofuran-2-yl group, a 5-fluoro-6-methoxybenzofuran-2-yl group, a 6-difluoromethoxybenzofuran-2-yl group, a 6-difluoromethoxy-5-fluorobenzofuran-2-yl group, a 6-methylthiobenzofuran-2-yl group, a 5-fluoro-6-methylthiobenzofuran-2-yl group, a benzo[b]thiophen-2-yl group, a 6-fluorobenzo[b]thiophen-2-yl group, a 5,6-difluorobenzo[b]thiophen-2-yl group, a 6-chlorobenzo[b]thiophen-2-yl group, a 6-chloro-5-fluorobenzo[b]thiophen-2-yl group, a 6-bromobenzo[b]thiophen-2-yl group, a 6-methylbenzo[b]thiophen-2-yl group, a 5-fluoro-6-methylbenzo[b]thiophen-2-yl group, a 6-ethylbenzo[b]thiophen-2-yl group, a 6-ethyl-5-fluorobenzo[b]thiophen-2-yl group, a 6-propylbenzo[b]thiophen-2-yl group, a 6-isopropylbenzo[b]thiophen-2-yl group, a 6-tert-butylbenzo[b]thiophen-2-yl group, a 6-trifluoromethylbenzo[b]thiophen-2-yl group, a 5-fluoro-6-trifluoromethylbenzo[b]-thiophen-2-yl group, a 6-difluoromethylbenzo[b]thiophen-2-yl group, a 6-trichloromethylbenzo[b]thiophen-2-yl group, a 6-dichloromethylbenzo[b]thiophen- 2-yl group, a 6-(2,2,2-trifluoroethyl)benzo[b]thiophen-2-yl group, a 6-(2,2,2-trichloroethyl)benzo[b]-thiophen-2-yl group, a 6-methoxybenzo[b]thiophen-2-yl group, a 5-fluoro-6-methoxybenzo[b]thiophen-2-yl group, a 6-ethoxybenzo[b]thiophen-2-yl group, a 6-propoxybenzo[b]thiophen-2-yl group, a 6-isopropoxybenzo[b]thiophen-2-yl group, a 6-tert-butoxybenzo[b]thiophen-2-yl group, a 6-trifluoromethoxybenzo[b]thiophen-2-yl group, a 6-difluoromethoxybenzo[b]thiophen-2-yl group, a 6-difluoromethoxy-5-fluorobenzo-[b]thiophen-2-yl group, a 6-trichloromethoxybenzo[b]thiophen-2-yl group, a 6-dichloromethoxybenzo[b]thiophen-2-yl group, a 6-methylthiobenzo[b]thiophen-2-yl group, a 5-fluoro-6-methylthiobenzo[b]thiophen-2-yl group, a 6-ethylthiobenzo[b]-thiophen-2-yl group, a 6-propylthiobenzo[b]thiophen-2-yl group, a 6-isopropylthiobenzo[b]thiophen-2-yl group, a 6-text-butylthiobenzo[b]thiophen-2-yl group, a benzoxazol-2-yl group, a 6-chlorobenzoxazol-2-yl group, a 6-methoxybenzoxazol-2-yl group, a benzothiazol-2-yl group, a 6-chlorobenzothiazol-2-yl group, a 6-methoxybenzothiazol-2-yl group, a biphenyl-3-yl group, a biphenyl-4-yl group, a 2'-fluorobiphenyl-4-yl group, a 3'-fluorobiphenyl-4-yl group, a 4'-fluorobiphenyl-4-yl group, a 2',4'-difluorobiphenyl-4-yl group, a 3',4'-difluorobiphenyl-4-yl group, a 2'-chlorobiphenyl-4-yl group, a 3'-chlorobiphenyl-4-yl group, a 4'-chlorobiphenyl-4-yl group, a 2',4'-dichlorobiphenyl-4-yl group, a 3',4'-dichlorobiphenyl-4-yl group, a 4'-chloro-2'-fluorobiphenyl-4-yl group, a 4'-chloro-3'-fluorobiphenyl-4-yl group, a 3'-bromobiphenyl-4-yl group, a 3'-hydroxybiphenyl-4-yl group, a 4'-hydroxybiphenyl-4-yl group, a 3'-methylbiphenyl-4-yl group, a 3'-ethylbiphenyl-4-yl group, a 3'-propylbiphenyl-4-yl group, a 3'-isopropylbiphenyl-4-yl group, a 3'-tert-butylbiphenyl-4-yl group, a 3'-trifluoromethylbiphenyl-4-yl group, a 3'-difluoromethylbiphenyl-4-yl group, a 3'-trichloromethylbiphenyl-4-yl group, a 3'-dichloromethylbiphenyl-4-yl group, a 3'-(2,2,2-trifluoroethyl)biphenyl-4-yl group, a 3'-(2,2,2-trichloroethyl)biphenyl-4-yl group, a 3'-methoxybiphenyl-4-yl group, a 3'-ethoxybiphenyl-4-yl group, a 3'-propoxybiphenyl-4-yl group, a 3'-isopropoxybiphenyl-4-yl group, a 3'-tert-butoxybiphenyl-4-yl group, a 3'-trifluoromethoxybiphenyl-4-yl group, a 3'-difluoromethoxybiphenyl-4-yl group, a 3'-trichloromethoxybiphenyl-4-yl group, a 3'-dichloromethoxybiphenyl-4-yl group, a 4-(thiophen-2-yl)phenyl group, a 4-(thiophen-3-yl)phenyl group, a 4-(pyrazol-1-yl)phenyl group, a 4-(4-fluoropyrazol-1-yl)phenyl group, a 4-(4-chloropyrazol-1-yl)phenyl group, a 4-(oxazol-2-yl)phenyl group, a 4-(oxazol-4-yl)phenyl group, a 4-(thiazol-2-yl)phenyl group, a 4-(4-fluorothiazol-2-yl)phenyl group, a 4-(4-chlorothiazol-2-yl)phenyl group, a 4-(5-chlorothiazol-2-yl)phenyl group, a 4-(4-methylthiazol-2-yl)phenyl group, a 4-(5-methylthiazol-2-yl)phenyl group, a 4-(4,5-dimethylthiazol-2-yl)phenyl group, a 4-(4-ethylthiazol-2-yl)phenyl group, a 4-(4-trifluoromethylthiazol-2-yl)phenyl group, a 4-(4-methoxythiazol-2-yl)phenyl group, a 4-(4-difluoromethoxythiazol-2-yl)phenyl group, a 4-(thiazol-4-yl)phenyl group, a 4-(2-fluorothiazol-4-yl)phenyl group, a 4-(2-chlorothiazol-4-yl)phenyl group, a 4-(2-methylthiazol-4-yl)phenyl group, a 4-(2-ethylthiazol-4-yl)phenyl group, a 4-(2-trifluoromethylthiazol-4-yl)phenyl group, a 4-(2-methoxythiazol-4-yl)phenyl group, a 4-(2-difluoromethoxythiazol-4-yl)phenyl group, a 4-(thiazol-5-yl)phenyl group, a 4-(1,2,4-triazol-1-yl)phenyl group, a 4-(pyridin-2-yl)phenyl group, a 4-(pyridin-3-yl)-phenyl group, a 4-(pyridin-4-yl)phenyl group, a 4-(pyridazin-3-yl)phenyl group, a 4-(pyridazin-4-yl)phenyl group, a 4-(pyrimidin-2-yl)phenyl group, a 4-(5-fluoropyrimidin-2-yl)phenyl group, a 4-(5-chloropyrimidin-2-yl)phenyl group, a 4-(5-hydroxypyrimidin-2-yl)phenyl group, a 4-(pyrimidin-4-yl)phenyl group, a 4-(pyrimidin-5-yl)phenyl group, a 4-(4,5-dihydrothiazol-2-yl)phenyl group, a 4-(pyrrolidin-1-yl)phenyl group, a 4-(piperidin-1-yl)phenyl group, a 5-phenylthiophen-2-yl group, a 5-(thiazol-2-yl)thiophen-2-yl group, a 5-(thiazol-4-yl)thiophen-2-yl group, a 6-phenylpyridazin-3-yl group, a 6-(thiazol-2-yl)pyridazin-3-yl group, a 6-(thiazol-4-yl)pyridazin-3-yl group, a 2-phenylpyrimidin-4-yl group, a 2-(thiazol-2-yl)pyrimidin-4-yl group or a 2-(thiazol-4-yl)pyrimidin-4-yl group.

It is more preferably a benzofuran-2-yl group, a 6-fluorobenzofuran-2-yl group, a 6-chlorobenzofuran-2-yl group, a 6-methoxybenzofuran-2-yl group, a benzo-[b]thiophen-2-yl group, a 6-fluorobenzo[b]thiophen-2-yl group, a 5,6-difluorobenzo-[b]thiophen-2-yl group, a 6-chlorobenzo[b]thiophen-2-yl group, a 6-chloro-5-fluorobenzo[b]thiophen-2-yl group, a 6-methylbenzo[b]thiophen-2-yl group, a 5-fluoro-6-methylbenzo[b]thiophen-2-yl group, a 6-ethylbenzo[b]thiophen-2-yl group, a 6-ethyl-5-fluorobenzo[b]thiophen-2-yl group, a 6-trifluoromethylbenzo[b]thiophen-2-yl group, a 5-fluoro-6-trifluoromethylbenzo[b]thiophen-2-yl group, a 6-methoxybenzo[b]thiophen-2-yl group, a 5-fluoro-6-methoxybenzo[b]thiophen-2-yl group, a 6-difluoromethoxybenzo[b]thiophen-2-yl group, a 6-difluoromethoxy-5-fluorobenzo[b]thiophen-2-yl group, a 6-methylthiobenzo[b]thiophen-2-yl group, a 5-fluoro-6-methylthiobenzo[b]-thiophen-2-yl group, a biphenyl-4-yl group, a 2'-fluorobiphenyl-4-yl group, a 3'-fluorobiphenyl-4-yl group, a 4'-fluorobiphenyl-4-yl group, a 2',4'-difluorobiphenyl-4-yl group, a 3',4'-difluorobiphenyl-4-yl group, a 2'-chlorobiphenyl-4-yl group, a 3'-chlorobiphenyl-4-yl group, a 4'-chlorobiphenyl-4-yl group, a 4'-chloro-2'-fluorobiphenyl-4-yl group, a 4'-chloro-3'-fluorobiphenyl-4-yl group, a 4'-hydroxybiphenyl-4-yl group, a 3'-methylbiphenyl-4-yl group, a 3'-ethylbiphenyl-4-yl group, a 3'-trifluoromethylbiphenyl-4-yl group, a 3'-methoxybiphenyl-4-yl group, a 3'-difluoromethoxybiphenyl-4-yl group, a 4-(thiophen-2-yl)phenyl group, a 4-(thiophen-3-yl)phenyl group, a 4-(pyrazol-1-yl)phenyl group, a 4-(oxazol-2-yl)phenyl group, a 4-(oxazol-4-yl)phenyl group, a 4-(thiazol-2-yl)phenyl group, a 4-(4-fluorothiazol-2-yl)phenyl group, a 4-(4-chlorothiazol-2-yl)phenyl group, a 4-(5-chlorothiazol-2-yl)phenyl group, a 4-(5-methylthiazol-2-yl)phenyl group, a 4-(4,5-dimethylthiazol-2-yl)phenyl group, a 4-(4-trifluoromethylthiazol-2-yl)phenyl group, a 4-(thiazol-4-yl)phenyl group, a 4-(2-fluorothiazol-4-yl)phenyl group, a 4-(2-chlorothiazol-4-yl)phenyl group, a 4-(thiazol-5-yl)-phenyl group, a 4-(1,2,4-triazol-1-yl)phenyl group, a 4-(pyridin-2-yl)phenyl group, a 4-(pyridazin-3-yl)phenyl group, a 4-(pyridazin-4-yl)phenyl group, a 4-(pyrimidin-2-yl)-phenyl group, a 4-(5-hydroxypyrimidin-2-yl)phenyl group, a 4-(pyrimidin-4-yl)phenyl group, a 4-(pyrimidin-5-yl)phenyl group, a 4-(4,5-dihydrothiazol-2-yl)phenyl group, a 6-phenylpyridazin-3-yl group, a 6-(thiazol-2-yl)pyridazin-3-yl group or a 6-(thiazol-4-yl)pyridazin-3-yl group. Y is particularly preferably a benzofuryl group or a benzothienyl group, each of which may be substituted with a group(s) selected from the group consisting of a halogen atom and a $C_1$-$C_4$ alkoxy group, or, in a -$Q^1$-$Q^2$ group represented by Y, $Q^1$ represents a phenylene group or a pyridazinylene group, and $Q^2$ is a phenyl group, a pyrazolyl group, a thiazolyl group, a 1,2,4-triazolyl group, a pyridyl group, a pyridazinyl group, a pyrimidinyl group or a 4,5-dihydrothiazolyl group, each of which may be substituted with a group(s) selected from the group consisting of a halogen atom, a $C_1$-$C_4$ alkyl group and a halogeno-$C_1$-$C_4$ alkyl group, for example, a benzofuran-2-yl group, a benzo[b]thiophen-2-yl group, a 6-chlorobenzo[b]thiophen-2-yl group, a 6-methoxybenzo[b]thiophen-2-yl group, a biphenyl-4-yl group, a 4'-fluorobiphenyl-4-yl group, a 4'-chlorobiphenyl-4-yl group, a 4-(pyrazol-1-yl)phenyl group, a 4-(thiazol-2-yl)phenyl group, a 4-(5-chlorothiazol-2-yl)phenyl group, a 4-(5-methylthiazol-2-yl)phenyl group, a 4-(4,5-dimethylthiazol-2-yl)phenyl group, a 4-(4-trifluoromethylthiazol-2-yl)phenyl group, a 4-(thiazol-4-yl)phenyl group, a 4-(1,2,4-triazol-1-yl)phenyl group, a 4-(pyridin-2-yl)phenyl group, a 4-(pyridazin-4-yl)phenyl group, a 4-(pyrimidin-2-yl)phenyl group, a 4-(4,5-dihydrothiazol-2-yl)phenyl group or a 6-phenylpyridazin-3-yl group.

The "5- to 6-membered heteroaromatic group" represented by Z indicates the same meaning and examples as those of the above-mentioned "fully unsaturated 5- to 6-membered heterocyclic group", and preferably it is a thienyl group, an imidazolyl group, a thiazolyl group, a pyridyl group or a pyrimidinyl group, more preferably a thienyl group or a pyridyl group, and particularly preferably a pyridyl group.

A substituent of an aromatic group or a 5- to 6-membered heteroaromatic group represented by Z is preferably a halogen atom, a $C_1$-$C_4$ alkyl group, a halogeno-$C_1$-$C_4$ alkyl group, a $C_1$-$C_4$ alkoxy group or a halogeno-$C_1$-$C_4$ alkoxy group, for example, a fluorine atom, a chlorine atom, a bromine atom, a methyl group, an ethyl group, a propyl group, an isopropyl group, a tert-butyl group, a trifluoromethyl group, a difluoromethyl group, a trichloromethyl group, a dichloromethyl group, a 2,2,2-trifluoroethyl group, a 2,2,2-trichloroethyl group, a methoxy group, an ethoxy group, a propoxy group, an isopropoxy group, a tert-butoxy group, a trifluoromethoxy group, a difluoromethoxy group, a trichloromethoxy group or a dichloromethoxy group, particularly a fluorine atom, a chlorine atom, a methyl group, an ethyl group, a trifluoromethyl group, a methoxy group or a difluoromethoxy group, and particularly preferably a halogen atom or a $C_1$-$C_4$ alkoxy group, for example, a fluorine atom, a chlorine atom or a methoxy group.

The number of substituent(s) on an aromatic group or a 5- to 6-membered heteroaromatic group represented by Z is, for example, 1 to 5, preferably 1 to 3, particularly preferably 1 to 2, and in the case of a plural number, these substituents may be the same or different from each other.

Examples of "an aromatic group which may be substituted with a group(s) selected from the group consisting of a halogen atom, a $C_1$-$C_6$ alkyl group, a halogeno-$C_1$-$C_6$ alkyl group, a $C_1$-$C_6$ alkoxy group and a halogeno-$C_1$-$C_6$ alkoxy group" represented by Z include a phenyl group, a 1-naphthyl group, a 2-naphthyl group, a 2-fluorophenyl group, a 3-fluorophenyl group, a 4-fluorophenyl group, a 3-fluoro-1-naphthyl group, a 4-fluoro-1-naphthyl group, a 4-fluoro-2-naphthyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,3,4-trifluorophenyl group, a 2,3,5-trifluorophenyl group, a 2,3,6-trifluorophenyl group, a 2,4,5-trifluorophenyl group, a 2,4,6-trifluorophenyl group, a 3,4,5-trifluorophenyl group, a 2,3,4,5,6-pentafluorophenyl group, a 2-chlorophenyl group, a 3-chlorophenyl group, a 4-chlorophenyl group, a 3-chloro-1-naphthyl group, a 4-chloro-1-naphthyl group, a 4-chloro-2-naphthyl group, a 2,3-dichlorophenyl group, a 2,4-dichlorophenyl group, a 2,5-dichlorophenyl group, a 2,6-dichlorophenyl group, a 3,4-dichlorophenyl group, a 3,5-dichlorophenyl group, a 4-chloro-2-fluorophenyl group, a 4-chloro-3-fluorophenyl group, a 4-chloro-2,3-difluorophenyl group, a 4-chloro-2,5-difluorophenyl group, a 4-chloro-2,6-difluorophenyl group, a 4-chloro-3,5-difluorophenyl group, a 3-bromophenyl group, a 4-bromophenyl group, a 4-iodophenyl group, a 2-methylphenyl group, a 3-methylphenyl group, a 4-methylphenyl group, a 3-fluoro-4-methylphenyl group, a 2-ethylphenyl group, a 3-ethylphenyl group, a 4-ethylphenyl group, a 4-ethyl-3-fluorophenyl group, a 3-propylphenyl group, a 4-propylphenyl group, a 3-isopropylphenyl group, a 4-isopropylphenyl group, a 4-butylphenyl group, a 4-isobutylphenyl group, a 4-sec-butylphenyl group, a 3-tert-butylphenyl group, a 4-tert-butylphenyl group, a 4-pentylphenyl group, a 4-hexylphenyl group, a 2-trifluoromethylphenyl group, a 3-trifluoromethylphenyl group, a 4-trifluoromethylphenyl group, a 3-fluoro-4-trifluoromethylphenyl group, a 3-difluoromethylphenyl group, a 4-difluoromethylphenyl group, a 3-trichloromethylphenyl group, a 4-trichloromethylphenyl group, a 3-dichloromethylphenyl group, a 4-dichloromethylphenyl group, a 3-(2,2,2-trifluoroethyl)phenyl group, a 4-(2,2,2-trifluoroethyl)phenyl group, a 3-(2,2,2-trichloroethyl)phenyl group, a 4-(2,2,2-trichloroethyl)phenyl group, a 2-methoxyphenyl group, a 3-methoxyphenyl group, a 4-methoxyphenyl group, a 3-methoxy-1-naphthyl group, a 4-methoxy-1-naphthyl group, a 4-methoxy-2-naphthyl group, a 2-fluoro-4-methoxyphenyl group, a 3-fluoro-4-methoxyphenyl group, a 2,3-difluoro-4-methoxyphenyl group, a 2,5-difluoro-4-methoxyphenyl group, a 2,6-difluoro-4-methoxyphenyl group, a 3,5-difluoro-4-methoxyphenyl group, a 3-ethoxyphenyl group, a 4-ethoxyphenyl group, a 3-propoxyphenyl group, a 4-propoxyphenyl group, a 3-isopropoxyphenyl group, a 4-isopropoxyphenyl group, a 4-butoxyphenyl group, a 4-isobutoxyphenyl group, a 4-sec-butoxyphenyl group, a 3-tert-butoxyphenyl group, a 4-tert-butoxyphenyl group, a 4-pentyloxyphenyl group, a 4-hexyloxyphenyl group, a 3-trifluoromethoxyphenyl group, a 4-trifluoromethoxyphenyl group, a 2-difluoromethoxyphenyl group, a 3-difluoromethoxyphenyl group, a 4-difluoromethoxyphenyl group, a 4-difluoromethoxy-3-fluorophenyl group, a 3-trichloromethoxyphenyl group, a 4-trichloromethoxyphenyl group, a 3-dichloromethoxyphenyl group or a 4-dichloromethoxyphenyl group, preferably a phenyl group, a 2-fluorophenyl group, a 3-fluorophenyl group, a 4-fluorophenyl group, a 3,4-difluorophenyl group, a 3,5-difluorophenyl group, a 3,4,5-trifluorophenyl group, a 2-chlorophenyl group, a 3-chlorophenyl group, a 4-chlorophenyl group, a 2,6-dichlorophenyl group, a 4-chloro-3-fluorophenyl group, a 4-chloro-3,5-difluorophenyl group, a 4-bromophenyl group, a 4-methylphenyl group, a 3-fluoro-4-methylphenyl group, a 4-ethylphenyl group, a 4-ethyl-3-fluorophenyl group, a 4-propylphenyl group, a 4-isopropylphenyl group, a 4-tert-butylphenyl group, a 4-trifluoromethylphenyl group, a 3-fluoro-4-trifluoromethylphenyl group, a 4-difluoromethylphenyl group, a 4-trichloromethylphenyl group, a 4-dichloromethylphenyl group, a 4-(2,2,2-trifluoroethyl)phenyl group, a 4-(2,2,2-trichloroethyl)phenyl group, a 4-methoxyphenyl group, a 3-fluoro-4-methoxyphenyl group, a 4-ethoxyphenyl group, a 4-propoxyphenyl group, a 4-isopropoxyphenyl group, a 4-tert-butoxyphenyl group, a 4-trifluoromethoxyphenyl group, a 4-difluoromethoxyphenyl group, a 4-difluoromethoxy-3-fluorophenyl group, a 4-trichloromethoxyphenyl group or a 4-dichloromethoxyphenyl group, more preferably a phenyl group, a 2-fluorophenyl group, a 3-fluorophenyl group, a 4-fluorophenyl group, a 3,4-difluorophenyl group, a 3,5-difluorophenyl group, a 2-chlorophenyl group, a 3-chlorophenyl group, a 4-chlorophenyl group, a 2,6-dichlorophenyl group, a 4-chloro-3-fluorophenyl group, a 4-methylphenyl group, a 3-fluoro-4-methylphenyl group, a 4-ethylphenyl group, a 4-ethyl-3-fluorophenyl group, a 4-trifluoromethylphenyl group, a 3-fluoro-4-trifluoromethylphenyl group, a 4-methoxyphenyl group, a 3-fluoro-4-methoxyphenyl group, a 4-difluoromethoxyphenyl group or a 4-difluoromethoxy-3-fluorophenyl group, and particularly preferably a phenyl group, a 2-fluorophenyl group, a 3-fluorophenyl group, a 4-fluorophenyl group, a 2-chlorophenyl group, a 3-chlorophenyl group, a 4-chlorophenyl group, a 2,6-dichlorophenyl group or a 4-methoxyphenyl group.

Examples of "a 5- to 6-membered hetero aromatic group which may be substituted with a group(s) selected from the group consisting of a halogen atom, a $C_1$-$C_6$ alkyl group, a halogeno-$C_1$-$C_6$ alkyl group, a $C_1$-$C_6$ alkoxy group and a halogen-$C_1$-$C_6$ alkoxy group" represented by Z include, for example, a pyrrol-1-yl group, a furan-2-yl group, a furan-3-yl group, a thiophen-2-yl group, a thiophen-3-yl group, a 5-fluorothiophen-2-yl group, a 5-chlorothiophen-2-yl group, a 5-methylthiophen-2-yl group, a 5-ethylthiophen-2-yl group, a 5-trifluoromethylthiophen-2-yl group, a 5-methoxythiophen-2-yl group, a 5-difluoromethoxythiophen-2-yl group, a pyrazol-1-yl group, a 1-methyl-1H-imidazol-4-yl group, a 1-ethyl-1H-imidazol-4-yl group, an oxazol-2-yl group, a thiazol-2-yl group, a pyridin-2-yl group, a 5-fluoropyridin-2-yl group, a 5-chloropyridin-2-yl group, a 5-bromopyridin-2-yl group, a 5-methylpyridin-2-yl group, a 5-ethylpyridin-2-yl group, a 5-propylpyridin-2-yl group, a 5-isopropylpyridin-2-yl group, a 5-butylpyridin-2-yl group, a 5-isobutylpyridin-2-yl group, a 5-sec-butylpyridin-2-yl group, a 5-tert-butylpyridin-2-yl group, a 5-pentylpyridin-2-yl group, a 5-hexylpyridin-2-yl group, a 5-trifluoromethylpyridin-2-yl group, a 5-difluoromethylpyridin-2-yl group, a 5-trichloromethylpyridin-2-yl group, a 5-dichloromethylpyridin-2-yl group, a 5-(2,2,2-trifluoroethyl)pyridin-2-yl group, a 5-(2,2,2-trichloro ethyl)pyridin-2-yl group, a 5-methoxypyridin-2-yl group, a 5-ethoxypyridin-2-yl group, a 5-propoxypyridin-2-yl group, a 5-isopropoxypyridin-2-yl group, a 5-tert-butoxypyridin-2-yl group, a 5-trifluoromethoxypyridin-2-yl group, a 5-difluoromethoxypyridin-2-yl group, a 5-trichloromethoxypyridin-2-yl group, a 5-dichloromethoxypyridin-2-yl group, a pyridin-3-yl group, a 6-fluoropyridin-3-yl group, a 6-chloropyridin-3-yl group, a 6-bromopyridin-3-yl group, a 6-methylpyridin-3-yl group, a 6-ethylpyridin-3-yl group, a 6-propylpyridin-3-yl group, a 6-isopropylpyridin-3-yl group, a 6-butylpyridin-3-yl group, a 6-isobutylpyridin-3-yl group, a 6-sec-butylpyridin-3-yl group, a 6-tert-butylpyridin-3-yl group, a 6-pentylpyridin-3-yl group, a 6-hexylpyridin-3-yl group, a 6-trifluoromethylpyridin-3-yl group, a 6-difluoromethylpyridin-3-yl group, a 6-trichloromethylpyridin-3-yl group, a 6-dichloromethylpyridin-3-yl group, a 6-(2,2,2-trifluoroethyl)pyridin-3-yl group, a 6-(2,2,2-trichloro ethyl)pyridin-3-yl group, a 6-methoxypyridin-3-yl group, a 6-ethoxypyridin-3-yl group, a 6-propoxypyridin-3-yl group, a 6-isopropoxypyridin-3-yl group, a 6-tert-butoxypyridin-3-yl group, a 6-trifluoromethoxypyridin-3-yl group, a 6-difluoromethoxypyridin-3-yl group, a 6-trichloromethoxypyridin-3-yl group, a 6-dichloromethoxypyridin-3-yl group, a pyridin-4-yl group, a pyridazin-3-yl group, a pyridazin-4-yl group, a pyrimidin-2-yl group, a pyrimidin-4-yl group, a pyrimidin-5-yl group or a pyrazin-2-yl group, preferably a thiophen-2-yl group, a thiophen-3-yl group, a 5-chlorothiophen-2-yl group, a 1-methyl-1H-imidazol-4-yl group, a thiazol-2-yl group, a pyridin-2-yl group, a 5-fluoropyridin-2-yl group, a 5-chloropyridin-2-yl group, a 5-methylpyridin-2-yl group, a 5-ethylpyridin-2-yl group, a 5-trifluoromethylpyridin-2-yl group, a 5-methoxypyridin-2-yl group, a 5-difluoromethoxypyridin-2-yl group, a pyridin-3-yl group, a 6-fluoropyridin-3-yl group, a 6-chloropyridin-3-yl group, a 6-methylpyridin-3-yl group, a 6-ethylpyridin-3-yl group, a 6-trifluoromethylpyridin-3-yl group, a 6-methoxypyridin-3-yl group, a 6-difluoromethoxypyridin-3-yl group, a pyridin-4-yl group or a pyrimidin-2-yl group, more preferably a thiophen-2-yl group, a thiophen-3-yl group, a pyridin-2-yl group, a 5-fluoropyridin-2-yl group, a 5-chloropyridin-2-yl group, a 5-methoxypyridin-2-yl group, a pyridin-3-yl group, a 6-fluoropyridin-3-yl group, a 6-chloropyridin-3-yl group, a 6-methoxypyridin-3-yl group or a pyridin-4-yl group, and particularly preferably a pyridin-2-yl group or a pyridin-3-yl group.

Z is preferably a phenyl group, a thienyl group, an imidazolyl group, a thiazolyl group, a pyridyl group or a pyrimidinyl group, each of which may be substituted with a group(s) selected from the group consisting of a halogen atom, a $C_1$-$C_4$ alkyl group, a halogeno-$C_1$-$C_4$ alkyl group, a $C_1$-$C_4$ alkoxy group or a halogeno-$C_1$-$C_4$ alkoxy group, for example, a fluorine atom, a chlorine atom, a bromine atom, a methyl group, an ethyl group, a propyl group, an isopropyl group, a tert-butyl group, a trifluoromethyl group, a difluoromethyl group, a trichloromethyl group, a dichloromethyl group, a 2,2,2-trifluoroethyl group, a 2,2,2-trichloroethyl group, a methoxy group, an ethoxy group, a propoxy group, an isopropoxy group, a tert-butoxy group, a trifluoromethoxy group, a difluoromethoxy group, a trichloromethoxy group and a dichloromethoxy group, more preferably a phenyl group, a 2-fluorophenyl group, a 3-fluorophenyl group, a 4-fluorophenyl group, a 3,4-difluorophenyl group, a 3,5-difluorophenyl group, a 3,4,5-trifluorophenyl group, a 2-chlorophenyl group, a 3-chlorophenyl group, a 4-chlorophenyl group, a 2,6-dichlorophenyl group, a 4-chloro-3-fluorophenyl group, a 4-chloro-3,5-difluorophenyl group, a 4-bromophenyl group, a 4-methylphenyl group, a 3-fluoro-4-methylphenyl group, a 4-ethylphenyl group, a 4-ethyl-3-fluorophenyl group, a 4-propylphenyl group, a 4-isopropylphenyl group, a 4-tert-butylphenyl group, a 4-trifluoromethylphenyl group, a 3-fluoro-4-trifluoromethylphenyl group, a 4-difluoromethylphenyl group, a 4-trichloromethylphenyl group, a 4-dichloromethylphenyl group, a 4-(2,2,2-trifluoroethyl)phenyl group, a 4-(2,2,2-trichloroethyl)phenyl group, a 4-methoxyphenyl group, a 3-fluoro-4-methoxyphenyl group, a 4-ethoxyphenyl group, a 4-propoxyphenyl group, a 4-isopropoxyphenyl group, a 4-tert-butoxyphenyl group, a 4-trifluoromethoxyphenyl group, a 4-difluoromethoxyphenyl group, a 4-difluoromethoxy-3-fluorophenyl group, a 4-trichloromethoxyphenyl group, a 4-dichloromethoxyphenyl group, a thiophen-2-yl group, a thiophen-3-yl group, a 5-chlorothiophen-2-yl group, a 1-methyl-1H-imidazol-4-yl group, a thiazol-2-yl group, a pyridin-2-yl group, a 5-fluoropyridin-2-yl group, a 5-chloropyridin-2-yl group, a 5-methylpyridin-2-yl group, a 5-ethylpyridin-2-yl group, a 5-trifluoromethylpyridin-2-yl group, a 5-methoxypyridin-2-yl group, a 5-difluoromethoxypyridin-2-yl group, a pyridin-3-yl group, a 6-fluoropyridin-3-yl group, a 6-chloropyridin-3-yl group, a 6-methylpyridin-3-yl group, a 6-ethylpyridin-3-yl group, a 6-trifluoromethylpyridin-3-yl group, a 6-methoxypyridin-3-yl group, a 6-difluoromethoxypyridin-3-yl group, a pyridin-4-yl group or a pyrimidin-2-yl group, even more preferably a phenyl group, a 2-fluorophenyl group, a 3-fluorophenyl group, a 4-fluorophenyl group, a 3,4-difluorophenyl group, a 3,5-difluorophenyl group, a 2-chlorophenyl group, a 3-chlorophenyl group, a 4-chlorophenyl group, a 2,6-dichlorophenyl group, a 4-chloro-3-fluorophenyl group, a 4-methylphenyl group, a 3-fluoro-4-methylphenyl group, a 4-ethylphenyl group, a 4-ethyl-3-fluorophenyl group, a 4-trifluoromethylphenyl group, 3-fluoro-4-trifluoromethylphenyl group, a 4-methoxyphenyl group, a 3-fluoro-4-methoxyphenyl group, a 4-difluoromethoxyphenyl group, a 4-difluoromethoxy-3-fluorophenyl group, a thiophen-2-yl group, a thiophen-3-yl group, a pyridin-2-yl group, a 5-fluoropyridin-2-yl group, a 5-chloropyridin-2-yl group, a 5-methoxypyridin-2-yl group, a pyridin-3-yl group, a 6-fluoropyridin-3-yl group, a 6-chloropyridin-3-yl group, a 6-methoxypyridin-3-yl group or a pyridin-4-yl group, and particularly preferably a phenyl group or a pyridyl group, each of which may be substituted with a group(s) selected from the group consisting of a halogen atom and a $C_1$-$C_4$ alkoxy group, for example, a phenyl group, a 2-fluorophenyl group, a 3-fluorophenyl group, a 4-fluorophenyl group, a 2-chlorophenyl group, a 3-chlorophenyl group, a 4-chlorophenyl group, a 2,6-dichlorophenyl group, a 4-methoxyphenyl group, a pyridin-2-yl group or a pyridin-3-yl group.

A substituent referred to in the present invention also includes each atom or each ring. When there is an optical isomer in the compound represented by the formula (1) of the present invention, such isomer is also included in the scope of the present invention, and when there is a proton tautomer, such tautomer is also included in the present invention.

The compound represented by the formula (1) of the present invention is easily converted into a pharmacologically acceptable salt by treating it with an acid. Examples of such a salt include, for example, inorganic acid salts such as hydrochloride, hydrobromide, hydroiodide, nitrate, sulfate or phosphate; or organic acid salts such as acetate, trifluoroacetate, benzoate, oxalate, malonate, succinate, maleate, fumarate, tartrate, citrate, methanesulfonate, ethanesulfonate, trifluoromethanesulfonate, benzenesulfonate, p-toluenesulfonate, glutamate or aspartate, preferably hydrochloride or trifluoroacetate.

The compound represented by the formula (1) of the present invention is easily converted into a pharmacologically acceptable salt by treating it with a base when $R^1$ is a hydrogen atom. Examples of such a salt include, for example, metal salts such as a sodium salt, a potassium salt, a calcium salt or a magnesium salt: inorganic salts such as an ammonium salt: or organic amine salts such as a triethylamine salt or a guanidine salt.

Further, the compound or pharmacologically acceptable salt thereof represented by the formula (1) of the present invention can be present as a hydrate or solvate, and they are also included in the present invention.

The compound represented by the formula (1) of the present invention is, preferably,
(1) a compound wherein $R^1$ is a hydrogen atom, a methyl group, an ethyl group, a propyl group, an isopropyl group, a butyl group, an isobutyl group, a sec-butyl group, a tert-butyl group, a pentyl group or a hexyl group,
(2) a compound wherein $R^1$ is a hydrogen atom, a methyl group, an ethyl group, a propyl group, an isopropyl group, a tert-butyl group or a hexyl group,
(3) a compound wherein $R^1$ is a hydrogen atom, a methyl group, an ethyl group, an isopropyl group or a hexyl group,
(4) a compound wherein $R^2$ and $R^3$ are each independently a hydrogen atom, a methyl group, an ethyl group, a propyl group or an isopropyl group,
(5) a compound wherein $R^2$ and $R^3$ are each independently a hydrogen atom or a methyl group,
(6) a compound wherein $R^2$ and $R^3$ are both hydrogen atoms,
(7) a compound wherein Y is a bicyclic heteroaromatic group, which may be substituted with a group(s) selected from the group consisting of a halogen atom, a $C_1$-$C_4$ alkyl group, a halogeno-$C_1$-$C_4$ alkyl group, a $C_1$-$C_4$ alkoxy group, a halogeno-$C_1$-$C_4$ alkoxy group and a $C_1$-$C_4$ alkylthio group, or a -$Q^1$-$Q^2$ group (wherein $Q^1$ represents an arylene group or a 5- to 6-membered heteroarylene ring group, and $Q^2$ represents an aromatic group or a 5- to 6-membered heterocyclic group, each of which may be substituted with a group(s) selected from the group consisting of a halogen atom, a hydroxy group, a $C_1$-$C_4$ alkyl group, a halogeno-$C_1$-$C_4$ alkyl group, a hydroxy group, a $C_1$-$C_4$ alkyl group, a halogeno-$C_1$-$C_4$ alkyl group, a $C_1$-$C_4$ alkoxy group and a halogeno-$C_1$-$C_4$ alkoxy group),
(8) a compound wherein Y is a benzofuryl group, a benzothienyl group, a benzoxazolyl group or a benzothiazolyl group, each of which may be substituted with a group(s) selected from the group consisting of a halogen atom, a $C_1$-$C_4$ alkyl group, a halogeno-$C_1$-$C_4$ alkyl group, a $C_1$-$C_4$ alkoxy group, a halogeno-$C_1$-$C_4$ alkoxy group and a $C_1$-$C_4$ alkylthio group, or a -$Q^1$-$Q^2$ group (wherein $Q^1$ represents a phenylene group, a thienylene group, a pyridazinylene group or a pyrimidinylene group, and $Q^2$ represents a phenyl group, a thienyl group, a pyrazolyl group, an oxazolyl group, a thiazolyl group, a 1,2,4-triazolyl group, a pyridyl group, a pyridazinyl group, a pyrimidinyl group, a 4,5-dihydrothiazolyl group, a pyrrolidinyl group or a piperidinyl group, each of which may be substituted with a group(s) selected from the group consisting of a halogen atom, a hydroxy group, a $C_1$-$C_4$ alkyl group, a halogeno-$C_1$-$C_4$ alkyl group, a $C_1$-$C_4$ alkoxy group and a halogeno-$C_1$-$C_4$ alkoxy group),
(9) a compound wherein Y is a benzofuryl group, a benzothienyl group, a benzoxazolyl group or a benzothiazolyl group, each of which may be substituted with a group(s) selected from the group consisting of a fluorine atom, a chlorine atom, a bromine atom, a methyl group, an ethyl group, a propyl group, an isopropyl group, a tert-butyl group, a trifluoromethyl group, a difluoromethyl group, a trichloromethyl group, a dichloromethyl group, a 2,2,2-trifluoroethyl group, a 2,2,2-trichloroethyl group, a methoxy group, an ethoxy group, a propoxy group, an isopropoxy group, a tert-butoxy group, a trifluoromethoxy group, a difluoromethoxy group, a trichloromethoxy group, a dichloromethoxy group, a methylthio group, an ethylthio group, a propylthio group, an isopropylthio group and a tert-butylthio group, or a -$Q^1$-$Q^2$ group (wherein $Q^1$ is a phenylene group, a thienylene group, a pyridazinylene group or a pyrimidinylene group, and $Q^2$ represents a phenyl group, a thienyl group, a pyrazolyl group, an oxazolyl group, a thiazolyl group, a 1,2,4-triazolyl group, a pyridyl group, a pyridazinyl group, a pyrimidinyl group, a 4,5-dihydrothiazolyl group, a pyrrolidinyl group or a piperidinyl group, each of which may be substituted with a group(s) selected from the group consisting of a fluorine atom, a chlorine atom, a bromine atom, a hydroxy group, a methyl group, an ethyl group, a propyl group, an isopropyl group, a tert-butyl group, a trifluoromethyl group, a difluoromethyl group, a trichloromethyl group, a dichloromethyl group, a 2,2,2-trifluoroethyl group, a 2,2,2-trichloroethyl group, a methoxy group, an ethoxy group, a propoxy group, an isopropoxy group, a tert-butoxy group, a trifluoromethoxy group, a difluoromethoxy group, a trichloromethoxy group and a dichloromethoxy group),
(10) a compound wherein Y is a benzofuran-2-yl group, a 6-fluorobenzofuran-2-yl group, a 5,6-difluorobenzofuran-2-yl group, a 6-chlorobenzofuran-2-yl group, a 6-chloro-5-fluorobenzofuran-2-yl group, a 6-methylbenzofuran-2-yl group, a 5-fluoro-6-methylbenzofuran-2-yl group, a 6-ethylbenzofuran-2-yl group, a 6-ethyl-5-fluorobenzofuran-2-yl group, a 6-trifluoromethylbenzofuran-2-yl group, a 5-fluoro-6-trifluoromethylbenzofuran-2-yl group, a 6-methoxybenzofuran-2-yl group, a 5-fluoro-6-methoxybenzofuran-2-yl group, a 6-difluoromethoxybenzofuran-2-yl group, a 6-difluoromethoxy-5-fluorobenzofuran-2-yl group, a 6-methylthiobenzofuran-2-yl group, a 5-fluoro-6-methylthiobenzofuran-2-yl group, a benzo[b]thiophen-2-yl group, a 6-fluorobenzo[b]thiophen-2-yl group, a 5,6-difluorobenzo[b]thiophen-2-yl group, a 6-chlorobenzo[b]thiophen-2-yl group, a 6-chloro-5-fluorobenzo[b]thiophen-2-yl group, a 6-bromobenzo[b]thiophen-2-yl group, a 6-methylbenzo[b]thiophen-2-yl group, a 5-fluoro-6-methylbenzo[b]thiophen-2-yl group, a 6-ethylbenzo[b]thiophen-2-yl group, a 6-ethyl-5-fluorobenzo[b]thiophen-2-yl group, a 6-propylbenzo[b]thiophen-2-yl group, a 6-isopropylbenzo[b]thiophen-2-yl group, a 6-tert-butylbenzo[b]thiophen-2-yl group, a 6-trifluoromethylbenzo[b]thiophen-2-yl group, a 5-fluoro-6-trifluoromethylbenzo[b]-thiophen-2-yl group, a 6-difluoromethylbenzo[b]thiophen-2-yl group, a 6-trichloromethylbenzo[b]thiophen-2-yl group, a 6-dichloromethylbenzo[b]thiophen-2-yl group, a 6-(2,2,2-trifluoroethyl)benzo[b]thiophen-2-yl group, a 6-(2,2,2-trichloroethyl)benzo[b]-thiophen-2-yl group, a 6-methoxybenzo[b]thiophen-2-yl group, a 5-fluoro-6-methoxybenzo[b]thiophen-2-yl group, a 6-ethoxybenzo[b]thiophen-2-yl group, a 6-propoxybenzo[b]thiophen-2-yl group, a 6-isopropoxybenzo[b]thiophen-2-yl group, a 6-tert-butoxybenzo[b]thiophen-2-yl group, a 6-trifluoromethoxybenzo[b]thiophen-2-yl group, a 6-difluoromethoxybenzo[b]thiophen-2-yl group, a 6-difluoromethoxy-5-fluorobenzo-[b]thiophen-2-yl group, a 6-trichloromethoxybenzo[b]thiophen-2-yl group, a 6-dichloromethoxybenzo[b]thiophen-2-yl group, a 6-methylthiobenzo[b]thiophen-2-yl group, a 5-fluoro-6-methylthiobenzo[b]thiophen-2-yl group, a 6-ethylthiobenzo[b]-thiophen-2-yl group, a 6-propylthiobenzo[b]thiophen-2-yl group, a 6-isopropylthiobenzo[b]thiophen-2-yl group, a 6-tert-butylthiobenzo[b]thiophen-2-yl group, a benzoxazol-2-yl group, a 6-chlorobenzoxazol-2-yl group, a 6-methoxybenzoxazol-2-yl group, a benzothiazol-2-yl group, a 6-chlorobenzothiazol-2-yl group, a 6-methoxybenzothiazol-2-yl group, a biphenyl-3-yl group, a biphenyl-4-yl group, a 2'-fluorobiphenyl-4-yl group, a 3'-fluorobiphenyl-4-yl group, a 4'-fluorobiphenyl-4-yl group, a 2',4'-difluorobiphenyl-4-yl group, a 3',4'-difluorobiphenyl-4-yl group, a 2'-chlorobiphenyl-4-yl group, a 3'-chlorobiphenyl-4-yl group, a 4'-chlorobiphenyl-4-yl group, a 2',4'-dichlorobiphenyl-4-yl group, a 3',4'-dichlorobiphenyl-4-yl group, a 4'-chloro-2'-fluorobiphenyl-4-yl group, a 4'-chloro-3'-fluorobiphenyl-4-yl group, a 3'-bromobiphenyl-4-yl group, a 3'-hydroxybiphenyl-4-yl group, a 4'-hydroxybiphenyl-4-yl group, a 3'-methylbiphenyl-4-yl group, a 3'-ethylbiphenyl-4-yl group, a 3'-propylbiphenyl-4-yl group, a 3'-isopropylbiphenyl-4-yl group, a 3'-tert-butylbiphenyl-4-yl group, a 3'-trifluoromethylbiphenyl-4-yl group, a 3'-difluoromethylbiphenyl-4-yl group, a 3'-trichloromethylbiphenyl-4-yl group, a 3'-dichloromethylbiphenyl-4-yl group, a 3'-(2,2,2-trifluoroethyl)biphenyl-4-yl group, a 3'-(2,2,2-trichloroethyl)biphenyl-4-yl group, a 3'-methoxybiphenyl-4-yl group, a 3% ethoxybiphenyl-4-yl group, a 3'-propoxybiphenyl-4-yl group, a 3'-isopropoxybiphenyl-4-yl group, a 3'-tert-butoxybiphenyl-4-yl group, a 3'-trifluoromethoxybiphenyl-4-yl group, a 3'-difluoromethoxybiphenyl-4-yl group, a 3'-trichloromethoxybiphenyl-4-yl group, a 3'-dichloromethoxybiphenyl-4-yl group, a 4-(thiophen-2-yl)phenyl group, a 4-(thiophen-3-yl)phenyl group, a 4-(pyrazol-1-yl)phenyl group, a 4-(4-fluoropyrazol-1-yl)phenyl group, a 4-(4-chloropyrazol-1-yl)phenyl group, a 4-(oxazol-2-yl)phenyl group, a 4-(oxazol-4-yl)phenyl group, a 4-(thiazol-2-yl)phenyl group, a 4-(4-fluorothiazol-2-yl)phenyl group, a 4-(4-chlorothiazol-2-yl)phenyl group, a 4-(5-chlorothiazol-2-yl)phenyl group, a 4-(4-methylthiazol-2-yl)phenyl group, a 4-(5-methylthiazol-2-yl)phenyl group, a 4-(4,5-dimethylthiazol-2-yl)phenyl group, a 4-(4-ethylthiazol-2-yl)phenyl group, a 4-(4-trifluoromethylthiazol-2-yl)phenyl group, a 4-(4-methoxythiazol-2-yl) phenyl group, a 4-(4-difluoromethoxythiazol-2-yl)phenyl group, a 4-(thiazol-4-yl)phenyl group, a 4-(2-fluorothiazol-4-yl)phenyl group, a 4-(2-chlorothiazol-4-yl)phenyl group, a 4-(2-methylthiazol-4-yl)phenyl group, a 4-(2-ethylthiazol-4-yl)phenyl group, a 4-(2-trifluoromethylthiazol-4-yl)phenyl group, a 4-(2-methoxythiazol-4-yl)phenyl group, a 4-(2-difluoromethoxythiazol-4-yl)phenyl group, a 4-(thiazol-5-yl)phenyl group, a 4-(1,2,4-triazol-1-yl)phenyl group, a 4-(pyridin-2-yl)phenyl group, a 4-(pyridin-3-yl)phenyl group, a 4-(pyridin-4-yl)phenyl group, a 4-(pyridazin-3-yl)phenyl group, a 4-(pyridazin-4-yl)phenyl group, a 4-(pyrimidin-2-yl)phenyl group, a 4-(5-fluoropyrimidin-2-yl)phenyl group, a 4-(5-chloropyrimidin-2-yl)phenyl group, a 4-(5-hydroxypyrimidin-2-yl)phenyl group, a 4-(pyrimidin-4-yl)phenyl group, a 4-(pyrimidin-5-yl)phenyl group, a 4-(4,5-dihydrothiazol-2-yl)phenyl group, a 4-(pyrrolidin-1-yl)phenyl group, a 4-(piperidin-1-yl)phenyl group, a 5-phenylthiophen-2-yl group, a 5-(thiazol-2-yl)thiophen-2-yl group, a 5-(thiazol-4-yl)thiophen-2-yl group, a 6-phenylpyridazin-3-yl group, a 6-(thiazol-2-yl)pyridazin-3-yl group, a 6-(thiazol-4-yl)pyridazin-3-yl group, a 2-phenylpyrimidin-4-yl group, a 2-(thiazol-2-yl)pyrimidin-4-yl group or a 2-(thiazol-4-yl)pyrimidin-4-yl group,

(11) a compound wherein Y is a benzofuran-2-yl group, a 6-fluorobenzofuran-2-yl group, a 6-chlorobenzofuran-2-yl group, a 6-methoxybenzofuran-2-yl group, a benzo-[b]thiophen-2-yl group, a 6-fluorobenzo[b]thiophen-2-yl group, a 5,6-difluorobenzo-[b]thiophen-2-yl group, a 6-chlorobenzo[b]thiophen-2-yl group, a 6-chloro-5-fluorobenzo[b]thiophen-2-yl group, a 6-methylbenzo[b]thiophen-2-yl group, a 5-fluoro-6-methylbenzo[b]thiophen-2-yl group, a 6-ethylbenzo[b]thiophen-2-yl group, a 6-ethyl-5-fluorobenzo[b]thiophen-2-yl group, a 6-trifluoromethylbenzo[b]thiophen-2-yl group, a 5-fluoro-6-trifluoromethylbenzo[b]thiophen-2-yl group, a 6-methoxybenzo[b]thiophen-2-yl group, a 5-fluoro-6-methoxybenzo[b]thiophen-2-yl group, a 6-difluoromethoxybenzo[b]thiophen-2-yl group, a 6-difluoromethoxy-5-fluorobenzo[b]thiophen-2-yl group, a 6-methylthiobenzo[b]thiophen-2-yl group, a 5-fluoro-6-methylthiobenzo[b]-thiophen-2-yl group, a biphenyl-4-yl group, a 2'-fluorobiphenyl-4-yl group, a 3% fluorobiphenyl-4-yl group, a 4'-fluorobiphenyl-4-yl group, a 2',4'-difluorobiphenyl-4-yl group, a 3',4'-difluorobiphenyl-4-yl group, a 2'-chlorobiphenyl-4-yl group, a 3'-chlorobiphenyl-4-yl group, a 4'-chlorobiphenyl-4-yl group, a 4'-chloro-2'-fluorobiphenyl-4-yl group, a 4'-chloro-3'-fluorobiphenyl-4-yl group, a 4'-hydroxybiphenyl-4-yl group, a 3'-methylbiphenyl-4-yl group, a 3'-ethylbiphenyl-4-yl group, a 3'-trifluoromethylbiphenyl-4-yl group, a 3'-methoxybiphenyl-4-yl group, a 3'-difluoromethoxybiphenyl-4-yl group, a 4-(thiophen-2-yl)phenyl group, a 4-(thiophen-3-yl)phenyl group, a 4-(pyrazol-1-yl) phenyl group, a 4-(oxazol-2-yl)phenyl group, a 4-(oxazol-4-yl)phenyl group, a 4-(thiazol-2-yl)phenyl group, a 4-(4-fluorothiazol-2-yl)phenyl group, a 4-(4-chlorothiazol-2-yl) phenyl group, a 4-(5-chlorothiazol-2-yl)phenyl group, a 4-(5-methylthiazol-2-yl)phenyl group, a 4-(4,5-dimethylthiazol-2-yl)phenyl group, a 4-(4-trifluoromethylthiazol-2-yl)phenyl group, a 4-(thiazol-4-yl)phenyl group, a 4-(2-fluorothiazol-4-yl)phenyl group, a 4-(2-chlorothiazol-4-yl) phenyl group, a 4-(thiazol-5-yl)phenyl group, a 4-(1,2,4-triazol-1-yl)phenyl group, a 4-(pyridin-2-yl)phenyl group, a 4-(pyridazin-3-yl) phenyl group, a 4-(pyridazin-4-yl)phenyl group, a 4-(pyrimidin-2-yl)phenyl group, a 4-(5-hydroxypyrimidin-2-yl)phenyl group, a 4-(pyrimidin-4-yl)phenyl group, a 4-(pyrimidin-5-yl)phenyl group, a 4-(4,5-dihydrothiazol-2-yl)phenyl group, a 6-phenylpyridazin-3-yl group, a 6-(thiazol-2-yl)pyridazin-3-yl group or a 6-(thiazol-4-yl)-pyridazin-3-yl group,

(12) a compound wherein Y is a benzofuran-2-yl group, a 6-fluorobenzofuran-2-yl group, a 6-chlorobenzofuran-2-yl group, a 6-methoxybenzofuran-2-yl group, a benzo-[b]thiophen-2-yl group, a 6-fluorobenzo[b]thiophen-2-yl group, a 6-chlorobenzo[b]-thiophen-2-yl group, a 6-methoxybenzo [b]thiophen-2-yl group, a biphenyl-4-yl group, a 2'-fluorobiphenyl-4-yl group, a 3'-fluorobiphenyl-4-yl group, a 4'-fluorobiphenyl-4-yl group, a 2'-chlorobiphenyl-4-yl group, a 3'-chlorobiphenyl-4-yl group, a 4'-chlorobiphenyl-4-yl group, a 3'-methylbiphenyl-4-yl group, a 3'-trifluoromethyl-biphenyl-4-yl group, a 4-(thiophen-2-yl)phenyl group, a 4-(thiophen-3-yl)phenyl group, a 4-(pyrazol-1-yl)phenyl group, a 4-(oxazol-2-yl)phenyl group, a 4-(oxazol-4-yl)phenyl group, a 4-(thiazol-2-yl)phenyl group, a 4-(4-fluorothiazol-2-yl)phenyl group, a 4-(4-chlorothiazol-2-yl)phenyl group, a 4-(5-chlorothiazol-2-yl)phenyl group, a 4-(5-methylthiazol-2-yl)-phenyl group, a 4-(4,5-dimethylthiazol-2-yl) phenyl group, a 4-(4-trifluoromethylthiazol-2-yl)phenyl group, a 4-(thiazol-4-yl)phenyl group, a 4-(2-fluorothiazol-4-yl)-phenyl group, a 4-(2-chlorothiazol-4-yl)phenyl group, a 4-(thiazol-5-yl)phenyl group, a 4-(1,2,4-triazol-1-yl)phenyl group, a 4-(pyridin-2-yl)phenyl group, a 4-(pyridazin-3-yl) phenyl group, a 4-(pyridazin-4-yl)phenyl group, a 4-(pyrimidin-2-yl)phenyl group, a 4-(pyrimidin-4-yl)phenyl group, a 4-(pyrimidin-5-yl)phenyl group, a 4-(4,5-dihydrothiazol-2-yl)phenyl group, a 6-phenylpyridazin-3-yl group,

(13) a compound wherein Y is a benzofuryl group or a benzothienyl group, each of which may be substituted with a group(s) selected from the group consisting of a halogen atom and a $C_1$-$C_4$ alkoxy group, or a compound wherein Y is a -$Q^1$-$Q^2$ group (wherein $Q^1$ represents a phenylene group or a pyridazinylene group, and $Q^2$ represents a phenyl group, a pyrazolyl group, a thiazolyl group, a 1,2,4-triazolyl group, a pyridyl group, a pyridazinyl group, a pyrimidinyl group or a 4,5-dihydrothiazolyl group, each of which may be substituted with a group(s) selected from the group consisting of a halogen atom, a $C_1$-$C_4$ alkyl group and a halogeno-$C_1$-$C_4$ alkyl group),

(14) a compound wherein Y is a benzofuran-2-yl group, a benzo[b]thiophen-2-yl group, a 6-chlorobenzo[b]thiophen-2-yl group, a 6-methoxybenzo[b]thiophen-2-yl group, a biphenyl-4-yl group, a 4'-fluorobiphenyl-4-yl group, a 4'-chlorobiphenyl-4-yl group, a 4-(pyrazol-1-yl)phenyl group, a 4-(thiazol-2-yl)phenyl group, a 4-(5-chlorothiazol-2-yl)phenyl group, a 4-(5-methylthiazol-2-yl)phenyl group, a 4-(4,5-dimethylthiazol-2-yl)phenyl group, a 4-(4-trifluoromethylthiazol-2-yl)phenyl group, a 4-(thiazol-4-yl)phenyl group, a 4-(1,2,4-triazol-1-yl)phenyl group, a 4-(pyridin-2-yl)phenyl group, a 4-(pyridazin-4-yl)phenyl group, a 4-(pyrimidin-2-yl)phenyl group, a 4-(4,5-dihydrothiazol-2-yl) phenyl group or a 6-phenylpyridazin-3-yl group,

(15) a compound wherein Z is an aromatic group or a 5- to 6-membered heteroaromatic group, each of which may be substituted with a group(s) selected from the group consisting of a halogen atom, a $C_1$-$C_4$ alkyl group, a halogeno-$C_1$-$C_4$ alkyl group, a $C_1$-$C_4$ alkoxy group and a halogeno-$C_1$-$C_4$ alkoxy group,

(16) a compound wherein Z is a phenyl group, a thienyl group, an imidazolyl group, a thiazolyl group, a pyridyl group or a pyrimidinyl group, each of which may be substituted with a group(s) selected from the group consisting of a halogen atom, a $C_1$-$C_4$ alkyl group, a halogeno-$C_1$-$C_4$ alkyl group, a $C_1$-$C_4$ alkoxy group and a halogeno-$C_1$-$C_4$ alkoxy group,

(17) a compound wherein Z is a phenyl group, a thienyl group, an imidazolyl group, a thiazolyl group, a pyridyl group or a pyrimidinyl group, each of which may be substituted with a group(s) selected from the group consisting of a fluorine atom, a chlorine atom, a bromine atom, a methyl group, an ethyl group, a propyl group, an isopropyl group, a tert-butyl group, a trifluoromethyl group, a difluoromethyl group, a trichloromethyl group, a dichloromethyl group, a 2,2,2-trifluoroethyl group, a 2,2,2-trichloroethyl group, a methoxy group, an ethoxy group, a propoxy group, an isopropoxy group, a tert-butoxy group, a trifluoromethoxy group, a difluoromethoxy group, a trichloromethoxy group and a dichloromethoxy group,

(18) a compound wherein Z is a phenyl group, a 2-fluorophenyl group, a 3-fluorophenyl group, a 4-fluorophenyl group, a 3,4-difluorophenyl group, a 3,5-difluorophenyl group, a 3,4,5-trifluorophenyl group, a 2-chlorophenyl group, a 3-chlorophenyl group, a 4-chlorophenyl group, a 2,6-dichlorophenyl group, a 4-chloro-3-fluorophenyl group, a 4-chloro-3,5-difluorophenyl group, a 4-bromophenyl group, a 4-methylphenyl group, a 3-fluoro-4-methylphenyl group, a 4-ethylphenyl group, a 4-ethyl-3-fluorophenyl group, a 4-propylphenyl group, a 4-isopropylphenyl group, a 4-tert-butylphenyl group, a 4-trifluoromethylphenyl group, a 3-fluoro-4-trifluoromethylphenyl group, a 4-difluoromethylphenyl group, a 4-trichloromethylphenyl group, a 4-dichloromethylphenyl group, a 4-(2,2,2-trifluoroethyl)phenyl group, a 4-(2,2,2-trichloroethyl)phenyl group, a 4-methoxyphenyl group, a 3-fluoro-4-methoxyphenyl group, a 4-ethoxyphenyl group, a 4-propoxyphenyl group, a 4-isopropoxyphenyl group, a 4-tert-butoxyphenyl group, a 4-trifluoromethoxyphenyl group, a 4-difluoromethoxyphenyl group, a 4-difluoromethoxy-3-fluorophenyl group, a 4-trichloromethoxyphenyl group, a 4-dichloromethoxyphenyl group, a thiophen-2-yl group, a thiophen-3-yl group, a 5-chlorothiophen-2-yl group, a 1-methyl-1H-imidazol-4-yl group, a thiazol-2-yl group, a pyridin-2-yl group, a 5-fluoropyridin-2-yl group, a 5-chloropyridin-2-yl group, a 5-methylpyridin-2-yl group, a 5-ethylpyridin-2-yl group, a 5-trifluoromethylpyridin-2-yl group, a 5-methoxypyridin-2-yl group, a 5-difluoromethoxypyridin-2-yl group, a pyridin-3-yl group, a 6-fluoropyridin-3-yl group, a 6-chloropyridin-3-yl group, a 6-methylpyridin-3-yl group, a 6-ethylpyridin-3-yl group, a 6-trifluoromethylpyridin-3-yl group, a 6-methoxypyridin-3-yl group, a 6-difluoromethoxypyridin-3-yl group, a pyridin-4-yl group or a pyrimidin-2-yl group,

(19) a compound wherein Z is a phenyl group, a 2-fluorophenyl group, a 3-fluorophenyl group, a 4-fluorophenyl group, a 3,4-difluorophenyl group, a 3,5-difluorophenyl group, a 2-chlorophenyl group, a 3-chlorophenyl group, a 4-chlorophenyl group, a 2,6-dichlorophenyl group, a 4-chloro-3-fluorophenyl group, a 4-methylphenyl group, a 3-fluoro-4-methylphenyl group, a 4-ethylphenyl group, a 4-ethyl-3-fluorophenyl group, a 4-trifluoromethylphenyl group, a 3-fluoro-4-trifluoromethylphenyl group, a 4-methoxyphenyl group, a 3-fluoro-4-methoxyphenyl group, a 4-difluoromethoxyphenyl group, a 4-difluoromethoxy-3-fluorophenyl group, a thiophen-2-yl group, a thiophen-3-yl group, a pyridin-2-yl group, a 5-fluoropyridin-2-yl group, a 5-chloropyridin-2-yl group, a 5-methoxypyridin-2-yl group, a pyridin-3-yl group, a 6-fluoropyridin-3-yl group, a 6-chloropyridin-3-yl group, a 6-methoxypyridin-3-yl group or a pyridin-4-yl group,

(20) a compound wherein Z is a phenyl group or a pyridyl group, each of which may be substituted with a group(s) selected from the group consisting of a halogen atom and a $C_1$-$C_4$ alkoxy group,

(21) a compound wherein Z is a phenyl group, a 2-fluorophenyl group, a 3-fluorophenyl group, a 4-fluorophenyl group, a 2-chlorophenyl group, a 3-chlorophenyl group, a 4-chlorophenyl group, a 2,6-dichlorophenyl group, a 4-methoxyphenyl group, a pyridin-2-yl group or a pyridin-3-yl group.

Further, in the above-mentioned groups of (1)-(3), (4)-(6), (7)-(14) and (15)-(21), as the number becomes larger, a more preferred compound is indicated, and a compound obtained by arbitrarily selecting $R^1$ from the groups (1)-(3), $R^2$ and $R^3$ from the groups (4)-(6), Y from the groups (7)-(14), and Z from the group (15)-(21), or by arbitrarily combining them is also a preferred compound.

Examples of such compound include:

(22) a compound wherein $R^1$ is a hydrogen atom, a methyl group, an ethyl group, a propyl group, an isopropyl group, a butyl group, an isobutyl group, a sec-butyl group, a tert-butyl group, a pentyl group or a hexyl group, $R^2$ and $R^3$ are respectively and independently a hydrogen atom, a methyl group, an ethyl group, a propyl group or an isopropyl group, Y is a benzofuryl group, a benzothienyl group, a benzoxazolyl group or a benzothiazolyl group, each of which may be substituted with a group(s) selected from the group consisting of a fluorine atom, a chlorine atom, a bromine atom, a methyl group, an ethyl group, a propyl group, an isopropyl group, a tert-butyl group, a trifluoromethyl group, a difluoromethyl group, a trichloromethyl group, a dichloromethyl group, a 2,2,2-trifluoroethyl group, a 2,2,2-trichloroethyl group, a methoxy group, an ethoxy group, a propoxy group, an isopropoxy group, a tert-butoxy group, a trifluoromethoxy group, a difluoromethoxy group, a trichloromethoxy group, a dichloromethoxy group, a methylthio group, an ethylthio group, a propylthio group, an isopropylthio group and a tert-butylthio group, or, in a -$Q^1$-$Q^2$ group represented by Y, $Q^1$ is a phenylene group, a thienylene group, a pyridazinylene group or a pyrimidinylene group, and $Q^2$ is a phenyl group, a thienyl group, a pyrazolyl group, an oxazolyl group, a thiazolyl group, a 1,2,4-triazolyl group, a pyridyl group, a pyridazinyl group, a pyrimidinyl group, a 4,5-dihydrothiazolyl group, a pyrrolidinyl group or a piperidinyl group, each of which may be substituted with a group(s) selected from the group consisting of a fluorine atom, a chlorine atom, a bromine atom, a hydroxy group, a methyl group, an ethyl group, a propyl group, an isopropyl group, a tert-butyl group, a trifluoromethyl group, a difluoromethyl group, a trichloromethyl group, a dichloromethyl group, a 2,2,2-trifluoroethyl group, a 2,2,2-trichloroethyl group, a methoxy group, an ethoxy group, a propoxy group, an isopropoxy group, a tert-butoxy group, a trifluoromethoxy group, a difluoromethoxy group, a trichloromethoxy group and a dichloromethoxy group, and Z is a phenyl group, a thienyl group, an imidazolyl group, a thiazolyl group, a pyridyl group or a pyrimidinyl group, each of which may be substituted with a group(s) selected from the group consisting of a fluorine atom, a chlorine atom, a bromine atom, a methyl group, an ethyl group, a propyl group, an isopropyl group, a tert-butyl group, a trifluoromethyl group, a difluoromethyl group, a trichloromethyl group, a dichloromethyl group, a 2,2,2-trifluoroethyl group, a 2,2,2-trichloroethyl group, a methoxy group, an ethoxy group, a propoxy group, an isopropoxy group, a tert-butoxy group, a trifluoromethoxy group, a difluoromethoxy group, a trichloromethoxy group and a dichloromethoxy group,

(23) a compound wherein $R^1$ is a hydrogen atom, a methyl group, an ethyl group, a propyl group, an isopropyl group, a butyl group, an isobutyl group, a sec-butyl group, a tert-butyl group, a pentyl group or a hexyl group, $R^2$ and $R^3$ are respectively and independently a hydrogen atom or a methyl group, Y is a benzofuran-2-yl group, a 6-fluorobenzofuran-2-yl group, a 6-chlorobenzofuran-2-yl group, a 6-methoxybenzofuran-2-yl group, a benzo[b]thiophen-2-yl group, a 6-fluorobenzo[b]thiophen-2-yl group, a 5,6-difluorobenzo[b]thiophen-2-yl group, a 6-chlorobenzo[b]thiophen-2-yl group, a 6-chloro-5-fluorobenzo[b]thiophen-2-yl group, a 6-methylbenzo[b]thiophen-2-yl group, a 5-fluoro-6-methylbenzo[b]thiophen-2-yl group, a 6-ethylbenzo[b]thiophen-2-yl group, a 6-ethyl-5-fluorobenzo[b]thiophen-2-yl group, a 6-trifluoromethylbenzo[b]thiophen-2-yl group, a 5-fluoro-6-trifluoromethylbenzo[b]thiophen-2-yl group, a 6-methoxybenzo[b]thiophen-2-yl group, a 5-fluoro-6-methoxybenzo[b]thiophen-2-yl group, a 6-difluoromethoxybenzo[b]thiophen-2-yl group, a 6-difluoromethoxy-5-fluorobenzo[b]thiophen-2-yl group, a 6-methylthiobenzo[b]thiophen-2-yl group, a 5-fluoro-6-methylthiobenzo[b]thiophen-2-yl group, a biphenyl-4-yl group, a 2'-fluorobiphenyl-4-yl group, a 3'-fluorobiphenyl-4-yl group, a 4'-fluorobiphenyl-4-yl group, a 2',4'-difluorobiphenyl-4-yl group, a 3',4'-difluorobiphenyl-4-yl group, a 2'-chlorobiphenyl-4-yl group, a 3'-chlorobiphenyl-4-yl group, a 4'-chlorobiphenyl-4-yl group, a 4'-chloro-2'-fluorobiphenyl-4-yl group, a 4'-chloro-3'-fluorobiphenyl-4-yl group, a 4'-hydroxybiphenyl-4-yl group, a 3'-methylbiphenyl-4-yl group, a 3'-ethylbiphenyl-4-yl group, a 3'-trifluoromethylbiphenyl-4-yl group, a 3'-methoxybiphenyl-4-yl group, a 3'-difluoromethoxybiphenyl-4-yl group, a 4-(thiophen-2-yl)phenyl group, a 4-(thiophen-3-yl)phenyl group, a 4-(pyrazol-1-yl)phenyl group, a 4-(oxazol-2-yl)phenyl group, a 4-(oxazol-4-yl)phenyl group, a 4-(thiazol-2-yl)phenyl group, a 4-(4-fluorothiazol-2-yl)phenyl group, a 4-(4-chlorothiazol-2-yl)phenyl group, a 4-(5-chlorothiazol-2-yl)phenyl group, a 4-(5-methylthiazol-2-yl)phenyl group, a 4-(4,5-dimethylthiazol-2-yl)phenyl group, a 4-(4-trifluoromethylthiazol-2-yl)phenyl group, a 4-(thiazol-4-yl)phenyl group, a 4-(2-fluorothiazol-4-yl)phenyl group, a 4-(2-chlorothiazol-4-yl)phenyl group, a 4-(thiazol-5-yl)phenyl group, a 4-(1,2,4-triazol-1-yl)phenyl group, a 4-(pyridin-2-yl)phenyl group, a 4-(pyridazin-3-yl)phenyl group, a 4-(pyridazin-4-yl)phenyl group, a 4-(pyrimidin-2-yl)phenyl group, a 4-(5-hydroxypyrimidin-2-yl)phenyl group, a 4-(pyrimidin-4-yl)phenyl group, a 4-(pyrimidin-5-yl)phenyl group, a 4-(4,5-dihydrothiazol-2-yl)phenyl group, a 6-phenylpyridazin-3-yl group, a 6-(thiazol-2-yl)pyridazin-3-yl group or a 6-(thiazol-4-yl)pyridazin-3-yl group, Z is a phenyl group, a 2-fluorophenyl group, a 3-fluorophenyl group, a 4-fluorophenyl group, a 3,4-difluorophenyl group, a 3,5-difluorophenyl group, a 3,4,5-trifluorophenyl group, a 2-chlorophenyl group, a 3-chlorophenyl group, a 4-chlorophenyl group, a 2,6-dichlorophenyl group, a 4-chloro-3-fluorophenyl group, a 4-chloro-3,5-difluorophenyl group, a 4-bromophenyl group, a 4-methylphenyl group, a 3-fluoro-4-methylphenyl group, a 4-ethylphenyl group, a 4-ethyl-3-fluorophenyl group, a 4-propylphenyl group, a 4-isopropylphenyl group, a 4-tert-butylphenyl group, a 4-trifluoromethylphenyl group, a 3-fluoro-4-trifluoromethylphenyl group, a 4-difluoromethylphenyl group, a 4-trichloromethylphenyl group, a 4-dichloromethylphenyl group, a 4-(2,2,2-trifluoroethyl)phenyl group, a 4-(2,2,2-trichloroethyl) phenyl group, a 4-methoxyphenyl group, a 3-fluoro-4-methoxyphenyl group, a 4-ethoxyphenyl group, a 4-propoxyphenyl group, a 4-isopropoxyphenyl group, a 4-tert-butoxyphenyl group, a 4-trifluoromethoxyphenyl group, a 4-difluoromethoxyphenyl group, a 4-difluoromethoxy-3-fluorophenyl group, a 4-trichloromethoxyphenyl group, a 4-dichloromethoxyphenyl group, a thiophen-2- yl group, a thiophen-3-yl group, a 5-chlorothiophen-2-yl group, a 1-methyl-1H-imidazol-4-yl group, a thiazol-2-yl group, a pyridin-2-yl group, a 5-fluoropyridin-2-yl group, a 5-chloropyridin-2-yl group, a 5-methylpyridin-2-yl group, a 5-ethylpyridin-2-yl group, a 5-trifluoromethylpyridin-2-yl group, a 5-methoxypyridin-2-yl group, a 5-difluoromethoxypyridin-2-yl group, a pyridin-3-yl group, a 6-fluoropyridin-3-yl group, a 6-chloropyridin-3-yl group, a 6-methylpyridin-3-yl group, a 6-ethylpyridin-3-yl group, a 6-trifluoromethylpyridin-3-yl group, a 6-methoxypyridin-3-yl group, a 6-difluoromethoxypyridin-3-yl group, a pyridin-4-yl group or a pyrimidin-2-yl group,

(24) a compound wherein $R^1$ is a hydrogen atom, a methyl group, an ethyl group, a propyl group, an isopropyl group, a tert-butyl group or a hexyl group, $R^2$ and $R^3$ are respectively and independently a hydrogen atom or a methyl group, Y is a benzofuran-2-yl group, a 6-fluorobenzofuran-2-yl group, a 6-chlorobenzofuran-2-yl group, a 6-methoxybenzofuran-2-yl group, a benzo[b]thiophen-2-yl group, a 6-fluorobenzo[b]thiophen-2-yl group, a 6-chlorobenzo[b]thiophen-2-yl group, a 6-methoxybenzo[b]thiophen-2-yl group, a biphenyl-4-yl group, a 2'-fluorobiphenyl-4-yl group, a 3'-fluorobiphenyl-4-yl group, a 4'-fluorobiphenyl-4-yl group, a 2'-chlorobiphenyl-4-yl group, a 3'-chlorobiphenyl-4-yl group, a 4'-chlorobiphenyl-4-yl group, a 3'-methylbiphenyl-4-yl group, a 3'-trifluoromethylbiphenyl-4-yl group, a 4-(thiophen-2-yl)phenyl group, a 4-(thiophen-3-yl)phenyl group, a 4-(pyrazol-1-yl)phenyl group, a 4-(oxazol-2-yl)phenyl group, a 4-(oxazol-4-yl)phenyl group, a 4-(thiazol-2-yl)phenyl group, a 4-(4-fluorothiazol-2-yl)phenyl group, a 4-(4-chlorothiazol-2-yl)phenyl group, a 4-(5-chlorothiazol-2-yl)phenyl group, a 4-(5-methylthiazol-2-yl)phenyl group, a 4-(4,5-dimethylthiazol-2-yl)phenyl group, a 4-(4-trifluoromethylthiazol-2-yl)phenyl group, a 4-(thiazol-4-yl)phenyl group, a 4-(2-fluorothiazol-4-yl)phenyl group, a 4-(2-chlorothiazol-4-yl)phenyl group, a 4-(thiazol-5-yl)phenyl group, a 4-(1,2,4-triazol-1-yl)phenyl group, a 4-(pyridin-2-yl)phenyl group, a 4-(pyridazin-3-yl)phenyl group, a 4-(pyridazin-4-yl)phenyl group, a 4-(pyrimidin-2-yl)phenyl group, a 4-(pyrimidin-4-yl)phenyl group, a 4-(pyrimidin-5-yl)phenyl group, a 4-(4,5-dihydrothiazol-2-yl)phenyl group, a 6-phenylpyridazin-3-yl group, Z is a phenyl group, a 2-fluorophenyl group, a 3-fluorophenyl group, a 4-fluorophenyl group, a 3,4-difluorophenyl group, a 3,5-difluorophenyl group, a 2-chlorophenyl group, a 3-chlorophenyl group, a 4-chlorophenyl group, a 2,6-dichlorophenyl group, a 4-chloro-3-fluorophenyl group, a 4-methylphenyl group, a 3-fluoro-4-methylphenyl group, a 4-ethylphenyl group, a 4-ethyl-3-fluorophenyl group, a 4-trifluoromethylphenyl group, a 3-fluoro-4-trifluoromethylphenyl group, a 4-methoxyphenyl group, a 3-fluoro-4-methoxyphenyl group, a 4-difluoromethoxyphenyl group, a 4-difluoromethoxy-3-fluorophenyl group, a thiophen-2-yl group, a thiophen-3-yl group, a pyridin-2-yl group, a 5-fluoropyridin-2-yl group, a 5-chloropyridin-2-yl group, a 5-methoxypyridin-2-yl group, a pyridin-3-yl group, a 6-fluoropyridin-3-yl group, a 6-chloropyridin-3-yl group, a 6-methoxypyridin-3-yl group or a pyridin-4-yl group,

(25) a compound wherein $R^1$ is a hydrogen atom, a methyl group, an ethyl group, an isopropyl group or a hexyl group, $R^2$ and $R^3$ are both hydrogen atoms, Y is a benzofuran-2-yl group, a 6-fluorobenzofuran-2-yl group, a 6-chlorobenzofuran-2-yl group, a 6-methoxybenzofuran-2-yl group, a benzo[b]thiophen-2-yl group, a 6-fluorobenzo[b]thiophen-2-yl group, a 6-chlorobenzo[b]thiophen-2-yl group, a 6-methoxybenzo[b]thiophen-2-yl group, a biphenyl-4-yl group, a 2'-fluorobiphenyl-4-yl group, a 3'-fluorobiphenyl-4-yl group, a 4'-fluorobiphenyl-4-yl group, a 2'-chlorobiphenyl-4-yl group, a 3'-chlorobiphenyl-4-yl group, a 4'-chlorobiphenyl-4-yl group, a 3'-methylbiphenyl-4-yl group, a 3'-trifluoromethylbiphenyl-4-yl group, a 4-(thiophen-2-yl)phenyl group, a 4-(thiophen-3-yl)phenyl group, a 4-(pyrazol-1-yl)phenyl group, a 4-(oxazol-2-yl)phenyl group, a 4-(oxazol-4-yl)phenyl group, a 4-(thiazol-2-yl)phenyl group, a 4-(4-fluorothiazol-2-yl)phenyl group, a 4-(4-chlorothiazol-2-yl)phenyl group, a 4-(5-chlorothiazol-2-yl)phenyl group, a 4-(5-methylthiazol-2-yl)phenyl group, a 4-(4,5-dimethylthiazol-2-yl)phenyl group, a 4-(4-trifluoromethylthiazol-2-yl)phenyl group, a 4-(thiazol-4-yl)phenyl group, a 4-(2-fluorothiazol-4-yl)phenyl group, a 4-(2-chlorothiazol-4-yl)phenyl group, a 4-(thiazol-5-yl)phenyl group, a 4-(1,2,4-triazol-1-yl)phenyl group, a 4-(pyridin-2-yl)phenyl group, a 4-(pyridazin-3-yl)phenyl group, a 4-(pyridazin-4-yl)phenyl group, a 4-(pyrimidin-2-yl)phenyl group, a 4-(pyrimidin-4-yl)phenyl group, a 4-(pyrimidin-5-yl)phenyl group, a 4-(4,5-dihydrothiazol-2-yl)phenyl group, a 6-phenylpyridazin-3-yl group, Z is a phenyl group, a 2-fluorophenyl group, a 3-fluorophenyl group, a 4-fluorophenyl group, a 2-chlorophenyl group, a 3-chlorophenyl group, a 4-chlorophenyl group, a 2,6-dichlorophenyl group, a 4-methoxyphenyl group, a pyridin-2-yl group or a pyridin-3-yl group, or

(26) a compound wherein $R^1$ is a hydrogen atom, a methyl group, an ethyl group, an isopropyl group or a hexyl group, $R^2$ and $R^3$ are both hydrogen atoms, Y is a benzofuran-2-yl group, a benzo[b]thiophen-2-yl group, a 6-chlorobenzo-[b]thiophen-2-yl group, a 6-methoxybenzo[b]thiophen-2-yl group, a biphenyl-4-yl group, a 4'-fluorobiphenyl-4-yl group, a 4'-chlorobiphenyl-4-yl group, a 4-(pyrazol-1-yl)phenyl group, a 4-(thiazol-2-yl)phenyl group, a 4-(5-chlorothiazol-2-yl)phenyl group, a 4-(5-methylthiazol-2-yl)phenyl group, a 4-(4,5-dimethylthiazol-2-yl)phenyl group, a 4-(4-trifluoromethylthiazol-2-yl)phenyl group, a 4-(thiazol-4-yl)phenyl group, a 4-(1,2,4-triazol-1-yl)phenyl group, a 4-(pyridin-2-yl)phenyl group, a 4-(pyridazin-4-yl)-phenyl group, a 4-(pyrimidin-2-yl)phenyl group, a 4-(4,5-dihydrothiazol-2-yl)phenyl group or a 6-phenylpyridazin-3-yl group, Z is a phenyl group, a 2-fluorophenyl group, a 3-fluorophenyl group, a 4-fluorophenyl group, a 2-chlorophenyl group, a 3-chlorophenyl group, a 4-chlorophenyl group, a 2,6-dichlorophenyl group, a 4-methoxyphenyl group, a pyridin-2-yl group or a pyridin-3-yl group.

(27) A compound wherein a pyridylaminoacetic acid compound is:

{6-[(benzofuran-2-ylmethyl)(pyridin-3-ylsulfonyl)aminomethyl]pyridin-2-ylamino}-acetic acid, {6-[(benzo[b]thiophen-2-ylmethyl)(pyridin-3-ylsulfonyl)aminomethyl]pyridin-2-ylamino}acetic acid, {6-[(6-chlorobenzo[b]thiophen-2-ylmethyl)(pyridin-3-ylsulfonyl)aminomethyl]pyridin-2-ylamino}acetic acid, {6-[(6-methoxybenzo[b]thiophen-2-ylmethyl)(pyridin-3-ylsulfonyl)aminomethyl]-pyridin-2-ylamino}acetic acid, {6-[(biphenyl-4-ylmethyl)(pyridin-2-ylsulfonyl)aminomethyl]pyridin-2-ylamino}acetic acid, {6-[(biphenyl-4-ylmethyl)(pyridin-3-ylsulfonyl)aminomethyl]pyridin-2-ylamino}acetic acid, {6-[(4'-fluorobiphenyl-4-ylmethyl)(pyridin-3-ylsulfonyl)amino methyl]pyridin-2-ylamino}acetic acid, {6-[(4'-chlorobiphenyl-4-ylmethyl)(pyridin-3-ylsulfonyl)
 aminomethyl]pyridin-2-ylamino}acetic acid, (6-{(4-fluorobenzenesulfonyl)[4-(pyrazol-1-yl)benzyl]
 aminomethyl}pyridin-2-ylamino)acetic acid, (6-{[4-(pyrazol-1-yl)benzyl](pyridin-2-ylsulfonyl)
 aminomethyl}pyridin-2-ylamino)-acetic acid, (6-{[4-(pyrazol-1-yl)benzyl](pyridin-3-ylsulfonyl)
 aminomethyl}pyridin-2-ylamino)-acetic acid, isopropyl (6-{(pyridin-2-ylsulfonyl)[4-(thiazol-2-yl)benzyl]
 aminomethyl}pyridin-2-ylamino)acetate, ethyl (6-{(pyridin-2-ylsulfonyl)[4-(thiazol-2-yl)benzyl]
 aminomethyl}pyridin-2-ylamino)acetate, (6-{(4-fluorobenzenesulfonyl)[4-(thiazol-2-yl)benzyl]
 aminomethyl}pyridin-2-ylamino)acetic acid, (6-{(pyridin-2-ylsulfonyl)[4-(thiazol-2-yl)benzyl]
 aminomethyl}pyridin-2-ylamino)-acetic acid, (6-{(pyridin-3-ylsulfonyl)[4-(thiazol-2-yl)benzyl]
 aminomethyl}pyridin-2-ylamino)-acetic acid, (6-{(pyridin-2-ylsulfonyl)[4-(4-trifluoromethylthiazol-2-yl)
 benzyl]aminomethyl}-pyridin-2-ylamino)acetic acid, (6-{(pyridin-2-ylsulfonyl)[4-(thiazol-4-yl)benzyl]
 aminomethyl}pyridin-2-ylamino)-acetic acid, (6-{[4-(pyridin-2-yl)benzyl] (pyridin-3-ylsulfonyl)
 aminomethyl}pyridin-2-ylamino)-acetic acid, (6-{[4-(pyridazin-4-yl)benzyl](pyridin-3-ylsulfonyl)
 aminomethyl}pyridin-2-ylamino)-acetic acid, (6-{(pyridin-2-ylsulfonyl) [4-(pyrimidin-2-yl)benzyl]amino
 methyl}pyridin-2-ylamino)-acetic acid, (6-{[4-(4,5-dihydrothiazol-2-yl)benzyl] (4-fluorobenzene-
 sulfonyl)aminomethyl}pyridin-2-ylamino)acetic acid, {6-[(6-phenylpyridazin-3-ylmethyl)(pyridin-3-ylsulfonyl)
 aminomethyl]pyridin-2-ylamino}acetic acid, hexyl (6-{(pyridin-2-ylsulfonyl)[4-(thiazol-2-yl)benzyl]
 aminomethyl}pyridin-2-ylamino)acetate, (6-{[4-(5-chlorothiazol-2-yl)benzyl](pyridin-2-ylsulfonyl)
 aminomethyl}pyridin-2-ylamino)acetic acid, (6-{[4-(5-methylthiazol-2-yl)benzyl](pyridin-2-ylsulfonyl)
 aminomethyl}pyridin-2-ylamino)acetic acid, (6-{[4-(4,5-dimethylthiazol-2-yl)benzyl] (pyridin-2-ylsulfo-
 nyl)aminomethyl}pyridin-2-ylamino)acetic acid, (6-{(pyridin-3-ylsulfonyl) [4-(1,2,4-triazol-1-yl)benzyl]
 aminomethyl}pyridin-2-ylamino)acetic acid, ethyl (6-{[4-(pyrazol-1-yl)benzyl](pyridin-3-ylsulfonyl)
 aminomethyl}pyridin-2-ylamino)acetate, or isopropyl (6-{[4-(pyrazol-1-yl)benzyl](pyridin-3-ylsulfo-
 nyl)aminomethyl}pyridin-2-ylamino)acetate.

Further, the present invention also provides:

(28) a pharmaceutical composition containing as an active ingredient the above-mentioned compound represented by the formula (1), a pyridylaminoacetic acid compound according to any one of (1) to (27) or a pharmacologically acceptable salt thereof, and

(29) a pharmaceutical composition according to (28) for the prevention or treatment of respiratory diseases.

Compounds in Table 1 can be specifically exemplified for preferred compounds represented by the formula (1) in the present invention.

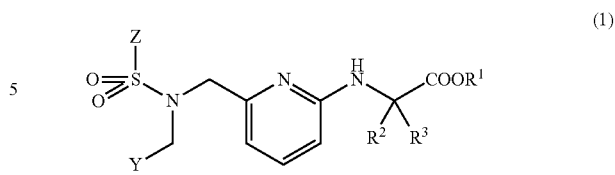

(1)

TABLE 1

| No. | R¹ | R² | R³ | Y | Z |
|---|---|---|---|---|---|
| 1 | H | H | H | Bfu-2-yl | Ph |
| 2 | H | H | H | Bfu-2-yl | 2-F—Ph |
| 3 | H | H | H | Bfu-2-yl | 3-F—Ph |
| 4 | H | H | H | Bfu-2-yl | 4-F—Ph |
| 5 | H | H | H | Bfu-2-yl | 3,4-diF—Ph |
| 6 | H | H | H | Bfu-2-yl | 3,5-diF—Ph |
| 7 | H | H | H | Bfu-2-yl | 2-Cl—Ph |
| 8 | H | H | H | Bfu-2-yl | 3-Cl—Ph |
| 9 | H | H | H | Bfu-2-yl | 4-Cl—Ph |
| 10 | H | H | H | Bfu-2-yl | 2,6-diCl—Ph |
| 11 | H | H | H | Bfu-2-yl | 4-Cl-3-F—Ph |
| 12 | H | H | H | Bfu-2-yl | 4-Me—Ph |
| 13 | H | H | H | Bfu-2-yl | 3-F-4-Me—Ph |
| 14 | H | H | H | Bfu-2-yl | 4-Et—Ph |
| 15 | H | H | H | Bfu-2-yl | 4-Et-3-F—Ph |
| 16 | H | H | H | Bfu-2-yl | 4-CF₃—Ph |
| 17 | H | H | H | Bfu-2-yl | 3-F-4-CF₃—Ph |
| 18 | H | H | H | Bfu-2-yl | 4-OMe—Ph |
| 19 | H | H | H | Bfu-2-yl | 3-F-4-OMe—Ph |
| 20 | H | H | H | Bfu-2-yl | 4-OCHF₂—Ph |
| 21 | H | H | H | Bfu-2-yl | 4-OCHF₂-3-F—Ph |
| 22 | H | H | H | Bfu-2-yl | Th-2-yl |
| 23 | H | H | H | Bfu-2-yl | Th-3-yl |
| 24 | H | H | H | Bfu-2-yl | Py-2-yl |
| 25 | H | H | H | Bfu-2-yl | 5-F—Py-2-yl |
| 26 | H | H | H | Bfu-2-yl | 5-Cl—Py-2-yl |
| 27 | H | H | H | Bfu-2-yl | 5-OMe—Py-2-yl |
| 28 | H | H | H | Bfu-2-yl | Py-3-yl |
| 29 | H | H | H | Bfu-2-yl | 6-F—Py-3-yl |
| 30 | H | H | H | Bfu-2-yl | 6-Cl—Py-3-yl |
| 31 | H | H | H | Bfu-2-yl | 6-OMe—Py-3-yl |
| 32 | H | H | H | Bfu-2-yl | Py-4-yl |
| 33 | H | H | H | 6-F-Bfu-2-yl | Ph |
| 34 | H | H | H | 6-F-Bfu-2-yl | 2-F—Ph |
| 35 | H | H | H | 6-F-Bfu-2-yl | 3-F—Ph |
| 36 | H | H | H | 6-F-Bfu-2-yl | 4-F—Ph |
| 37 | H | H | H | 6-F-Bfu-2-yl | 2-Cl—Ph |
| 38 | H | H | H | 6-F-Bfu-2-yl | 3-Cl—Ph |
| 39 | H | H | H | 6-F-Bfu-2-yl | 4-Cl—Ph |
| 40 | H | H | H | 6-F-Bfu-2-yl | 2,6-diCl—Ph |
| 41 | H | H | H | 6-F-Bfu-2-yl | 4-OMe—Ph |
| 42 | H | H | H | 6-F-Bfu-2-yl | Py-2-yl |
| 43 | H | H | H | 6-F-Bfu-2-yl | Py-3-yl |
| 44 | H | H | H | 5,6-diF-Bfu-2-yl | 4-F—Ph |
| 45 | H | H | H | 5,6-diF-Bfu-2-yl | Py-2-yl |
| 46 | H | H | H | 5,6-diF-Bfu-2-yl | Py-3-yl |
| 47 | H | H | H | 6-Cl-Bfu-2-yl | Ph |
| 48 | H | H | H | 6-Cl-Bfu-2-yl | 2-F—Ph |
| 49 | H | H | H | 6-Cl-Bfu-2-yl | 3-F—Ph |
| 50 | H | H | H | 6-Cl-Bfu-2-yl | 4-F—Ph |
| 51 | H | H | H | 6-Cl-Bfu-2-yl | 2-Cl—Ph |
| 52 | H | H | H | 6-Cl-Bfu-2-yl | 3-Cl—Ph |
| 53 | H | H | H | 6-Cl-Bfu-2-yl | 4-Cl—Ph |
| 54 | H | H | H | 6-Cl-Bfu-2-yl | 2,6-diCl—Ph |
| 55 | H | H | H | 6-Cl-Bfu-2-yl | 4-OMe—Ph |
| 56 | H | H | H | 6-Cl-Bfu-2-yl | Py-2-yl |
| 57 | H | H | H | 6-Cl-Bfu-2-yl | Py-3-yl |
| 58 | H | H | H | 6-Cl-5-F-Bfu-2-yl | 4-F—Ph |
| 59 | H | H | H | 6-Cl-5-F-Bfu-2-yl | Py-2-yl |
| 60 | H | H | H | 6-Cl-5-F-Bfu-2-yl | Py-3-yl |
| 61 | H | H | H | 6-Me-Bfu-2-yl | 4-F—Ph |
| 62 | H | H | H | 6-Me-Bfu-2-yl | Py-2-yl |
| 63 | H | H | H | 6-Me-Bfu-2-yl | Py-3-yl |

TABLE 1-continued

Compounds

| No. | R¹ | R² | R³ | Y | Z |
|---|---|---|---|---|---|
| 64 | H | H | H | 5-F-6-Me-Bfu-2-yl | 4-F—Ph |
| 65 | H | H | H | 5-F-6-Me-Bfu-2-yl | Py-2-yl |
| 66 | H | H | H | 5-F-6-Me-Bfu-2-yl | Py-3-yl |
| 67 | H | H | H | 6-Et-Bfu-2-yl | 4-F—Ph |
| 68 | H | H | H | 6-Et-Bfu-2-yl | Py-2-yl |
| 69 | H | H | H | 6-Et-Bfu-2-yl | Py-3-yl |
| 70 | H | H | H | 6-Et-5-F-Bfu-2-yl | 4-F—Ph |
| 71 | H | H | H | 6-Et-5-F-Bfu-2-yl | Py-2-yl |
| 72 | H | H | H | 6-Et-5-F-Bfu-2-yl | Py-3-yl |
| 73 | H | H | H | 6-CF₃-Bfu-2-yl | 4-F—Ph |
| 74 | H | H | H | 6-CF₃-Bfu-2-yl | Py-2-yl |
| 75 | H | H | H | 6-CF₃-Bfu-2-yl | Py-3-yl |
| 76 | H | H | H | 5-F-6-CF₃-Bfu-2-yl | 4-F—Ph |
| 77 | H | H | H | 5-F-6-CF₃-Bfu-2-yl | Py-2-yl |
| 78 | H | H | H | 5-F-6-CF₃-Bfu-2-yl | Py-3-yl |
| 79 | H | H | H | 6-OMe-Bfu-2-yl | Ph |
| 80 | H | H | H | 6-OMe-Bfu-2-yl | 2-F—Ph |
| 81 | H | H | H | 6-OMe-Bfu-2-yl | 3-F—Ph |
| 82 | H | H | H | 6-OMe-Bfu-2-yl | 4-F—Ph |
| 83 | H | H | H | 6-OMe-Bfu-2-yl | 2-Cl—Ph |
| 84 | H | H | H | 6-OMe-Bfu-2-yl | 3-Cl—Ph |
| 85 | H | H | H | 6-OMe-Bfu-2-yl | 4-Cl—Ph |
| 86 | H | H | H | 6-OMe-Bfu-2-yl | 2,6-diCl—Ph |
| 87 | H | H | H | 6-OMe-Bfu-2-yl | 4-OMe—Ph |
| 88 | H | H | H | 6-OMe-Bfu-2-yl | Py-2-yl |
| 89 | H | H | H | 6-OMe-Bfu-2-yl | Py-3-yl |
| 90 | H | H | H | 5-F-6-OMe-Bfu-2-yl | 4-F—Ph |
| 91 | H | H | H | 5-F-6-OMe-Bfu-2-yl | Py-2-yl |
| 92 | H | H | H | 5-F-6-OMe-Bfu-2-yl | Py-3-yl |
| 93 | H | H | H | 6-OCHF₂-Bfu-2-yl | 4-F—Ph |
| 94 | H | H | H | 6-OCHF₂-Bfu-2-yl | Py-2-yl |
| 95 | H | H | H | 6-OCHF₂-Bfu-2-yl | Py-3-yl |
| 96 | H | H | H | 6-OCHF₂-5-F-Bfu-2-yl | 4-F—Ph |
| 97 | H | H | H | 6-OCHF₂-5-F-Bfu-2-yl | Py-2-yl |
| 98 | H | H | H | 6-OCHF₂-5-F-Bfu-2-yl | Py-3-yl |
| 99 | H | H | H | 6-SMe-Bfu-2-yl | 4-F—Ph |
| 100 | H | H | H | 6-SMe-Bfu-2-yl | Py-2-yl |
| 101 | H | H | H | 6-SMe-Bfu-2-yl | Py-3-yl |
| 102 | H | H | H | 5-F-6-SMe-Bfu-2-yl | 4-F—Ph |
| 103 | H | H | H | 5-F-6-SMe-Bfu-2-yl | Py-2-yl |
| 104 | H | H | H | 5-F-6-SMe-Bfu-2-yl | Py-3-yl |
| 105 | H | H | H | Bth-2-yl | Ph |
| 106 | H | H | H | Bth-2-yl | 2-F—Ph |
| 107 | H | H | H | Bth-2-yl | 3-F—Ph |
| 108 | H | H | H | Bth-2-yl | 4-F—Ph |
| 109 | H | H | H | Bth-2-yl | 3,4-diF—Ph |
| 110 | H | H | H | Bth-2-yl | 3,5-diF—Ph |
| 111 | H | H | H | Bth-2-yl | 2-Cl—Ph |
| 112 | H | H | H | Bth-2-yl | 3-Cl—Ph |
| 113 | H | H | H | Bth-2-yl | 4-Cl—Ph |
| 114 | H | H | H | Bth-2-yl | 2,6-diCl—Ph |
| 115 | H | H | H | Bth-2-yl | 4-Cl-3-F—Ph |
| 116 | H | H | H | Bth-2-yl | 4-Me—Ph |
| 117 | H | H | H | Bth-2-yl | 3-F-4-Me—Ph |
| 118 | H | H | H | Bth-2-yl | 4-Et—Ph |
| 119 | H | H | H | Bth-2-yl | 4-Et-3-F—Ph |
| 120 | H | H | H | Bth-2-yl | 4-CF₃—Ph |
| 121 | H | H | H | Bth-2-yl | 3-F-4-CF₃—Ph |
| 122 | H | H | H | Bth-2-yl | 4-OMe—Ph |
| 123 | H | H | H | Bth-2-yl | 3-F-4-OMe—Ph |
| 124 | H | H | H | Bth-2-yl | 4-OCHF₂—Ph |
| 125 | H | H | H | Bth-2-yl | 4-OCHF₂-3-F—Ph |
| 126 | H | H | H | Bth-2-yl | Th-2-yl |
| 127 | H | H | H | Bth-2-yl | Th-3-yl |
| 128 | H | H | H | Bth-2-yl | Py-2-yl |
| 129 | H | H | H | Bth-2-yl | 5-F—Py-2-yl |
| 130 | H | H | H | Bth-2-yl | 5-Cl—Py-2-yl |
| 131 | H | H | H | Bth-2-yl | 5-OMe—Py-2-yl |
| 132 | H | H | H | Bth-2-yl | Py-3-yl |
| 133 | H | H | H | Bth-2-yl | 6-F—Py-3-yl |
| 134 | H | H | H | Bth-2-yl | 6-Cl—Py-3-yl |
| 135 | H | H | H | Bth-2-yl | 6-OMe—Py-3-yl |
| 136 | H | H | H | Bth-2-yl | Py-4-yl |
| 137 | H | H | H | 6-F-Bth-2-yl | Ph |
| 138 | H | H | H | 6-F-Bth-2-yl | 2-F—Ph |
| 139 | H | H | H | 6-F-Bth-2-yl | 3-F—Ph |
| 140 | H | H | H | 6-F-Bth-2-yl | 4-F—Ph |
| 141 | H | H | H | 6-F-Bth-2-yl | 2-Cl—Ph |
| 142 | H | H | H | 6-F-Bth-2-yl | 3-Cl—Ph |
| 143 | H | H | H | 6-F-Bth-2-yl | 4-Cl—Ph |
| 144 | H | H | H | 6-F-Bth-2-yl | 2,6-diCl—Ph |
| 145 | H | H | H | 6-F-Bth-2-yl | 4-OMe—Ph |
| 146 | H | H | H | 6-F-Bth-2-yl | Py-2-yl |
| 147 | H | H | H | 6-F-Bth-2-yl | Py-3-yl |
| 148 | H | H | H | 5,6-diF-Bth-2-yl | Ph |
| 149 | H | H | H | 5,6-diF-Bth-2-yl | 2-F—Ph |
| 150 | H | H | H | 5,6-diF-Bth-2-yl | 3-F—Ph |
| 151 | H | H | H | 5,6-diF-Bth-2-yl | 4-F—Ph |
| 152 | H | H | H | 5,6-diF-Bth-2-yl | 2-Cl—Ph |
| 153 | H | H | H | 5,6-diF-Bth-2-yl | 3-Cl—Ph |
| 154 | H | H | H | 5,6-diF-Bth-2-yl | 4-Cl—Ph |
| 155 | H | H | H | 5,6-diF-Bth-2-yl | 2,6-diCl—Ph |
| 156 | H | H | H | 5,6-diF-Bth-2-yl | 4-OMe—Ph |
| 157 | H | H | H | 5,6-diF-Bth-2-yl | Py-2-yl |
| 158 | H | H | H | 5,6-diF-Bth-2-yl | Py-3-yl |
| 159 | H | H | H | 6-Cl-Bth-2-yl | Ph |
| 160 | H | H | H | 6-Cl-Bth-2-yl | 2-F—Ph |
| 161 | H | H | H | 6-Cl-Bth-2-yl | 3-F—Ph |
| 162 | H | H | H | 6-Cl-Bth-2-yl | 4-F—Ph |
| 163 | H | H | H | 6-Cl-Bth-2-yl | 3,4-diF—Ph |
| 164 | H | H | H | 6-Cl-Bth-2-yl | 3,5-diF—Ph |
| 165 | H | H | H | 6-Cl-Bth-2-yl | 2-Cl—Ph |
| 166 | H | H | H | 6-Cl-Bth-2-yl | 3-Cl—Ph |
| 167 | H | H | H | 6-Cl-Bth-2-yl | 4-Cl—Ph |
| 168 | H | H | H | 6-Cl-Bth-2-yl | 2,6-diCl—Ph |
| 169 | H | H | H | 6-Cl-Bth-2-yl | 4-Cl-3-F—Ph |
| 170 | H | H | H | 6-Cl-Bth-2-yl | 4-Me—Ph |
| 171 | H | H | H | 6-Cl-Bth-2-yl | 3-F-4-Me—Ph |
| 172 | H | H | H | 6-Cl-Bth-2-yl | 4-Et—Ph |
| 173 | H | H | H | 6-Cl-Bth-2-yl | 4-Et-3-F—Ph |
| 174 | H | H | H | 6-Cl-Bth-2-yl | 4-CF₃—Ph |
| 175 | H | H | H | 6-Cl-Bth-2-yl | 3-F-4-CF₃—Ph |
| 176 | H | H | H | 6-Cl-Bth-2-yl | 4-OMe—Ph |
| 177 | H | H | H | 6-Cl-Bth-2-yl | 3-F-4-OMe—Ph |
| 178 | H | H | H | 6-Cl-Bth-2-yl | 4-OCHF₂—Ph |
| 179 | H | H | H | 6-Cl-Bth-2-yl | 4-OCHF₂-3-F—Ph |
| 180 | H | H | H | 6-Cl-Bth-2-yl | Th-2-yl |
| 181 | H | H | H | 6-Cl-Bth-2-yl | Th-3-yl |
| 182 | H | H | H | 6-Cl-Bth-2-yl | Py-2-yl |
| 183 | H | H | H | 6-Cl-Bth-2-yl | 5-F—Py-2-yl |
| 184 | H | H | H | 6-Cl-Bth-2-yl | 5-Cl—Py-2-yl |
| 185 | H | H | H | 6-Cl-Bth-2-yl | 5-OMe—Py-2-yl |
| 186 | H | H | H | 6-Cl-Bth-2-yl | Py-3-yl |
| 187 | H | H | H | 6-Cl-Bth-2-yl | 6-F—Py-3-yl |
| 188 | H | H | H | 6-Cl-Bth-2-yl | 6-Cl—Py-3-yl |
| 189 | H | H | H | 6-Cl-Bth-2-yl | 6-OMe—Py-3-yl |
| 190 | H | H | H | 6-Cl-Bth-2-yl | Py-4-yl |
| 191 | H | H | H | 6-Cl-5-F-Bth-2-yl | Ph |
| 192 | H | H | H | 6-Cl-5-F-Bth-2-yl | 2-F—Ph |
| 193 | H | H | H | 6-Cl-5-F-Bth-2-yl | 3-F—Ph |
| 194 | H | H | H | 6-Cl-5-F-Bth-2-yl | 4-F—Ph |
| 195 | H | H | H | 6-Cl-5-F-Bth-2-yl | 2-Cl—Ph |
| 196 | H | H | H | 6-Cl-5-F-Bth-2-yl | 3-Cl—Ph |
| 197 | H | H | H | 6-Cl-5-F-Bth-2-yl | 4-Cl—Ph |
| 198 | H | H | H | 6-Cl-5-F-Bth-2-yl | 2,6-diCl—Ph |
| 199 | H | H | H | 6-Cl-5-F-Bth-2-yl | 4-OMe—Ph |
| 200 | H | H | H | 6-Cl-5-F-Bth-2-yl | Py-2-yl |
| 201 | H | H | H | 6-Cl-5-F-Bth-2-yl | Py-3-yl |
| 202 | H | H | H | 6-Br-Bth-2-yl | 4-F—Ph |
| 203 | H | H | H | 6-Br-Bth-2-yl | Py-2-yl |
| 204 | H | H | H | 6-Br-Bth-2-yl | Py-3-yl |
| 205 | H | H | H | 6-Me-Bth-2-yl | Ph |
| 206 | H | H | H | 6-Me-Bth-2-yl | 2-F—Ph |
| 207 | H | H | H | 6-Me-Bth-2-yl | 3-F—Ph |
| 208 | H | H | H | 6-Me-Bth-2-yl | 4-F—Ph |
| 209 | H | H | H | 6-Me-Bth-2-yl | 2-Cl—Ph |
| 210 | H | H | H | 6-Me-Bth-2-yl | 3-Cl—Ph |
| 211 | H | H | H | 6-Me-Bth-2-yl | 4-Cl—Ph |
| 212 | H | H | H | 6-Me-Bth-2-yl | 2,6-diCl—Ph |
| 213 | H | H | H | 6-Me-Bth-2-yl | 4-OMe—Ph |
| 214 | H | H | H | 6-Me-Bth-2-yl | Py-2-yl |
| 215 | H | H | H | 6-Me-Bth-2-yl | Py-3-yl |

TABLE 1-continued

Compounds

| No. | R¹ | R² | R³ | Y | Z |
|---|---|---|---|---|---|
| 216 | H | H | H | 5-F-6-Me-Bth-2-yl | Ph |
| 217 | H | H | H | 5-F-6-Me-Bth-2-yl | 2-F—Ph |
| 218 | H | H | H | 5-F-6-Me-Bth-2-yl | 3-F—Ph |
| 219 | H | H | H | 5-F-6-Me-Bth-2-yl | 4-F—Ph |
| 220 | H | H | H | 5-F-6-Me-Bth-2-yl | 2-Cl—Ph |
| 221 | H | H | H | 5-F-6-Me-Bth-2-yl | 3-Cl—Ph |
| 222 | H | H | H | 5-F-6-Me-Bth-2-yl | 4-Cl—Ph |
| 223 | H | H | H | 5-F-6-Me-Bth-2-yl | 2,6-diCl—Ph |
| 224 | H | H | H | 5-F-6-Me-Bth-2-yl | 4-OMe—Ph |
| 225 | H | H | H | 5-F-6-Me-Bth-2-yl | Py-2-yl |
| 226 | H | H | H | 5-F-6-Me-Bth-2-yl | Py-3-yl |
| 227 | H | H | H | 6-Et-Bth-2-yl | Ph |
| 228 | H | H | H | 6-Et-Bth-2-yl | 2-F—Ph |
| 229 | H | H | H | 6-Et-Bth-2-yl | 3-F—Ph |
| 230 | H | H | H | 6-Et-Bth-2-yl | 4-F—Ph |
| 231 | H | H | H | 6-Et-Bth-2-yl | 2-Cl—Ph |
| 232 | H | H | H | 6-Et-Bth-2-yl | 3-Cl—Ph |
| 233 | H | H | H | 6-Et-Bth-2-yl | 4-Cl—Ph |
| 234 | H | H | H | 6-Et-Bth-2-yl | 2,6-diCl—Ph |
| 235 | H | H | H | 6-Et-Bth-2-yl | 4-OMe—Ph |
| 236 | H | H | H | 6-Et-Bth-2-yl | Py-2-yl |
| 237 | H | H | H | 6-Et-Bth-2-yl | Py-3-yl |
| 238 | H | H | H | 6-Et-5-F-Bth-2-yl | Ph |
| 239 | H | H | H | 6-Et-5-F-Bth-2-yl | 2-F—Ph |
| 240 | H | H | H | 6-Et-5-F-Bth-2-yl | 3-F—Ph |
| 241 | H | H | H | 6-Et-5-F-Bth-2-yl | 4-F—Ph |
| 242 | H | H | H | 6-Et-5-F-Bth-2-yl | 2-Cl—Ph |
| 243 | H | H | H | 6-Et-5-F-Bth-2-yl | 3-Cl—Ph |
| 244 | H | H | H | 6-Et-5-F-Bth-2-yl | 4-Cl—Ph |
| 245 | H | H | H | 6-Et-5-F-Bth-2-yl | 2,6-diCl—Ph |
| 246 | H | H | H | 6-Et-5-F-Bth-2-yl | 4-OMe—Ph |
| 247 | H | H | H | 6-Et-5-F-Bth-2-yl | Py-2-yl |
| 248 | H | H | H | 6-Et-5-F-Bth-2-yl | Py-3-yl |
| 249 | H | H | H | 6-Pr-Bth-2-yl | 4-F—Ph |
| 250 | H | H | H | 6-Pr-Bth-2-yl | Py-2-yl |
| 251 | H | H | H | 6-Pr-Bth-2-yl | Py-3-yl |
| 252 | H | H | H | 6-iPr-Bth-2-yl | 4-F—Ph |
| 253 | H | H | H | 6-iPr-Bth-2-yl | Py-2-yl |
| 254 | H | H | H | 6-iPr-Bth-2-yl | Py-3-yl |
| 255 | H | H | H | 6-tBu-Bth-2-yl | 4-F—Ph |
| 256 | H | H | H | 6-tBu-Bth-2-yl | Py-2-yl |
| 257 | H | H | H | 6-tBu-Bth-2-yl | Py-3-yl |
| 258 | H | H | H | 6-CF₃-Bth-2-yl | Ph |
| 259 | H | H | H | 6-CF₃-Bth-2-yl | 2-F—Ph |
| 260 | H | H | H | 6-CF₃-Bth-2-yl | 3-F—Ph |
| 261 | H | H | H | 6-CF₃-Bth-2-yl | 4-F—Ph |
| 262 | H | H | H | 6-CF₃-Bth-2-yl | 2-Cl—Ph |
| 263 | H | H | H | 6-CF₃-Bth-2-yl | 3-Cl—Ph |
| 264 | H | H | H | 6-CF₃-Bth-2-yl | 4-Cl—Ph |
| 265 | H | H | H | 6-CF₃-Bth-2-yl | 2,6-diCl—Ph |
| 266 | H | H | H | 6-CF₃-Bth-2-yl | 4-OMe—Ph |
| 267 | H | H | H | 6-CF₃-Bth-2-yl | Py-2-yl |
| 268 | H | H | H | 6-CF₃-Bth-2-yl | Py-3-yl |
| 269 | H | H | H | 5-F-6-CF₃-Bth-2-yl | Ph |
| 270 | H | H | H | 5-F-6-CF₃-Bth-2-yl | 2-F—Ph |
| 271 | H | H | H | 5-F-6-CF₃-Bth-2-yl | 3-F—Ph |
| 272 | H | H | H | 5-F-6-CF₃-Bth-2-yl | 4-F—Ph |
| 273 | H | H | H | 5-F-6-CF₃-Bth-2-yl | 2-Cl—Ph |
| 274 | H | H | H | 5-F-6-CF₃-Bth-2-yl | 3-Cl—Ph |
| 275 | H | H | H | 5-F-6-CF₃-Bth-2-yl | 4-Cl—Ph |
| 276 | H | H | H | 5-F-6-CF₃-Bth-2-yl | 2,6-diCl—Ph |
| 277 | H | H | H | 5-F-6-CF₃-Bth-2-yl | 4-OMe—Ph |
| 278 | H | H | H | 5-F-6-CF₃-Bth-2-yl | Py-2-yl |
| 279 | H | H | H | 5-F-6-CF₃-Bth-2-yl | Py-3-yl |
| 280 | H | H | H | 6-CHF₂-Bth-2-yl | 4-F—Ph |
| 281 | H | H | H | 6-CHF₂-Bth-2-yl | Py-2-yl |
| 282 | H | H | H | 6-CHF₂-Bth-2-yl | Py-3-yl |
| 283 | H | H | H | 6-CCl₃-Bth-2-yl | 4-F—Ph |
| 284 | H | H | H | 6-CCl₃-Bth-2-yl | Py-2-yl |
| 285 | H | H | H | 6-CCl₃-Bth-2-yl | Py-3-yl |
| 286 | H | H | H | 6-CHCl₂-Bth-2-yl | 4-F—Ph |
| 287 | H | H | H | 6-CHCl₂-Bth-2-yl | Py-2-yl |
| 288 | H | H | H | 6-CHCl₂-Bth-2-yl | Py-3-yl |
| 289 | H | H | H | 6-CH₂CF₃-Bth-2-yl | 4-F—Ph |
| 290 | H | H | H | 6-CH₂CF₃-Bth-2-yl | Py-2-yl |
| 291 | H | H | H | 6-CH₂CF₃-Bth-2-yl | Py-3-yl |
| 292 | H | H | H | 6-CH₂CCl₃-Bth-2-yl | 4-F—Ph |
| 293 | H | H | H | 6-CH₂CCl₃-Bth-2-yl | Py-2-yl |
| 294 | H | H | H | 6-CH₂CCl₃-Bth-2-yl | Py-3-yl |
| 295 | Me | H | H | 6-OMe-Bth-2-yl | 4-F—Ph |
| 296 | Me | H | H | 6-OMe-Bth-2-yl | Py-2-yl |
| 297 | Me | H | H | 6-OMe-Bth-2-yl | Py-3-yl |
| 298 | Et | H | H | 6-OMe-Bth-2-yl | 4-F—Ph |
| 299 | Et | H | H | 6-OMe-Bth-2-yl | Py-2-yl |
| 300 | Et | H | H | 6-OMe-Bth-2-yl | Py-3-yl |
| 301 | Me | Me | Me | 6-OMe-Bth-2-yl | Py-2-yl |
| 302 | Et | Me | Me | 6-OMe-Bth-2-yl | Py-2-yl |
| 303 | H | Me | Me | 6-OMe-Bth-2-yl | 4-F—Ph |
| 304 | H | Me | Me | 6-OMe-Bth-2-yl | Py-2-yl |
| 305 | H | Me | Me | 6-OMe-Bth-2-yl | Py-3-yl |
| 306 | H | Me | H | 6-OMe-Bth-2-yl | 4-F—Ph |
| 307 | H | Me | H | 6-OMe-Bth-2-yl | Py-2-yl |
| 308 | H | Me | H | 6-OMe-Bth-2-yl | Py-3-yl |
| 309 | H | H | H | 6-OMe-Bth-2-yl | Ph |
| 310 | H | H | H | 6-OMe-Bth-2-yl | 2-F—Ph |
| 311 | H | H | H | 6-OMe-Bth-2-yl | 3-F—Ph |
| 312 | H | H | H | 6-OMe-Bth-2-yl | 4-F—Ph |
| 313 | H | H | H | 6-OMe-Bth-2-yl | 3,4-diF—Ph |
| 314 | H | H | H | 6-OMe-Bth-2-yl | 3,5-diF—Ph |
| 315 | H | H | H | 6-OMe-Bth-2-yl | 3,4,5-triF—Ph |
| 316 | H | H | H | 6-OMe-Bth-2-yl | 2-Cl—Ph |
| 317 | H | H | H | 6-OMe-Bth-2-yl | 3-Cl—Ph |
| 318 | H | H | H | 6-OMe-Bth-2-yl | 4-Cl—Ph |
| 319 | H | H | H | 6-OMe-Bth-2-yl | 2,6-diCl—Ph |
| 320 | H | H | H | 6-OMe-Bth-2-yl | 4-Cl-3-F—Ph |
| 321 | H | H | H | 6-OMe-Bth-2-yl | 4-Cl-3,5-diF—Ph |
| 322 | H | H | H | 6-OMe-Bth-2-yl | 4-Br—Ph |
| 323 | H | H | H | 6-OMe-Bth-2-yl | 4-Me—Ph |
| 324 | H | H | H | 6-OMe-Bth-2-yl | 3-F-4-Me—Ph |
| 325 | H | H | H | 6-OMe-Bth-2-yl | 4-Et—Ph |
| 326 | H | H | H | 6-OMe-Bth-2-yl | 4-Et-3-F—Ph |
| 327 | H | H | H | 6-OMe-Bth-2-yl | 4-Pr—Ph |
| 328 | H | H | H | 6-OMe-Bth-2-yl | 4-iPr—Ph |
| 329 | H | H | H | 6-OMe-Bth-2-yl | 4-tBu—Ph |
| 330 | H | H | H | 6-OMe-Bth-2-yl | 4-CF₃—Ph |
| 331 | H | H | H | 6-OMe-Bth-2-yl | 3-F-4-CF₃—Ph |
| 332 | H | H | H | 6-OMe-Bth-2-yl | 4-CHF₂—Ph |
| 333 | H | H | H | 6-OMe-Bth-2-yl | 4-CCl₃—Ph |
| 334 | H | H | H | 6-OMe-Bth-2-yl | 4-CHCl₂—Ph |
| 335 | H | H | H | 6-OMe-Bth-2-yl | 4-CH₂CF₃—Ph |
| 336 | H | H | H | 6-OMe-Bth-2-yl | 4-CH₂CCl₃—Ph |
| 337 | H | H | H | 6-OMe-Bth-2-yl | 4-OMe—Ph |
| 338 | H | H | H | 6-OMe-Bth-2-yl | 3-F-4-OMe—Ph |
| 339 | H | H | H | 6-OMe-Bth-2-yl | 4-OEt—Ph |
| 340 | H | H | H | 6-OMe-Bth-2-yl | 4-OPr—Ph |
| 341 | H | H | H | 6-OMe-Bth-2-yl | 4-OiPr—Ph |
| 342 | H | H | H | 6-OMe-Bth-2-yl | 4-OtBu—Ph |
| 343 | H | H | H | 6-OMe-Bth-2-yl | 4-OCF₃—Ph |
| 344 | H | H | H | 6-OMe-Bth-2-yl | 4-OCHF₂—Ph |
| 345 | H | H | H | 6-OMe-Bth-2-yl | 4-OCHF₂-3-F—Ph |
| 346 | H | H | H | 6-OMe-Bth-2-yl | 4-OCCl₃—Ph |
| 347 | H | H | H | 6-OMe-Bth-2-yl | 4-OCHCl₂—Ph |
| 348 | H | H | H | 6-OMe-Bth-2-yl | Th-2-yl |
| 349 | H | H | H | 6-OMe-Bth-2-yl | Th-3-yl |
| 350 | H | H | H | 6-OMe-Bth-2-yl | 5-Cl-Th-2-yl |
| 351 | H | H | H | 6-OMe-Bth-2-yl | 1-Me-1H-Imz-4-yl |
| 352 | H | H | H | 6-OMe-Bth-2-yl | Thz-2-yl |
| 353 | H | H | H | 6-OMe-Bth-2-yl | Py-2-yl |
| 354 | H | H | H | 6-OMe-Bth-2-yl | 5-F—Py-2-yl |
| 355 | H | H | H | 6-OMe-Bth-2-yl | 5-Cl—Py-2-yl |
| 356 | H | H | H | 6-OMe-Bth-2-yl | 5-Me—Py-2-yl |
| 357 | H | H | H | 6-OMe-Bth-2-yl | 5-Et—Py-2-yl |
| 358 | H | H | H | 6-OMe-Bth-2-yl | 5-CF₃—Py-2-yl |
| 359 | H | H | H | 6-OMe-Bth-2-yl | 5-OMe—Py-2-yl |
| 360 | H | H | H | 6-OMe-Bth-2-yl | 5-OCHF₂—Py-2-yl |
| 361 | H | H | H | 6-OMe-Bth-2-yl | Py-3-yl |
| 362 | H | H | H | 6-OMe-Bth-2-yl | 6-F—Py-3-yl |
| 363 | H | H | H | 6-OMe-Bth-2-yl | 6-Cl—Py-3-yl |
| 364 | H | H | H | 6-OMe-Bth-2-yl | 6-Me—Py-3-yl |
| 365 | H | H | H | 6-OMe-Bth-2-yl | 6-Et—Py-3-yl |
| 366 | H | H | H | 6-OMe-Bth-2-yl | 6-CF₃—Py-3-yl |
| 367 | H | H | H | 6-OMe-Bth-2-yl | 6-OMe—Py-3-yl |

TABLE 1-continued

Compounds

| No. | R¹ | R² | R³ | Y | Z |
|---|---|---|---|---|---|
| 368 | H | H | H | 6-OMe-Bth-2-yl | 6-OCHF$_2$—Py-3-yl |
| 369 | H | H | H | 6-OMe-Bth-2-yl | Py-4-yl |
| 370 | H | H | H | 6-OMe-Bth-2-yl | Pym-2-yl |
| 371 | H | H | H | 5-F-6-OMe-Bth-2-yl | Ph |
| 372 | H | H | H | 5-F-6-OMe-Bth-2-yl | 2-F—Ph |
| 373 | H | H | H | 5-F-6-OMe-Bth-2-yl | 3-F—Ph |
| 374 | H | H | H | 5-F-6-OMe-Bth-2-yl | 4-F—Ph |
| 375 | H | H | H | 5-F-6-OMe-Bth-2-yl | 2-Cl—Ph |
| 376 | H | H | H | 5-F-6-OMe-Bth-2-yl | 3-Cl—Ph |
| 377 | H | H | H | 5-F-6-OMe-Bth-2-yl | 4-Cl—Ph |
| 378 | H | H | H | 5-F-6-OMe-Bth-2-yl | 2,6-diCl—Ph |
| 379 | H | H | H | 5-F-6-OMe-Bth-2-yl | 4-OMe—Ph |
| 380 | H | H | H | 5-F-6-OMe-Bth-2-yl | Py-2-yl |
| 381 | H | H | H | 5-F-6-OMe-Bth-2-yl | Py-3-yl |
| 382 | H | H | H | 6-OEt-Bth-2-yl | 4-F—Ph |
| 383 | H | H | H | 6-OEt-Bth-2-yl | Py-2-yl |
| 384 | H | H | H | 6-OEt-Bth-2-yl | Py-3-yl |
| 385 | H | H | H | 6-OPr-Bth-2-yl | 4-F—Ph |
| 386 | H | H | H | 6-OPr-Bth-2-yl | Py-2-yl |
| 387 | H | H | H | 6-OPr-Bth-2-yl | Py-3-yl |
| 388 | H | H | H | 6-OiPr-Bth-2-yl | 4-F—Ph |
| 389 | H | H | H | 6-OiPr-Bth-2-yl | Py-2-yl |
| 390 | H | H | H | 6-OiPr-Bth-2-yl | Py-3-yl |
| 391 | H | H | H | 6-OtBu-Bth-2-yl | 4-F—Ph |
| 392 | H | H | H | 6-OtBu-Bth-2-yl | Py-2-yl |
| 393 | H | H | H | 6-OtBu-Bth-2-yl | Py-3-yl |
| 394 | H | H | H | 6-OCF$_3$-Bth-2-yl | 4-F—Ph |
| 395 | H | H | H | 6-OCF$_3$-Bth-2-yl | Py-2-yl |
| 396 | H | H | H | 6-OCF$_3$-Bth-2-yl | Py-3-yl |
| 397 | H | H | H | 6-OCHF$_2$-Bth-2-yl | Ph |
| 398 | H | H | H | 6-OCHF$_2$-Bth-2-yl | 2-F—Ph |
| 399 | H | H | H | 6-OCHF$_2$-Bth-2-yl | 3-F—Ph |
| 400 | H | H | H | 6-OCHF$_2$-Bth-2-yl | 4-F—Ph |
| 401 | H | H | H | 6-OCHF$_2$-Bth-2-yl | 2-Cl—Ph |
| 402 | H | H | H | 6-OCHF$_2$-Bth-2-yl | 3-Cl—Ph |
| 403 | H | H | H | 6-OCHF$_2$-Bth-2-yl | 4-Cl—Ph |
| 404 | H | H | H | 6-OCHF$_2$-Bth-2-yl | 2,6-diCl—Ph |
| 405 | H | H | H | 6-OCHF$_2$-Bth-2-yl | 4-OMe—Ph |
| 406 | H | H | H | 6-OCHF$_2$-Bth-2-yl | Py-2-yl |
| 407 | H | H | H | 6-OCHF$_2$-Bth-2-yl | Py-3-yl |
| 408 | H | H | H | 6-OCHF$_2$-5-F-Bth-2-yl | Ph |
| 409 | H | H | H | 6-OCHF$_2$-5-F-Bth-2-yl | 2-F—Ph |
| 410 | H | H | H | 6-OCHF$_2$-5-F-Bth-2-yl | 3-F—Ph |
| 411 | H | H | H | 6-OCHF$_2$-5-F-Bth-2-yl | 4-F—Ph |
| 412 | H | H | H | 6-OCHF$_2$-5-F-Bth-2-yl | 2-Cl—Ph |
| 413 | H | H | H | 6-OCHF$_2$-5-F-Bth-2-yl | 3-Cl—Ph |
| 414 | H | H | H | 6-OCHF$_2$-5-F-Bth-2-yl | 4-Cl—Ph |
| 415 | H | H | H | 6-OCHF$_2$-5-F-Bth-2-yl | 2,6-diCl—Ph |
| 416 | H | H | H | 6-OCHF$_2$-5-F-Bth-2-yl | 4-OMe—Ph |
| 417 | H | H | H | 6-OCHF$_2$-5-F-Bth-2-yl | Py-2-yl |
| 418 | H | H | H | 6-OCHF$_2$-5-F-Bth-2-yl | Py-3-yl |
| 419 | H | H | H | 6-OCCl$_3$-Bth-2-yl | 4-F—Ph |
| 420 | H | H | H | 6-OCCl$_3$-Bth-2-yl | Py-2-yl |
| 421 | H | H | H | 6-OCCl$_3$-Bth-2-yl | Py-3-yl |
| 422 | H | H | H | 6-OCHCl$_2$-Bth-2-yl | 4-F—Ph |
| 423 | H | H | H | 6-OCHCl$_2$-Bth-2-yl | Py-2-yl |
| 424 | H | H | H | 6-OCHCl$_2$-Bth-2-yl | Py-3-yl |
| 425 | H | H | H | 6-SMe-Bth-2-yl | Ph |
| 426 | H | H | H | 6-SMe-Bth-2-yl | 2-F—Ph |
| 427 | H | H | H | 6-SMe-Bth-2-yl | 3-F—Ph |
| 428 | H | H | H | 6-SMe-Bth-2-yl | 4-F—Ph |
| 429 | H | H | H | 6-SMe-Bth-2-yl | 2-Cl—Ph |
| 430 | H | H | H | 6-SMe-Bth-2-yl | 3-Cl—Ph |
| 431 | H | H | H | 6-SMe-Bth-2-yl | 4-Cl—Ph |
| 432 | H | H | H | 6-SMe-Bth-2-yl | 2,6-diCl—Ph |
| 433 | H | H | H | 6-SMe-Bth-2-yl | 4-OMe—Ph |
| 434 | H | H | H | 6-SMe-Bth-2-yl | Py-2-yl |
| 435 | H | H | H | 6-SMe-Bth-2-yl | Py-3-yl |
| 436 | H | H | H | 5-F-6-SMe-Bth-2-yl | Ph |
| 437 | H | H | H | 5-F-6-SMe-Bth-2-yl | 2-F—Ph |
| 438 | H | H | H | 5-F-6-SMe-Bth-2-yl | 3-F—Ph |
| 439 | H | H | H | 5-F-6-SMe-Bth-2-yl | 4-F—Ph |
| 440 | H | H | H | 5-F-6-SMe-Bth-2-yl | 2-Cl—Ph |
| 441 | H | H | H | 5-F-6-SMe-Bth-2-yl | 3-Cl—Ph |
| 442 | H | H | H | 5-F-6-SMe-Bth-2-yl | 4-Cl—Ph |
| 443 | H | H | H | 5-F-6-SMe-Bth-2-yl | 2,6-diCl—Ph |
| 444 | H | H | H | 5-F-6-SMe-Bth-2-yl | 4-OMe—Ph |
| 445 | H | H | H | 5-F-6-SMe-Bth-2-yl | Py-2-yl |
| 446 | H | H | H | 5-F-6-SMe-Bth-2-yl | Py-3-yl |
| 447 | H | H | H | 6-SEt-Bth-2-yl | 4-F—Ph |
| 448 | H | H | H | 6-SEt-Bth-2-yl | Py-2-yl |
| 449 | H | H | H | 6-SEt-Bth-2-yl | Py-3-yl |
| 450 | H | H | H | 6-SPr-Bth-2-yl | 4-F—Ph |
| 451 | H | H | H | 6-SPr-Bth-2-yl | Py-2-yl |
| 452 | H | H | H | 6-SPr-Bth-2-yl | Py-3-yl |
| 453 | H | H | H | 6-SiPr-Bth-2-yl | 4-F—Ph |
| 454 | H | H | H | 6-SiPr-Bth-2-yl | Py-2-yl |
| 455 | H | H | H | 6-SiPr-Bth-2-yl | Py-3-yl |
| 456 | H | H | H | 6-StBu-Bth-2-yl | 4-F—Ph |
| 457 | H | H | H | 6-StBu-Bth-2-yl | Py-2-yl |
| 458 | H | H | H | 6-StBu-Bth-2-yl | Py-3-yl |
| 459 | H | H | H | Boxz-2-yl | 4-F—Ph |
| 460 | H | H | H | Boxz-2-yl | Py-2-yl |
| 461 | H | H | H | Boxz-2-yl | Py-3-yl |
| 462 | H | H | H | 6-Cl-Boxz-2-yl | 4-F—Ph |
| 463 | H | H | H | 6-Cl-Boxz-2-yl | Py-2-yl |
| 464 | H | H | H | 6-Cl-Boxz-2-yl | Py-3-yl |
| 465 | H | H | H | 6-OMe-Boxz-2-yl | 4-F—Ph |
| 466 | H | H | H | 6-OMe-Boxz-2-yl | Py-2-yl |
| 467 | H | H | H | 6-OMe-Boxz-2-yl | Py-3-yl |
| 468 | H | H | H | Bthz-2-yl | 4-F—Ph |
| 469 | H | H | H | Bthz-2-yl | Py-2-yl |
| 470 | H | H | H | Bthz-2-yl | Py-3-yl |
| 471 | H | H | H | 6-Cl-Bthz-2-yl | 4-F—Ph |
| 472 | H | H | H | 6-Cl-Bthz-2-yl | Py-2-yl |
| 473 | H | H | H | 6-Cl-Bthz-2-yl | Py-3-yl |
| 474 | H | H | H | 6-OMe-Bthz-2-yl | 4-F—Ph |
| 475 | H | H | H | 6-OMe-Bthz-2-yl | Py-2-yl |
| 476 | H | H | H | 6-OMe-Bthz-2-yl | Py-3-yl |
| 477 | H | H | H | biPh-3-yl | 4-F—Ph |
| 478 | H | H | H | biPh-3-yl | Py-2-yl |
| 479 | H | H | H | biPh-3-yl | Py-3-yl |
| 480 | Me | H | H | biPh-4-yl | 4-F—Ph |
| 481 | Me | H | H | biPh-4-yl | Py-2-yl |
| 482 | Me | H | H | biPh-4-yl | Py-3-yl |
| 483 | Et | H | H | biPh-4-yl | 4-F—Ph |
| 484 | Et | H | H | biPh-4-yl | Py-2-yl |
| 485 | Et | H | H | biPh-4-yl | Py-3-yl |
| 486 | Me | Me | Me | biPh-4-yl | Py-2-yl |
| 487 | Et | Me | Me | biPh-4-yl | Py-3-yl |
| 488 | H | Me | Me | biPh-4-yl | 4-F—Ph |
| 489 | H | Me | Me | biPh-4-yl | Py-2-yl |
| 490 | H | Me | Me | biPh-4-yl | Py-3-yl |
| 491 | H | Me | H | biPh-4-yl | 4-F—Ph |
| 492 | H | Me | H | biPh-4-yl | Py-2-yl |
| 493 | H | Me | H | biPh-4-yl | Py-3-yl |
| 494 | H | H | H | biPh-4-yl | Ph |
| 495 | H | H | H | biPh-4-yl | 2-F—Ph |
| 496 | H | H | H | biPh-4-yl | 3-F—Ph |
| 497 | H | H | H | biPh-4-yl | 4-F—Ph |
| 498 | H | H | H | biPh-4-yl | 3,4-diF—Ph |
| 499 | H | H | H | biPh-4-yl | 3,5-diF—Ph |
| 500 | H | H | H | biPh-4-yl | 3,4,5-triF—Ph |
| 501 | H | H | H | biPh-4-yl | 2-Cl—Ph |
| 502 | H | H | H | biPh-4-yl | 3-Cl—Ph |
| 503 | H | H | H | biPh-4-yl | 4-Cl—Ph |
| 504 | H | H | H | biPh-4-yl | 2,6-diCl—Ph |
| 505 | H | H | H | biPh-4-yl | 4-Cl-3-F—Ph |
| 506 | H | H | H | biPh-4-yl | 4-Cl-3,5-diF—Ph |
| 507 | H | H | H | biPh-4-yl | 4-Br-Ph |
| 508 | H | H | H | biPh-4-yl | 4-Me—Ph |
| 509 | H | H | H | biPh-4-yl | 3-F-4-Me—Ph |
| 510 | H | H | H | biPh-4-yl | 4-Et—Ph |
| 511 | H | H | H | biPh-4-yl | 4-Et-3-F—Ph |
| 512 | H | H | H | biPh-4-yl | 4-Pr—Ph |
| 513 | H | H | H | biPh-4-yl | 4-iPr—Ph |
| 514 | H | H | H | biPh-4-yl | 4-tBu—Ph |
| 515 | H | H | H | biPh-4-yl | 4-CF$_3$—Ph |
| 516 | H | H | H | biPh-4-yl | 3-F-4-CF$_3$—Ph |
| 517 | H | H | H | biPh-4-yl | 4-CHF$_2$—Ph |
| 518 | H | H | H | biPh-4-yl | 4-CCl$_3$—Ph |
| 519 | H | H | H | biPh-4-yl | 4-CHCl$_2$—Ph |

TABLE 1-continued

Compounds

| No. | R¹ | R² | R³ | Y | Z |
|---|---|---|---|---|---|
| 520 | H | H | H | biPh-4-yl | 4-CH$_2$CF$_3$—Ph |
| 521 | H | H | H | biPh-4-yl | 4-CH$_2$CCl$_3$—Ph |
| 522 | H | H | H | biPh-4-yl | 4-OMe—Ph |
| 523 | H | H | H | biPh-4-yl | 3-F-4-OMe—Ph |
| 524 | H | H | H | biPh-4-yl | 4-OEt—Ph |
| 525 | H | H | H | biPh-4-yl | 4-OPr—Ph |
| 526 | H | H | H | biPh-4-yl | 4-OiPr—Ph |
| 527 | H | H | H | biPh-4-yl | 4-OtBu—Ph |
| 528 | H | H | H | biPh-4-yl | 4-OCF$_3$—Ph |
| 529 | H | H | H | biPh-4-yl | 4-OCHF$_2$—Ph |
| 530 | H | H | H | biPh-4-yl | 4-OCHF$_2$-3-F—Ph |
| 531 | H | H | H | biPh-4-yl | 4-OCCl$_3$—Ph |
| 532 | H | H | H | biPh-4-yl | 4-OCHCl$_2$—Ph |
| 533 | H | H | H | biPh-4-yl | Th-2-yl |
| 534 | H | H | H | biPh-4-yl | Th-3-yl |
| 535 | H | H | H | biPh-4-yl | 5-Cl-Th-2-yl |
| 536 | H | H | H | biPh-4-yl | 1-Me-1H-Imz-4-yl |
| 537 | H | H | H | biPh-4-yl | Thz-2-yl |
| 538 | H | H | H | biPh-4-yl | Py-2-yl |
| 539 | H | H | H | biPh-4-yl | 5-F—Py-2-yl |
| 540 | H | H | H | biPh-4-yl | 5-Cl—Py-2-yl |
| 541 | H | H | H | biPh-4-yl | 5-Me—Py-2-yl |
| 542 | H | H | H | biPh-4-yl | 5-Et—Py-2-yl |
| 543 | H | H | H | biPh-4-yl | 5-CF$_3$—Py-2-yl |
| 544 | H | H | H | biPh-4-yl | 5-OMe—Py-2-yl |
| 545 | H | H | H | biPh-4-yl | 5-OCHF$_2$—Py-2-yl |
| 546 | H | H | H | biPh-4-yl | Py-3-yl |
| 547 | H | H | H | biPh-4-yl | 6-F—Py-3-yl |
| 548 | H | H | H | biPh-4-yl | 6-Cl—Py-3-yl |
| 549 | H | H | H | biPh-4-yl | 6-Me—Py-3-yl |
| 550 | H | H | H | biPh-4-yl | 6-Et—Py-3-yl |
| 551 | H | H | H | biPh-4-yl | 6-CF$_3$—Py-3-yl |
| 552 | H | H | H | biPh-4-yl | 6-OMe—Py-3-yl |
| 553 | H | H | H | biPh-4-yl | 6-OCHF$_2$—Py-3-yl |
| 554 | H | H | H | biPh-4-yl | Py-4-yl |
| 555 | H | H | H | biPh-4-yl | Pym-2-yl |
| 556 | H | H | H | 2'-F-biPh-4-yl | Ph |
| 557 | H | H | H | 2'-F-biPh-4-yl | 2-F—Ph |
| 558 | H | H | H | 2'-F-biPh-4-yl | 3-F—Ph |
| 559 | H | H | H | 2'-F-biPh-4-yl | 4-F—Ph |
| 560 | H | H | H | 2'-F-biPh-4-yl | 2-Cl—Ph |
| 561 | H | H | H | 2'-F-biPh-4-yl | 3-Cl—Ph |
| 562 | H | H | H | 2'-F-biPh-4-yl | 4-Cl—Ph |
| 563 | H | H | H | 2'-F-biPh-4-yl | 2,6-diCl—Ph |
| 564 | H | H | H | 2'-F-biPh-4-yl | 4-OMe—Ph |
| 565 | H | H | H | 2'-F-biPh-4-yl | Py-2-yl |
| 566 | H | H | H | 2'-F-biPh-4-yl | Py-3-yl |
| 567 | H | H | H | 3'-F-biPh-4-yl | Ph |
| 568 | H | H | H | 3'-F-biPh-4-yl | 2-F—Ph |
| 569 | H | H | H | 3'-F-biPh-4-yl | 3-F—Ph |
| 570 | H | H | H | 3'-F-biPh-4-yl | 4-F—Ph |
| 571 | H | H | H | 3'-F-biPh-4-yl | 2-Cl—Ph |
| 572 | H | H | H | 3'-F-biPh-4-yl | 3-Cl—Ph |
| 573 | H | H | H | 3'-F-biPh-4-yl | 4-Cl—Ph |
| 574 | H | H | H | 3'-F-biPh-4-yl | 2,6-diCl—Ph |
| 575 | H | H | H | 3'-F-biPh-4-yl | 4-OMe—Ph |
| 576 | H | H | H | 3'-F-biPh-4-yl | Py-2-yl |
| 577 | H | H | H | 3'-F-biPh-4-yl | Py-3-yl |
| 578 | H | H | H | 4'-F-biPh-4-yl | Ph |
| 579 | H | H | H | 4'-F-biPh-4-yl | 2-F—Ph |
| 580 | H | H | H | 4'-F-biPh-4-yl | 3-F—Ph |
| 581 | H | H | H | 4'-F-biPh-4-yl | 4-F—Ph |
| 582 | H | H | H | 4'-F-biPh-4-yl | 3,4-diF—Ph |
| 583 | H | H | H | 4'-F-biPh-4-yl | 3,5-diF—Ph |
| 584 | H | H | H | 4'-F-biPh-4-yl | 2-Cl—Ph |
| 585 | H | H | H | 4'-F-biPh-4-yl | 3-Cl—Ph |
| 586 | H | H | H | 4'-F-biPh-4-yl | 4-Cl—Ph |
| 587 | H | H | H | 4'-F-biPh-4-yl | 2,6-diCl—Ph |
| 588 | H | H | H | 4'-F-biPh-4-yl | 4-Cl-3-F—Ph |
| 589 | H | H | H | 4'-F-biPh-4-yl | 4-Me—Ph |
| 590 | H | H | H | 4'-F-biPh-4-yl | 3-F-4-Me—Ph |
| 591 | H | H | H | 4'-F-biPh-4-yl | 4-Et—Ph |
| 592 | H | H | H | 4'-F-biPh-4-yl | 4-Et-3-F—Ph |
| 593 | H | H | H | 4'-F-biPh-4-yl | 4-CF$_3$—Ph |
| 594 | H | H | H | 4'-F-biPh-4-yl | 3-F-4-CF$_3$—Ph |
| 595 | H | H | H | 4'-F-biPh-4-yl | 4-OMe—Ph |
| 596 | H | H | H | 4'-F-biPh-4-yl | 3-F-4-OMe—Ph |
| 597 | H | H | H | 4'-F-biPh-4-yl | 4-OCHF$_2$—Ph |
| 598 | H | H | H | 4'-F-biPh-4-yl | 4-OCHF$_2$-3-F—Ph |
| 599 | H | H | H | 4'-F-biPh-4-yl | Th-2-yl |
| 600 | H | H | H | 4'-F-biPh-4-yl | Th-3-yl |
| 601 | H | H | H | 4'-F-biPh-4-yl | Py-2-yl |
| 602 | H | H | H | 4'-F-biPh-4-yl | 5-F—Py-2-yl |
| 603 | H | H | H | 4'-F-biPh-4-yl | 5-Cl—Py-2-yl |
| 604 | H | H | H | 4'-F-biPh-4-yl | 5-OMe—Py-2-yl |
| 605 | H | H | H | 4'-F-biPh-4-yl | Py-3-yl |
| 606 | H | H | H | 4'-F-biPh-4-yl | 6-F—Py-3-yl |
| 607 | H | H | H | 4'-F-biPh-4-yl | 6-Cl—Py-3-yl |
| 608 | H | H | H | 4'-F-biPh-4-yl | 6-OMe—Py-3-yl |
| 609 | H | H | H | 4'-F-biPh-4-yl | Py-4-yl |
| 610 | H | H | H | 2',4'-diF-biPh-4-yl | Ph |
| 611 | H | H | H | 2',4'-diF-biPh-4-yl | 2-F—Ph |
| 612 | H | H | H | 2',4'-diF-biPh-4-yl | 3-F—Ph |
| 613 | H | H | H | 2',4'-diF-biPh-4-yl | 4-F—Ph |
| 614 | H | H | H | 2',4'-diF-biPh-4-yl | 2-Cl—Ph |
| 615 | H | H | H | 2',4'-diF-biPh-4-yl | 3-Cl—Ph |
| 616 | H | H | H | 2',4'-diF-biPh-4-yl | 4-Cl—Ph |
| 617 | H | H | H | 2',4'-diF-biPh-4-yl | 2,6-diCl—Ph |
| 618 | H | H | H | 2',4'-diF-biPh-4-yl | 4-OMe—Ph |
| 619 | H | H | H | 2',4'-diF-biPh-4-yl | Py-2-yl |
| 620 | H | H | H | 2',4'-diF-biPh-4-yl | Py-3-yl |
| 621 | H | H | H | 3',4'-diF-biPh-4-yl | Ph |
| 622 | H | H | H | 3',4'-diF-biPh-4-yl | 2-F—Ph |
| 623 | H | H | H | 3',4'-diF-biPh-4-yl | 3-F—Ph |
| 624 | H | H | H | 3',4'-diF-biPh-4-yl | 4-F—Ph |
| 625 | H | H | H | 3',4'-diF-biPh-4-yl | 2-Cl—Ph |
| 626 | H | H | H | 3',4'-diF-biPh-4-yl | 3-Cl—Ph |
| 627 | H | H | H | 3',4'-diF-biPh-4-yl | 4-Cl—Ph |
| 628 | H | H | H | 3',4'-diF-biPh-4-yl | 2,6-diCl—Ph |
| 629 | H | H | H | 3',4'-diF-biPh-4-yl | 4-OMe—Ph |
| 630 | H | H | H | 3',4'-diF-biPh-4-yl | Py-2-yl |
| 631 | H | H | H | 3',4'-diF-biPh-4-yl | Py-3-yl |
| 632 | H | H | H | 2'-Cl-biPh-4-yl | Ph |
| 633 | H | H | H | 2'-Cl-biPh-4-yl | 2-F—Ph |
| 634 | H | H | H | 2'-Cl-biPh-4-yl | 3-F—Ph |
| 635 | H | H | H | 2'-Cl-biPh-4-yl | 4-F—Ph |
| 636 | H | H | H | 2'-Cl-biPh-4-yl | 2-Cl—Ph |
| 637 | H | H | H | 2'-Cl-biPh-4-yl | 3-Cl—Ph |
| 638 | H | H | H | 2'-Cl-biPh-4-yl | 4-Cl—Ph |
| 639 | H | H | H | 2'-Cl-biPh-4-yl | 2,6-diCl—Ph |
| 640 | H | H | H | 2'-Cl-biPh-4-yl | 4-OMe—Ph |
| 641 | H | H | H | 2'-Cl-biPh-4-yl | Py-2-yl |
| 642 | H | H | H | 2'-Cl-biPh-4-yl | Py-3-yl |
| 643 | H | H | H | 3'-Cl-biPh-4-yl | Ph |
| 644 | H | H | H | 3'-Cl-biPh-4-yl | 2-F—Ph |
| 645 | H | H | H | 3'-Cl-biPh-4-yl | 3-F—Ph |
| 646 | H | H | H | 3'-Cl-biPh-4-yl | 4-F—Ph |
| 647 | H | H | H | 3'-Cl-biPh-4-yl | 2-Cl—Ph |
| 648 | H | H | H | 3'-Cl-biPh-4-yl | 3-Cl—Ph |
| 649 | H | H | H | 3'-Cl-biPh-4-yl | 4-Cl—Ph |
| 650 | H | H | H | 3'-Cl-biPh-4-yl | 2,6-diCl—Ph |
| 651 | H | H | H | 3'-Cl-biPh-4-yl | 4-OMe—Ph |
| 652 | H | H | H | 3'-Cl-biPh-4-yl | Py-2-yl |
| 653 | H | H | H | 3'-Cl-biPh-4-yl | Py-3-yl |
| 654 | H | H | H | 4'-Cl-biPh-4-yl | Ph |
| 655 | H | H | H | 4'-Cl-biPh-4-yl | 2-F—Ph |
| 656 | H | H | H | 4'-Cl-biPh-4-yl | 3-F—Ph |
| 657 | H | H | H | 4'-Cl-biPh-4-yl | 4-F—Ph |
| 658 | H | H | H | 4'-Cl-biPh-4-yl | 3,4-diF—Ph |
| 659 | H | H | H | 4'-Cl-biPh-4-yl | 3,5-diF—Ph |
| 660 | H | H | H | 4'-Cl-biPh-4-yl | 2-Cl—Ph |
| 661 | H | H | H | 4'-Cl-biPh-4-yl | 3-Cl—Ph |
| 662 | H | H | H | 4'-Cl-biPh-4-yl | 4-Cl—Ph |
| 663 | H | H | H | 4'-Cl-biPh-4-yl | 2,6-diCl—Ph |
| 664 | H | H | H | 4'-Cl-biPh-4-yl | 4-Cl-3-F—Ph |
| 665 | H | H | H | 4'-Cl-biPh-4-yl | 4-Me—Ph |
| 666 | H | H | H | 4'-Cl-biPh-4-yl | 3-F-4-Me—Ph |
| 667 | H | H | H | 4'-Cl-biPh-4-yl | 4-Et—Ph |
| 668 | H | H | H | 4'-Cl-biPh-4-yl | 4-Et-3-F—Ph |
| 669 | H | H | H | 4'-Cl-biPh-4-yl | 4-CF$_3$—Ph |
| 670 | H | H | H | 4'-Cl-biPh-4-yl | 3-F-4-CF$_3$—Ph |
| 671 | H | H | H | 4'-Cl-biPh-4-yl | 4-OMe—Ph |

TABLE 1-continued

Compounds

| No. | R¹ | R² | R³ | Y | Z |
|---|---|---|---|---|---|
| 672 | H | H | H | 4'-Cl-biPh-4-yl | 3-F-4-OMe-Ph |
| 673 | H | H | H | 4'-Cl-biPh-4-yl | 4-OCHF$_2$—Ph |
| 674 | H | H | H | 4'-Cl-biPh-4-yl | 4-OCHF$_2$-3-F—Ph |
| 675 | H | H | H | 4'-Cl-biPh-4-yl | Th-2-yl |
| 676 | H | H | H | 4'-Cl-biPh-4-yl | Th-3-yl |
| 677 | H | H | H | 4'-Cl-biPh-4-yl | Py-2-yl |
| 678 | H | H | H | 4'-Cl-biPh-4-yl | 5-F—Py-2-yl |
| 679 | H | H | H | 4'-Cl-biPh-4-yl | 5-Cl—Py-2-yl |
| 680 | H | H | H | 4'-Cl-biPh-4-yl | 5-OMe—Py-2-yl |
| 681 | H | H | H | 4'-Cl-biPh-4-yl | Py-3-yl |
| 682 | H | H | H | 4'-Cl-biPh-4-yl | 6-F—Py-3-yl |
| 683 | H | H | H | 4'-Cl-biPh-4-yl | 6-Cl—Py-3-yl |
| 684 | H | H | H | 4'-Cl-biPh-4-yl | 6-OMe—Py-3-yl |
| 685 | H | H | H | 4'-Cl-biPh-4-yl | Py-4-yl |
| 686 | H | H | H | 2',4'-diCl-biPh-4-yl | 4-F—Ph |
| 687 | H | H | H | 2',4'-diCl-biPh-4-yl | Py-2-yl |
| 688 | H | H | H | 2',4'-diCl-biPh-4-yl | Py-3-yl |
| 689 | H | H | H | 3',4'-diCl-biPh-4-yl | 4-F—Ph |
| 690 | H | H | H | 3',4'-diCl-biPh-4-yl | Py-2-yl |
| 691 | H | H | H | 3',4'-diCl-biPh-4-yl | Py-3-yl |
| 692 | H | H | H | 4'-Cl-2'-F-biPh-4-yl | Ph |
| 693 | H | H | H | 4'-Cl-2'-F-biPh-4-yl | 2-F—Ph |
| 694 | H | H | H | 4'-Cl-2'-F-biPh-4-yl | 3-F—Ph |
| 695 | H | H | H | 4'-Cl-2'-F-biPh-4-yl | 4-F—Ph |
| 696 | H | H | H | 4'-Cl-2'-F-biPh-4-yl | 2-Cl—Ph |
| 697 | H | H | H | 4'-Cl-2'-F-biPh-4-yl | 3-Cl—Ph |
| 698 | H | H | H | 4'-Cl-2'-F-biPh-4-yl | 4-Cl—Ph |
| 699 | H | H | H | 4'-Cl-2'-F-biPh-4-yl | 2,6-diCl—Ph |
| 700 | H | H | H | 4'-Cl-2'-F-biPh-4-yl | 4-OMe—Ph |
| 701 | H | H | H | 4'-Cl-2'-F-biPh-4-yl | Py-2-yl |
| 702 | H | H | H | 4'-Cl-2'-F-biPh-4-yl | Py-3-yl |
| 703 | H | H | H | 4'-Cl-3'-F-biPh-4-yl | Ph |
| 704 | H | H | H | 4'-Cl-3'-F-biPh-4-yl | 2-F—Ph |
| 705 | H | H | H | 4'-Cl-3'-F-biPh-4-yl | 3-F—Ph |
| 706 | H | H | H | 4'-Cl-3'-F-biPh-4-yl | 4-F—Ph |
| 707 | H | H | H | 4'-Cl-3'-F-biPh-4-yl | 2-Cl—Ph |
| 708 | H | H | H | 4'-Cl-3'-F-biPh-4-yl | 3-Cl—Ph |
| 709 | H | H | H | 4'-Cl-3'-F-biPh-4-yl | 4-Cl—Ph |
| 710 | H | H | H | 4'-Cl-3'-F-biPh-4-yl | 2,6-diCl—Ph |
| 711 | H | H | H | 4'-Cl-3'-F-biPh-4-yl | 4-OMe—Ph |
| 712 | H | H | H | 4'-Cl-3'-F-biPh-4-yl | Py-2-yl |
| 713 | H | H | H | 4'-Cl-3'-F-biPh-4-yl | Py-3-yl |
| 714 | H | H | H | 3'-Br-biPh-4-yl | 4-F—Ph |
| 715 | H | H | H | 3'-Br-biPh-4-yl | Py-2-yl |
| 716 | H | H | H | 3'-Br-biPh-4-yl | Py-3-yl |
| 717 | H | H | H | 3'-OH-biPh-4-yl | 4-F—Ph |
| 718 | H | H | H | 3'-OH-biPh-4-yl | Py-2-yl |
| 719 | H | H | H | 3'-OH-biPh-4-yl | Py-3-yl |
| 720 | H | H | H | 4'-OH-biPh-4-yl | Ph |
| 721 | H | H | H | 4'-OH-biPh-4-yl | 2-F—Ph |
| 722 | H | H | H | 4'-OH-biPh-4-yl | 3-F—Ph |
| 723 | H | H | H | 4'-OH-biPh-4-yl | 4-F—Ph |
| 724 | H | H | H | 4'-OH-biPh-4-yl | 2-Cl—Ph |
| 725 | H | H | H | 4'-OH-biPh-4-yl | 3-Cl—Ph |
| 726 | H | H | H | 4'-OH-biPh-4-yl | 4-Cl—Ph |
| 727 | H | H | H | 4'-OH-biPh-4-yl | 2,6-diCl—Ph |
| 728 | H | H | H | 4'-OH-biPh-4-yl | 4-OMe—Ph |
| 729 | H | H | H | 4'-OH-biPh-4-yl | Py-2-yl |
| 730 | H | H | H | 4'-OH-biPh-4-yl | Py-3-yl |
| 731 | H | H | H | 3'-Me-biPh-4-yl | Ph |
| 732 | H | H | H | 3'-Me-biPh-4-yl | 2-F—Ph |
| 733 | H | H | H | 3'-Me-biPh-4-yl | 3-F—Ph |
| 734 | H | H | H | 3'-Me-biPh-4-yl | 4-F—Ph |
| 735 | H | H | H | 3'-Me-biPh-4-yl | 2-Cl—Ph |
| 736 | H | H | H | 3'-Me-biPh-4-yl | 3-Cl—Ph |
| 737 | H | H | H | 3'-Me-biPh-4-yl | 4-Cl—Ph |
| 738 | H | H | H | 3'-Me-biPh-4-yl | 2,6-diCl—Ph |
| 739 | H | H | H | 3'-Me-biPh-4-yl | 4-OMe—Ph |
| 740 | H | H | H | 3'-Me-biPh-4-yl | Py-2-yl |
| 741 | H | H | H | 3'-Me-biPh-4-yl | Py-3-yl |
| 742 | H | H | H | 3'-Et-biPh-4-yl | Ph |
| 743 | H | H | H | 3'-Et-biPh-4-yl | 2-F—Ph |
| 744 | H | H | H | 3'-Et-biPh-4-yl | 3-F—Ph |
| 745 | H | H | H | 3'-Et-biPh-4-yl | 4-F—Ph |
| 746 | H | H | H | 3'-Et-biPh-4-yl | 2-Cl—Ph |
| 747 | H | H | H | 3'-Et-biPh-4-yl | 3-Cl—Ph |
| 748 | H | H | H | 3'-Et-biPh-4-yl | 4-Cl—Ph |
| 749 | H | H | H | 3'-Et-biPh-4-yl | 2,6-diCl—Ph |
| 750 | H | H | H | 3'-Et-biPh-4-yl | 4-OMe—Ph |
| 751 | H | H | H | 3'-Et-biPh-4-yl | Py-2-yl |
| 752 | H | H | H | 3'-Et-biPh-4-yl | Py-3-yl |
| 753 | H | H | H | 3'-Pr-biPh-4-yl | 4-F—Ph |
| 754 | H | H | H | 3'-Pr-biPh-4-yl | Py-2-yl |
| 755 | H | H | H | 3'-Pr-biPh-4-yl | Py-3-yl |
| 756 | H | H | H | 3'-iPr-biPh-4-yl | 4-F—Ph |
| 757 | H | H | H | 3'-iPr-biPh-4-yl | Py-2-yl |
| 758 | H | H | H | 3'-iPr-biPh-4-yl | Py-3-yl |
| 759 | H | H | H | 3'-tBu-biPh-4-yl | 4-F—Ph |
| 760 | H | H | H | 3'-tBu-biPh-4-yl | Py-2-yl |
| 761 | H | H | H | 3'-tBu-biPh-4-yl | Py-3-yl |
| 762 | H | H | H | 3'-CF$_3$-biPh-4-yl | Ph |
| 763 | H | H | H | 3'-CF$_3$-biPh-4-yl | 2-F—Ph |
| 764 | H | H | H | 3'-CF$_3$-biPh-4-yl | 3-F—Ph |
| 765 | H | H | H | 3'-CF$_3$-biPh-4-yl | 4-F—Ph |
| 766 | H | H | H | 3'-CF$_3$-biPh-4-yl | 2-Cl—Ph |
| 767 | H | H | H | 3'-CF$_3$-biPh-4-yl | 3-Cl—Ph |
| 768 | H | H | H | 3'-CF$_3$-biPh-4-yl | 4-Cl—Ph |
| 769 | H | H | H | 3'-CF$_3$-biPh-4-yl | 2,6-diCl—Ph |
| 770 | H | H | H | 3'-CF$_3$-biPh-4-yl | 4-OMe—Ph |
| 771 | H | H | H | 3'-CF$_3$-biPh-4-yl | Py-2-yl |
| 772 | H | H | H | 3'-CF$_3$-biPh-4-yl | Py-3-yl |
| 773 | H | H | H | 3'-CHF$_2$-biPh-4-yl | 4-F—Ph |
| 774 | H | H | H | 3'-CHF$_2$-biPh-4-yl | Py-2-yl |
| 775 | H | H | H | 3'-CHF$_2$-biPh-4-yl | Py-3-yl |
| 776 | H | H | H | 3'-CCl$_3$-biPh-4-yl | 4-F—Ph |
| 777 | H | H | H | 3'-CCl$_3$-biPh-4-yl | Py-2-yl |
| 778 | H | H | H | 3'-CCl$_3$-biPh-4-yl | Py-3-yl |
| 779 | H | H | H | 3'-CHCl$_2$-biPh-4-yl | 4-F—Ph |
| 780 | H | H | H | 3'-CHCl$_2$-biPh-4-yl | Py-2-yl |
| 781 | H | H | H | 3'-CHCl$_2$-biPh-4-yl | Py-3-yl |
| 782 | H | H | H | 3'-CH$_2$CF$_3$-biPh-4-yl | 4-F—Ph |
| 783 | H | H | H | 3'-CH$_2$CF$_3$-biPh-4-yl | Py-2-yl |
| 784 | H | H | H | 3'-CH$_2$CF$_3$-biPh-4-yl | Py-3-yl |
| 785 | H | H | H | 3'-CH$_2$CCl$_3$-biPh-4-yl | 4-F—Ph |
| 786 | H | H | H | 3'-CH$_2$CCl$_3$-biPh-4-yl | Py-2-yl |
| 787 | H | H | H | 3'-CH$_2$CCl$_3$-biPh-4-yl | Py-3-yl |
| 788 | H | H | H | 3'-OMe-biPh-4-yl | Ph |
| 789 | H | H | H | 3'-OMe-biPh-4-yl | 2-F—Ph |
| 790 | H | H | H | 3'-OMe-biPh-4-yl | 3-F—Ph |
| 791 | H | H | H | 3'-OMe-biPh-4-yl | 4-F—Ph |
| 792 | H | H | H | 3'-OMe-biPh-4-yl | 2-Cl—Ph |
| 793 | H | H | H | 3'-OMe-biPh-4-yl | 3-Cl—Ph |
| 794 | H | H | H | 3'-OMe-biPh-4-yl | 4-Cl—Ph |
| 795 | H | H | H | 3'-OMe-biPh-4-yl | 2,6-diCl—Ph |
| 796 | H | H | H | 3'-OMe-biPh-4-yl | 4-OMe—Ph |
| 797 | H | H | H | 3'-OMe-biPh-4-yl | Py-2-yl |
| 798 | H | H | H | 3'-OMe-biPh-4-yl | Py-3-yl |
| 799 | H | H | H | 3'-OEt-biPh-4-yl | 4-F—Ph |
| 800 | H | H | H | 3'-OEt-biPh-4-yl | Py-2-yl |
| 801 | H | H | H | 3'-OEt-biPh-4-yl | Py-3-yl |
| 802 | H | H | H | 3'-OPr-biPh-4-yl | 4-F—Ph |
| 803 | H | H | H | 3'-OPr-biPh-4-yl | Py-2-yl |
| 804 | H | H | H | 3'-OPr-biPh-4-yl | Py-3-yl |
| 805 | H | H | H | 3'-OiPr-biPh-4-yl | 4-F—Ph |
| 806 | H | H | H | 3'-OiPr-biPh-4-yl | Py-2-yl |
| 807 | H | H | H | 3'-OiPr-biPh-4-yl | Py-3-yl |
| 808 | H | H | H | 3'-OtBu-biPh-4-yl | 4-F—Ph |
| 809 | H | H | H | 3'-OtBu-biPh-4-yl | Py-2-yl |
| 810 | H | H | H | 3'-OtBu-biPh-4-yl | Py-3-yl |
| 811 | H | H | H | 3'-OCF$_3$-biPh-4-yl | 4-F—Ph |
| 812 | H | H | H | 3'-OCF$_3$-biPh-4-yl | Py-2-yl |
| 813 | H | H | H | 3'-OCF$_3$-biPh-4-yl | Py-3-yl |
| 814 | H | H | H | 3'-OCHF$_2$-biPh-4-yl | Ph |
| 815 | H | H | H | 3'-OCHF$_2$-biPh-4-yl | 2-F—Ph |
| 816 | H | H | H | 3'-OCHF$_2$-biPh-4-yl | 3-F—Ph |
| 817 | H | H | H | 3'-OCHF$_2$-biPh-4-yl | 4-F—Ph |
| 818 | H | H | H | 3'-OCHF$_2$-biPh-4-yl | 2-Cl—Ph |
| 819 | H | H | H | 3'-OCHF$_2$-biPh-4-yl | 3-Cl—Ph |
| 820 | H | H | H | 3'-OCHF$_2$-biPh-4-yl | 4-Cl—Ph |
| 821 | H | H | H | 3'-OCHF$_2$-biPh-4-yl | 2,6-diCl—Ph |
| 822 | H | H | H | 3'-OCHF$_2$-biPh-4-yl | 4-OMe—Ph |
| 823 | H | H | H | 3'-OCHF$_2$-biPh-4-yl | Py-2-yl |

TABLE 1-continued

Compounds

| No. | R¹ | R² | R³ | Y | Z |
|---|---|---|---|---|---|
| 824 | H | H | H | 3'-OCHF$_2$-biPh-4-yl | Py-3-yl |
| 825 | H | H | H | 3'-OCCl$_3$-biPh-4-yl | 4-F—Ph |
| 826 | H | H | H | 3'-OCCl$_3$-biPh-4-yl | Py-2-yl |
| 827 | H | H | H | 3'-OCCl$_3$-biPh-4-yl | Py-3-yl |
| 828 | H | H | H | 3'-OCHCl$_2$-biPh-4-yl | 4-F—Ph |
| 829 | H | H | H | 3'-OCHCl$_2$-biPh-4-yl | Py-2-yl |
| 830 | H | H | H | 3'-OCHCl$_2$-biPh-4-yl | Py-3-yl |
| 831 | H | H | H | 4-(Th-2-yl)Ph | Ph |
| 832 | H | H | H | 4-(Th-2-yl)Ph | 2-F—Ph |
| 833 | H | H | H | 4-(Th-2-yl)Ph | 3-F—Ph |
| 834 | H | H | H | 4-(Th-2-yl)Ph | 4-F—Ph |
| 835 | H | H | H | 4-(Th-2-yl)Ph | 2-Cl—Ph |
| 836 | H | H | H | 4-(Th-2-yl)Ph | 3-Cl—Ph |
| 837 | H | H | H | 4-(Th-2-yl)Ph | 4-Cl—Ph |
| 838 | H | H | H | 4-(Th-2-yl)Ph | 2,6-diCl—Ph |
| 839 | H | H | H | 4-(Th-2-yl)Ph | 4-OMe—Ph |
| 840 | H | H | H | 4-(Th-2-yl)Ph | Py-2-yl |
| 841 | H | H | H | 4-(Th-2-yl)Ph | Py-3-yl |
| 842 | H | H | H | 4-(Th-3-yl)Ph | Ph |
| 843 | H | H | H | 4-(Th-3-yl)Ph | 2-F—Ph |
| 844 | H | H | H | 4-(Th-3-yl)Ph | 3-F—Ph |
| 845 | H | H | H | 4-(Th-3-yl)Ph | 4-F—Ph |
| 846 | H | H | H | 4-(Th-3-yl)Ph | 2-Cl—Ph |
| 847 | H | H | H | 4-(Th-3-yl)Ph | 3-Cl—Ph |
| 848 | H | H | H | 4-(Th-3-yl)Ph | 4-Cl—Ph |
| 849 | H | H | H | 4-(Th-3-yl)Ph | 2,6-diCl—Ph |
| 850 | H | H | H | 4-(Th-3-yl)Ph | 4-OMe—Ph |
| 851 | H | H | H | 4-(Th-3-yl)Ph | Py-2-yl |
| 852 | H | H | H | 4-(Th-3-yl)Ph | Py-3-yl |
| 853 | H | H | H | 4-(Pyz-1-yl)Ph | Ph |
| 854 | H | H | H | 4-(Pyz-1-yl)Ph | 2-F—Ph |
| 855 | H | H | H | 4-(Pyz-1-yl)Ph | 3-F—Ph |
| 856 | H | H | H | 4-(Pyz-1-yl)Ph | 4-F—Ph |
| 857 | H | H | H | 4-(Pyz-1-yl)Ph | 3,4-diF—Ph |
| 858 | H | H | H | 4-(Pyz-1-yl)Ph | 3,5-diF—Ph |
| 859 | H | H | H | 4-(Pyz-1-yl)Ph | 2-Cl—Ph |
| 860 | H | H | H | 4-(Pyz-1-yl)Ph | 3-Cl—Ph |
| 861 | H | H | H | 4-(Pyz-1-yl)Ph | 4-Cl—Ph |
| 862 | H | H | H | 4-(Pyz-1-yl)Ph | 2,6-diCl—Ph |
| 863 | H | H | H | 4-(Pyz-1-yl)Ph | 4-Cl-3-F—Ph |
| 864 | H | H | H | 4-(Pyz-1-yl)Ph | 4-Me—Ph |
| 865 | H | H | H | 4-(Pyz-1-yl)Ph | 3-F-4-Me—Ph |
| 866 | H | H | H | 4-(Pyz-1-yl)Ph | 4-Et—Ph |
| 867 | H | H | H | 4-(Pyz-1-yl)Ph | 4-Et-3-F—Ph |
| 868 | H | H | H | 4-(Pyz-1-yl)Ph | 4-CF$_3$—Ph |
| 869 | H | H | H | 4-(Pyz-1-yl)Ph | 3-F-4-CF$_3$—Ph |
| 870 | H | H | H | 4-(Pyz-1-yl)Ph | 4-OMe—Ph |
| 871 | H | H | H | 4-(Pyz-1-yl)Ph | 3-F-4-OMe—Ph |
| 872 | H | H | H | 4-(Pyz-1-yl)Ph | 4-OCHF$_2$—Ph |
| 873 | H | H | H | 4-(Pyz-1-yl)Ph | 4-OCHF$_2$-3-F—Ph |
| 874 | H | H | H | 4-(Pyz-1-yl)Ph | Th-2-yl |
| 875 | H | H | H | 4-(Pyz-1-yl)Ph | Th-3-yl |
| 876 | H | H | H | 4-(Pyz-1-yl)Ph | Py-2-yl |
| 877 | H | H | H | 4-(Pyz-1-yl)Ph | 5-F—Py-2-yl |
| 878 | H | H | H | 4-(Pyz-1-yl)Ph | 5-Cl—Py-2-yl |
| 879 | H | H | H | 4-(Pyz-1-yl)Ph | 5-OMe—Py-2-yl |
| 880 | H | H | H | 4-(Pyz-1-yl)Ph | Py-3-yl |
| 881 | H | H | H | 4-(Pyz-1-yl)Ph | 6-F—Py-3-yl |
| 882 | H | H | H | 4-(Pyz-1-yl)Ph | 6-Cl—Py-3-yl |
| 883 | H | H | H | 4-(Pyz-1-yl)Ph | 6-OMe—Py-3-yl |
| 884 | H | H | H | 4-(Pyz-1-yl)Ph | Py-4-yl |
| 885 | H | H | H | 4-(4-F-Pyz-1-yl)Ph | 4-F—Ph |
| 886 | H | H | H | 4-(4-F-Pyz-1-yl)Ph | Py-2-yl |
| 887 | H | H | H | 4-(4-F-Pyz-1-yl)Ph | Py-3-yl |
| 888 | H | H | H | 4-(4-Cl-Pyz-1-yl)Ph | 4-F—Ph |
| 889 | H | H | H | 4-(4-Cl-Pyz-1-yl)Ph | Py-2-yl |
| 890 | H | H | H | 4-(4-Cl-Pyz-1-yl)Ph | Py-3-yl |
| 891 | H | H | H | 4-(Oxz-2-yl)Ph | Ph |
| 892 | H | H | H | 4-(Oxz-2-yl)Ph | 2-F—Ph |
| 893 | H | H | H | 4-(Oxz-2-yl)Ph | 3-F—Ph |
| 894 | H | H | H | 4-(Oxz-2-yl)Ph | 4-F—Ph |
| 895 | H | H | H | 4-(Oxz-2-yl)Ph | 2-Cl—Ph |
| 896 | H | H | H | 4-(Oxz-2-yl)Ph | 3-Cl—Ph |
| 897 | H | H | H | 4-(Oxz-2-yl)Ph | 4-Cl—Ph |
| 898 | H | H | H | 4-(Oxz-2-yl)Ph | 2,6-diCl—Ph |
| 899 | H | H | H | 4-(Oxz-2-yl)Ph | 4-OMe—Ph |
| 900 | H | H | H | 4-(Oxz-2-yl)Ph | Py-2-yl |
| 901 | H | H | H | 4-(Oxz-2-yl)Ph | Py-3-yl |
| 902 | H | H | H | 4-(Oxz-4-yl)Ph | Ph |
| 903 | H | H | H | 4-(Oxz-4-yl)Ph | 2-F—Ph |
| 904 | H | H | H | 4-(Oxz-4-yl)Ph | 3-F—Ph |
| 905 | H | H | H | 4-(Oxz-4-yl)Ph | 4-F—Ph |
| 906 | H | H | H | 4-(Oxz-4-yl)Ph | 2-Cl—Ph |
| 907 | H | H | H | 4-(Oxz-4-yl)Ph | 3-Cl—Ph |
| 908 | H | H | H | 4-(Oxz-4-yl)Ph | 4-Cl—Ph |
| 909 | H | H | H | 4-(Oxz-4-yl)Ph | 2,6-diCl—Ph |
| 910 | H | H | H | 4-(Oxz-4-yl)Ph | 4-OMe—Ph |
| 911 | H | H | H | 4-(Oxz-4-yl)Ph | Py-2-yl |
| 912 | H | H | H | 4-(Oxz-4-yl)Ph | Py-3-yl |
| 913 | Pr | H | H | 4-(Thz-2-yl)Ph | Py-2-yl |
| 914 | iPr | H | H | 4-(Thz-2-yl)Ph | Py-2-yl |
| 915 | tBu | H | H | 4-(Thz-2-yl)Ph | Py-2-yl |
| 916 | Me | H | H | 4-(Thz-2-yl)Ph | 4-F—Ph |
| 917 | Me | H | H | 4-(Thz-2-yl)Ph | Py-2-yl |
| 918 | Me | H | H | 4-(Thz-2-yl)Ph | Py-3-yl |
| 919 | Et | H | H | 4-(Thz-2-yl)Ph | 4-F—Ph |
| 920 | Et | H | H | 4-(Thz-2-yl)Ph | Py-2-yl |
| 921 | Et | H | H | 4-(Thz-2-yl)Ph | Py-3-yl |
| 922 | Me | Me | Me | 4-(Thz-2-yl)Ph | Py-2-yl |
| 923 | Et | Me | Me | 4-(Thz-2-yl)Ph | Py-2-yl |
| 924 | H | Et | Et | 4-(Thz-2-yl)Ph | Py-2-yl |
| 925 | H | Pr | Pr | 4-(Thz-2-yl)Ph | Py-2-yl |
| 926 | H | iPr | iPr | 4-(Thz-2-yl)Ph | Py-2-yl |
| 927 | H | Me | Me | 4-(Thz-2-yl)Ph | 4-F—Ph |
| 928 | H | Me | Me | 4-(Thz-2-yl)Ph | Py-2-yl |
| 929 | H | Me | Me | 4-(Thz-2-yl)Ph | Py-3-yl |
| 930 | H | Me | H | 4-(Thz-2-yl)Ph | 4-F—Ph |
| 931 | H | Me | H | 4-(Thz-2-yl)Ph | Py-2-yl |
| 932 | H | Me | H | 4-(Thz-2-yl)Ph | Py-3-yl |
| 933 | H | H | H | 4-(Thz-2-yl)Ph | Ph |
| 934 | H | H | H | 4-(Thz-2-yl)Ph | 2-F—Ph |
| 935 | H | H | H | 4-(Thz-2-yl)Ph | 3-F—Ph |
| 936 | H | H | H | 4-(Thz-2-yl)Ph | 4-F—Ph |
| 937 | H | H | H | 4-(Thz-2-yl)Ph | 3,4-diF—Ph |
| 938 | H | H | H | 4-(Thz-2-yl)Ph | 3,5-diF—Ph |
| 939 | H | H | H | 4-(Thz-2-yl)Ph | 3,4,5-triF—Ph |
| 940 | H | H | H | 4-(Thz-2-yl)Ph | 2-Cl—Ph |
| 941 | H | H | H | 4-(Thz-2-yl)Ph | 3-Cl—Ph |
| 942 | H | H | H | 4-(Thz-2-yl)Ph | 4-Cl—Ph |
| 943 | H | H | H | 4-(Thz-2-yl)Ph | 2,6-diCl—Ph |
| 944 | H | H | H | 4-(Thz-2-yl)Ph | 4-Cl-3-F—Ph |
| 945 | H | H | H | 4-(Thz-2-yl)Ph | 4-Cl-3,5-diF—Ph |
| 946 | H | H | H | 4-(Thz-2-yl)Ph | 4-Br—Ph |
| 947 | H | H | H | 4-(Thz-2-yl)Ph | 4-Me—Ph |
| 948 | H | H | H | 4-(Thz-2-yl)Ph | 3-F-4-Me—Ph |
| 949 | H | H | H | 4-(Thz-2-yl)Ph | 4-Et—Ph |
| 950 | H | H | H | 4-(Thz-2-yl)Ph | 4-Et-3-F—Ph |
| 951 | H | H | H | 4-(Thz-2-yl)Ph | 4-Pr—Ph |
| 952 | H | H | H | 4-(Thz-2-yl)Ph | 4-iPr—Ph |
| 953 | H | H | H | 4-(Thz-2-yl)Ph | 4-tBu—Ph |
| 954 | H | H | H | 4-(Thz-2-yl)Ph | 4-CF$_3$—Ph |
| 955 | H | H | H | 4-(Thz-2-yl)Ph | 3-F-4-CF$_3$—Ph |
| 956 | H | H | H | 4-(Thz-2-yl)Ph | 4-CHF$_2$—Ph |
| 957 | H | H | H | 4-(Thz-2-yl)Ph | 4-CCl$_3$—Ph |
| 958 | H | H | H | 4-(Thz-2-yl)Ph | 4-CHCl$_2$—Ph |
| 959 | H | H | H | 4-(Thz-2-yl)Ph | 4-CH$_2$CF$_3$—Ph |
| 960 | H | H | H | 4-(Thz-2-yl)Ph | 4-CH$_2$CCl$_3$—Ph |
| 961 | H | H | H | 4-(Thz-2-yl)Ph | 4-OMe—Ph |
| 962 | H | H | H | 4-(Thz-2-yl)Ph | 3-F-4-OMe—Ph |
| 963 | H | H | H | 4-(Thz-2-yl)Ph | 4-OEt—Ph |
| 964 | H | H | H | 4-(Thz-2-yl)Ph | 4-OPr—Ph |
| 965 | H | H | H | 4-(Thz-2-yl)Ph | 4-OiPr—Ph |
| 966 | H | H | H | 4-(Thz-2-yl)Ph | 4-OtBu—Ph |
| 967 | H | H | H | 4-(Thz-2-yl)Ph | 4-OCF$_3$—Ph |
| 968 | H | H | H | 4-(Thz-2-yl)Ph | 4-OCHF$_2$—Ph |
| 969 | H | H | H | 4-(Thz-2-yl)Ph | 4-OCHF$_2$-3-F—Ph |
| 970 | H | H | H | 4-(Thz-2-yl)Ph | 4-OCCl$_3$—Ph |
| 971 | H | H | H | 4-(Thz-2-yl)Ph | 4-OCHCl$_2$—Ph |
| 972 | H | H | H | 4-(Thz-2-yl)Ph | Th-2-yl |
| 973 | H | H | H | 4-(Thz-2-yl)Ph | Th-3-yl |
| 974 | H | H | H | 4-(Thz-2-yl)Ph | 5-Cl-Th-2-yl |
| 975 | H | H | H | 4-(Thz-2-yl)Ph | 1-Me-1H-Imz-4-yl |

TABLE 1-continued

Compounds

| No. | R¹ | R² | R³ | Y | Z |
|---|---|---|---|---|---|
| 976 | H | H | H | 4-(Thz-2-yl)Ph | Thz-2-yl |
| 977 | H | H | H | 4-(Thz-2-yl)Ph | Py-2-yl |
| 978 | H | H | H | 4-(Thz-2-yl)Ph | 5-F-Py-2-yl |
| 979 | H | H | H | 4-(Thz-2-yl)Ph | 5-Cl—Py-2-yl |
| 980 | H | H | H | 4-(Thz-2-yl)Ph | 5-Me—Py-2-yl |
| 981 | H | H | H | 4-(Thz-2-yl)Ph | 5-Et—Py-2-yl |
| 982 | H | H | H | 4-(Thz-2-yl)Ph | 5-CF₃—Py-2-yl |
| 983 | H | H | H | 4-(Thz-2-yl)Ph | 5-OMe—Py-2-yl |
| 984 | H | H | H | 4-(Thz-2-yl)Ph | 5-OCHF₂—Py-2-yl |
| 985 | H | H | H | 4-(Thz-2-yl)Ph | Py-3-yl |
| 986 | H | H | H | 4-(Thz-2-yl)Ph | 6-F—Py-3-yl |
| 987 | H | H | H | 4-(Thz-2-yl)Ph | 6-Cl—Py-3-yl |
| 988 | H | H | H | 4-(Thz-2-yl)Ph | 6-Me—Py-3-yl |
| 989 | H | H | H | 4-(Thz-2-yl)Ph | 6-Et—Py-3-yl |
| 990 | H | H | H | 4-(Thz-2-yl)Ph | 6-CF₃—Py-3-yl |
| 991 | H | H | H | 4-(Thz-2-yl)Ph | 6-OMe—Py-3-yl |
| 992 | H | H | H | 4-(Thz-2-yl)Ph | 6-OCHF₂—Py-3-yl |
| 993 | H | H | H | 4-(Thz-2-yl)Ph | Py-4-yl |
| 994 | H | H | H | 4-(Thz-2-yl)Ph | Pym-2-yl |
| 995 | H | H | H | 4-(4-F-Thz-2-yl)Ph | Ph |
| 996 | H | H | H | 4-(4-F-Thz-2-yl)Ph | 2-F—Ph |
| 997 | H | H | H | 4-(4-F-Thz-2-yl)Ph | 3-F—Ph |
| 998 | H | H | H | 4-(4-F-Thz-2-yl)Ph | 4-F—Ph |
| 999 | H | H | H | 4-(4-F-Thz-2-yl)Ph | 2-Cl—Ph |
| 1000 | H | H | H | 4-(4-F-Thz-2-yl)Ph | 3-Cl—Ph |
| 1001 | H | H | H | 4-(4-F-Thz-2-yl)Ph | 4-Cl—Ph |
| 1002 | H | H | H | 4-(4-F-Thz-2-yl)Ph | 2,6-diCl—Ph |
| 1003 | H | H | H | 4-(4-F-Thz-2-yl)Ph | 4-OMe—Ph |
| 1004 | H | H | H | 4-(4-F-Thz-2-yl)Ph | Py-2-yl |
| 1005 | H | H | H | 4-(4-F-Thz-2-yl)Ph | Py-3-yl |
| 1006 | H | H | H | 4-(4-Cl-Thz-2-yl)Ph | Ph |
| 1007 | H | H | H | 4-(4-Cl-Thz-2-yl)Ph | 2-F—Ph |
| 1008 | H | H | H | 4-(4-Cl-Thz-2-yl)Ph | 3-F—Ph |
| 1009 | H | H | H | 4-(4-Cl-Thz-2-yl)Ph | 4-F—Ph |
| 1010 | H | H | H | 4-(4-Cl-Thz-2-yl)Ph | 2-Cl—Ph |
| 1011 | H | H | H | 4-(4-Cl-Thz-2-yl)Ph | 3-Cl—Ph |
| 1012 | H | H | H | 4-(4-Cl-Thz-2-yl)Ph | 4-Cl—Ph |
| 1013 | H | H | H | 4-(4-Cl-Thz-2-yl)Ph | 2,6-diCl—Ph |
| 1014 | H | H | H | 4-(4-Cl-Thz-2-yl)Ph | 4-OMe—Ph |
| 1015 | H | H | H | 4-(4-Cl-Thz-2-yl)Ph | Py-2-yl |
| 1016 | H | H | H | 4-(4-Cl-Thz-2-yl)Ph | Py-3-yl |
| 1017 | H | H | H | 4-(4-Me-Thz-2-yl)Ph | 4-F—Ph |
| 1018 | H | H | H | 4-(4-Me-Thz-2-yl)Ph | Py-2-yl |
| 1019 | H | H | H | 4-(4-Me-Thz-2-yl)Ph | Py-3-yl |
| 1020 | H | H | H | 4-(4-Et-Thz-2-yl)Ph | 4-F—Ph |
| 1021 | H | H | H | 4-(4-Et-Thz-2-yl)Ph | Py-2-yl |
| 1022 | H | H | H | 4-(4-Et-Thz-2-yl)Ph | Py-3-yl |
| 1023 | H | H | H | 4-(4-CF₃-Thz-2-yl)Ph | 4-F—Ph |
| 1024 | H | H | H | 4-(4-CF₃-Thz-2-yl)Ph | Py-2-yl |
| 1025 | H | H | H | 4-(4-CF₃-Thz-2-yl)Ph | Py-3-yl |
| 1026 | H | H | H | 4-(4-OMe-Thz-2-yl)Ph | 4-F—Ph |
| 1027 | H | H | H | 4-(4-OMe-Thz-2-yl)Ph | Py-2-yl |
| 1028 | H | H | H | 4-(4-OMe-Thz-2-yl)Ph | Py-3-yl |
| 1029 | H | H | H | 4-(4-OCHF₂-Thz-2-yl)Ph | 4-F—Ph |
| 1030 | H | H | H | 4-(4-OCHF₂-Thz-2-yl)Ph | Py-2-yl |
| 1031 | H | H | H | 4-(4-OCHF₂-Thz-2-yl)Ph | Py-3-yl |
| 1032 | Me | H | H | 4-(Thz-4-yl)Ph | 4-F—Ph |
| 1033 | Me | H | H | 4-(Thz-4-yl)Ph | Py-2-yl |
| 1034 | Me | H | H | 4-(Thz-4-yl)Ph | Py-3-yl |
| 1035 | Et | H | H | 4-(Thz-4-yl)Ph | 4-F—Ph |
| 1036 | Et | H | H | 4-(Thz-4-yl)Ph | Py-2-yl |
| 1037 | Et | H | H | 4-(Thz-4-yl)Ph | Py-3-yl |
| 1038 | Me | Me | Me | 4-(Thz-4-yl)Ph | Py-2-yl |
| 1039 | Et | Me | Me | 4-(Thz-4-yl)Ph | Py-2-yl |
| 1040 | H | Me | Me | 4-(Thz-4-yl)Ph | 4-F—Ph |
| 1041 | H | Me | Me | 4-(Thz-4-yl)Ph | Py-2-yl |
| 1042 | H | Me | Me | 4-(Thz-4-yl)Ph | Py-3-yl |
| 1043 | H | Me | H | 4-(Thz-4-yl)Ph | 4-F—Ph |
| 1044 | H | Me | H | 4-(Thz-4-yl)Ph | Py-2-yl |
| 1045 | H | Me | H | 4-(Thz-4-yl)Ph | Py-3-yl |
| 1046 | H | H | H | 4-(Thz-4-yl)Ph | Ph |
| 1047 | H | H | H | 4-(Thz-4-yl)Ph | 2-F—Ph |
| 1048 | H | H | H | 4-(Thz-4-yl)Ph | 3-F—Ph |
| 1049 | H | H | H | 4-(Thz-4-yl)Ph | 4-F—Ph |
| 1050 | H | H | H | 4-(Thz-4-yl)Ph | 3,4-diF—Ph |
| 1051 | H | H | H | 4-(Thz-4-yl)Ph | 3,5-diF—Ph |
| 1052 | H | H | H | 4-(Thz-4-yl)Ph | 3,4,5-triF—Ph |
| 1053 | H | H | H | 4-(Thz-4-yl)Ph | 2-Cl—Ph |
| 1054 | H | H | H | 4-(Thz-4-yl)Ph | 3-Cl—Ph |
| 1055 | H | H | H | 4-(Thz-4-yl)Ph | 4-Cl—Ph |
| 1056 | H | H | H | 4-(Thz-4-yl)Ph | 2,6-diCl—Ph |
| 1057 | H | H | H | 4-(Thz-4-yl)Ph | 4-Cl-3-F—Ph |
| 1058 | H | H | H | 4-(Thz-4-yl)Ph | 4-Cl-3,5-diF—Ph |
| 1059 | H | H | H | 4-(Thz-4-yl)Ph | 4-Br-Ph |
| 1060 | H | H | H | 4-(Thz-4-yl)Ph | 4-Me—Ph |
| 1061 | H | H | H | 4-(Thz-4-yl)Ph | 3-F-4-Me-Ph |
| 1062 | H | H | H | 4-(Thz-4-yl)Ph | 4-Et—Ph |
| 1063 | H | H | H | 4-(Thz-4-yl)Ph | 4-Et-3-F—Ph |
| 1064 | H | H | H | 4-(Thz-4-yl)Ph | 4-Pr—Ph |
| 1065 | H | H | H | 4-(Thz-4-yl)Ph | 4-iPr—Ph |
| 1066 | H | H | H | 4-(Thz-4-yl)Ph | 4-tBu—Ph |
| 1067 | H | H | H | 4-(Thz-4-yl)Ph | 4-CF₃—Ph |
| 1068 | H | H | H | 4-(Thz-4-yl)Ph | 3-F-4-CF₃—Ph |
| 1069 | H | H | H | 4-(Thz-4-yl)Ph | 4-CHF₂—Ph |
| 1070 | H | H | H | 4-(Thz-4-yl)Ph | 4-CCl₃—Ph |
| 1071 | H | H | H | 4-(Thz-4-yl)Ph | 4-CHCl₂—Ph |
| 1072 | H | H | H | 4-(Thz-4-yl)Ph | 4-CH₂CF₃—Ph |
| 1073 | H | H | H | 4-(Thz-4-yl)Ph | 4-CH₂CCl₃—Ph |
| 1074 | H | H | H | 4-(Thz-4-yl)Ph | 4-OMe—Ph |
| 1075 | H | H | H | 4-(Thz-4-yl)Ph | 3-F-4-OMe—Ph |
| 1076 | H | H | H | 4-(Thz-4-yl)Ph | 4-OEt—Ph |
| 1077 | H | H | H | 4-(Thz-4-yl)Ph | 4-OPr—Ph |
| 1078 | H | H | H | 4-(Thz-4-yl)Ph | 4-OiPr—Ph |
| 1079 | H | H | H | 4-(Thz-4-yl)Ph | 4-OtBu—Ph |
| 1080 | H | H | H | 4-(Thz-4-yl)Ph | 4-OCF₃—Ph |
| 1081 | H | H | H | 4-(Thz-4-yl)Ph | 4-OCHF₂—Ph |
| 1082 | H | H | H | 4-(Thz-4-yl)Ph | 4-OCHF₂-3-F—Ph |
| 1083 | H | H | H | 4-(Thz-4-yl)Ph | 4-OCCl₃—Ph |
| 1084 | H | H | H | 4-(Thz-4-yl)Ph | 4-OCHCl₂—Ph |
| 1085 | H | H | H | 4-(Thz-4-yl)Ph | Th-2-yl |
| 1086 | H | H | H | 4-(Thz-4-yl)Ph | Th-3-yl |
| 1087 | H | H | H | 4-(Thz-4-yl)Ph | 5-Cl—Th-2-yl |
| 1088 | H | H | H | 4-(Thz-4-yl)Ph | 1-Me-1H-Imz-4-yl |
| 1089 | H | H | H | 4-(Thz-4-yl)Ph | Thz-2-yl |
| 1090 | H | H | H | 4-(Thz-4-yl)Ph | Py-2-yl |
| 1091 | H | H | H | 4-(Thz-4-yl)Ph | 5-F—Py-2-yl |
| 1092 | H | H | H | 4-(Thz-4-yl)Ph | 5-Cl—Py-2-yl |
| 1093 | H | H | H | 4-(Thz-4-yl)Ph | 5-Me—Py-2-yl |
| 1094 | H | H | H | 4-(Thz-4-yl)Ph | 5-Et—Py-2-yl |
| 1095 | H | H | H | 4-(Thz-4-yl)Ph | 5-CF₃—Py-2-yl |
| 1096 | H | H | H | 4-(Thz-4-yl)Ph | 5-OMe—Py-2-yl |
| 1097 | H | H | H | 4-(Thz-4-yl)Ph | 5-OCHF₂—Py-2-yl |
| 1098 | H | H | H | 4-(Thz-4-yl)Ph | Py-3-yl |
| 1099 | H | H | H | 4-(Thz-4-yl)Ph | 6-F—Py-3-yl |
| 1100 | H | H | H | 4-(Thz-4-yl)Ph | 6-Cl—Py-3-yl |
| 1101 | H | H | H | 4-(Thz-4-yl)Ph | 6-Me—Py-3-yl |
| 1102 | H | H | H | 4-(Thz-4-yl)Ph | 6-Et—Py-3-yl |
| 1103 | H | H | H | 4-(Thz-4-yl)Ph | 6-CF₃—Py-3-yl |
| 1104 | H | H | H | 4-(Thz-4-yl)Ph | 6-OMe—Py-3-yl |
| 1105 | H | H | H | 4-(Thz-4-yl)Ph | 6-OCHF₂—Py-3-yl |
| 1106 | H | H | H | 4-(Thz-4-yl)Ph | Py-4-yl |
| 1107 | H | H | H | 4-(Thz-4-yl)Ph | Pym-2-yl |
| 1108 | H | H | H | 4-(2-F-Thz-4-yl)Ph | Ph |
| 1109 | H | H | H | 4-(2-F-Thz-4-yl)Ph | 2-F—Ph |
| 1110 | H | H | H | 4-(2-F-Thz-4-yl)Ph | 3-F—Ph |
| 1111 | H | H | H | 4-(2-F-Thz-4-yl)Ph | 4-F—Ph |
| 1112 | H | H | H | 4-(2-F-Thz-4-yl)Ph | 2-Cl—Ph |
| 1113 | H | H | H | 4-(2-F-Thz-4-yl)Ph | 3-Cl—Ph |
| 1114 | H | H | H | 4-(2-F-Thz-4-yl)Ph | 4-Cl—Ph |
| 1115 | H | H | H | 4-(2-F-Thz-4-yl)Ph | 2,6-diCl—Ph |
| 1116 | H | H | H | 4-(2-F-Thz-4-yl)Ph | 4-OMe—Ph |
| 1117 | H | H | H | 4-(2-F-Thz-4-yl)Ph | Py-2-yl |
| 1118 | H | H | H | 4-(2-F-Thz-4-yl)Ph | Py-3-yl |
| 1119 | H | H | H | 4-(2-Cl-Thz-4-yl)Ph | Ph |
| 1120 | H | H | H | 4-(2-Cl-Thz-4-yl)Ph | 2-F—Ph |
| 1121 | H | H | H | 4-(2-Cl-Thz-4-yl)Ph | 3-F—Ph |
| 1122 | H | H | H | 4-(2-Cl-Thz-4-yl)Ph | 4-F—Ph |
| 1123 | H | H | H | 4-(2-Cl-Thz-4-yl)Ph | 2-Cl—Ph |
| 1124 | H | H | H | 4-(2-Cl-Thz-4-yl)Ph | 3-Cl—Ph |
| 1125 | H | H | H | 4-(2-Cl-Thz-4-yl)Ph | 4-Cl—Ph |
| 1126 | H | H | H | 4-(2-Cl-Thz-4-yl)Ph | 2,6-diCl—Ph |
| 1127 | H | H | H | 4-(2-Cl-Thz-4-yl)Ph | 4-OMe—Ph |

TABLE 1-continued

Compounds

| No. | R¹ | R² | R³ | Y | Z |
|---|---|---|---|---|---|
| 1128 | H | H | H | 4-(2-Cl-Thz-4-yl)Ph | Py-2-yl |
| 1129 | H | H | H | 4-(2-Cl-Thz-4-yl)Ph | Py-3-yl |
| 1130 | H | H | H | 4-(2-Me-Thz-4-yl)Ph | 4-F—Ph |
| 1131 | H | H | H | 4-(2-Me-Thz-4-yl)Ph | Py-2-yl |
| 1132 | H | H | H | 4-(2-Me-Thz-4-yl)Ph | Py-3-yl |
| 1133 | H | H | H | 4-(2-Et-Thz-4-yl)Ph | 4-F—Ph |
| 1134 | H | H | H | 4-(2-Et-Thz-4-yl)Ph | Py-2-yl |
| 1135 | H | H | H | 4-(2-Et-Thz-4-yl)Ph | Py-3-yl |
| 1136 | H | H | H | 4-(2-CF₃-Thz-4-yl)Ph | 4-F—Ph |
| 1137 | H | H | H | 4-(2-CF₃-Thz-4-yl)Ph | Py-2-yl |
| 1138 | H | H | H | 4-(2-CF₃-Thz-4-yl)Ph | Py-3-yl |
| 1139 | H | H | H | 4-(2-OMe-Thz-4-yl)Ph | 4-F—Ph |
| 1140 | H | H | H | 4-(2-OMe-Thz-4-yl)Ph | Py-2-yl |
| 1141 | H | H | H | 4-(2-OMe-Thz-4-yl)Ph | Py-3-yl |
| 1142 | H | H | H | 4-(2-OCHF₂-Thz-4-yl)Ph | 4-F—Ph |
| 1143 | H | H | H | 4-(2-OCHF₂-Thz-4-yl)Ph | Py-2-yl |
| 1144 | H | H | H | 4-(2-OCHF₂-Thz-4-yl)Ph | Py-3-yl |
| 1145 | H | H | H | 4-(Thz-5-yl)Ph | Ph |
| 1146 | H | H | H | 4-(Thz-5-yl)Ph | 2-F—Ph |
| 1147 | H | H | H | 4-(Thz-5-yl)Ph | 3-F—Ph |
| 1148 | H | H | H | 4-(Thz-5-yl)Ph | 4-F—Ph |
| 1149 | H | H | H | 4-(Thz-5-yl)Ph | 2-Cl—Ph |
| 1150 | H | H | H | 4-(Thz-5-yl)Ph | 3-Cl—Ph |
| 1151 | H | H | H | 4-(Thz-5-yl)Ph | 4-Cl—Ph |
| 1152 | H | H | H | 4-(Thz-5-yl)Ph | 2,6-diCl—Ph |
| 1153 | H | H | H | 4-(Thz-5-yl)Ph | 4-OMe—Ph |
| 1154 | H | H | H | 4-(Thz-5-yl)Ph | Py-2-yl |
| 1155 | H | H | H | 4-(Thz-5-yl)Ph | Py-3-yl |
| 1156 | H | H | H | 4-(Py-2-yl)Ph | 4-F—Ph |
| 1157 | H | H | H | 4-(Py-2-yl)Ph | Py-2-yl |
| 1158 | H | H | H | 4-(Py-2-yl)Ph | Py-3-yl |
| 1159 | H | H | H | 4-(Py-3-yl)Ph | 4-F—Ph |
| 1160 | H | H | H | 4-(Py-3-yl)Ph | Py-2-yl |
| 1161 | H | H | H | 4-(Py-3-yl)Ph | Py-3-yl |
| 1162 | H | H | H | 4-(Py-4-yl)Ph | 4-F—Ph |
| 1163 | H | H | H | 4-(Py-4-yl)Ph | Py-2-yl |
| 1164 | H | H | H | 4-(Py-4-yl)Ph | Py-3-yl |
| 1165 | H | H | H | 4-(Pyd-3-yl)Ph | Ph |
| 1166 | H | H | H | 4-(Pyd-3-yl)Ph | 2-F—Ph |
| 1167 | H | H | H | 4-(Pyd-3-yl)Ph | 3-F—Ph |
| 1168 | H | H | H | 4-(Pyd-3-yl)Ph | 4-F—Ph |
| 1169 | H | H | H | 4-(Pyd-3-yl)Ph | 2-Cl—Ph |
| 1170 | H | H | H | 4-(Pyd-3-yl)Ph | 3-Cl—Ph |
| 1171 | H | H | H | 4-(Pyd-3-yl)Ph | 4-Cl—Ph |
| 1172 | H | H | H | 4-(Pyd-3-yl)Ph | 2,6-diCl—Ph |
| 1173 | H | H | H | 4-(Pyd-3-yl)Ph | 4-OMe—Ph |
| 1174 | H | H | H | 4-(Pyd-3-yl)Ph | Py-2-yl |
| 1175 | H | H | H | 4-(Pyd-3-yl)Ph | Py-3-yl |
| 1176 | H | H | H | 4-(Pyd-4-yl)Ph | Ph |
| 1177 | H | H | H | 4-(Pyd-4-yl)Ph | 2-F—Ph |
| 1178 | H | H | H | 4-(Pyd-4-yl)Ph | 3-F—Ph |
| 1179 | H | H | H | 4-(Pyd-4-yl)Ph | 4-F—Ph |
| 1180 | H | H | H | 4-(Pyd-4-yl)Ph | 3,4-diF—Ph |
| 1181 | H | H | H | 4-(Pyd-4-yl)Ph | 3,5-diF—Ph |
| 1182 | H | H | H | 4-(Pyd-4-yl)Ph | 2-Cl—Ph |
| 1183 | H | H | H | 4-(Pyd-4-yl)Ph | 3-Cl—Ph |
| 1184 | H | H | H | 4-(Pyd-4-yl)Ph | 4-Cl—Ph |
| 1185 | H | H | H | 4-(Pyd-4-yl)Ph | 2,6-diCl—Ph |
| 1186 | H | H | H | 4-(Pyd-4-yl)Ph | 4-Cl-3-F—Ph |
| 1187 | H | H | H | 4-(Pyd-4-yl)Ph | 4-Me—Ph |
| 1188 | H | H | H | 4-(Pyd-4-yl)Ph | 3-F-4-Me—Ph |
| 1189 | H | H | H | 4-(Pyd-4-yl)Ph | 4-Et—Ph |
| 1190 | H | H | H | 4-(Pyd-4-yl)Ph | 4-Et-3-F—Ph |
| 1191 | H | H | H | 4-(Pyd-4-yl)Ph | 4-CF₃—Ph |
| 1192 | H | H | H | 4-(Pyd-4-yl)Ph | 3-F-4-CF₃—Ph |
| 1193 | H | H | H | 4-(Pyd-4-yl)Ph | 4-OMe—Ph |
| 1194 | H | H | H | 4-(Pyd-4-yl)Ph | 3-F-4-OMe—Ph |
| 1195 | H | H | H | 4-(Pyd-4-yl)Ph | 4-OCHF₂—Ph |
| 1196 | H | H | H | 4-(Pyd-4-yl)Ph | 4-OCHF₂-3-F—Ph |
| 1197 | H | H | H | 4-(Pyd-4-yl)Ph | Th-2-yl |
| 1198 | H | H | H | 4-(Pyd-4-yl)Ph | Th-3-yl |
| 1199 | H | H | H | 4-(Pyd-4-yl)Ph | Py-2-yl |
| 1200 | H | H | H | 4-(Pyd-4-yl)Ph | 5-F—Py-2-yl |
| 1201 | H | H | H | 4-(Pyd-4-yl)Ph | 5-Cl—Py-2-yl |
| 1202 | H | H | H | 4-(Pyd-4-yl)Ph | 5-OMe—Py-2-yl |
| 1203 | H | H | H | 4-(Pyd-4-yl)Ph | Py-3-yl |
| 1204 | H | H | H | 4-(Pyd-4-yl)Ph | 6-F—Py-3-yl |
| 1205 | H | H | H | 4-(Pyd-4-yl)Ph | 6-Cl—Py-3-yl |
| 1206 | H | H | H | 4-(Pyd-4-yl)Ph | 6-OMe—Py-3-yl |
| 1207 | H | H | H | 4-(Pyd-4-yl)Ph | Py-4-yl |
| 1208 | Me | H | H | 4-(Pym-2-yl)Ph | 4-F—Ph |
| 1209 | Me | H | H | 4-(Pym-2-yl)Ph | Py-2-yl |
| 1210 | Me | H | H | 4-(Pym-2-yl)Ph | Py-3-yl |
| 1211 | Et | H | H | 4-(Pym-2-yl)Ph | 4-F—Ph |
| 1212 | Et | H | H | 4-(Pym-2-yl)Ph | Py-2-yl |
| 1213 | Et | H | H | 4-(Pym-2-yl)Ph | Py-3-yl |
| 1214 | Me | Me | Me | 4-(Pym-2-yl)Ph | Py-2-yl |
| 1215 | Et | Me | Me | 4-(Pym-2-yl)Ph | Py-2-yl |
| 1216 | H | Me | Me | 4-(Pym-2-yl)Ph | 4-F—Ph |
| 1217 | H | Me | Me | 4-(Pym-2-yl)Ph | Py-2-yl |
| 1218 | H | Me | Me | 4-(Pym-2-yl)Ph | Py-3-yl |
| 1219 | H | Me | H | 4-(Pym-2-yl)Ph | 4-F—Ph |
| 1220 | H | Me | H | 4-(Pym-2-yl)Ph | Py-2-yl |
| 1221 | H | Me | H | 4-(Pym-2-yl)Ph | Py-3-yl |
| 1222 | H | H | H | 4-(Pym-2-yl)Ph | Ph |
| 1223 | H | H | H | 4-(Pym-2-yl)Ph | 2-F—Ph |
| 1224 | H | H | H | 4-(Pym-2-yl)Ph | 3-F—Ph |
| 1225 | H | H | H | 4-(Pym-2-yl)Ph | 4-F—Ph |
| 1226 | H | H | H | 4-(Pym-2-yl)Ph | 3,4-diF—Ph |
| 1227 | H | H | H | 4-(Pym-2-yl)Ph | 3,5-diF—Ph |
| 1228 | H | H | H | 4-(Pym-2-yl)Ph | 3,4,5-triF—Ph |
| 1229 | H | H | H | 4-(Pym-2-yl)Ph | 2-Cl—Ph |
| 1230 | H | H | H | 4-(Pym-2-yl)Ph | 3-Cl—Ph |
| 1231 | H | H | H | 4-(Pym-2-yl)Ph | 4-Cl—Ph |
| 1232 | H | H | H | 4-(Pym-2-yl)Ph | 2,6-diCl—Ph |
| 1233 | H | H | H | 4-(Pym-2-yl)Ph | 4-Cl-3-F—Ph |
| 1234 | H | H | H | 4-(Pym-2-yl)Ph | 4-Cl-3,5-diF—Ph |
| 1235 | H | H | H | 4-(Pym-2-yl)Ph | 4-Br—Ph |
| 1236 | H | H | H | 4-(Pym-2-yl)Ph | 4-Me—Ph |
| 1237 | H | H | H | 4-(Pym-2-yl)Ph | 3-F-4-Me—Ph |
| 1238 | H | H | H | 4-(Pym-2-yl)Ph | 4-Et—Ph |
| 1239 | H | H | H | 4-(Pym-2-yl)Ph | 4-Et-3-F—Ph |
| 1240 | H | H | H | 4-(Pym-2-yl)Ph | 4-Pr—Ph |
| 1241 | H | H | H | 4-(Pym-2-yl)Ph | 4-iPr—Ph |
| 1242 | H | H | H | 4-(Pym-2-yl)Ph | 4-tBu—Ph |
| 1243 | H | H | H | 4-(Pym-2-yl)Ph | 4-CF₃—Ph |
| 1244 | H | H | H | 4-(Pym-2-yl)Ph | 3-F-4-CF₃—Ph |
| 1245 | H | H | H | 4-(Pym-2-yl)Ph | 4-CHF₂—Ph |
| 1246 | H | H | H | 4-(Pym-2-yl)Ph | 4-CCl₃—Ph |
| 1247 | H | H | H | 4-(Pym-2-yl)Ph | 4-CHCl₂-Ph |
| 1248 | H | H | H | 4-(Pym-2-yl)Ph | 4-CH₂CF₃-Ph |
| 1249 | H | H | H | 4-(Pym-2-yl)Ph | 4-CH₂CCl₃-Ph |
| 1250 | H | H | H | 4-(Pym-2-yl)Ph | 4-OMe—Ph |
| 1251 | H | H | H | 4-(Pym-2-yl)Ph | 3-F-4-OMe—Ph |
| 1252 | H | H | H | 4-(Pym-2-yl)Ph | 4-OEt—Ph |
| 1253 | H | H | H | 4-(Pym-2-yl)Ph | 4-OPr-Ph |
| 1254 | H | H | H | 4-(Pym-2-yl)Ph | 4-OiPr-Ph |
| 1255 | H | H | H | 4-(Pym-2-yl)Ph | 4-OtBu-Ph |
| 1256 | H | H | H | 4-(Pym-2-yl)Ph | 4-OCF₃—Ph |
| 1257 | H | H | H | 4-(Pym-2-yl)Ph | 4-OCHF₂—Ph |
| 1258 | H | H | H | 4-(Pym-2-yl)Ph | 4-OCHF₂-3-F—Ph |
| 1259 | H | H | H | 4-(Pym-2-yl)Ph | 4-OCCl₃-Ph |
| 1260 | H | H | H | 4-(Pym-2-yl)Ph | 4-OCHCl₂-Ph |
| 1261 | H | H | H | 4-(Pym-2-yl)Ph | Th-2-yl |
| 1262 | H | H | H | 4-(Pym-2-yl)Ph | Th-3-yl |
| 1263 | H | H | H | 4-(Pym-2-yl)Ph | 5-Cl-Th-2-yl |
| 1264 | H | H | H | 4-(Pym-2-yl)Ph | 1-Me-1H-Imz-4-yl |
| 1265 | H | H | H | 4-(Pym-2-yl)Ph | Thz-2-yl |
| 1266 | H | H | H | 4-(Pym-2-yl)Ph | Py-2-yl |
| 1267 | H | H | H | 4-(Pym-2-yl)Ph | 5-F-Py-2-yl |
| 1268 | H | H | H | 4-(Pym-2-yl)Ph | 5-Cl-Py-2-yl |
| 1269 | H | H | H | 4-(Pym-2-yl)Ph | 5-Me-Py-2-yl |
| 1270 | H | H | H | 4-(Pym-2-yl)Ph | 5-Et-Py-2-yl |
| 1271 | H | H | H | 4-(Pym-2-yl)Ph | 5-CF₃-Py-2-yl |
| 1272 | H | H | H | 4-(Pym-2-yl)Ph | 5-OMe-Py-2-yl |
| 1273 | H | H | H | 4-(Pym-2-yl)Ph | 5-OCHF₂-Py-2-yl |
| 1274 | H | H | H | 4-(Pym-2-yl)Ph | Py-3-yl |
| 1275 | H | H | H | 4-(Pym-2-yl)Ph | 6-F-Py-3-yl |
| 1276 | H | H | H | 4-(Pym-2-yl)Ph | 6-Cl-Py-3-yl |
| 1277 | H | H | H | 4-(Pym-2-yl)Ph | 6-Me-Py-3-yl |
| 1278 | H | H | H | 4-(Pym-2-yl)Ph | 6-Et-Py-3-yl |
| 1279 | H | H | H | 4-(Pym-2-yl)Ph | 6-CF₃-Py-3-yl |

TABLE 1-continued

Compounds

| No. | R¹ | R² | R³ | Y | Z |
|---|---|---|---|---|---|
| 1280 | H | H | H | 4-(Pym-2-yl)Ph | 6-OMe-Py-3-yl |
| 1281 | H | H | H | 4-(Pym-2-yl)Ph | 6-OCHF$_2$-Py-3-yl |
| 1282 | H | H | H | 4-(Pym-2-yl)Ph | Py-4-yl |
| 1283 | H | H | H | 4-(Pym-2-yl)Ph | Pym-2-yl |
| 1284 | H | H | H | 4-(5-F-Pym-2-yl)Ph | 4-F—Ph |
| 1285 | H | H | H | 4-(5-F-Pym-2-yl)Ph | Py-2-yl |
| 1286 | H | H | H | 4-(5-F-Pym-2-yl)Ph | Py-3-yl |
| 1287 | H | H | H | 4-(5-Cl-Pym-2-yl)Ph | 4-F—Ph |
| 1288 | H | H | H | 4-(5-Cl-Pym-2-yl)Ph | Py-2-yl |
| 1289 | H | H | H | 4-(5-Cl-Pym-2-yl)Ph | Py-3-yl |
| 1290 | H | H | H | 4-(5-OH-Pym-2-yl)Ph | Ph |
| 1291 | H | H | H | 4-(5-OH-Pym-2-yl)Ph | 2-F—Ph |
| 1292 | H | H | H | 4-(5-OH-Pym-2-yl)Ph | 3-F—Ph |
| 1293 | H | H | H | 4-(5-OH-Pym-2-yl)Ph | 4-F—Ph |
| 1294 | H | H | H | 4-(5-OH-Pym-2-yl)Ph | 2-Cl—Ph |
| 1295 | H | H | H | 4-(5-OH-Pym-2-yl)Ph | 3-Cl—Ph |
| 1296 | H | H | H | 4-(5-OH-Pym-2-yl)Ph | 4-Cl—Ph |
| 1297 | H | H | H | 4-(5-OH-Pym-2-yl)Ph | 2,6-diCl—Ph |
| 1298 | H | H | H | 4-(5-OH-Pym-2-yl)Ph | 4-OMe—Ph |
| 1299 | H | H | H | 4-(5-OH-Pym-2-yl)Ph | Py-2-yl |
| 1300 | H | H | H | 4-(5-OH-Pym-2-yl)Ph | Py-3-yl |
| 1301 | H | H | H | 4-(Pym-4-yl)Ph | Ph |
| 1302 | H | H | H | 4-(Pym-4-yl)Ph | 2-F—Ph |
| 1303 | H | H | H | 4-(Pym-4-yl)Ph | 3-F—Ph |
| 1304 | H | H | H | 4-(Pym-4-yl)Ph | 4-F—Ph |
| 1305 | H | H | H | 4-(Pym-4-yl)Ph | 2-Cl—Ph |
| 1306 | H | H | H | 4-(Pym-4-yl)Ph | 3-Cl—Ph |
| 1307 | H | H | H | 4-(Pym-4-yl)Ph | 4-Cl—Ph |
| 1308 | H | H | H | 4-(Pym-4-yl)Ph | 2,6-diCl—Ph |
| 1309 | H | H | H | 4-(Pym-4-yl)Ph | 4-OMe—Ph |
| 1310 | H | H | H | 4-(Pym-4-yl)Ph | Py-2-yl |
| 1311 | H | H | H | 4-(Pym-4-yl)Ph | Py-3-yl |
| 1312 | H | H | H | 4-(Pym-5-yl)Ph | Ph |
| 1313 | H | H | H | 4-(Pym-5-yl)Ph | 2-F—Ph |
| 1314 | H | H | H | 4-(Pym-5-yl)Ph | 3-F—Ph |
| 1315 | H | H | H | 4-(Pym-5-yl)Ph | 4-F—Ph |
| 1316 | H | H | H | 4-(Pym-5-yl)Ph | 2-Cl—Ph |
| 1317 | H | H | H | 4-(Pym-5-yl)Ph | 3-Cl—Ph |
| 1318 | H | H | H | 4-(Pym-5-yl)Ph | 4-Cl—Ph |
| 1319 | H | H | H | 4-(Pym-5-yl)Ph | 2,6-diCl—Ph |
| 1320 | H | H | H | 4-(Pym-5-yl)Ph | 4-OMe—Ph |
| 1321 | H | H | H | 4-(Pym-5-yl)Ph | Py-2-yl |
| 1322 | H | H | H | 4-(Pym-5-yl)Ph | Py-3-yl |
| 1323 | H | H | H | 4-(4,5-diH-Thz-2-yl)Ph | Ph |
| 1324 | H | H | H | 4-(4,5-diH-Thz-2-yl)Ph | 2-F—Ph |
| 1325 | H | H | H | 4-(4,5-diH-Thz-2-yl)Ph | 3-F—Ph |
| 1326 | H | H | H | 4-(4,5-diH-Thz-2-yl)Ph | 4-F—Ph |
| 1327 | H | H | H | 4-(4,5-diH-Thz-2-yl)Ph | 3,4-diF—Ph |
| 1328 | H | H | H | 4-(4,5-diH-Thz-2-yl)Ph | 3,5-diF—Ph |
| 1329 | H | H | H | 4-(4,5-diH-Thz-2-yl)Ph | 2-Cl—Ph |
| 1330 | H | H | H | 4-(4,5-diH-Thz-2-yl)Ph | 3-Cl—Ph |
| 1331 | H | H | H | 4-(4,5-diH-Thz-2-yl)Ph | 4-Cl—Ph |
| 1332 | H | H | H | 4-(4,5-diH-Thz-2-yl)Ph | 2,6-diCl—Ph |
| 1333 | H | H | H | 4-(4,5-diH-Thz-2-yl)Ph | 4-Cl-3-F—Ph |
| 1334 | H | H | H | 4-(4,5-diH-Thz-2-yl)Ph | 4-Me—Ph |
| 1335 | H | H | H | 4-(4,5-diH-Thz-2-yl)Ph | 3-F-4-Me—Ph |
| 1336 | H | H | H | 4-(4,5-diH-Thz-2-yl)Ph | 4-Et—Ph |
| 1337 | H | H | H | 4-(4,5-diH-Thz-2-yl)Ph | 4-Et-3-F—Ph |
| 1338 | H | H | H | 4-(4,5-diH-Thz-2-yl)Ph | 4-CF$_3$—Ph |
| 1339 | H | H | H | 4-(4,5-diH-Thz-2-yl)Ph | 3-F-4-CF$_3$—Ph |
| 1340 | H | H | H | 4-(4,5-diH-Thz-2-yl)Ph | 4-OMe—Ph |
| 1341 | H | H | H | 4-(4,5-diH-Thz-2-yl)Ph | 3-F-4-OMe—Ph |
| 1342 | H | H | H | 4-(4,5-diH-Thz-2-yl)Ph | 4-OCHF$_2$—Ph |
| 1343 | H | H | H | 4-(4,5-diH-Thz-2-yl)Ph | 4-OCHF$_2$-3-F—Ph |
| 1344 | H | H | H | 4-(4,5-diH-Thz-2-yl)Ph | Th-2-yl |
| 1345 | H | H | H | 4-(4,5-diH-Thz-2-yl)Ph | Th-3-yl |
| 1346 | H | H | H | 4-(4,5-diH-Thz-2-yl)Ph | Py-2-yl |
| 1347 | H | H | H | 4-(4,5-diH-Thz-2-yl)Ph | 5-F-Py-2-yl |
| 1348 | H | H | H | 4-(4,5-diH-Thz-2-yl)Ph | 5-Cl-Py-2-yl |
| 1349 | H | H | H | 4-(4,5-diH-Thz-2-yl)Ph | 5-OMe-Py-2-yl |
| 1350 | H | H | H | 4-(4,5-diH-Thz-2-yl)Ph | Py-3-yl |
| 1351 | H | H | H | 4-(4,5-diH-Thz-2-yl)Ph | 6-F-Py-3-yl |
| 1352 | H | H | H | 4-(4,5-diH-Thz-2-yl)Ph | 6-Cl-Py-3-yl |
| 1353 | H | H | H | 4-(4,5-diH-Thz-2-yl)Ph | 6-OMe-Py-3-yl |
| 1354 | H | H | H | 4-(4,5-diH-Thz-2-yl)Ph | Py-4-yl |
| 1355 | H | H | H | 4-(Pyr-1-yl)Ph | 4-F—Ph |
| 1356 | H | H | H | 4-(Pyr-1-yl)Ph | Py-2-yl |
| 1357 | H | H | H | 4-(Pyr-1-yl)Ph | Py-3-yl |
| 1358 | H | H | H | 4-(Pip-1-yl)Ph | 4-F—Ph |
| 1359 | H | H | H | 4-(Pip-1-yl)Ph | Py-2-yl |
| 1360 | H | H | H | 4-(Pip-1-yl)Ph | Py-3-yl |
| 1361 | H | H | H | 5-Ph-Th-2-yl | 4-F—Ph |
| 1362 | H | H | H | 5-Ph-Th-2-yl | Py-2-yl |
| 1363 | H | H | H | 5-Ph-Th-2-yl | Py-3-yl |
| 1364 | H | H | H | 5-(Thz-2-yl)-Th-2-yl | 4-F—Ph |
| 1365 | H | H | H | 5-(Thz-2-yl)-Th-2-yl | Py-2-yl |
| 1366 | H | H | H | 5-(Thz-2-yl)-Th-2-yl | Py-3-yl |
| 1367 | H | H | H | 5-(Thz-4-yl)-Th-2-yl | 4-F—Ph |
| 1368 | H | H | H | 5-(Thz-4-yl)-Th-2-yl | Py-2-yl |
| 1369 | H | H | H | 5-(Thz-4-yl)-Th-2-yl | Py-3-yl |
| 1370 | H | H | H | 6-Ph-Pyd-3-yl | Ph |
| 1371 | H | H | H | 6-Ph-Pyd-3-yl | 2-F—Ph |
| 1372 | H | H | H | 6-Ph-Pyd-3-yl | 3-F—Ph |
| 1373 | H | H | H | 6-Ph-Pyd-3-yl | 4-F—Ph |
| 1374 | H | H | H | 6-Ph-Pyd-3-yl | 3,4-diF—Ph |
| 1375 | H | H | H | 6-Ph-Pyd-3-yl | 3,5-diF—Ph |
| 1376 | H | H | H | 6-Ph-Pyd-3-yl | 2-Cl—Ph |
| 1377 | H | H | H | 6-Ph-Pyd-3-yl | 3-Cl—Ph |
| 1378 | H | H | H | 6-Ph-Pyd-3-yl | 4-Cl—Ph |
| 1379 | H | H | H | 6-Ph-Pyd-3-yl | 2,6-diCl—Ph |
| 1380 | H | H | H | 6-Ph-Pyd-3-yl | 4-Cl-3-F—Ph |
| 1381 | H | H | H | 6-Ph-Pyd-3-yl | 4-Me—Ph |
| 1382 | H | H | H | 6-Ph-Pyd-3-yl | 3-F-4-Me—Ph |
| 1383 | H | H | H | 6-Ph-Pyd-3-yl | 4-Et—Ph |
| 1384 | H | H | H | 6-Ph-Pyd-3-yl | 4-Et-3-F—Ph |
| 1385 | H | H | H | 6-Ph-Pyd-3-yl | 4-CF$_3$—Ph |
| 1386 | H | H | H | 6-Ph-Pyd-3-yl | 3-F-4-CF$_3$—Ph |
| 1387 | H | H | H | 6-Ph-Pyd-3-yl | 4-OMe—Ph |
| 1388 | H | H | H | 6-Ph-Pyd-3-yl | 3-F-4-OMe—Ph |
| 1389 | H | H | H | 6-Ph-Pyd-3-yl | 4-OCHF$_2$—Ph |
| 1390 | H | H | H | 6-Ph-Pyd-3-yl | 4-OCHF$_2$-3-F—Ph |
| 1391 | H | H | H | 6-Ph-Pyd-3-yl | Th-2-yl |
| 1392 | H | H | H | 6-Ph-Pyd-3-yl | Th-3-yl |
| 1393 | H | H | H | 6-Ph-Pyd-3-yl | Py-2-yl |
| 1394 | H | H | H | 6-Ph-Pyd-3-yl | 5-F-Py-2-yl |
| 1395 | H | H | H | 6-Ph-Pyd-3-yl | 5-Cl-Py-2-yl |
| 1396 | H | H | H | 6-Ph-Pyd-3-yl | 5-OMe-Py-2-yl |
| 1397 | H | H | H | 6-Ph-Pyd-3-yl | Py-3-yl |
| 1398 | H | H | H | 6-Ph-Pyd-3-yl | 6-F-Py-3-yl |
| 1399 | H | H | H | 6-Ph-Pyd-3-yl | 6-Cl-Py-3-yl |
| 1400 | H | H | H | 6-Ph-Pyd-3-yl | 6-OMe-Py-3-yl |
| 1401 | H | H | H | 6-Ph-Pyd-3-yl | Py-4-yl |
| 1402 | H | H | H | 6-(Thz-2-yl)-Pyd-3-yl | Ph |
| 1403 | H | H | H | 6-(Thz-2-yl)-Pyd-3-yl | 2-F—Ph |
| 1404 | H | H | H | 6-(Thz-2-yl)-Pyd-3-yl | 3-F—Ph |
| 1405 | H | H | H | 6-(Thz-2-yl)-Pyd-3-yl | 4-F—Ph |
| 1406 | H | H | H | 6-(Thz-2-yl)-Pyd-3-yl | 2-Cl—Ph |
| 1407 | H | H | H | 6-(Thz-2-yl)-Pyd-3-yl | 3-Cl—Ph |
| 1408 | H | H | H | 6-(Thz-2-yl)-Pyd-3-yl | 4-Cl—Ph |
| 1409 | H | H | H | 6-(Thz-2-yl)-Pyd-3-yl | 2,6-diCl—Ph |
| 1410 | H | H | H | 6-(Thz-2-yl)-Pyd-3-yl | 4-OMe—Ph |
| 1411 | H | H | H | 6-(Thz-2-yl)-Pyd-3-yl | Py-2-yl |
| 1412 | H | H | H | 6-(Thz-2-yl)-Pyd-3-yl | Py-3-yl |
| 1413 | H | H | H | 6-(Thz-4-yl)-Pyd-3-yl | Ph |
| 1414 | H | H | H | 6-(Thz-4-yl)-Pyd-3-yl | 2-F—Ph |
| 1415 | H | H | H | 6-(Thz-4-yl)-Pyd-3-yl | 3-F—Ph |
| 1416 | H | H | H | 6-(Thz-4-yl)-Pyd-3-yl | 4-F—Ph |
| 1417 | H | H | H | 6-(Thz-4-yl)-Pyd-3-yl | 2-Cl—Ph |
| 1418 | H | H | H | 6-(Thz-4-yl)-Pyd-3-yl | 3-Cl—Ph |
| 1419 | H | H | H | 6-(Thz-4-yl)-Pyd-3-yl | 4-Cl—Ph |
| 1420 | H | H | H | 6-(Thz-4-yl)-Pyd-3-yl | 2,6-diCl—Ph |
| 1421 | H | H | H | 6-(Thz-4-yl)-Pyd-3-yl | 4-OMe—Ph |
| 1422 | H | H | H | 6-(Thz-4-yl)-Pyd-3-yl | Py-2-yl |
| 1423 | H | H | H | 6-(Thz-4-yl)-Pyd-3-yl | Py-3-yl |
| 1424 | H | H | H | 2-Ph-Pym-4-yl | 4-F—Ph |
| 1425 | H | H | H | 2-Ph-Pym-4-yl | Py-2-yl |
| 1426 | H | H | H | 2-Ph-Pym-4-yl | Py-3-yl |
| 1427 | H | H | H | 2-(Thz-2-yl)-Pym-4-yl | 4-F—Ph |
| 1428 | H | H | H | 2-(Thz-2-yl)-Pym-4-yl | Py-2-yl |
| 1429 | H | H | H | 2-(Thz-2-yl)-Pym-4-yl | Py-3-yl |
| 1430 | H | H | H | 2-(Thz-4-yl)-Pym-4-yl | 4-F—Ph |
| 1431 | H | H | H | 2-(Thz-4-yl)-Pym-4-yl | Py-2-yl |

TABLE 1-continued

Compounds

| No. | R¹ | R² | R³ | Y | Z |
|---|---|---|---|---|---|
| 1432 | H | H | H | 2-(Thz-4-yl)-Pym-4-yl | Py-3-yl |
| 1433 | Hx | H | H | 4-(Thz-2-yl)Ph | Py-2-yl |
| 1434 | H | H | H | 4-(5-Cl-Thz-2-yl)Ph | Ph |
| 1435 | H | H | H | 4-(5-Cl-Thz-2-yl)Ph | 3-F—Ph |
| 1436 | H | H | H | 4-(5-Cl-Thz-2-yl)Ph | 4-F—Ph |
| 1437 | H | H | H | 4-(5-Cl-Thz-2-yl)Ph | 4-Cl—Ph |
| 1438 | H | H | H | 4-(5-Cl-Thz-2-yl)Ph | 4-OMe—Ph |
| 1439 | H | H | H | 4-(5-Cl-Thz-2-yl)Ph | Py-2-yl |
| 1440 | H | H | H | 4-(5-Cl-Thz-2-yl)Ph | Py-3-yl |
| 1441 | H | H | H | 4-(5-Me-Thz-2-yl)Ph | Ph |
| 1442 | H | H | H | 4-(5-Me-Thz-2-yl)Ph | 3-F—Ph |
| 1443 | H | H | H | 4-(5-Me-Thz-2-yl)Ph | 4-F—Ph |
| 1444 | H | H | H | 4-(5-Me-Thz-2-yl)Ph | 4-Cl—Ph |
| 1445 | H | H | H | 4-(5-Me-Thz-2-yl)Ph | 4-OMe—Ph |
| 1446 | H | H | H | 4-(5-Me-Thz-2-yl)Ph | Py-2-yl |
| 1447 | H | H | H | 4-(5-Me-Thz-2-yl)Ph | Py-3-yl |
| 1448 | H | H | H | 4-(4,5-diMe-Thz-2-yl)Ph | Ph |
| 1449 | H | H | H | 4-(4,5-diMe-Thz-2-yl)Ph | 3-F—Ph |
| 1450 | H | H | H | 4-(4,5-diMe-Thz-2-yl)Ph | 4-F—Ph |
| 1451 | H | H | H | 4-(4,5-diMe-Thz-2-yl)Ph | 4-Cl—Ph |
| 1452 | H | H | H | 4-(4,5-diMe-Thz-2-yl)Ph | 4-OMe—Ph |
| 1453 | H | H | H | 4-(4,5-diMe-Thz-2-yl)Ph | Py-2-yl |
| 1454 | H | H | H | 4-(4,5-diMe-Thz-2-yl)Ph | Py-3-yl |
| 1455 | H | H | H | 4-(1,2,4-Trz-1-yl)Ph | Ph |
| 1456 | H | H | H | 4-(1,2,4-Trz-1-yl)Ph | 3-F—Ph |
| 1457 | H | H | H | 4-(1,2,4-Trz-1-yl)Ph | 4-F—Ph |
| 1458 | H | H | H | 4-(1,2,4-Trz-1-yl)Ph | 4-Cl—Ph |
| 1459 | H | H | H | 4-(1,2,4-Trz-1-yl)Ph | 4-OMe—Ph |
| 1460 | H | H | H | 4-(1,2,4-Trz-1-yl)Ph | Py-2-yl |
| 1461 | H | H | H | 4-(1,2,4-Trz-1-yl)Ph | Py-3-yl |
| 1462 | Me | H | H | 4-(Pyz-1-yl)Ph | 4-F—Ph |
| 1463 | Me | H | H | 4-(Pyz-1-yl)Ph | Py-2-yl |
| 1464 | Me | H | H | 4-(Pyz-1-yl)Ph | Py-3-yl |
| 1465 | Et | H | H | 4-(Pyz-1-yl)Ph | 4-F—Ph |
| 1466 | Et | H | H | 4-(Pyz-1-yl)Ph | Py-2-yl |
| 1467 | Et | H | H | 4-(Pyz-1-yl)Ph | Py-3-yl |
| 1468 | Pr | H | H | 4-(Pyz-1-yl)Ph | 4-F—Ph |
| 1469 | Pr | H | H | 4-(Pyz-1-yl)Ph | Py-2-yl |
| 1470 | Pr | H | H | 4-(Pyz-1-yl)Ph | Py-3-yl |
| 1471 | iPr | H | H | 4-(Pyz-1-yl)Ph | 4-F—Ph |
| 1472 | iPr | H | H | 4-(Pyz-1-yl)Ph | Py-2-yl |
| 1473 | iPr | H | H | 4-(Pyz-1-yl)Ph | Py-3-yl |
| 1474 | Bu | H | H | 4-(Pyz-1-yl)Ph | 4-F—Ph |
| 1475 | Bu | H | H | 4-(Pyz-1-yl)Ph | Py-2-yl |
| 1476 | Bu | H | H | 4-(Pyz-1-yl)Ph | Py-3-yl |
| 1477 | iBu | H | H | 4-(Pyz-1-yl)Ph | 4-F—Ph |
| 1478 | iBu | H | H | 4-(Pyz-1-yl)Ph | Py-2-yl |
| 1479 | iBu | H | H | 4-(Pyz-1-yl)Ph | Py-3-yl |
| 1480 | sBu | H | H | 4-(Pyz-1-yl)Ph | 4-F—Ph |
| 1481 | sBu | H | H | 4-(Pyz-1-yl)Ph | Py-2-yl |
| 1482 | sBu | H | H | 4-(Pyz-1-yl)Ph | Py-3-yl |
| 1483 | tBu | H | H | 4-(Pyz-1-yl)Ph | 4-F—Ph |
| 1484 | tBu | H | H | 4-(Pyz-1-yl)Ph | Py-2-yl |
| 1485 | tBu | H | H | 4-(Pyz-1-yl)Ph | Py-3-yl |
| 1486 | Pn | H | H | 4-(Pyz-1-yl)Ph | 4-F—Ph |
| 1487 | Pn | H | H | 4-(Pyz-1-yl)Ph | Py-2-yl |
| 1488 | Pn | H | H | 4-(Pyz-1-yl)Ph | Py-3-yl |
| 1489 | Hx | H | H | 4-(Pyz-1-yl)Ph | 4-F—Ph |
| 1490 | Hx | H | H | 4-(Pyz-1-yl)Ph | Py-2-yl |
| 1491 | Hx | H | H | 4-(Pyz-1-yl)Ph | Py-3-yl |

Further, abbreviations in the above table represent the following groups.
H: hydrogen atom,
Me: methyl group,
Et: ethyl group,
Pr: propyl group,
iPr: isopropyl group,
Bu: butyl group,
iBu: isobutyl group,
sBu: sec-butyl group,
tBu: tert-butyl group,
Pn: pentyl group,
Hx: hexyl group,
Bfu-2-yl: benzofuran-2-yl group,
6-F-Bfu-2-yl: 6-fluorobenzofuran-2-yl group,
5,6-diF-Bfu-2-yl: 5,6-difluorobenzofuran-2-yl group,
6-Cl-Bfu-2-yl: 6-chlorobenzofuran-2-yl group,
6-Cl-5-F-Bfu-2-yl: 6-chloro-5-fluorobenzofuran-2-yl group,
6-Me-Bfu-2-yl: 6-methylbenzofuran-2-yl group,
5-F-6-Me-Bfu-2-yl: 5-fluoro-6-methylbenzofuran-2-yl group,
6-Et-Bfu-2-yl: 6-ethylbenzofuran-2-yl group,
6-Et-5-F-Bfu-2-yl: 6-ethyl-5-fluorobenzofuran-2-yl group,
6-CF$_3$-Bfu-2-yl: 6-trifluoromethylbenzofuran-2-yl group,
5-F-6-CF$_3$-Bfu-2-yl: 5-fluoro-6-trifluoromethylbenzofuran-2-yl group,
6-OMe-Bfu-2-yl: 6-methoxybenzofuran-2-yl group,
5-F-6-OMe-Bfu-2-yl: 5-fluoro-6-methoxybenzofuran-2-yl group,
6-OCHF$_2$-Bfu-2-yl: 6-difluoromethoxybenzofuran-2-yl group,
6-OCHF$_2$-5-F-Bfu-2-yl: 6-difluoromethoxy-5-fluorobenzofuran-2-yl group,
6-SMe-Bfu-2-yl: 6-methylthiobenzofuran-2-yl group, 5-F-6-SMe-Bfu-2-yl: 5-fluoro-6-methylthiobenzofuran-2-yl group,
Bth-2-yl: benzo[b]thiophen-2-yl group,
6-F-Bth-2-yl: 6-fluorobenzo[b]thiophen-2-yl group,
5,6-diF-Bth-2-yl: 5,6-difluorobenzo[b]thiophen-2-yl group,
6-Cl-Bth-2-yl: 6-chlorobenzo[b]thiophen-2-yl group,
6-Cl-5-F-Bth-2-yl: 6-chloro-5-fluorobenzo[b]thiophen-2-yl group,
6-Br-Bth-2-yl: 6-bromobenzo[b]thiophen-2-yl group,
6-Me-Bth-2-yl: 6-methylbenzo[b]thiophen-2-yl group,
5-F-6-Me-Bth-2-yl: 5-fluoro-6-methylbenzo[b]thiophen-2-yl group,
6-Et-Bth-2-yl: 6-ethylbenzo[b]thiophen-2-yl group,
6-Et-5-F-Bth-2-yl: 6-ethyl-5-fluorobenzo[b]thiophen-2-yl group,
6-Pr-Bth-2-yl: 6-propylbenzo[b]thiophen-2-yl group,
6-iPr-Bth-2-yl: 6-isopropylbenzo[b]thiophen-2-yl group,
6-tBu-Bth-2-yl: 6-tert-butylbenzo[b]thiophen-2-yl group,
6-CF$_3$-Bth-2-yl: 6-trifluoromethylbenzo[b]thiophen-2-yl group,
5-F-6-CF$_3$-Bth-2-yl: 5-fluoro-6-trifluoromethylbenzo[b]thiophen-2-yl group,
6-CHF$_2$-Bth-2-yl: 6-difluoromethylbenzo[b]thiophen-2-yl group,
6-CCl$_3$-Bth-2-yl: 6-trichloromethylbenzo[b]thiophen-2-yl group,
6-CHCl$_2$-Bth-2-yl: 6-dichloromethylbenzo[b]thiophen-2-yl group,
6-CH$_2$CF$_3$-Bth-2-yl: 6-(2,2,2-trifluoroethyl)benzo[b]thiophen-2-yl group,
6-CH$_2$CCl$_3$-Bth-2-yl: 6-(2,2,2-trichloroethyl)benzo[b]thiophen-2-yl group,
6-OMe-Bth-2-yl: 6-methoxybenzo[b]thiophen-2-yl group,
5-F-6-OMe-Bth-2-yl: 5-fluoro-6-methoxybenzo[b]thiophen-2-yl group,
6-OEt-Bth-2-yl: 6-ethoxybenzo[b]thiophen-2-yl group,
6-OPr-Bth-2-yl: 6-propoxybenzo[b]thiophen-2-yl group,
6-OiPr-Bth-2-yl: 6-isopropoxybenzo[b]thiophen-2-yl group,
6-OtBu-Bth-2-yl: 6-tert-butoxybenzo[b]thiophen-2-yl group,
6-OCF$_3$-Bth-2-yl: 6-trifluoromethoxybenzo[b]thiophen-2-yl group,
6-OCHF$_2$-Bth-2-yl: 6-difluoromethoxybenzo[b]thiophen-2-yl group,
6-OCHF$_2$-5-F-Bth-2-yl: 6-difluoromethoxy-5-fluorobenzo[b]thiophen-2-yl group, 6-OCCl₃-Bth-2-yl: 6-trichloromethoxybenzo[b]thiophen-2-yl group,
6-OCHCl₂-Bth-2-yl: 6-dichloromethoxybenzo[b]thiophen-2-yl group,
6-SMe-Bth-2-yl: 6-methylthiobenzo[b]thiophen-2-yl group,
5-F-6-SMe-Bth-2-yl: 5-fluoro-6-methylthiobenzo[b]thiophen-2-yl group,
6-SEt-Bth-2-yl: 6-ethylthiobenzo[b]thiophen-2-yl group,
6-SPr-Bth-2-yl: 6-propylthiobenzo[b]thiophen-2-yl group,
6-SiPr-Bth-2-yl: 6-isopropylthiobenzo[b]thiophen-2-yl group,
6-StBu-Bth-2-yl: 6-tert-butylthiobenzo[b]thiophen-2-yl group,
Boxz-2-yl: benzoxazol-2-yl group,
6-Cl-Boxz-2-yl: 6-chlorobenzoxazol-2-yl group,
6-OMe-Boxz-2-yl: 6-methoxybenzoxazol-2-yl group,
Bthz-2-yl: benzothiazol-2-yl group,
6-Cl-Bthz-2-yl: 6-chlorobenzothiazol-2-yl group,
6-OMe-Bthz-2-yl: 6-methoxybenzothiazol-2-yl group,
biPh-3-yl: biphenyl-3-yl group,
biPh-4-yl: biphenyl-4-yl group,
2'-F-biPh-4-yl: 2'-fluorobiphenyl-4-yl group,
3'-F-biPh-4-yl: 3'-fluorobiphenyl-4-yl group,
4'-F-biPh-4-yl: 4'-fluorobiphenyl-4-yl group,
2',4'-diF-biPh-4-yl: 2',4'-difluorobiphenyl-4-yl group,
3',4'-diF-biPh-4-yl: 3',4'-difluorobiphenyl-4-yl group,
2'-Cl-biPh-4-yl: 2'-chlorobiphenyl-4-yl group,
3'-Cl-biPh-4-yl: 3'-chlorobiphenyl-4-yl group,
4'-Cl-biPh-4-yl: 4'-chlorobiphenyl-4-yl group,
2',4'-diCl-biPh-4-yl: 2',4'-dichlorobiphenyl-4-yl group,
3',4'-diCl-biPh-4-yl: 3',4'-dichlorobiphenyl-4-yl group,
4'-Cl-2'-F-biPh-4-yl: 4'-chloro-2'-fluorobiphenyl-4-yl group,
4'-Cl-3'-F-biPh-4-yl: 4'-chloro-3'-fluorobiphenyl-4-yl group,
3'-Br-biPh-4-yl: 3'-bromobiphenyl-4-yl group,
3'-OH-biPh-4-yl: 3'-hydroxybiphenyl-4-yl group,
4'-OH-biPh-4-yl: 4'-hydroxybiphenyl-4-yl group,
3'-Me-biPh-4-yl: 3'-methylbiphenyl-4-yl group,
3'-Et-biPh-4-yl: 3'-ethylbiphenyl-4-yl group,
3'-Pr-biPh-4-yl: 3'-propylbiphenyl-4-yl group,
3'-iPr-biPh-4-yl: 3'-isopropylbiphenyl-4-yl group,
3'-tBu-biPh-4-yl: 3'-tert-butylbiphenyl-4-yl group,
3'-CF₃-biPh-4-yl: 3'-trifluoromethylbiphenyl-4-yl group,
3'-CHF₂-biPh-4-yl: 3'-difluoromethylbiphenyl-4-yl group,
3'-CCl₃-biPh-4-yl: 3'-trichloromethylbiphenyl-4-yl group,
3'-CHCl₂-biPh-4-yl: 3'-dichloromethylbiphenyl-4-yl group,
3'-CH₂CF₃-biPh-4-yl: 3'-(2,2,2-trifluoroethyl)biphenyl-4-yl group,
3'-CH₂CCl₃-biPh-4-yl: 3'-(2,2,2-trichloroethyl)biphenyl-4-yl group,
3'-OMe-biPh-4-yl: 3'-methoxybiphenyl-4-yl group,
3'-OEt-biPh-4-yl: 3'-ethoxybiphenyl-4-yl group,
3'-OPr-biPh-4-yl: 3'-propoxybiphenyl-4-yl group,
3'-OiPr-biPh-4-yl: 3'-isopropoxybiphenyl-4-yl group,
3'-OtBu-biPh-4-yl: 3'-tert-butoxybiphenyl-4-yl group,
3'-OCF₃-biPh-4-yl: 3'-trifluoromethoxybiphenyl-4-yl group,
3'-OCHF₂-biPh-4-yl: 3'-difluoromethoxybiphenyl-4-yl group,
3'-OCCl₃-biPh-4-yl: 3'-trichloromethoxybiphenyl-4-yl group,
3'-OCHCl₂-biPh-4-yl: 3'-dichloromethoxybiphenyl-4-yl group,
4-(Th-2-yl)Ph: 4-(thiophen-2-yl)phenyl group,
4-(Th-3-yl)Ph: 4-(thiophen-3-yl)phenyl group,
4-(Pyz-1-yl)Ph: 4-(pyrazol-1-yl)phenyl group,
4-(4-F-Pyz-1-yl)Ph: 4-(4-fluoropyrazol-1-yl)phenyl group,
4-(4-Cl-Pyz-1-yl)Ph: 4-(4-chloropyrazol-1-yl)phenyl group,
4-(Oxz-2-yl)Ph: 4-(oxazol-2-yl)phenyl group,
4-(Oxz-4-yl)Ph: 4-(oxazol-4-yl)phenyl group,
4-(Thz-2-yl)Ph: 4-(thiazol-2-yl)phenyl group,
4-(4-F-Thz-2-yl)Ph: 4-(4-fluorothiazol-2-yl)phenyl group,
4-(4-Cl-Thz-2-yl)Ph: 4-(4-chlorothiazol-2-yl)phenyl group,
4-(5-Cl-Thz-2-yl)Ph: 4-(5-chlorothiazol-2-yl)phenyl group,
4-(4-Me-Thz-2-yl)Ph: 4-(4-methylthiazol-2-yl)phenyl group,
4-(5-Me-Thz-2-yl)Ph: 4-(5-methylthiazol-2-yl)phenyl group,
4-(4,5-diMe-Thz-2-yl)Ph: 4-(4,5-dimethylthiazol-2-yl)phenyl group,
4-(4-Et-Thz-2-yl)Ph: 4-(4-ethylthiazol-2-yl)phenyl group,
4-(4-CF₃-Thz-2-yl)Ph: 4-(4-trifluoromethylthiazol-2-yl)phenyl group,
4-(4-OMe-Thz-2-yl)Ph: 4-(4-methoxythiazol-2-yl)phenyl group,
4-(4-OCHF₂-Thz-2-yl)Ph: 4-(4-difluoromethoxythiazol-2-yl)phenyl group,
4-(Thz-4-yl)Ph: 4-(thiazol-4-yl)phenyl group,
4-(2-F-Thz-4-yl)Ph: 4-(2-fluorothiazol-4-yl)phenyl group,
4-(2-Cl-Thz-4-yl)Ph: 4-(2-chlorothiazol-4-yl)phenyl group,
4-(2-Me-Thz-4-yl)Ph: 4-(2-methylthiazol-4-yl)phenyl group,
4-(2-Et-Thz-4-yl)Ph: 4-(2-ethylthiazol-4-yl)phenyl group,
4-(2-CF₃-Thz-4-yl)Ph: 4-(2-trifluoromethylthiazol-4-yl)phenyl group,
4-(2-OMe-Thz-4-yl)Ph: 4-(2-methoxythiazol-4-yl)phenyl group,
4-(2-OCHF₂-Thz-4-yl)Ph: 4-(2-difluoromethoxythiazol-4-yl)phenyl group,
4-(Thz-5-yl)Ph: 4-(thiazol-5-yl)phenyl group,
4-(1,2,4-Trz-1-yl)Ph: 4-(1,2,4-triazol-1-yl)phenyl group,
4-(Py-2-yl)Ph: 4-(pyridin-2-yl)phenyl group,
4-(Py-3-yl)Ph: 4-(pyridin-3-yl)phenyl group,
4-(Py-4-yl)Ph: 4-(pyridin-4-yl)phenyl group,
4-(Pyd-3-yl)Ph: 4-(pyridazin-3-yl)phenyl group,
4-(Pyd-4-yl)Ph: 4-(pyridazin-4-yl)phenyl group,
4-(Pym-2-yl)Ph: 4-(pyrimidin-2-yl)phenyl group,
4-(5-F-Pym-2-yl)Ph: 4-(5-fluoropyrimidin-2-yl)phenyl group,
4-(5-Cl-Pym-2-yl)Ph: 4-(5-chloropyrimidin-2-yl)phenyl group,
4-(5-OH-Pym-2-yl)Ph: 4-(5-hydroxypyrimidin-2-yl)phenyl group,
4-(Pym-4-yl)Ph: 4-(pyrimidin-4-yl)phenyl group,
4-(Pym-5-yl)Ph: 4-(pyrimidin-5-yl)phenyl group,
4-(4,5-diH-Thz-2-yl)Ph: 4-(4,5-dihydrothiazol-2-yl)phenyl group,
4-(Pyr-1-yl)Ph: 4-(pyrrolidin-1-yl)phenyl group,
4-(Pip-1-yl)Ph: 4-(piperidin-1-yl)phenyl group,
5-Ph-Th-2-yl: 5-phenylthiophen-2-yl group,
5-(Thz-2-yl)-Th-2-yl: 5-(thiazol-2-yl)thiophen-2-yl group,
5-(Thz-4-yl)-Th-2-yl: 5-(thiazol-4-yl)thiophen-2-yl group,
6-Ph-Pyd-3-yl: 6-phenylpyridazin-3-yl group,
6-(Thz-2-yl)-Pyd-3-yl: 6-(thiazol-2-yl)pyridazin-3-yl group,
6-(Thz-4-yl)-Pyd-3-yl: 6-(thiazol-4-yl)pyridazin-3-yl group,
2-Ph-Pym-4-yl: 2-phenylpyrimidin-4-yl group,
2-(Thz-2-yl)-Pym-4-yl: 2-(thiazol-2-yl)pyrimidin-4-yl group,
2-(Thz-4-yl)-Pym-4-yl: 2-(thiazol-4-yl)pyrimidin-4-yl group,
Ph: phenyl group,
2-F-Ph: 2-fluorophenyl group,
3-F-Ph: 3-fluorophenyl group,
4-F-Ph: 4-fluorophenyl group,
3,4-diF-Ph: 3,4-difluorophenyl group,
3,5-diF-Ph: 3,5-difluorophenyl group, 3,4,5-triF-Ph: 3,4,5-trifluorophenyl group,
2-Cl-Ph: 2-chlorophenyl group,
3-Cl-Ph: 3-chlorophenyl group,
4-Cl-Ph: 4-chlorophenyl group,
2,6-diCl-Ph: 2,6-dichlorophenyl group,
4-Cl-3-F-Ph: 4-chloro-3-fluorophenyl group,
4-Cl-3,5-diF-Ph: 4-chloro-3,5-difluorophenyl group,
4-Br-Ph: 4-bromophenyl group,
4-Me-Ph: 4-methylphenyl group,
3-F-4-Me-Ph: 3-fluoro-4-methylphenyl group,
4-Et-Ph: 4-ethylphenyl group,
4-Et-3-F-Ph: 4-ethyl-3-fluorophenyl group,
4-Pr-Ph: 4-propylphenyl group,
4-iPr-Ph: 4-isopropylphenyl group,
4-tBu-Ph: 4-tert-butylphenyl group,
4-CF$_3$-Ph: 4-trifluoromethylphenyl group,
3-F-4-CF$_3$-Ph: 3-fluoro-4-trifluoromethylphenyl group,
4-CHF$_2$-Ph: 4-difluoromethylphenyl group,
4-CCl$_3$-Ph: 4-trichloromethylphenyl group,
4-CHCl$_2$-Ph: 4-dichloromethylphenyl group,
4-CH$_2$CF$_3$-Ph: 4-(2,2,2-trifluoroethyl)phenyl group,
4-CH$_2$CO$_3$-Ph: 4-(2,2,2-trichloroethyl)phenyl group,
4-OMe-Ph: 4-methoxyphenyl group,
3-F-4-OMe-Ph: 3-fluoro-4-methoxyphenyl group,
4-OEt-Ph: 4-ethoxyphenyl group,
4-OPr-Ph: 4-propoxyphenyl group,
4-OiPr-Ph: 4-isopropoxyphenyl group,
4-OtBu-Ph: 4-tert-butoxyphenyl group,
4-OCF$_3$-Ph: 4-trifluoromethoxyphenyl group,
4-OCHF$_2$-Ph: 4-difluoromethoxyphenyl group,
4-OCHF$_2$-3-F-Ph: 4-difluoromethoxy-3-fluorophenyl group,
4-OCCl$_3$-Ph: 4-trichloromethoxyphenyl group,
4-OCHCl$_2$-Ph: 4-dichloromethoxyphenyl group,
Th-2-yl: thiophen-2-yl group,
Th-3-yl: thiophen-3-yl group,
5-Cl-Th-2-yl: 5-chlorothiophen-2-yl group,
1-Me-1H-Imz-4-yl: 1-methyl-1H-imidazol-4-yl group,
Thz-2-yl: thiazol-2-yl group,
Py-2-yl: pyridin-2-yl group,
5-F-Py-2-yl: 5-fluoropyridin-2-yl group,
5-Cl-Py-2-yl: 5-chloropyridin-2-yl group,
5-Me-Py-2-yl: 5-methylpyridin-2-yl group,
5-Et-Py-2-yl: 5-ethylpyridin-2-yl group,
5-CF$_3$-Py-2-yl: 5-trifluoromethylpyridin-2-yl group,
5-OMe-Py-2-yl: 5-methoxypyridin-2-yl group,
5-OCHF$_2$-Py-2-yl: 5-difluoromethoxypyridin-2-yl group,
Py-3-yl: pyridin-3-yl group,
6-F-Py-3-yl: 6-fluoropyridin-3-yl group,
6-Cl-Py-3-yl: 6-chloropyridin-3-yl group,
6-Me-Py-3-yl: 6-methylpyridin-3-yl group,
6-Et-Py-3-yl: 6-ethylpyridin-3-yl group,
6-CF$_3$-Py-3-yl: 6-trifluoromethylpyridin-3-yl group,
6-OMe-Py-3-yl: 6-methoxypyridin-3-yl group,
6-OCHF$_2$-Py-3-yl: 6-difluoromethoxypyridin-3-yl group,
Py-4-yl: pyridin-4-yl group or
Pym-2-yl: pyrimidin-2-yl group.

In the above table, a more preferred compound is that of compound No. 1, 2, 3, 4, 7, 8, 9, 10, 18, 24, 28, 36, 42, 43, 50, 56, 57, 82, 88, 89, 105, 106, 107, 108, 111, 112, 113, 114, 122, 128, 132, 140, 146, 147, 151, 157, 158, 159, 160, 161, 162, 165, 166, 167, 168, 176, 182, 186, 194, 200, 201, 208, 214, 215, 219, 225, 226, 230, 236, 237, 241, 247, 248, 261, 267, 268, 272, 278, 279, 309, 310, 311, 312, 313, 314, 316, 317, 318, 319, 320, 323, 324, 325, 326, 330, 331, 337, 338, 344, 345, 348, 349, 353, 354, 355, 359, 361, 362, 363, 367, 369, 374, 380, 381, 400, 406, 407, 411, 417, 418, 428, 434, 435, 439, 445, 446, 494, 495, 496, 497, 498, 499, 501, 502, 503, 504, 505, 508, 509, 510, 511, 515, 516, 522, 523, 529, 530, 533, 534, 538, 539, 540, 544, 546, 547, 548, 552, 554, 559, 565, 566, 570, 576, 577, 578, 579, 580, 581, 584, 585, 586, 587, 595, 601, 605, 613, 619, 620, 624, 630, 631, 635, 641, 642, 646, 652, 653, 654, 655, 656, 657, 660, 661, 662, 663, 671, 677, 681, 695, 701, 702, 706, 712, 713, 723, 729, 730, 734, 740, 741, 745, 751, 752, 765, 771, 772, 791, 797, 798, 817, 823, 824, 834, 840, 841, 845, 851, 852, 853, 854, 855, 856, 859, 860, 861, 862, 870, 876, 880, 894, 900, 901, 905, 911, 912, 914, 917, 920, 928, 931, 933, 934, 935, 936, 937, 938, 940, 941, 942, 943, 944, 947, 948, 949, 950, 954, 955, 961, 962, 968, 969, 972, 973, 977, 978, 979, 983, 985, 986, 987, 991, 993, 998, 1004, 1005, 1009, 1015, 1016, 1024, 1046, 1047, 1048, 1049, 1050, 1051, 1053, 1054, 1055, 1056, 1057, 1060, 1061, 1062, 1063, 1067, 1068, 1074, 1075, 1081, 1082, 1085, 1086, 1090, 1091, 1092, 1096, 1098, 1099, 1100, 1104, 1106, 1111, 1117, 1118, 1122, 1128, 1129, 1148, 1154, 1155, 1158, 1168, 1174, 1175, 1176, 1177, 1178, 1179, 1182, 1183, 1184, 1185, 1193, 1199, 1203, 1222, 1223, 1224, 1225, 1226, 1227, 1229, 1230, 1231, 1232, 1233, 1236, 1237, 1238, 1239, 1243, 1244, 1250, 1251, 1257, 1258, 1261, 1262, 1266, 1267, 1268, 1272, 1274, 1275, 1276, 1280, 1282, 1293, 1299, 1300, 1304, 1310, 1311, 1315, 1321, 1322, 1323, 1324, 1325, 1326, 1329, 1330, 1331, 1332, 1340, 1346, 1350, 1370, 1371, 1372, 1373, 1376, 1377, 1378, 1379, 1387, 1393, 1397, 1405, 1411, 1412, 1416, 1422, 1423, 1433, 1436, 1439, 1440, 1443, 1446, 1447, 1450, 1453, 1454, 1457, 1460, 1461, 1464, 1467, 1470, 1473, 1476, 1479, 1482, 1485, 1488 or 1491, an even more preferred compound is that of compound No. 1, 2, 3, 4, 7, 8, 9, 10, 18, 24, 28, 105, 106, 107, 108, 111, 112, 113, 114, 122, 128, 132, 159, 160, 161, 162, 165, 166, 167, 168, 176, 182, 186, 309, 310, 311, 312, 316, 317, 318, 319, 337, 353, 361, 494, 495, 496, 497, 501, 502, 503, 504, 522, 538, 546, 578, 579, 580, 581, 584, 585, 586, 587, 595, 601, 605, 654, 655, 656, 657, 660, 661, 662, 663, 671, 677, 681, 853, 854, 855, 856, 859, 860, 861, 862, 870, 876, 880, 914, 920, 933, 934, 935, 936, 940, 941, 942, 943, 961, 977, 985, 1024, 1046, 1047, 1048, 1049, 1053, 1054, 1055, 1056, 1074, 1090, 1098, 1158, 1176, 1177, 1178, 1179, 1182, 1183, 1184, 1185, 1193, 1199, 1203, 1222, 1223, 1224, 1225, 1229, 1230, 1231, 1232, 1250, 1266, 1274, 1323, 1324, 1325, 1326, 1329, 1330, 1331, 1332, 1340, 1346, 1350, 1370, 1371, 1372, 1373, 1376, 1377, 1378, 1379, 1387, 1393, 1397, 1433, 1439, 1446, 1453, 1461, 1467 or 1473, a particularly preferred compound is that of compound No. 4, 24, 28, 108, 128, 132, 162, 182, 186, 309, 312, 318, 353, 361, 494, 497, 503, 538, 546, 581, 601, 605, 657, 677, 681, 856, 876, 880, 914, 920, 933, 936, 942, 977, 985, 1024, 1046, 1049, 1055, 1090, 1098, 1158, 1179, 1199, 1203, 1222, 1225, 1231, 1266, 1274, 1326, 1346, 1350, 1373, 1393, 1397, 1433, 1439, 1446, 1453, 1461, 1467 or 1473, and a most preferred compound is that of
Compound No. 28: {6-[(benzofuran-2-ylmethyl)(pyridin-3-ylsulfonyl)aminomethyl]-pyridin-2-ylamino}acetic acid,
Compound No. 132: {6-[(benzo[b]thiophen-2-ylmethyl)(pyridin-3-ylsulfonyl)aminomethyl]pyridin-2-ylamino}acetic acid,
Compound No. 186: {6-[(6-chlorobenzo[b]thiophen-2-ylmethyl)(pyridin-3-ylsulfonyl)-aminomethyl]pyridin-2-ylamino}acetic acid,
Compound No. 361: {6-[(6-methoxybenzo[b]thiophen-2-ylmethyl)(pyridin-3-ylsulfonyl)aminomethyl]pyridin-2-ylamino}acetic acid,
Compound No. 538: {6-[(biphenyl-4-ylmethyl)(pyridin-2-ylsulfonyl)aminomethyl]-pyridin-2-ylamino}acetic acid,
Compound No. 546: {6-[(biphenyl-4-ylmethyl)(pyridin-3-ylsulfonyl)aminomethyl]-pyridin-2-ylamino}acetic acid, Compound No. 605: {6-[(4'-fluorobiphenyl-4-ylmethyl)(pyridin-3-ylsulfonyl)aminomethyl]pyridin-2-ylamino}acetic acid, Compound No. 681: {6-[(4'-chlorobiphenyl-4-ylmethyl)(pyridin-3-ylsulfonyl)aminomethyl]pyridin-2-ylamino}acetic acid, Compound No. 856: (6-{(4-fluorobenzenesulfonyl)[4-(pyrazol-1-yl)benzyl]aminomethyl}pyridin-2-ylamino)acetic acid, Compound No. 876: (6-{[4-(pyrazol-1-yl)benzyl](pyridin-2-ylsulfonyl)aminomethyl}-pyridin-2-ylamino)acetic acid, Compound No. 880: (6-{[4-(pyrazol-1-yl)benzyl](pyridin-3-ylsulfonyl)aminomethyl}-pyridin-2-ylamino)acetic acid, Compound No. 914: isopropyl (6-{(pyridin-2-ylsulfonyl)[4-(thiazol-2-yl)benzyl]aminomethyl}pyridin-2-ylamino)acetate, Compound No. 920: ethyl (6-{(pyridin-2-ylsulfonyl)[4-(thiazol-2-yl)benzyl]aminomethyl}pyridin-2-ylamino)acetate, Compound No. 936: (6-{(4-fluorobenzenesulfonyl)[4-(thiazol-2-yl)benzyl]aminomethyl}pyridin-2-ylamino)acetic acid, Compound No. 977: (6-{(pyridin-2-ylsulfonyl)[4-(thiazol-2-yl)benzyl]aminomethyl}-pyridin-2-ylamino)acetic acid, Compound No. 985: (6-{(pyridin-3-ylsulfonyl)[4-(thiazol-2-yl)benzyl]aminomethyl}-pyridin-2-ylamino)acetic acid, Compound No. 1024: (6-{(pyridin-2-ylsulfonyl)[4-(4-trifluoromethylthiazol-2-yl)-benzyl]aminomethyl}pyridin-2-ylamino)acetic acid, Compound No. 1090: (6-{(pyridin-2-ylsulfonyl) [4-(thiazol-4-yl)benzyl]aminomethyl}-pyridin-2-ylamino)acetic acid, Compound No. 1158: (6-{[4-(pyridin-2-yl)benzyl](pyridin-3-ylsulfonyl)aminomethyl}-pyridin-2-ylamino)acetic acid, Compound No. 1203: (6-{[4-(pyridazin-4-yl)benzyl](pyridin-3-ylsulfonyl)aminomethyl}pyridin-2-ylamino)acetic acid, Compound No. 1266: (6-{(pyridin-2-ylsulfonyl)[4-(pyrimidin-2-yl)benzyl]aminomethyl}pyridin-2-ylamino)acetic acid, Compound No. 1326: (6-{[4-(4,5-dihydrothiazol-2-yl)benzyl](4-fluorobenzenesulfonyl)aminomethyl}pyridin-2-ylamino)acetic acid, Compound No. 1397: {6-[(6-phenylpyridazin-3-ylmethyl)(pyridin-3-ylsulfonyl)aminomethyl]pyridin-2-ylamino}acetic acid, Compound No. 1433: hexyl (6-{(pyridin-2-ylsulfonyl) [4-(thiazol-2-yl)benzyl]aminomethyl}pyridin-2-ylamino)acetate, Compound No. 1439: (6-{[4-(5-chlorothiazol-2-yl)benzyl](pyridin-2-ylsulfonyl)aminomethyl}pyridin-2-ylamino) acetic acid, Compound No. 1446: (6-{[4-(5-methylthiazol-2-yl)benzyl](pyridin-2-ylsulfonyl)aminomethyl}pyridin-2-ylamino) acetic acid, Compound No. 1453: (6-{[4-(4,5-dimethylthiazol-2-yl)benzyl](pyridin-2-ylsulfonyl)-aminomethyl}pyridin-2-ylamino)acetic acid, Compound No. 1461: (6-{(pyridin-3-ylsulfonyl)[4-(1,2,4-triazol-1-yl)benzyl]aminomethyl}pyridin-2-ylamino)acetic acid, Compound No. 1467: ethyl (6-{[4-(pyrazol-1-yl)benzyl](pyridin-3-ylsulfonyl)aminomethyl}pyridin-2-ylamino)acetate or Compound No. 1473: isopropyl (6-{[4-(pyrazol-1-yl)benzyl](pyridin-3-ylsulfonyl)-aminomethyl}pyridin-2-ylamino) acetate.

A compound represented by the formula (1) of the present invention can be prepared by the following methods:

[Preparation Method 1]

"Preparation Method 1" is a method for preparing a compound (1a) of the present invention, in which $R^1$ in the formula (1) is a hydrogen atom, and a compound (1b) of the present invention, in which $R^1$ in the formula (1) is a $C_1$-$C_6$ alkyl group:

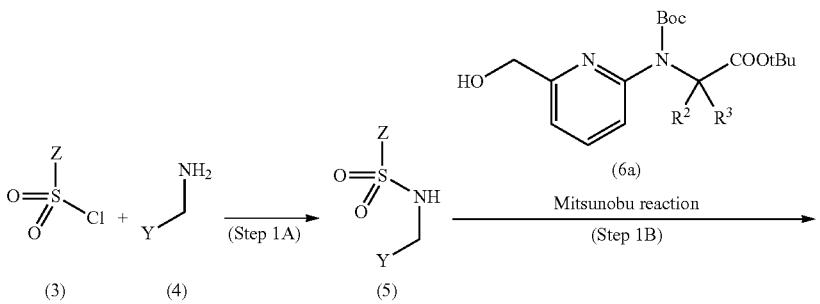

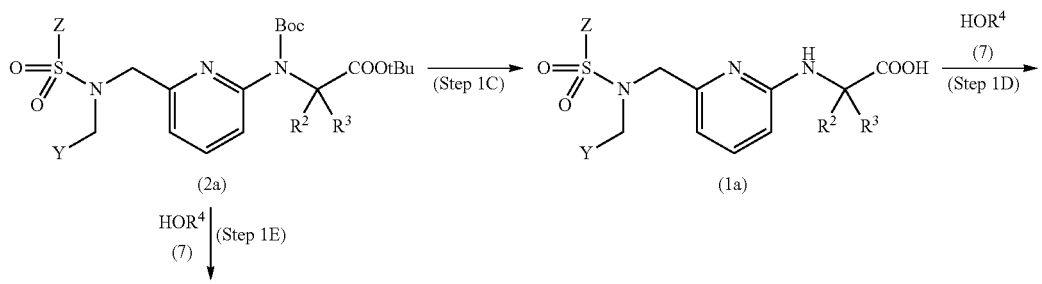

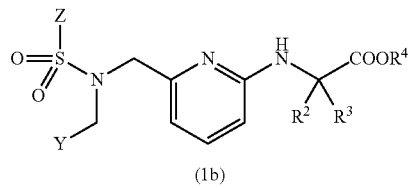

(1b)

[wherein $R^2$, $R^3$, Y and Z are the same as previously defined, $R^4$ represents a $C_1$-$C_6$ alkyl group that is the same as previously defined, Boc represents a tert-butoxycarbonyl group, and tBu represents a tert-butyl group].

"Step 1A" is a step for preparing a sulfonamide compound (5) by reacting a chlorosulfonyl compound (3) and an amine compound (4) in an inert solvent and in the presence or absence (and preferably in the presence) of a base.

The compound (3) and the compound (4) are known or can be prepared in compliance with known methods from known compounds.

Although there are no particular limitations on the inert solvent used provided it does not inhibit the reaction and dissolves the raw materials to a certain degree, examples include aromatic hydrocarbons such as benzene, toluene and xylene; halogenated aliphatic hydrocarbons such as methylene chloride, chloroform and 1,2-dichloroethane; ethers such as 1,4-dioxane, tetrahydrofuran, diethyl ether and 1,2-dimethoxyethane; amides such as N,N-dimethylformamide, N,N-dimethylacetamide and N-methylpyrrolidone; nitriles such as acetonitrile and propionitrile; and arbitrary mixed solvents thereof, and preferably methylene chloride, 1,2-dichloroethane, N,N-dimethylformamide, acetonitrile or a mixed solvent thereof.

Examples of bases used include organic bases such as triethylamine and diisopropylethylamine, and inorganic bases such as sodium hydrogen carbonate, potassium hydrogen carbonate, sodium carbonate and potassium carbonate, and preferably triethylamine or diisopropylethylamine. A molar amount of the base used is generally 0.9 to 20-fold and preferably 1 to 10-fold based on 1 mol of the compound (3).

A molar amount of the compound (4) used is generally 0.7 to 5-fold and preferably 0.8 to 1.5-fold based on 1 mol of the compound (3).

Although varying according to the types and amounts used of the raw materials, solvent and the like, the reaction temperature is normally −20 to 100° C. and preferably −5 to 50° C.

Although varying according to the reaction temperature and the like, the reaction time is normally 1 minute to 36 hours and preferably 1 hour to 18 hours.

"Step 1B" is a so-called Mitsunobu reaction, and is a step in which an intermediate compound (2a) is prepared by reacting the compound (5) and a hydroxymethylpyridine compound (6a) in an inert solvent and in the presence of a phosphine compound and an azo compound.

Compound (6a) is a compound that is included in a hydroxymethylpyridine compound (6) that can be prepared according to "Preparation Method 11" to be described later.

Although there are no particular limitations on the inert solvent used provided it does not inhibit the reaction and dissolves the raw materials to a certain degree, examples include aromatic hydrocarbons such as benzene, toluene and xylene; ethers such as diethyl ether, tetrahydrofuran, 1,4-dioxane and 1,2-dimethoxyethane; amides such as N,N-dimethylformamide, N,N-dimethylacetamide and N-methylpyrrolidone; nitriles such as acetonitrile and propionitrile; esters such as methyl acetate, ethyl acetate and isopropyl acetate; and arbitrary mixed solvents thereof, and preferably tetrahydrofuran, N,N-dimethylformamide, acetonitrile or a mixed solvent thereof.

Examples of the phosphine compound used include trimethylphosphine, triethylphosphine, tri-n-butylphosphine or triphenylphosphine, and preferably tri-n-butylphosphine or triphenylphosphine. A molar amount of the phosphine compound used is generally 0.9 to 10-fold and preferably 1 to 5-fold based on 1 mol of the compound (5).

Examples of the azo compound used include diethylazodicarboxylate (DEAD), diisopropylazodicarboxylate (DIAD), N,N,N',N'-tetraisopropylazodicarboxamide (TIPA), 1,1'-(azodicarbonyl)dipiperidine (ADDP), N,N,N',N'-tetramethylazodicarboxamide (TMAD) and 1,6-dimethyl-1,5,7-hexahydro-1,4,6,7-tetrazocin-2,5-dione (DHTD), and preferably diethylazodicarboxylate (DEAD) or N,N,N',N'-tetramethylazodicarboxamide (TMAD). A molar amount of the azo compound used is generally 0.9 to 10-fold and preferably 1 to 5-fold based on 1 mol of the compound (5).

A molar amount of the compound (6a) used is generally 0.8 to 2-fold and preferably 0.9 to 1.5-fold based on 1 mol of the compound (5).

Although varying according to the types and amounts used of the raw materials, solvent and the like, the reaction temperature is normally −20° C. to 100° C. and preferably −5° C. to 50° C.

Although varying according to the reaction temperature and the like, the reaction time is normally 30 minutes to 48 hours and preferably 1 hour to 24 hours.

"Step 1C" is a step for preparing the compound (1a) by simultaneously removing the Boc group and tBu group of the compound (2a). This step can be carried out by referring to the literature (see T. W. Greene & P. G. M. Wuts, Protective Groups in Organic Synthesis, 4th Ed., John Wiley & Sons, Inc., pp. 582 and 725), and although it can be carried out by, for example, treating the compound (2a) with an acid in an inert solvent, the method used is not limited thereto.

Although there are no particular limitations on the inert solvent used provided it does not inhibit the reaction and dissolves the raw materials to a certain degree, examples include ethers such as tetrahydrofuran, 1,4-dioxane and 1,2-dimethoxyethane; halogenated aliphatic hydrocarbons such as methylene chloride, chloroform and 1,2-dichloroethane; organic acids such as formic acid, acetic acid, propionic acid or trifluoroacetic acid; water; and arbitrary mixed solvents thereof, and preferably tetrahydrofuran, 1,4-dioxane, methylene chloride, water or a mixed solvent thereof.

Examples of the acid used include hydrogen chloride, hydrochloric acid, hydrobromic acid, hydroiodic acid, sulfuric acid, phosphoric acid, p-toluenesulfonic acid, methanesulfonic acid and trifluoroacetic acid, and preferably hydrogen chloride, hydrochloric acid or trifluoroacetic acid. A molar amount of the acid used is generally 1 to 200-fold and preferably 5 to 100-fold based on 1 mol of the compound (2a).

An anisole compound such as anisole or thioanisole may be added to accelerate the reaction. A molar amount of anisole compound used is generally 1 to 200-fold and preferably 5 to 100-fold based on 1 mol of the compound (2a).

Although varying according to the types and amounts used of the raw materials, solvent and the like, the reaction temperature is normally 0° C. to 150° C. and preferably 5° C. to 100° C.

Although varying according to the reaction temperature and the like, the reaction time is normally 10 minutes to 48 hours and preferably 1 hour to 24 hours.

"Step 1D" is a step for preparing the compound (1b) by esterifying the carboxyl group of the compound (1a). This step can be carried out by referring to the literature (see T. W. Greene & P. G. M. Wuts, Protective Groups in Organic Synthesis, 4th Ed., John Wiley & Sons, Inc., p. 538). Although this step can be carried out by reacting the compound (1a) with the compound (7) in the presence of an acid or after activating the carboxyl group of the compound (1a), the method used is not limited thereto.

The compound (7) is known or can be prepared in compliance with a known method from a known compound.

In the case the reaction of "Step 1D" is carried out in the presence of an acid, the reaction with the compound (7) can be carried out in an inert solvent or in the absence of a solvent and in the presence of an acid.

Although there are no particular limitations on the inert solvent used provided it does not inhibit the reaction and dissolves the raw materials to a certain degree, examples include aromatic hydrocarbons such as benzene, toluene and xylene; ethers such as tetrahydrofuran, 1,4-dioxane and 1,2-dimethoxyethane; halogenated aliphatic hydrocarbons such as methylene chloride, chloroform and 1,2-dichloroethane; and arbitrary mixed solvents thereof, and preferably 1,4-dioxane, methylene chloride, 1,2-dichloroethane or a mixed solvent thereof.

Examples of the acid used include hydrogen chloride, sulfuric acid, methanesulfonic acid, p-toluenesulfonic acid and trifluoroacetic acid, and preferably hydrogen chloride, sulfuric acid or p-toluenesulfonic acid. A molar amount of the acid used is generally 1 to 200-fold and preferably 1 to 100-fold based on 1 mol of the compound (1a).

Although the amount of the compound (7) used is generally 1 to 100-fold and preferably 1 to 5-fold based on 1 mol of the compound (1a), it can also be used in excess as a solvent.

Although varying according to the types and amounts used of the raw materials, solvent and the like, the reaction temperature is normally −20° C. to 150° C. and preferably −5° C. to 100° C.

Although varying according to the reaction temperature and the like, the reaction time is normally 1 minute to 72 hours and preferably 1 hour to 48 hours.

In the case the reaction of "Step 1D" is carried out by activating the carboxyl group of the compound (1a), it is carried out by converting the carboxyl group to "an active form of a carboxy group" such as an acid chloride, mixed acid anhydride and imidazolide in an inert solvent or in the absence of a solvent and using an activating agent, followed by reacting with the compound (7) in the presence or absence (and preferably in the presence) of a base. Furthermore, "the active form of a carboxy group" obtained by this reaction can be used in the reaction with the compound (7) without isolating.

Although there are no particular limitations on the inert solvent used provided it does not inhibit the reaction and dissolves the raw materials to a certain degree, examples include aromatic hydrocarbons such as benzene, toluene and xylene; halogenated aliphatic hydrocarbons such as methylene chloride, chloroform and 1,2-dichloroethane; ethers such as tetrahydrofuran, 1,2-dimethoxyethane and 1,4-dioxane; nitriles such as acetonitrile and propionitrile; amides such as N,N-dimethylformamide, N,N-dimethylacetamide and N-methylpyrrolidone; and arbitrary mixed solvents thereof, and preferably methylene chloride, tetrahydrofuran or acetonitrile.

Examples of the carboxy group activating agent include chlorides such as thionyl chloride, oxalyl chloride, phosphorous oxychloride and phosphorous pentachloride; 1,1′-carbonyldiimidazole; and chloroformic acid esters such as methyl chloroformate and ethyl chloroformate; and preferably thionyl chloride or 1,1′-carbonyldiimidazole. A molar amount of the activating agent used is generally 1 to 5-fold and preferably 1 to 1.5-fold based on 1 mol of the compound (1a).

Examples of the base used include organic bases such as triethylamine and diisopropylethylamine; and inorganic bases such as sodium hydrogen carbonate, potassium hydrogen carbonate, sodium carbonate and potassium carbonate, and preferably triethylamine or diisopropylethylamine. A molar amount of the base used is generally 1 to 100-fold and preferably 1 to 10-fold based on 1 mol of the compound (1a).

A molar amount of the compound (7) used is generally 1 to 100-fold and preferably 1 to 5-fold based on 1 mol of the compound (1a).

Although varying according to the types and amounts used of the raw materials, solvent and the like, the reaction temperature is normally −20° C. to 150° C. and preferably −5° C. to 100° C.

Although varying according to the reaction temperature and the like, the reaction time is normally 1 minute to 24 hours and preferably 1 hour to 12 hours.

"Step 1E" is a step for preparing the compound (1b) by removing the Boc group of the compound (2a) and simultaneously converting the tBu group to $R^4$. This step is carried out in compliance with the case of reacting in the presence of an acid in the aforementioned "Step 1D".

[Preparation Method 2]

Preparation Method 2 is another method for preparing the aforementioned the compound (1b).

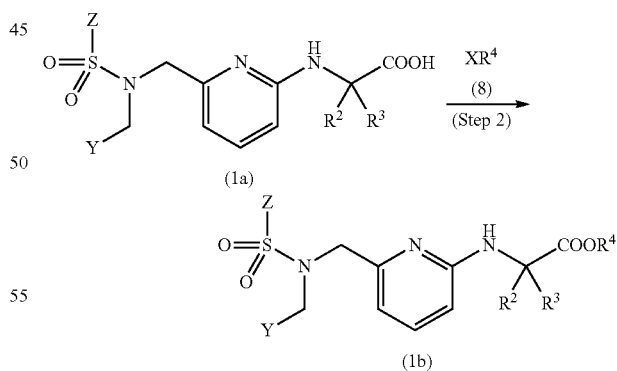

[wherein $R^2$, $R^3$, $R^4$, Y and Z are the same as previously defined, and X represents a chlorine atom, a bromine atom, an iodine atom, a methanesulfonyloxy group, a benzenesulfonyloxy group, a p-toluenesulfonyloxy group or a trifluoromethanesulfonyloxy group].

"Step 2" is carried out by reacting the compound (1a) and an alkylating agent (8) in an inert solvent and in the presence of a base.

The alkylating agent (8) is known or can be prepared in compliance with a known method from a known compound.

Although there are no particular limitations on the inert solvent used provided it does not inhibit the reaction and dissolves the raw materials to a certain degree, examples include aromatic hydrocarbons such as benzene, toluene and xylene; halogenated aliphatic hydrocarbons such as methylene chloride, chloroform and 1,2-dichloroethane; ethers such as diethyl ether, tetrahydrofuran, 1,4-dioxane and 1,2-dimethoxyethane; ketones such as acetone, methyl ethyl ketone, methyl isobutyl ketone and methyl tert-butyl ketone; amides such as N,N-dimethylformamide, N,N-dimethylacetamide and N-methylpyrrolidone; nitriles such as acetonitrile and propionitrile; and arbitrary mixed solvents thereof, and preferably methylene chloride, 1,2-dichloroethane, acetone, N,N-dimethylformamide, acetonitrile or a mixed solvent thereof.

Examples of the base used include organic bases such as triethylamine, diisopropylethylamine, pyridine, 4-dimethylaminopyridine or picoline, and inorganic bases such as sodium hydrogen carbonate, potassium hydrogen carbonate, sodium carbonate and potassium carbonate, and preferably triethylamine, diisopropylethylamine or potassium carbonate. A molar amount of the base used is generally 1 to 100-fold and preferably 1 to 10-fold based on t 1 mol of the compound (1a).

A molar amount of the alkylating agent (8) used is generally 0.9 to 10-fold and preferably 1 to 1.5-fold based on 1 mol of the compound (1a).

Although varying according to the types and amounts used of the raw materials, solvent and the like, the reaction temperature is normally −20° C. to 100° C. and preferably −5° C. to 60° C.

Although varying according to the reaction temperature and the like, the reaction time is normally 1 minute to 24 hours and preferably 1 hour to 6 hours.

[Preparation Method 3]

Preparation Method 3 is another method for preparing the compound (1a') of the present invention in which Y is $Y^1$ and Z is $Z^1$ in the aforementioned the compound (1a).

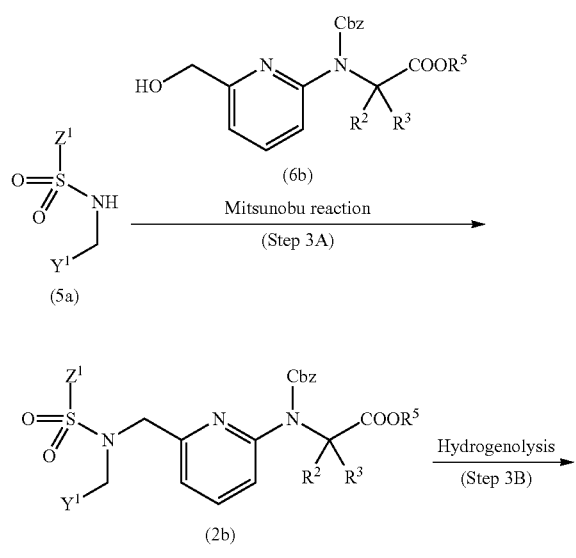

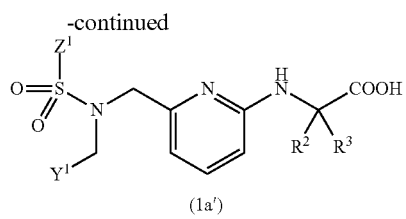

[wherein $R^2$ and $R^3$ are the same as previously defined, $R^5$ represents a benzyl group or a p-methoxybenzyl group, $Y^1$ represents a bicyclic heteroaromatic group, which may be substituted with a group(s) selected from the group consisting of a fluorine atom, a $C_1$-$C_6$ alkyl group, a fluoro-$C_1$-$C_6$ alkyl group, a $C_1$-$C_6$ alkoxy group, a fluoro-$C_1$-$C_6$ alkoxy group and a $C_1$-$C_6$ alkylthio group, or a -$Q^1$-$Q^{2'}$ group (wherein $Q^1$ is the same as previously defined and $Q^{2'}$ represents an aromatic group or a 5- to 6-membered heterocyclic group, each of which may be optionally substituted with a group(s) selected from the group consisting of a fluorine atom, a hydroxy group, a $C_1$-$C_6$ alkyl group, a fluoro-$C_1$-$C_6$ alkyl group, a $C_1$-$C_6$ alkoxy group and a fluoro-$C_1$-$C_6$ alkoxy group), $Z^1$ represents an aromatic group or a 5- to 6-membered heteroaromatic group, each of which may be substituted with a group(s) selected from the group consisting of a fluorine atom, a $C_1$-$C_6$ alkyl group, a fluoro-$C_1$-$C_6$ alkyl group, a $C_1$-$C_6$ alkoxy group and a fluoro-$C_1$-$C_6$ alkoxy group, and Cbz represents a benzyloxycarbonyl group].

"Step 3A" is a so-called Mitsunobu reaction, and is a step for preparing an intermediate compound (2b) by reacting a sulfonamide compound (5a) and a hydroxydimethylpyridine compound (6b) in an inert solvent and in the presence of a phosphine compound and an azo compound. This step is carried out in compliance with the aforementioned "Step 1B" except for using the compound (5a) in place of the compound (5) and the compound (6b) in place of the compound (6a), respectively.

The compound (5a) is a compound in which Y is $Y^1$ and Z is $Z^1$ in the compound (5) that can be prepared according the aforementioned "Step 1A". The compound (6b) is a compound that is included in the compound (6) that can be prepared according the Preparation Method 11 to be described later.

"Step 3B" is step for preparing the compound (1a') by simultaneously removing the Cbz group and $R^2$ group of the compound (2b) by a hydrogenolysis reaction. This step is carried out by reacting the compound (2b) with hydrogen in an inert solvent and in the presence of a catalyst.

Although there are no particular limitations on the inert solvent used provided it does not inhibit the reaction and dissolves the raw materials to a certain degree, examples include alcohols such as methanol, ethanol, propanol and isopropanol; ethers such as tetrahydrofuran, 1,4-dioxane and 1,2-dimethoxyethane; halogenated aliphatic hydrocarbons such as methylene chloride, chloroform and 1,2-dichloroethane; esters such as methyl formate, ethyl formate, methyl acetate and ethyl acetate; aromatic hydrocarbons such as benzene and toluene; water; and arbitrary mixed solvents thereof, and preferably methanol or ethanol.

Examples of the catalyst used include palladium-activated carbon, platinum-activated carbon, platinum black, rhodium-activated carbon and Raney nickel, and preferably palladium-activated carbon, platinum black or Raney nickel. A molar amount of the catalyst used is generally 0.0005 to 1-fold and preferably 0.01 to 0.3-fold based on 1 mol of the compound (2b).

Hydrogen partial pressure of the hydrogenolysis conditions is normally 1 atm to 10 atm and preferably 1 atm to 5 atm.

Although varying according to the types and amounts used of the raw materials, solvent and the like, the reaction temperature is normally 0° C. to 100° C. and preferably 15° C. to 80° C.

Although varying according to the reaction temperature and the like, the reaction time is normally 15 minutes to 72 hours and preferably 30 minutes to 48 hours.

[Preparation Method 4]

"Preparation Method 4" is another method for preparing the aforementioned compound (1a), compound (1b) and compound (1a'), and a compound (1b') in which Y is $Y^1$ and Z is $Z^1$ in the formula (1b). This preparation method is composed of steps for preparing the compound (1b) by removing the Boc group from an intermediate compound (2d) and then preparing the compound (1a) by an ester hydrogenolysis reaction (Step 4B1 to Step 4C1), and steps for preparing the compound (1b') by removing the Cbz group from an intermediate compound (2e) and then preparing the compound (1a') by an ester hydrolysis reaction (Step 4B2 to Step 4C2).

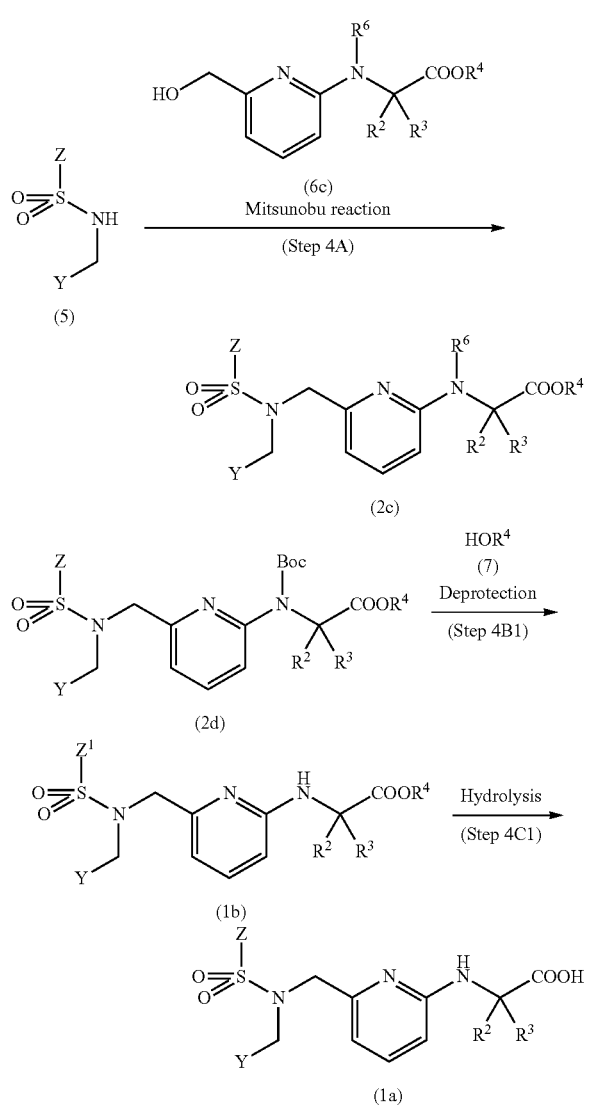

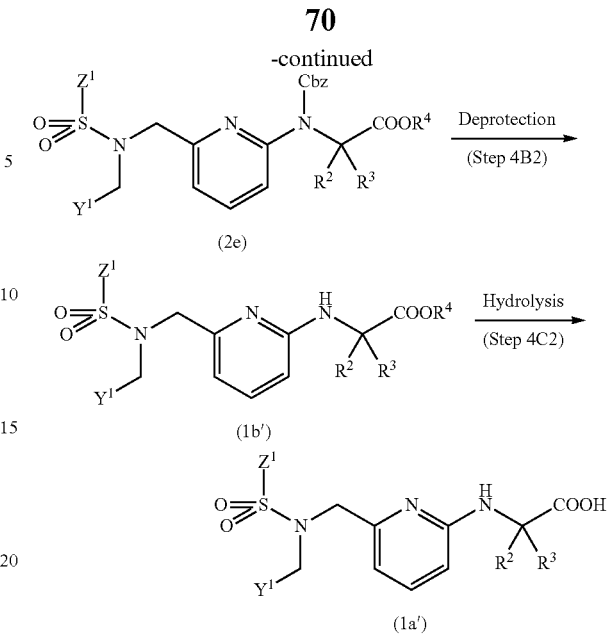

[wherein $R^2$, $R^3$, $R^4$, Y, Z, $Y^1$ and $Z^1$ are the same as previously defined, and $R^6$ represents a Boc group or a Cbz group].

"Step 4A" is a so-called Mitsunobu reaction, and is a step for preparing an intermediate compound (2c) by reacting the compound (5) and a hydroxymethylpyridine compound (6c) in an inert solvent and in the presence of a phosphine compound and an azo compound. This step is carried out in compliance with the aforementioned "Step 1B" except for using the compound (6c) in place of the compound (6a).

The compound (6c) is a compound that is included in the compound (6) that can be prepared according to "Preparation Method 11" to be described later.

"Step 4B1" is carried out by treating the compound (2d) with an acid in an inert solvent or in the absence of solvent and in the presence of the compound (7).

Although there are no particular limitations on the inert solvent used provided it does not inhibit the reaction and dissolves the raw materials to a certain degree, examples include aromatic hydrocarbons such as benzene, toluene and xylene; ethers such as tetrahydrofuran, 1,4-dioxane and 1,2-dimethoxyethane; halogenated aliphatic hydrocarbons such as methylene chloride, chloroform and 1,2-dichloroethane; and arbitrary mixed solvents thereof, and preferably 1,4-dioxane, methylene chloride, 1,2-dichloroethane or a mixed solvent thereof.

A molar amount of the compound (7) used is generally 1 to 1000-fold and preferably 10 to 100-fold based on 1 mol of the compound (2d).

Examples of the acid used include hydrogen chloride, hydrochloric acid, sulfuric acid, methanesulfonic acid, p-toluenesulfonic acid and trifluoroacetic acid, and preferably hydrogen chloride, sulfuric acid or p-toluenesulfonic acid. A molar amount of the acid used is generally 1 to 200-fold and preferably 1.5 to 100-fold based on 1 mol of the compound (2d).

Although varying according to the types and amounts used of the raw materials, solvent and the like, the reaction temperature is normally −20° C. to 150° C. and preferably −5° C. to 100° C.

Although varying according to the reaction temperature and the like, the reaction time is normally 30 minutes to 72 hours and preferably 1 hour to 48 hours.

"Step 4C1" is a step for preparing the compound (1a) by an ester hydrolysis reaction of the compound (1b). This step is carried out under acidic conditions or basic conditions.

In the case where "Step 4C1" is carried out under acidic conditions, it is carried out by treating the compound (1b) with an acid in an organic solvent and in the presence of water.

Although there are no particular limitations on the inert solvent used provided it does not inhibit the reaction and dissolves the raw materials to a certain degree, examples include alcohols such as methanol, ethanol, propanol and isopropanol; ethers such as tetrahydrofuran, 1,4-dioxane and 1,2-dimethoxyethane; acetic acid; and arbitrary mixed solvents thereof, and preferably methanol, ethanol, tetrahydrofuran, acetic acid or a mixed solvent thereof.

Although a molar amount of water used is generally 10 to 1000-fold based on 1 mol of the compound (1b), it can also be used in excess as a solvent.

Examples of the acid used include inorganic acids such as hydrochloric acid, hydrobromic acid, hydroiodic acid, sulfuric acid and phosphoric acid; and sulfonic acids such as methanesulfonic acid, benzenesulfonic acid and p-toluenesulfonic acid, and preferably hydrochloric acid, hydrobromic acid or sulfuric acid. A molar amount of the acid used is generally 1 to 1000-fold and preferably 10 to 100-fold based on 1 mol of the compound (1b).

Although varying according to the types and amounts used of the raw materials, solvent and the like, the reaction temperature is normally −5° C. to 150° C. and preferably 0° C. to 100° C.

Although varying according to the reaction temperature and the like, the reaction time is normally 15 minutes to 72 hours and preferably 30 minutes to 48 hours.

"Step 4C1" is carried out by treating the compound (1b) with a base in an organic solvent and in the presence of water in the case it is carried out under basic conditions.

Although there are no particular limitations on the solvent used provided it does not inhibit the reaction and dissolves the raw materials to a certain degree, examples include alcohols such as methanol, ethanol, propanol and isopropanol; ethers such as tetrahydrofuran, 1,4-dioxane and 1,2-dimethoxyethane; and arbitrary mixed solvents thereof, and preferably methanol, ethanol, tetrahydrofuran or a mixed solvent thereof.

Although a molar amount of water used is generally 10 to 1000-fold based on 1 mol of the compound (1b), it can also be used in excess as a solvent.

Examples of the base used include alkali metal hydroxides such as lithium hydroxide, sodium hydroxide and potassium hydroxide; and alkali metal carbonates such as sodium carbonate and potassium carbonate, and preferably lithium hydroxide, sodium hydroxide or potassium hydroxide. A molar amount of the base used is generally 0.9 to 10-fold and preferably 1 to 5-fold based on 1 mol of the compound (1b).

Although varying according to the types and amounts used of the raw materials, solvent and the like, the reaction temperature is normally −5° C. to 150° C. and preferably 0° C. to 80° C.

Although varying according to the reaction temperature and the like, the reaction time is normally 15 minutes to 72 hours and preferably 30 minutes to 48 hours.

"Step 4B2" is a step for preparing the compound (1b') by reacting the compound (2e) with hydrogen in an inert solvent and in the presence of a catalyst. This step is carried out in compliance with the aforementioned "Step 3B" except for using the compound (2e) in place of the compound (2b).

"Step 4C2" is a step for preparing the compound (1a') by an ester hydrolysis reaction of the compound (1b'), and is carried out under acidic conditions or basic conditions. This step is carried out in compliance with the aforementioned "Step 4C1" except for using the compound (1b') in place of the compound (1b).

[Preparation Method 5]

"Preparation Method 5" is a typical preparation method for preparing the intermediate compound (2).

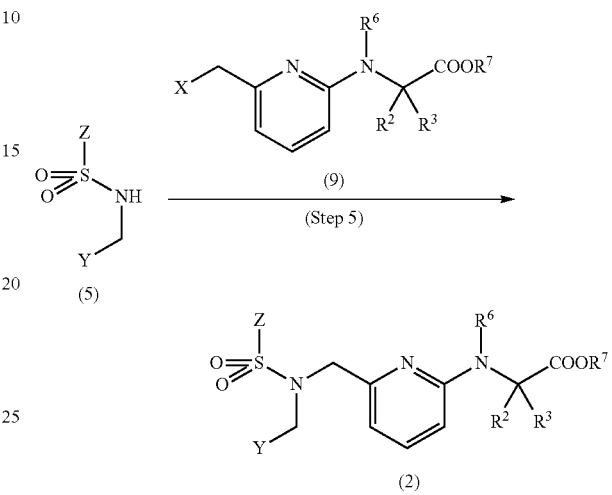

[wherein $R^2$, $R^3$, $R^6$, X, Y and Z are the same as previously defined, and $R^7$ represents a $C_1$-$C_6$ alkyl, a benzyl group or a p-methoxybenzyl group as previously defined].

"Step 5" is a step for preparing the compound (2) by reacting the compound (5) and a compound (9) in an inert solvent and in the presence of a base.

The compound (9) can be prepared according to "Preparation Method 15" to be described later.

Although there are no particular limitations on the inert solvent used provided it does not inhibit the reaction and dissolves the raw materials to a certain degree, examples include ethers such as tetrahydrofuran, 1,4-dioxane and 1,2-dimethoxyethane; halogenated aliphatic hydrocarbons such as methylene chloride, chloroform and 1,2-dichloroethane; nitriles such as acetonitrile and propionitrile; esters such as methyl formate, ethyl formate, methyl acetate and ethyl acetate; aromatic hydrocarbons such as benzene and toluene; amides such as N,N-dimethylformamide, N,N-dimethylacetamide and N-methylpyrrolidone; sulfoxides such as dimethylsulfoxide; and arbitrary mixed solvents thereof, and preferably tetrahydrofuran, N,N-dimethylformamide, methylene chloride or 1,2-dichloroethane.

Examples of the base used include alkali metal hydrides such as sodium hydride and potassium hydride; alkali metal amides such as lithium amide, sodium amide, lithium diisopropylamide and lithium bistrimethylsilylamide; alkali metal alkoxides such as sodium methoxide, sodium ethoxide, sodium tert-butoxide and potassium tert-butoxide; alkali metal carbonates such as sodium carbonate and potassium carbonate; and amines such as triethylamine, tributylamine, diisopropylethylamine, pyridine, picoline, 2,6-lutidine and 4-dimethylaminopyridine, and preferably sodium hydride, potassium carbonate, triethylamine or diisopropylethylamine. However, in the case the inert solvent used is an ester, nitrile or halogenated aliphatic hydrocarbon, the base is preferably triethylamine or diisopropylethylamine. A molar of the base used is generally 1 to 5-fold and preferably 1 to 2.5-fold based on 1 mol of the compound (5).

A molar amount of the compound (9) used is generally 0.5 to 3-fold and preferably 0.5 to 1.5-fold based on 1 mol of the compound (5).

Although varying according to the types and amounts used of the raw materials, solvent and the like, the reaction temperature is normally −80° C. to 100° C. and preferably 0° C. to 80° C.

Although varying according to the reaction temperature and the like, the reaction time is normally 10 minutes to 48 hours and preferably 1 hour to 24 hours.

[Preparation Method 6]

"Preparation Method 6" is another method for preparing the compound (2d) in which $R^6$ is a Boc group and $R^7$ is $R^4$ in the aforementioned compound (2).

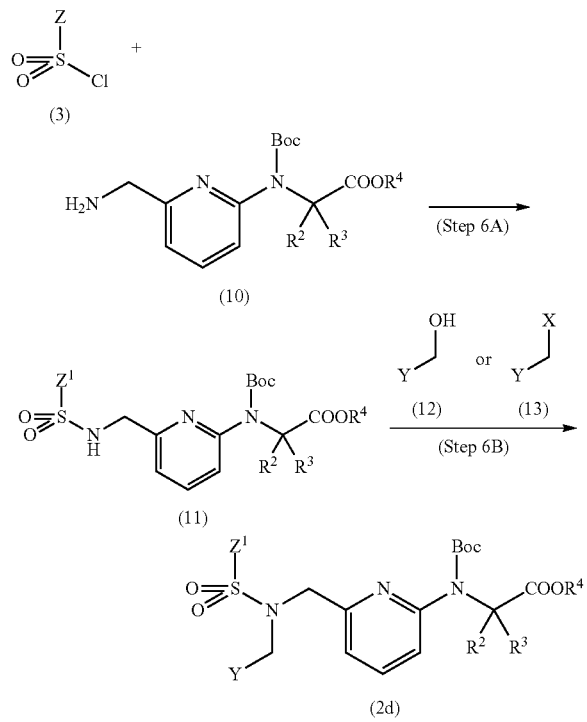

[wherein $R^2$, $R^3$, $R^4$, X, Y and Z are the same as previously defined].

"Step 6A" is a step for preparing a sulfonylaminomethylpyridine compound (11) by reacting the compound (3) and an aminomethylpyridine compound (10) in an inert solvent and in the presence or absence (and preferably in the presence) of a base. This step is carried out in compliance with the aforementioned "Step 1A" except for using the compound (10) in place of the compound (4).

The compound (10) can be prepared according to "Preparation Method 14" to be described later.

"Step 6B" is a step for preparing the compound (2d) by reacting the compound (11) with a hydroxy compound (12) or a compound (13).

In the case of using the compound (12), "Step 6B" is a so-called Mitsunobu reaction, and is carried out in an inert solvent and in the presence of a phosphine compound and an azo compound. This is carried out in compliance with the aforementioned "Step 1B" except for using the compound (11) in place of the compound (5) and the compound (12) in place of the compound (6a), respectively.

The compound (12) is either known or can be prepared in compliance with a known method from a known compound.

In the case of using the compound (13), "Step 6B" is carried out by reacting the compound (11) and the compound (13) in an inert solvent and in the presence of a base. This step is carried out in compliance with the aforementioned "Step 5" except for using the compound (11) in place of the compound (5) and the compound (13) in place of the compound (9), respectively.

The compound (13) is known or can be prepared in compliance with a known method from a known compound.

[Preparation Method 7]

"Preparation Method 7" is another method for preparing an intermediate compound (2f) in which $R^6$ is a Boc group, $R^7$ is $R^4$, Y is $Y^1$ and Z is $Z^1$ in the aforementioned compound (2).

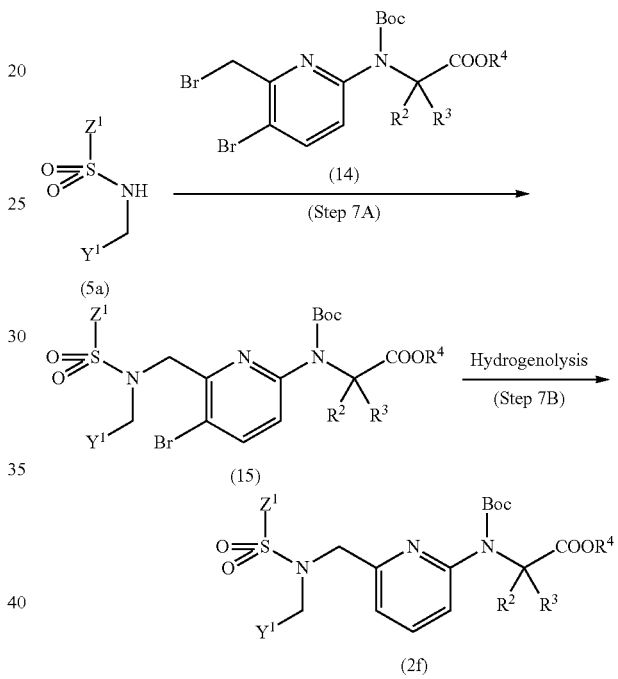

[wherein $R^2$, $R^3$, $R^4$, $Y^1$ and $Z^1$ are the same as previously defined].

"Step 7A" is a step for preparing an intermediate compound (15) by reacting the compound (5a) with a bromomethylpyridine compound (14) in an inert solvent and in the presence of a base. This step is carried out in compliance with the aforementioned "Step 5" except for using the compound (5a) in place of the compound (5) and the compound (14) in place of the compound (9), respectively.

The compound (14) can be prepared according to "Preparation Method 16" to be described later.

"Step 7B" is a step for preparing the compound (2f) by reacting the compound (15) with hydrogen in an inert solvent, in the presence or absence (and preferably in the presence) of a base, and in the presence of a catalyst.

Although there are no particular limitations on the inert solvent used provided it does not inhibit the reaction and dissolves the raw materials to a certain degree, examples include alcohols such as methanol, ethanol, propanol and isopropanol; ethers such as tetrahydrofuran, 1,4-dioxane and 1,2-dimethoxyethane; halogenated aliphatic hydrocarbons such as methylene chloride, chloroform and 1,2-dichloroethane; esters such as methyl formate, ethyl formate, methyl acetate and ethyl acetate; aromatic hydrocarbons such as benzene and toluene; water; and arbitrary mixed solvents thereof, and preferably methanol or ethanol.

Examples of the base used include organic bases such as triethylamine, diisopropylethylamine, pyridine, 4-dimethylaminopyridine, picoline and 2,6-lutidine, and inorganic bases such as sodium hydrogen carbonate, potassium hydrogen carbonate, sodium carbonate and potassium carbonate, and preferably triethylamine or diisopropylethylamine. A molar amount of the based used is generally 1 to 100-fold and preferably 1 to 10-fold based on 1 mol of the compound (15).

Examples of the catalyst used include palladium-activated carbon, platinum-activated carbon, platinum black, rhodium-activated carbon and Raney nickel, and preferably palladium-activated carbon, platinum black or Raney nickel. A molar amount of the catalyst used is generally 0.0005 to 1-fold and preferably 0.01 to 0.3-fold based on 1 mol of the compound (15).

Hydrogen partial pressure is normally 1 atm to 10 atm and preferably 1 atm to 5 atm.

Although varying according to the types and amounts used of the raw materials, solvent and the like, the reaction temperature is normally 0° C. to 100° C. and preferably 15° C. to 80° C.

Although varying according to the reaction temperature and the like, the reaction time is normally 15 minutes to 72 hours and preferably 30 minutes to 24 hours.

[Preparation Method 8]

"Preparation Method 8" is another method for preparing the aforementioned compound (2).

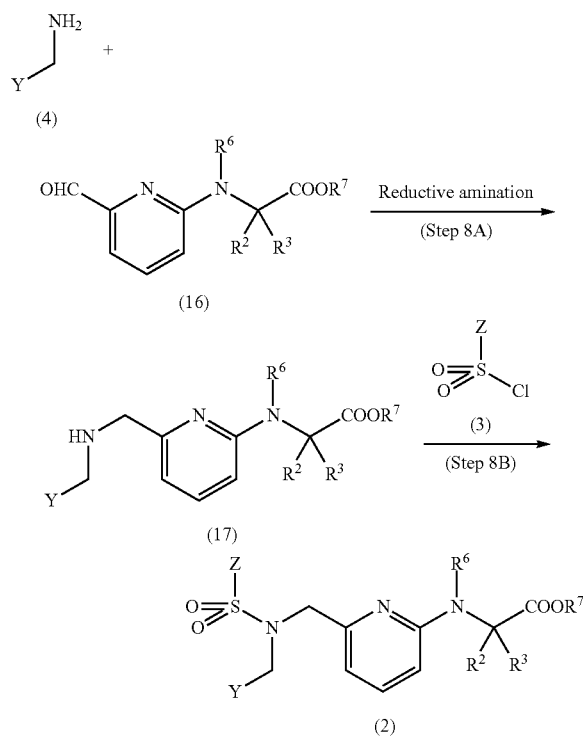

[wherein $R^2$, $R^3$, $R^6$, $R^7$, Y and Z are the same as previously defined].

"Step 8A" is a step for preparing a compound (17) by reacting the compound (4) and a formylpyridine compound (16) in an inert solvent and in the presence or absence of a dehydrating agent to obtain an imine form followed by reducing the imine form using a borohydride compound.

The compound (16) can be prepared according to "Preparation Method 13" to be described later.

Although there are no particular limitations on the inert solvent used provided it does not inhibit the reaction and dissolves the raw materials to a certain degree, examples include halogenated aliphatic hydrocarbons such as methylene chloride, chloroform and 1,2-dichloroethane; aromatic hydrocarbons such as benzene and toluene; and alcohols such as methanol, ethanol or propanol, and preferably methylene chloride, 1,2-dichloroethane, methanol or ethanol.

Examples of the dehydrating agent used include molecular sieves and anhydrous magnesium sulfate. An amount of the dehydrating agent used is generally 100 g to 2000 g and preferably 500 g to 1000 g based on 1 mol of the compound (16).

A molar amount of the compound (4) used is generally 0.4 to 10-fold and preferably 0.5 to 3-fold based on 1 mol of the compound (16). Furthermore, in the case the compound (4) is an acid addition salt (such as a hydrochloride and a hydrobromide), a base may also be added, and in that case, examples of the base used include triethylamine and diisopropylethylamine. A molar amount of the base used is generally 1 to 10-fold and preferably 1 to 3-fold based on 1 mol of the compound (4).

Although varying according to the types and amounts used of the raw materials, solvent and the like, the reaction temperature is normally −5° C. to 100° C. and preferably 0° C. to 50° C.

Although varying according to the reaction temperature and the like, the reaction time is normally 10 minutes to 24 hours and preferably 1 hour to 12 hours.

The resulting imine form is subsequently reduced using a borohydride compound either after having isolated the imine form or without isolating the imine form. Examples of the borohydride compound used include sodium borohydride, sodium cyanoborohydride and sodium triacetoxyborohydride, and preferably sodium borohydride or sodium triacetoxyborohydride. A molar amount of the borohydride compound used is generally 1 to 10-fold and preferably 1 to 3-fold based on 1 mol of the compound (16).

In the case of having isolated the resulting imine form, although there are no particular limitations on the inert solvent used for the reduction provided it does not inhibit the reaction and dissolves the raw materials to a certain degree, examples include halogenated aliphatic hydrocarbons such as methylene chloride, chloroform and 1,2-dichloroethane; aromatic hydrocarbons such as benzene and toluene; and alcohols such as methanol, ethanol or propanol, and preferably methylene chloride, 1,2-dichloroethane, methanol or ethanol.

Although varying according to the types and amounts used of the raw materials, solvent and the like, the reaction temperature is normally −5° C. to 100° C. and preferably 0° C. to 50° C.

Although varying according to the reaction temperature and the like, the reaction time is normally 10 minutes to 12 hours and preferably 1 hour to 6 hours.

"Step 8B" is a step for preparing the compound (2) by reacting the compound (3) and the compound (17) in the presence of a base. This step is carried out in compliance with the aforementioned "Step 1A" except for using the compound (17) in place of the compound (4).

[Preparation Method 9]

"Preparation Method 9" is another method for preparing a substituted aminomethylpyridine compound (17a) in which $R^6$ is a Boc group and $R^7$ is $R^4$ in the aforementioned compound (17).

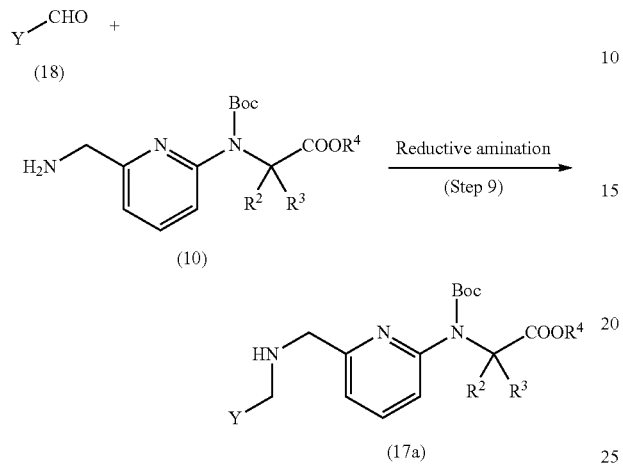

[wherein $R^2$, $R^3$, $R^4$ and Y are the same as previously defined].

"Step 9" is a step for preparing the compound (17a) by reacting the compound (10) and a formyl compound (18) in an inert solvent and in the presence or absence of a dehydrating agent to obtain an imine form, followed by reducing the imine form using a borohydride compound. This step is carried out in compliance with the aforementioned "Step 8A" except for using the compound (10) in place of the compound (4) and the compound (18) in place of the compound (16), respectively.

The compound (18) is known or can be prepared in compliance with a known method from a known compound.

[Preparation Method 10]

"Preparation Method 10" is another method for preparing an intermediate compound (2g) in which Z is $Z^2$ and Y is a $-Q^1-Q^2$ group in the aforementioned compound (2).

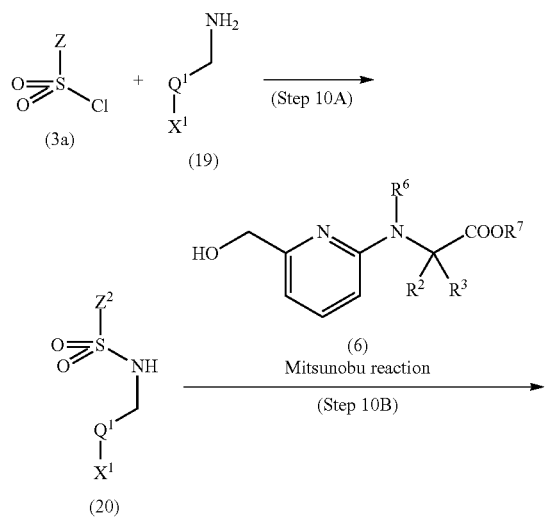

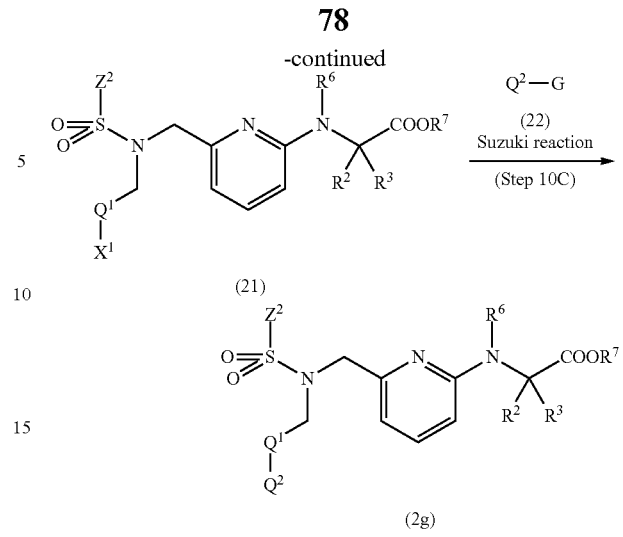

[wherein $R^2$, $R^3$, $R^6$, $R^7$, $Q^1$ and $Q^2$ are the same as previously defined, G represents a boronic acid derivative group such as a dihydroxyboryl group and a 4,4,5,5-tetramethyl-[1,3,2]dioxaborolanyl group, $X^1$ represents a chlorine atom, a bromine atom or an iodine atom, and $Z^2$ represents an aromatic group or a 5- to 6-membered heteroaromatic group, each of which may be substituted with a group(s) selected from the group consisting of a fluorine atom, a chlorine atom, a $C_1$-$C_6$ alkyl group, a halogeno-$C_1$-$C_6$ alkyl group, a $C_1$-$C_6$ alkoxy group and a halogeno-$C_1$-$C_6$ alkoxy group].

"Step 10A" is a step for preparing a sulfonamide compound (20) by reacting a chlorosulfonyl compound (3a) and an amine compound (19) in an inert solvent and in the presence or absence (and preferably the presence) of a base. This step is carried out in compliance with the aforementioned "Step 1A" except for using the compound (3a) in place of the compound (3) and the compound (19) in place of the compound (4), respectively.

The compound (3a) is a compound in which Z is $Z^2$ in the compound (3). The compound (19) is known or can be prepared in compliance with a known method from a known compound.

"Step 10B" is a so-called Mitsunobu reaction, and is a step for preparing an intermediate compound (21) by reacting the compound (20) and the compound (6) in an inert solvent and in the presence of a phosphine compound and an azo compound. This step is carried out in compliance with "Step 1B" except for using the compound (20) in place of the compound (5) and the compound (6) in place of the compound (6a), respectively.

The compound (6) can be prepared according to "Preparation Method 11" to be described later.

"Step 10C" is a so-called Suzuki reaction, and is a step for preparing the compound (2g) by reacting the compound (21) and a boronic acid compound (22) in an inert solvent, in an inert gas atmosphere, and in the presence of either a base or a fluoride and a palladium catalyst.

The compound (22) is known or can be prepared in compliance with a known method from a known compound.

Although there are no particular limitations on the inert solvent used provided it does not inhibit the reaction and dissolves the raw materials to a certain degree, examples include aromatic hydrocarbons such as benzene and toluene; ethers such as tetrahydrofuran, 1,2-dimethoxyethane and 1,4-dioxane; alcohol such as methanol, ethanol, propanol and isopropanol; esters such as methyl acetate and ethyl acetate;

amides such as N,N-dimethylformamide, N,N-dimethylacetamide and N-methylpyrrolidone; sulfoxides such as dimethylsulfoxide, nitriles such as acetonitrile; water; and arbitrary mixed solvents thereof, and preferably toluene, toluene-ethanol-water mixed solvent or toluene-water mixed solvent.

Examples of the inert gas used include nitrogen, helium and argon.

Examples of the palladium catalyst used include palladium metals such as palladium-active carbon and palladium black; organic palladium complexes such as tetrakis(triphenylphosphine)palladium, bis(triphenylphosphine)palladium chloride, 1,1'-bis(diphenylphosphino)ferrocene palladium chloride and tris(dibenzylideneacetone)-dipalladium; and palladium salts such as palladium chloride and palladium acetate, and preferably tetrakis(triphenylphosphine)palladium or palladium acetate. A molar amount of palladium used as catalyst is generally 0.0001 to 1-fold and preferably 0.005 to 0.3-fold based on 1 mol of the compound (21).

In the case of using tris(dibenzylideneacetone)dipalladium, palladium chloride or palladium acetate as a catalyst, it is preferably used in the presence of an organic phosphine compound. Examples of the organic phosphine compound used include tri-n-butylphosphine, tri-tert-butylphosphine, tricyclohexylphosphine, butyldi-1-adamantylphosphine, triphenylphosphine, tri(o-tolyl)phosphine, 2-dicyclohexylphosphino-2',6'-dimethoxybiphenyl, 1,1'-bis(diphenylphosphino)ferrocene and 1,2,3,4,5-pentaphenyl-1'-(di-tert-butylphosphino)ferrocene, and preferably tricyclohexylphosphine, dibutyl-1-adamantylphosphine, triphenylphosphine or 2-dicyclohexylphosphino-2',6'-dimethoxybiphenyl. A molar amount of the organic phosphine compound used is generally 1 to 5-fold and preferably 1.5 to 2.5-fold based on 1 mol of palladium.

Examples of the base or the fluoride used include alkali metal acetates such as sodium acetate and potassium acetate; alkali metal carbonates such as sodium carbonate, potassium carbonate and cesium carbonate; alkali metal phosphates such as trisodium phosphate and tripotassium phosphate; alkali metal hydroxides such as lithium hydroxide, sodium hydroxide and potassium hydroxide; quaternary ammonium hydroxides such as tetramethylammonium hydroxide, tetraethylammonium hydroxide and tetrabutylammonium hydroxide; and fluorides such as cesium fluoride, tetramethylammonium fluoride, tetraethylammonium fluoride and tetrabutylammonium fluoride, and preferably sodium carbonate or tripotassium phosphate. A molar amount of the base or the fluoride used is generally 1 to 10-fold and preferably 1.5 to 5-fold based on 1 mol of the compound (21).

A molar amount of the compound (22) used is generally 1 to 3-fold and preferably 1 to 2-fold based on 1 mol of the compound (21).

Although varying according to the types and amounts used of the raw materials, solvent and the like, the reaction temperature is normally 0° C. to 200° C. and preferably 50° C. to 150° C.

Although varying according to the reaction temperature and the like, the reaction time is normally 10 minutes to 120 hours and preferably 1 hour to 48 hours.

[Preparation Method 11]

"Preparation Method 11" is a typical method for preparing the compound (6).

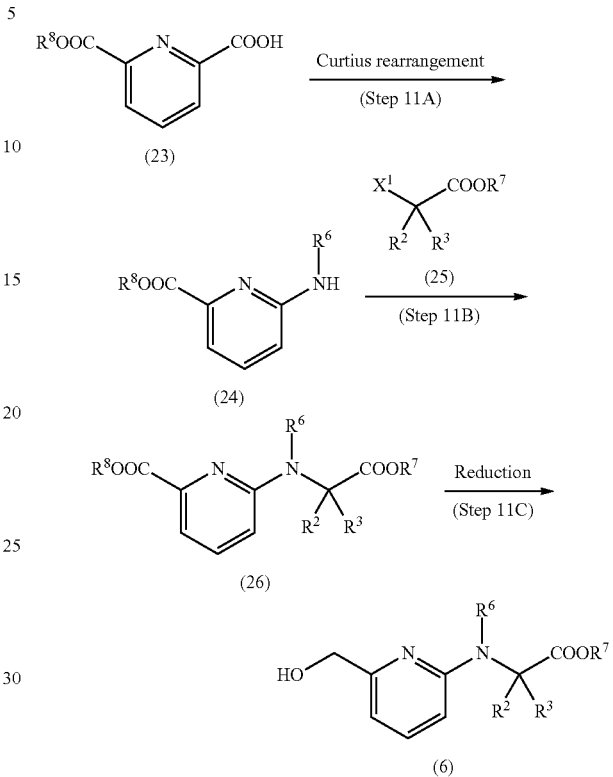

[wherein $R^2$, $R^3$, $R^6$, $R^7$ and $X^1$ are the same as previously defined, and $R^8$ represents a methyl group or an ethyl group].

"Step 11A" is a step for preparing an aminopyridyl ester compound (24) from a half ester compound (23) by a so-called Curtius rearrangement reaction, and in the case $R^6$ is a Boc group, is carried out in the same manner as the method described in WO 2006/074884A, while in the case $R^6$ is a Cbz group, is carried out in compliance with the method in the aforementioned publication except for using benzyl alcohol in place of tert-butanol.

The compound (23) is known or can be prepared in compliance with a known method from a known compound.

"Step 11B" is a step for preparing a pyridine ester compound (26) by reacting the compound (24) and a halogenoacetic acid compound (25) in an inert solvent and in the presence of a base. This step is carried out in compliance with the aforementioned "Step 5" except for using the compound (24) in place of the compound (5) and the compound (25) in place of the compound (9), respectively.

The compound (25) is known or can be prepared in compliance with a known method from a known compound.

"Step 11C" is a step for preparing the compound (6) by reducing the compound (26) using a sodium borohydride in an inert solvent and in the presence or absence (and preferably in the presence) of calcium chloride.

Although there are no particular limitations on the inert solvent used provided it does not inhibit the reaction and dissolves the raw materials to a certain degree, examples include alcohols such as methanol, ethanol, propanol, isopropanol, butanol, isobutanol, sec-butanol and tert-butanol; ethers such as tetrahydrofuran, 1,4-dioxane, 1,2-dimethoxyethane, diethylene glycol dimethyl ether, triethylene glycol dimethyl ether and tetraethylene glycol dimethyl ether; nitriles such as acetonitrile and propionitrile; amides such as N,N-dimethylformamide, N,N-dimethylacetamide and N-methylpyrrolidone; sulfoxides such as dimethylsulfoxide; and arbitrary mixed solvents thereof, and preferably methanol, ethanol, tetrahydrofuran, triethylene glycol dimethyl ether, tetraethylene glycol dimethyl ether or a mixed solvent thereof.

A molar amount of calcium chloride used is generally 0.5 to 10-fold and preferably 1 to 3-fold based on 1 mol of the compound (26).

A molar amount of sodium borohydride used is generally 0.5 to 10-fold and preferably 1 to 3-fold based on 1 mol of the compound (26).

Although varying according to the types and amounts used of the raw materials, solvent and the like, the reaction temperature is normally −10° C. to 100° C. and preferably 0° C. to 50° C.

Although varying according to the reaction temperature and the like, the reaction time is normally 10 minutes to 12 hours and preferably 15 minutes to 6 hours.

[Preparation Method 12]

"Preparation Method 12" is another method for preparing a hydroxymethylpyridine compound (6d) in which $R^7$ is a tBu group in the aforementioned compound (6).

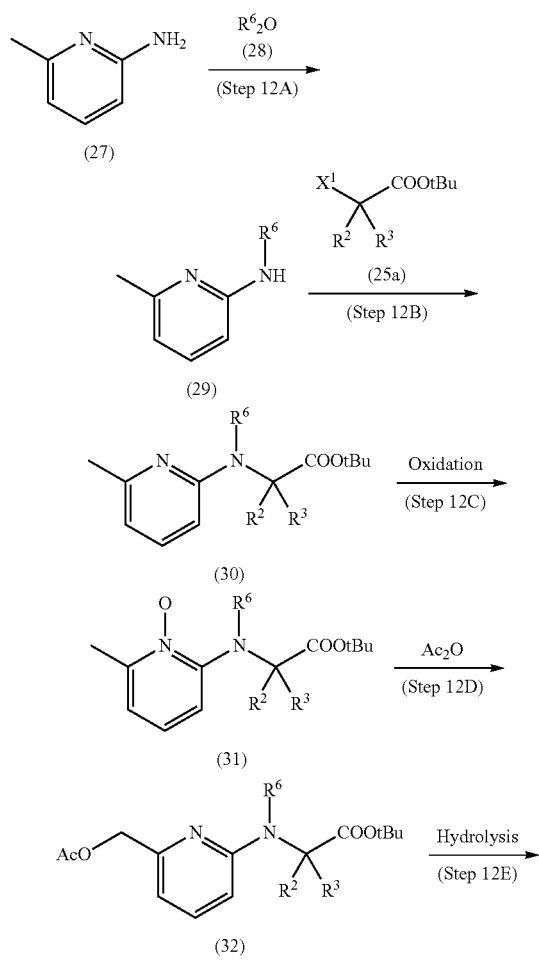

-continued

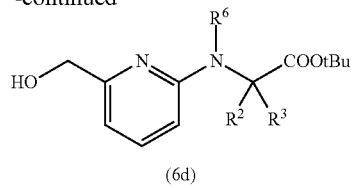

(6d)

[wherein $R^2$, $R^3$, $R^6$ and $X^1$ are the same as previously defined, and Ac represents an acetyl group].

"Step 12A" is a step for preparing a picoline compound (29) by reacting a known compound (28) and a known compound (27) in an inert solvent and in the presence of a base.

Although there are no particular limitations on the inert solvent used provided it does not inhibit the reaction and dissolves the raw materials to a certain degree, examples include alcohols such as methanol, ethanol, propanol, isopropanol, butanol, isobutanol, sec-butanol, tert-butanol and benzyl alcohol; ethers such as tetrahydrofuran, 1,4-dioxane and 1,2-dimethoxyethane; nitriles such as acetonitrile and propionitrile; amides such as N,N-dimethylformamide, N,N-dimethylacetamide and N-methylpyrrolidone; sulfoxides such as dimethylsulfoxide; and arbitrary mixed solvents thereof, and preferably tert-butanol or benzyl alcohol.

Examples of the base used include organic amines such as triethylamine, diisopropylethylamine, pyridine, 4-dimethylaminopyridine, picoline and 2,6-lutidine, and preferably 4-dimethylaminopyridine. A molar amount of the base used is generally 0.01 to 10-fold and preferably 0.05 to 1-fold based on 1 mol of the compound (27).

A molar amount of the compound (28) used is generally 0.9 to 5-fold and preferably 1 to 3-fold based on 1 mol of the compound (27).

Although varying according to the types and amounts used of the raw materials, solvent and the like, the reaction temperature is normally −10° C. to 100° C. and preferably 0° C. to 50° C.

Although varying according to the reaction temperature and the like, the reaction time is normally 10 minutes to 24 hours and preferably 1 hour to 12 hours.

"Step 12B" is a step for preparing a substituted aminopicoline compound (30) by reacting the compound (29) and a halogenoacetic acid compound (25a) in an inert solvent and in the presence of a base. This step is carried out in compliance with the aforementioned "Step 11B" except for using the compound (29) in place of the compound (24) and the compound (25a) in place of the compound (25), respectively.

The compound (25a) is a compound in which $R^7$ is a tBu group in the aforementioned compound (25).

"Step 12C" is a step for preparing an N-oxide compound (31) by oxidizing the compound (30) using an oxidizing agent in an inert solvent.

Although there are no particular limitations on the inert solvent used provided it does not inhibit the reaction and dissolves the raw materials to a certain degree, examples include halogenated aliphatic hydrocarbons such as methylene chloride, chloroform and 1,2-dichloro ethane; and preferably methylene chloride.

Examples of the oxidizing agent used include oxidizing agents such as m-chloroperbenzoic acid and hydrogen peroxide, and preferably m-chloroperbenzoic acid. A molar amount of the oxidizing agent used is generally 1 to 10-fold amount and preferably 1 to 3-fold based on 1 mol of the compound (30).

Although varying according to the types and amounts used of the raw materials, solvent and the like, the reaction temperature is normally 0° C. to 100° C. and preferably 10° C. to 50° C.

Although varying according to the reaction temperature and the like, the reaction time is normally 30 minutes to 24 hours and preferably 1 hour to 6 hours.

"Step 12D" is a step for preparing an acetoxymethylpyridine compound (32) from the compound (31) by a rearrangement reaction in acetic anhydride.

Although a molar amount of acetic anhydride used is generally 1 to 100-fold and preferably 5 to 30-fold based on 1 mol of the compound (31), it can also be used in excess as a solvent.

Although varying according to the types and amounts used of the raw materials, solvent and the like, the reaction temperature is normally 0° C. to 150° C. and preferably 50° C. to 120° C.

Although varying according to the reaction temperature and the like, the reaction time is normally 30 minutes to 24 hours and preferably 1 hour to 12 hours.

"Step 12E" is a step for preparing the compound (6d) by treating the compound (32) with a base in an inert solvent and in the presence of water. This step is carried out in compliance with the reaction of the aforementioned Step 4C1 under basic conditions except for using a molar amount of the base 0.9 to 1.1-fold based on 1 mol of the compound (32).

[Preparation Method 13]

"Preparation Method 13" is a typical method for preparing the aforementioned compound (16).

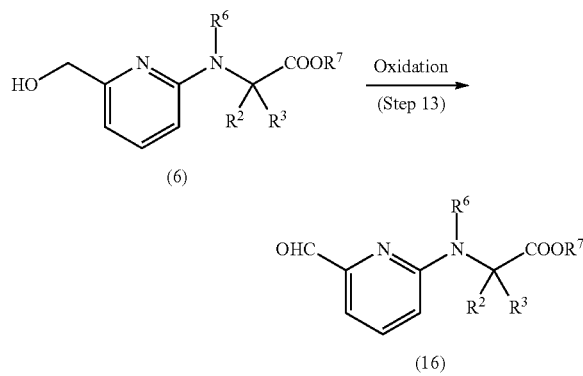

[wherein $R^2$, $R^3$, $R^6$ and $R^7$ are the same as previously defined].

"Step 13" is a step for preparing the compound (16) by oxidizing the compound (6) using an oxidizing agent in an inert solvent. Examples of the oxidizing agent of this step include manganese dioxide, pyridinium chlorochromate (PCC), pyridinium dichromate (PDC), 1,1,1-tris(acetoxy)-1,1-dihydro-1,2-benziodoxol-3-(1H)-one (abbreviated as Dess-Martin reagent), and so-called TEMPO oxidizing agents combining the use of sodium hypochlorite and 2,2,6,6-tetramethylpiperidine 1-oxyl (abbreviated as TEMPO), and it is necessary to select the reaction conditions corresponding to the type of the oxidizing agent used.

The reaction is carried out in an inert solvent in the case of using manganese dioxide, pyridinium chlorochromate (PCC), pyridinium dichromate (PDC) or Dess-Martin reagent for the oxidizing agent.

Although there are no particular limitations on the inert solvent used provided it does not inhibit the reaction and dissolves the raw materials to a certain degree, examples include halogenated aliphatic hydrocarbons such as methylene chloride, chloroform and 1,2-dichloroethane; nitriles such as acetonitrile; and esters such as methyl acetate, ethyl acetate and isopropyl acetate; and preferably methylene chloride.

A molar amount of the oxidizing agent used is generally 0.9 to 100-fold and preferably 1 to 20-fold based on 1 mol of the compound (61).

Although varying according to the types and amounts used of the raw materials, solvent and the like, the reaction temperature is normally 0° C. to 150° C. and preferably 0° C. to 100° C.

Although varying according to the reaction temperature and the like, the reaction time is normally 30 minutes to 24 hours and preferably 1 hour to 12 hours.

The reaction is carried out in an inert solvent and in the presence of potassium bromide in the case of carrying out a so-called TEMPO oxidation using sodium hypochlorite and TEMPO as oxidizing agents.

Although there are no particular limitations on the inert solvent used provided it does not inhibit the reaction and dissolves the raw materials to a certain degree, examples include halogenated aliphatic hydrocarbons such as methylene chloride, chloroform and 1,2-dichloroethane; water; and arbitrary mixed solvents thereof, and preferably a mixed solvent of methylene chloride and water.

A molar amount of sodium hypochlorite used is generally 0.8 to 3-fold and preferably 0.9 to 1.5-fold based on 1 mol of the compound (6). Furthermore, the sodium hypochlorite may be added as an aqueous solution that has been adjusted to pH 8 to 10 with sodium hydrogen carbonate.

A molar amount of TEMPO used is generally 0.001 to 0.1-fold and preferably 0.005 to 0.05-fold based on 1 mol of the compound (6).

A molar amount of potassium bromide used is generally 0.01 to 1-fold and preferably 0.05 to 0.2-fold based on t 1 mol of the compound (6).

Although varying according to the types and amounts used of the raw materials, solvent and the like, the reaction temperature is normally −30° C. to 30° C. and preferably −15° C. to 15° C.

Although varying according to the reaction temperature and the like, the reaction time is normally 10 minutes to 12 hours and preferably 30 minutes to 6 hours.

[Preparation Method 14]

"Preparation Method 14" is a typical method for preparing the aforementioned compound (10).

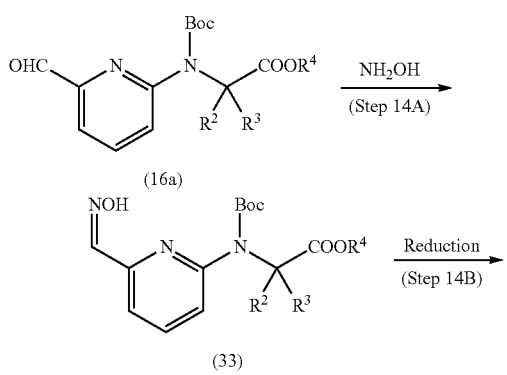

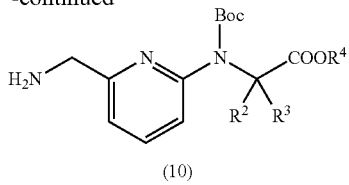

[wherein $R^2$, $R^3$ and $R^4$ are the same as previously defined].

"Step 14A" is a step for preparing an oxime compound (33) by reacting a hydroxylamine and a formyl pyridine compound (16a) in an inert solvent.

The compound (16a) is a compound in which $R^6$ is a Boc group and $R^7$ is $R^4$ in the aforementioned compound (16).

Although there are no particular limitations on the inert solvent used provided it does not inhibit the reaction and dissolves the raw materials to a certain degree, examples include alcohols such as methanol, ethanol and isopropanol; halogenated aliphatic hydrocarbons such as methylene chloride, chloroform and 1,2-dichloroethane; nitriles such as acetonitrile; and esters such as methyl acetate, ethyl acetate and isopropyl acetate; and preferably methanol.

A molar amount of the hydroxylamine used is generally 1 to 5-fold and preferably 1 to 2-fold.

A base such as triethylamine, diisopropylethylamine and pyridine may be added to accelerate the reaction. A molar amount of the base used is generally 0.5 to 20-fold and preferably 1 to 10-fold based on 1 mol of the compound (16a).

Although varying according to the types and amounts used of the raw materials, solvent and the like, the reaction temperature is normally 0° C. to 100° C. and preferably 0° C. to 60° C.

Although varying according to the reaction temperature and the like, the reaction time is normally 30 minutes to 24 hours and preferably 1 hour to 12 hours.

"Step 14B" is a step for preparing the compound (10) by reacting the compound (33) with hydrogen in an inert solvent and in the presence of a catalyst. This step is carried out in compliance with the aforementioned "Step 3B" except for using the compound (33) in place of the compound (2b).

[Preparation Method 15]

"Preparation Method 15" is a typical method for preparing the aforementioned compound (9).

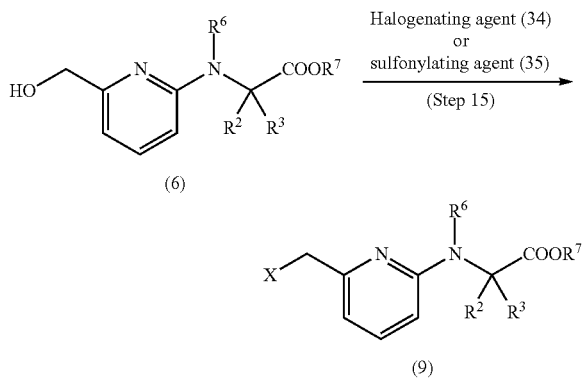

[wherein $R^2$, $R^3$, $R^6$, $R^7$ and X are the same as previously defined].

"Step 15" is a step for preparing the compound (9) by reacting the compound (6) with a halogenating agent (34) or a sulfonylating agent (35). In the case of using the halogenating agent (34) in this step, a compound can be prepared in which X is a chlorine atom, a bromine atom or an iodine atom in the formula (9), and in the case of using the sulfonylating agent (35), a compound can be prepared in which X is a methanesulfonyloxy group, a benzenesulfonyloxy group, a p-toluenesulfonyloxy group or a trifluoromethanesulfonyloxy group in the formula (9).

In the case of using the halogenating agent (34) in "Step 15", it is necessary to select the reaction conditions corresponding to the type of halogenating agent (34).

Examples of the halogenating agent (34) used include thionyl chloride, oxalyl chloride, phosphorous oxychloride, phosphorous pentachloride, thionyl bromide, N-chlorosuccinimide (abbreviated as NCS), N-bromosuccinimide (abbreviated as NBS), carbon tetrachloride, carbon tetrabromide and iodine.

The reaction is carried out in an inert solvent in the case of using thionyl chloride, oxalyl chloride, phosphorous oxychloride, phosphorous pentachloride or thionyl bromide for the halogenating agent (34).

Although there are no particular limitations on the inert solvent used provided it does not inhibit the reaction and dissolves the raw materials to a certain degree, examples include aromatic hydrocarbons such as benzene, toluene and xylene; halogenated aliphatic hydrocarbons such as methylene chloride, chloroform and 1,2-dichloroethane; ethers such as tetrahydrofuran, 1,2-dimethoxyethane and 1,4-dioxane; nitriles such as acetonitrile and propionitrile; amides such as N,N-dimethylformamide, N,N-dimethylacetamide and N-methylpyrrolidone; and arbitrary mixed solvents thereof; and preferably toluene, methylene chloride, tetrahydrofuran or acetonitrile.

A molar amount of the halogenating agent (34) used is generally 0.9 to 10-fold and preferably 1 to 1.5-fold based on 1 mol of the compound (6).

A base such as triethylamine, diisopropylethylamine, imidazole, pyridine and 4-dimethylaminopyridine may be added to accelerate the reaction. A molar amount of the base used is generally 1 to 10-fold and preferably 1 to 1.5-fold based on 1 mol of the compound (6).

Although varying according to the types and amounts used of the raw materials, solvent and the like, the reaction temperature is normally −20° C. to 150° C. and preferably 0° C. to 50° C.

Although varying according to the reaction temperature and the like, the reaction time is normally 1 minute to 24 hours and preferably 1 hour to 12 hours.

The reaction is carried out in an inert solvent and in the presence of a phosphine compound in the case of using NCS, NBS, carbon tetrachloride, carbon tetrabromide or iodine for the halogenating agent (34).

Although there are no particular limitations on the inert solvent used provided it does not inhibit the reaction and dissolves the raw materials to a certain degree, examples include ethers such as tetrahydrofuran, 1,2-dimethoxyethane and 1,4-dioxane; nitriles such as acetonitrile and propionitrile; amides such as N,N-dimethylformamide, N,N-dimethylacetamide and N-methylpyrrolidone; and arbitrary mixed solvents thereof; and preferably tetrahydrofuran or acetonitrile.

Examples of the phosphine compound used include trimethylphosphine, triethylphosphine, tri-n-butylphosphine and triphenylphosphine, and preferably triphenylphosphine. A molar amount of the phosphine compound used is generally 0.9 to 10-fold and preferably 1 to 2-fold based on 1 mol of the compound (6).

A molar amount of the halogenating agent (34) used is generally 0.9 to 10-fold and preferably 1 to 2-fold based on 1 mol of the compound (6). A base such as imidazole may be added to accelerate the reaction in the case of using iodine for the halogenating agent. A molar amount of the base used is generally 1 to 10-fold and preferably 1 to 2-fold based on 1 mol of the compound (6).

Although varying according to the types and amounts used of the raw materials, solvent and the like, the reaction temperature is normally 0° C. to 100° C. and preferably 0° C. to 50° C.

Although varying according to the reaction temperature and the like, the reaction time is normally 1 minute to 24 hours and preferably 1 hour to 12 hours.

The reaction is carried out in an inert solvent and in the presence of a base in the case of using the sulfonylating agent (35) in "Step 15".

Although there are no particular limitations on the inert solvent used provided it does not inhibit the reaction and dissolves the raw materials to a certain degree, examples include aromatic hydrocarbons such as benzene, toluene and xylene; halogenated aliphatic hydrocarbons such as methylene chloride, chloroform and 1,2-dichloroethane; ethers such as tetrahydrofuran, 1,2-dimethoxyethane and 1,4-dioxane; nitriles such as acetonitrile and propionitrile; amides such as N,N-dimethylformamide, N,N-dimethylacetamide and N-methylpyrrolidone; and arbitrary mixed solvents thereof, and preferably toluene, methylene chloride, tetrahydrofuran or acetonitrile.

Examples of the base used include organic bases such as triethylamine, diisopropylethylamine, pyridine and 4-dimethylaminopyridine, and preferably triethylamine, diisopropylethylamine or pyridine. A molar amount of the base used is generally 0.9 to 10-fold and preferably 1 to 1.5-fold based on 1 mol of the compound (6).

Examples of the sulfonylating agent (35) used include methanesulfonyl chloride, benzenesulfonyl chloride, p-toluenesulfonyl chloride and trifluoromethanesulfonic anhydride. A molar amount of the sulfonylating agent (35) used is generally 0.9 to 10-fold and preferably 1 to 1.5-fold based on 1 mol of the compound (6).

Although varying according to the types and amounts used of the raw materials, solvent and the like, the reaction temperature is normally −20° C. to 130° C. and preferably −5° C. to 30° C.

Although varying according to the reaction temperature and the like, the reaction time is normally 1 minute to 24 hours and preferably 1 hour to 12 hours.

[Preparation Method 16]

"Preparation Method 16" is a typical method for preparing the aforementioned compound (14).

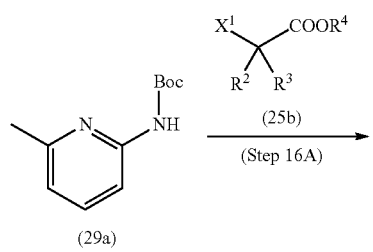

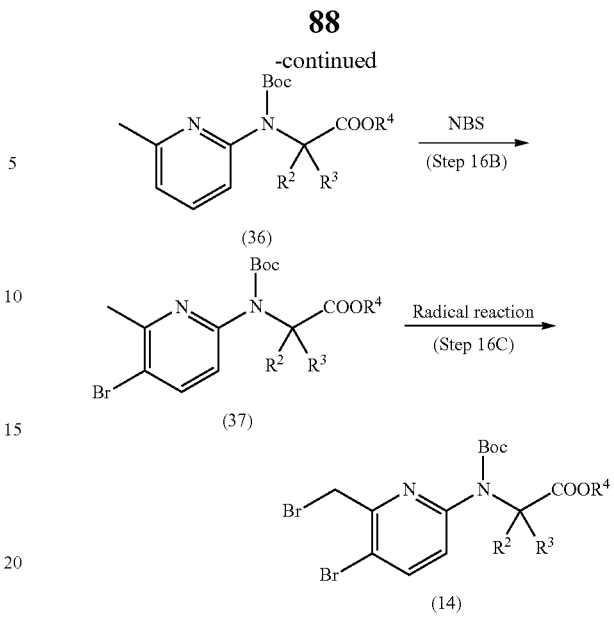

[wherein $R^2$, $R^3$, $R^4$ and $X^1$ are the same as previously defined].

"Step 16A" is a step for preparing a substituted aminopicoline compound (36) by reacting a picoline compound (29a) and a halogenoacetic acid compound (25b) in an inert solvent and in the presence of a base. This step is carried out in compliance with the aforementioned "Step 12B" except for using the compound (29b) in place of the compound (29) and the compound (25b) in place of the compound (25a), respectively.

The compound (25b) is a compound in which $R^7$ is $R^4$ is the aforementioned compound (25). The compound (29a) is a compound in which $R^6$ is a Boc group in the compound (29) that can be prepared in the aforementioned "Step 12A".

"Step 16B" is a step for preparing a bromopyridine compound (37) by treating the compound (36) with NBS in an inert solvent.

Although there are no particular limitations on the inert solvent used provided it does not inhibit the reaction and dissolves the raw materials to a certain degree, examples include aromatic hydrocarbons such as benzene and chlorobenzene; halogenated aliphatic hydrocarbons such as methylene chloride, chloroform and 1,2-dichloroethane; ethers such as tetrahydrofuran, 1,2-dimethoxyethane and 1,4-dioxane; nitriles such as acetonitrile and propionitrile; amides such as N,N-dimethylformamide, N,N-dimethylacetamide and N-methylpyrrolidone; and arbitrary mixed solvents thereof, and preferably acetonitrile.

A molar amount of NBS used is generally 0.9 to 5-fold and preferably 1 to 2-fold based on 1 mol of the compound (36).

Although varying according to the types and amounts used of the raw materials, solvent and the like, the reaction temperature is normally −20° C. to 100° C. and preferably 0° C. to 60° C.

Although varying according to the reaction temperature and the like, the reaction time is normally 1 minute to 24 hours and preferably 1 hour to 12 hours.

"Step 16C" is a step for preparing the compound (14) by treating the compound (37) with NBS in an inert solvent and in the presence of a radical initiator or while irradiating with light.

Although there are no particular limitations on the inert solvent used provided it does not inhibit the reaction and dissolves the raw materials to a certain degree, examples include halogenated aliphatic hydrocarbons such as methylene chloride, chloroform and 1,2-dichloroethane; and aromatic hydrocarbons such as benzene, chlorobenzene and dichlorobenzene, and preferably 1,2-dichloroethane or chlorobenzene.

A molar amount of NBS used is generally 0.9 to 5-fold and preferably 1 to 3-fold based on 1 mol of the compound (37).

Examples of the radical initiator used include azobisisobutyronitrile, 2,2'-azobis(2,4-dimethylvaleronitrile), 2,2'-azobis(2-methylbutyronitrile) and benzoyl peroxide.

A molar amount of the radical initiator used is generally 0.001 to 1-fold and preferably 0.01 to 0.5-fold based on 1 mol of the compound (37).

Although varying according to the types and amounts used of the raw materials, solvent and the like, the reaction temperature is normally 0° C. to 150° C. and preferably 30° C. to 100° C.

Although varying according to the reaction temperature and the like, the reaction time is normally 10 minutes to 12 hours and preferably 15 minutes to 6 hours.

In the case of carrying out the reaction by generating radicals under photoirradiation, the reaction is carried out in the same manner as in the case where the radical initiator is used except for irradiating light using a mercury lamp as a light source in place of the radical initiator.

[Preparation Method 17]

"Preparation Method 17" is another method for preparing a sulfonamide compound (5b) in which $Q^2$ of the $-Q^1-Q^2$ group represented by Y in the aforementioned compound (5) is a 5,6-dihydro-4H-1,3-thiazin-2-yl group or a 4,5-dihydrothiazol-2-yl group.

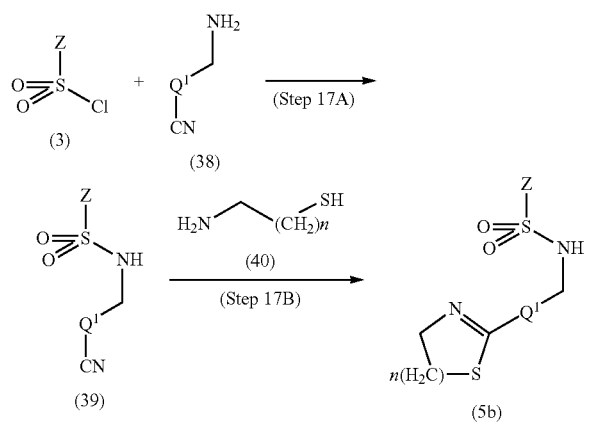

[wherein $Q^1$ and Z are the same as previously defined, and n represents an integer of 1 to 2].

"Step 17A" is a step for preparing a sulfonamide compound (39) having a cyano group by reacting the compound (3) and an amine compound (38) having a cyano group in an inert solvent and in the presence of a base. This step is carried out in compliance with the aforementioned "Step 1A" except for using the compound (38) in place of the compound (4).

The compound (38) is known or can be prepared in compliance with a known method from a known compound.

"Step 17B" is a step for preparing the compound (5b) by reacting the compound (39) with a known compound (40). This step is carried out in compliance with a known method (for example, European Journal of Medicinal Chemistry, 20, 16 (1985)).

[Preparation Method 18]

"Preparation Method 18" is another method for preparing an intermediate compound (2h) in which $R^6$ is a Boc group and $R^7$ is $R^4$ in the aforementioned compound (2g).

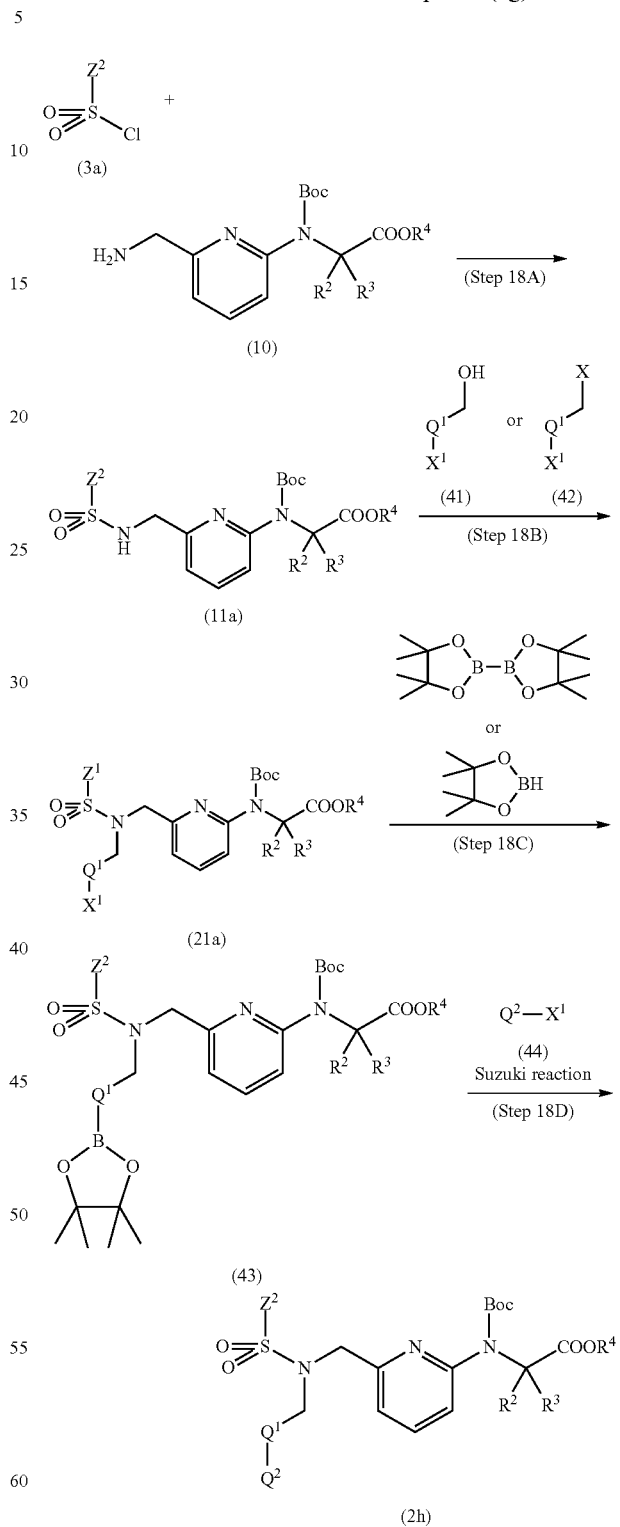

[wherein $R^2$, $R^3$, $R^4$, $Q^1$, $Q^2$, X, $X^1$ and $Z^1$ are the same as previously defined].

"Step 18A" is a step for preparing a compound (11a), in which Z is $Z^2$ in the aforementioned compound (11), by reacting the compound (3a) and the compound (10) in an inert solvent and in the presence or absence (and preferably the presence) of a base. This step is carried out in compliance with the aforementioned "Step 6A" except for using the compound (3a) in place of the compound (3).

"Step 18B" is a step for preparing a compound (21a), in which $R^6$ is a Boc group and $R^1$ is $R^4$ in the aforementioned compound (21), by reacting the compound (11a) with a compound (41) or a compound (42).

The compound (41) and the compound (42) are known or can be prepared in compliance with known methods from known compounds.

In the case of using the compound (41), "Step 18B" is a so-called Mitsunobu reaction, and is carried out in an inert solvent and in the presence of a phosphine compound and an azo compound. This step is carried out in compliance with the aforementioned "Step 16B" except for using the compound (11a) in place of the compound (11) and the compound (41) in place of the compound (12), respectively.

In the case of using the compound (42), "Step 18B" is carried out in an inert solvent and in the presence of a base. This step is carried out in compliance with the aforementioned "Step 16B" except for using the compound (11a) in place of the compound (11) and the compound (42) in place of the compound (13), respectively.

"Step 18C" is carried out by reacting the compound (21a) with 4,4,5,5,4',4',5',5'-octamethyl-[2,2']bi([1,3,2]dioxaborolanyl) (to be referred to as bis(pinacolato)diboron) or 4,4,5,5-tetramethyl-[1,3,2]dioxaborolane (to be referred to as pinacolborane) in an inert solvent, in an inert gas atmosphere and in the presence of base and a palladium catalyst. This step can be carried out with reference to, for example, The Journal of Organic Chemistry, 60, 7508 (1995) or The Journal of Organic Chemistry, 65, 164 (2000).

Although there are no particular limitations on the inert solvent used provided it does not inhibit the reaction and dissolves the raw materials to a certain degree, examples include aromatic hydrocarbons such as benzene and toluene; ethers such as tetrahydrofuran, 1,2-dimethoxyethane and 1,4-dioxane; alcohols such as methanol, ethanol, propanol and isopropanol; amides such as N,N-dimethylformamide, N,N-dimethylacetamide and N-methylpyrrolidone; sulfoxides such as dimethylsulfoxide; nitriles such as acetonitrile; water; and arbitrary mixed solvents thereof, and preferably toluene, 1,4-dioxane, N,N-dimethylformamide, dimethylsulfoxide or acetonitrile.

Examples of the inert gas used include nitrogen, helium and argon.

Examples of the palladium catalyst used include organic palladium complexes such as tetrakis(triphenylphosphine) palladium, bis(triphenylphosphine)palladium chloride and 1,1'-bis(diphenylphosphino)ferrocene palladium chloride, and preferably 1,1'-bis(diphenylphosphino)ferrocene palladium chloride. A molar amount of palladium used as catalyst is generally 0.0001 to 1-fold and preferably 0.005 to 0.3-fold based on 1 mol of the compound (21a).

Examples of the base used include alkali metal acetates such as sodium acetate and potassium acetate; alkali metal carbonates such as sodium carbonate, potassium carbonate and cesium carbonate; and organic bases such as triethylamine and diisopropylethylamine, and preferably sodium acetate, potassium acetate or triethylamine. A molar amount of the base used is generally 1 to 10-fold and preferably 1 to 5-fold based on 1 mol of the compound (21a).

A molar amount of the bis(pinacolato)diboron or pinacolborane used is generally 1 to 5-fold and preferably 1 to 3-fold based on 1 mol of the compound (21a).

Although varying according to the types and amounts used of the raw materials, solvent and the like, the reaction temperature is normally 0° C. to 200° C. and preferably 30° C. to 150° C.

Although varying according to the reaction temperature and the like, the reaction time is normally 10 minutes to 120 hours and preferably 1 hour to 48 hours.

"Step 18D" is a so-called Suzuki reaction, and is a step for preparing the compound (2h) by reacting a compound (43) and a compound (44) in an inert solvent, in an inert gas atmosphere and in the presence of either a base or a fluoride and a palladium catalyst. This is step is carried out in compliance with the aforementioned "Step 10C" except for using the compound (44) in place of the compound (21) and the compound (43) in place of the compound (22), respectively.

The compound (44) is known or can be prepared in compliance with a known method from a known compound.

The target compounds formed in each of the aforementioned reactions can be obtained from a reaction mixture in accordance with ordinary methods. For example, after suitably neutralizing the reaction mixture, or removing insolubles by filtration in the case such insolubles are present, an organic solvent such as ethyl acetate that is not miscible with water is added followed by rinsing with water, separating the organic layer containing the target compound, drying with a drying agent such as anhydrous magnesium sulfate and distilling off the solvent to obtain the target compound.

The resulting target compound can be separated and purified as necessary by suitably combining ordinary methods, examples of which include recrystallization; reprecipitation; or a method commonly used to separate and purify ordinary organic compounds (such as adsorption chromatography using a carrier such as silica gel or alumina; ion exchange chromatography; or normal or reverse phase column chromatography using silica gel or alkylated silica gel (and preferably, high-performance liquid chromatography)).

Although a compound represented by the formula (1) of the present invention can be converted into a pharmacologically acceptable salt in accordance with ordinary methods as necessary, it can also be separated directly from the reaction mixture as a salt.

In the case of using a compound represented by the formula (1), or a pharmacologically acceptable salt thereof of the present invention, as a pharmaceutical, the compound, or pharmacologically acceptable salt thereof, per se can be administered (as a bulk powder), or can be administered orally or parenterally (such as intravenous administration, intramuscular administration, intraperitoneal administration, trans-cutaneous administration, transtracheal administration, intracutaneous administration or subcutaneous administration) in a form such as a tablet, capsule, powder, syrup, granule, fine particles, pill, suspension, emulsion, transdermal preparation, suppository, ointment, lotion, inhalant and injection, which is prepared by mixing with a suitable pharmacologically acceptable vehicle or diluent and the like.

These preparations are prepared by commonly known methods using additives such as vehicles, lubricants, binders, disintegrators, emulsifiers, stabilizers, corrigents or diluents and the like.

Examples of vehicles include organic vehicles and inorganic vehicles. Examples of organic vehicles include sugar derivatives such as lactose, sucrose, glucose, mannitol and sorbitol; starch derivatives such as cornstarch, potato starch, alpha-starch and dextrin; cellulose derivatives such as crystalline cellulose; gum Arabic; dextran; and pullulan. Examples of inorganic vehicles include light silicic acid anhydride; and sulfates such as calcium sulfate.

Examples of lubricants include stearic acid; stearic acid metal salts such as calcium stearate and magnesium stearate; talc; colloidal silica; waxes such as beeswax and spermaceti; boric acid; adipic acid; sulfates such as sodium sulfate; glycol; fumaric acid; sodium benzoate; D,L-leucine; sodium lauryl sulfate; silicic acids such as silicic acid anhydride and silicic acid hydrate; and the aforementioned starch derivatives listed as examples of the vehicles.

Examples of binders include hydroxypropyl cellulose, hydroxypropyl methyl-cellulose, polyvinyl pyrrolidone, Macrogol and the aforementioned compounds listed as examples of the vehicles.

Examples of disintegrators include cellulose derivatives such as low substitution-degree hydroxypropyl cellulose, carboxymethyl cellulose, calcium carboxymethyl cellulose and internally crosslinked calcium carboxymethyl cellulose; crosslinked polyvinyl pyrrolidone; and chemically modified starch or cellulose derivatives such as carboxymethyl starch and sodium carboxymethyl starch.

Examples of emulsifiers include colloidal clays such as bentonite and bee gum; anionic surfactants such as sodium lauryl sulfate; cationic surfactants such as benzalkonium chloride; and nonionic surfactants such as polyoxyethylene alkyl ethers, polyoxyethylene sorbitan fatty acid esters and sucrose fatty acid esters.

Examples of stabilizers include para-hydroxybenzoic acid esters such as methyl para-hydroxybenzoate and propyl para-hydroxybenzoate; alcohols such as chlorobutanol, benzyl alcohol and phenylethyl alcohol; benzalkonium chloride; phenols such as phenol and cresol; thimerosal; acetic anhydride; and sorbic acid.

Examples of corrigents include sweeteners such as sodium saccharin and aspartame; sour flavorings such as citric acid, malic acid and tartaric acid; and aromatics such as menthol, lemon extract and orange extract.

Examples of diluents include compounds ordinarily used as diluents, such as lactose, mannitol, glucose, sucrose, calcium sulfate, hydroxypropyl cellulose, microcrystalline cellulose, water, ethanol, polyethylene glycol, propylene glycol, glycerol, starch, polyvinyl pyrrolidone or mixtures thereof.

Although the dosage of a compound represented by the formula (1) or a pharmacologically acceptable salt thereof of the present invention can be varied according to conditions such as patient symptoms, age or body weight, the adult dosage per administration in the case of oral administration has a lower limit of 0.001 mg/kg (preferably 0.01 mg/kg) and an upper limit of 20 mg/kg (preferably 10 mg/kg), while the adult dosage per administration in the case of parenteral administration has a lower limit of 0.0001 mg/kg (preferably 0.0005 mg/kg) and an upper limit of 10 mg/kg (preferably 5 mg/kg), administered corresponding to symptoms from 1 to 6 times per day.

EXAMPLES

Although the following provides a more detailed explanation of the present invention through Examples, Reference Examples and Test examples thereof, the scope of the present invention is not limited thereby.

Example 1

{6-[(6-Phenylpyridazin-3-ylmethyl)(pyridin-3-ylsulfonyl)aminomethyl]pyridin-2-ylamino}acetic acid hydrochloride (Exemplified Compound No. 1397)

1-(a) tert-Butyl({5-bromo-6-[(6-phenylpyridazin-3-ylmethyl)(pyridin-3-ylsulfonyl)-aminomethyl]pyridin-2-yl}tert-butoxycarbonylamino)acetate To a solution of N-(6-phenylpyridazin-3-ylmethyl)pyridin-3-ylsulfonamide (114 mg, 0.349 mmol) obtained in Reference Example 2-(d) in N,N-dimethylformamide (1.75 ml) were added tert-butyl[(5-bromo-6-bromomethylpyridin-2-yl)tert-butoxycarbonylamino]acetate (233 mg, containing 0.35 mmol of a pure content) obtained in Reference Example 1-(c) and potassium carbonate (98.0 mg, 0.709 mmol), followed by stirring at room temperature for 20 hours. After completion of the reaction, water (5.3 ml) was added to the reaction solution, followed by extraction with ethyl acetate. The separated organic layer was washed with a saturated aqueous sodium chloride solution, dried over anhydrous sodium sulfate, and then concentrated under reduced pressure. The resulting residue was subjected to silica gel column chromatography (eluent; hexane:ethyl acetate=3:1→1:5 (V/V)), and fractions containing the desired compound were concentrated under reduced pressure to afford the title compound (242 mg) as a slightly yellow foam. (Yield: 96%)

Mass spectrum (FAB, m/z): 725 ($M^++1$).

$^1$H-NMR spectrum (CDCl$_3$, δppm): 9.04 (dd, J=2.3, 0.8 Hz, 1H), 8.74 (dd, J=4.8, 1.7 Hz, 1H), 8.06-8.00 (m, 3H), 7.81 (d, J=8.8 Hz, 1H), 7.72 (d, J=8.8 Hz, 1H), 7.64-7.49 (m, 5H), 7.37 (ddd, J=8.1, 4.8, 0.8 Hz, 1H), 4.95 (s, 2H), 4.75 (s, 2H), 4.41 (s, 2H), 1.53 (s, 9H), 1.47 (s, 9H).

1-(b) tert-Butyl(tert-butoxycarbonyl{6-[(6-phenylpyridazin-3-ylmethyl)(pyridin-3-ylsulfonyl)aminomethyl]pyridin-2-yl}amino)acetate To a solution of tert-butyl({5-bromo-6-[(6-phenylpyridazin-3-ylmethyl)-(pyridin-3-ylsulfonyl)aminomethyl]pyridin-2-yl}tert-butoxycarbonylamino)acetate (239 mg, 0.329 mmol) obtained in Example 1-(a) in ethanol (3.3 ml) were added triethylamine (322 μl, 2.31 mmol) and 10% palladium-active carbon (55% hydrate) (48 mg), followed by stirring at room temperature for 6 hours under hydrogen atmosphere at 1 atm. After completion of the reaction, insolubles were filtered off, and the filtrate was concentrated under reduced pressure. The resulting residue was subjected to silica gel column chromatography (eluent; hexane:ethyl acetate=1:1→1:10 (V/V)) and then to reversed phase column chromatography (column; Megabond Elut™ C18 (manufactured by Varian, Inc.), eluent; acetonitrile:water=0:1→1:0 (V/V)), and fractions containing the desired compound were concentrated under reduced pressure to afford the title compound (153 mg) as a white foam. (Yield: 72%)

Mass spectrum (FAB, m/z): 647 ($M^++1$).

$^1$H-NMR spectrum (CDCl$_3$, δppm): 9.01 (dd, J=2.4, 0.8 Hz, 1H), 8.74 (dd, J=4.8, 1.7 Hz, 1H), 8.06-8.03 (m, 2H), 7.99 (ddd, J=8.1, 2.4, 1.7 Hz, 1H), 7.79 (d, J=8.8 Hz, 1H), 7.69 (d, J=8.4 Hz, 1H), 7.69 (d, J=8.8 Hz, 1H), 7.55-7.49 (m, 3H), 7.48 (dd, J=8.4, 7.3 Hz, 1H), 7.37 (ddd, J=8.1, 4.8, 0.8 Hz, 1H), 6.89 (dd, J=7.3, 0.4 Hz, 1H), 4.91 (s, 2H), 4.55 (s, 2H), 4.43 (s, 2H), 1.51 (s, 9H), 1.44 (s, 9H).

1-(c) {6-[(6-Phenylpyridazin-3-ylmethyl)(pyridin-3-ylsulfonyl)aminomethyl]pyridin-2-ylamino}acetic acid hydrochloride To a solution of tert-butyl(tert-butoxycarbonyl{6-[(6-phenylpyridazin-3-ylmethyl)(pyridin-3-ylsulfonyl)aminomethyl]pyridin-2-yl}amino)acetate (150 mg, 0.232 mmol) obtained in Example 1-(b) in methylene chloride (9.2 ml) was added a 4N hydrogen chloride/1,4-dioxane solution (2.3 ml), and the mixture was left at room temperature for 23 hours. After completion of the reaction, the reaction solution was concentrated under reduced pressure to afford the title compound (144 mg) substantially quantitatively as a white solid.

Rf value: 0.52 (n-butanol:acetic acid:water-3:1:1).

Mass spectrum (FAB, m/z): 491 (M$^+$+1).

$^1$H-NMR spectrum (CD$_3$OD, δppm): 9.28 (dd, J=2.3, 0.7 Hz, 1H), 9.01 (dd, J=5.3, 1.5 Hz, 1H), 8.70 (ddd, J=8.2, 2.3, 1.5 Hz, 1H), 8.43 (d, J=8.8 Hz, 1H), 8.11-8.06 (m, 3H), 7.98 (ddd, J=8.2, 5.3, 0.7 Hz, 1H), 7.93 (dd, J=8.8, 7.5 Hz, 1H), 7.64-7.59 (m, 3H), 7.05 (d, J=8.8 Hz, 1H), 7.01 (dd, J=7.5, 0.7 Hz, 1H), 5.13 (s, 2H), 4.83 (s, 2H), 4.41 (s, 2H).

Example 2

(6-{(Pyridin-3-ylsulfonyl)[4-(thiazol-2-yl)benzyl]aminomethyl}pyridin-2-ylamino)-acetic acid (Exemplified Compound No. 985)

2-(a) tert-Butyl[tert-butoxycarbonyl(6-{(pyridin-3-ylsulfonyl)[4-(thiazol-2-yl)benzyl]-aminomethyl}pyridin-2-yl)amino]acetate To a solution of N-[4-(thiazol-2-yl)benzyl]pyridin-3-ylsulfonamide (686 mg, 2.07 mmol) obtained in Reference Example 4-(e) in tetrahydrofuran (20 ml) were added tert-butyl[tert-butoxycarbonyl(6-hydroxymethylpyridin-2-yl)-amino]acetate (743 mg, 2.20 mmol) obtained in Reference Example 3-(b), tri-n-butylphosphine (980 μl, 3.92 mmol) and N,N,N',N'-tetramethylazodicarboxamide (562 mg, 3.26 mmol), followed by stirring at room temperature for 11 hours. After completion of the reaction, a saturated aqueous sodium chloride solution was added to the reaction solution, followed by extraction with ethyl acetate. The separated organic layer was washed with a saturated aqueous sodium chloride solution, dried over anhydrous magnesium sulfate, and then concentrated under reduced pressure. The resulting residue was subjected to silica gel column chromatography (eluent; hexane:ethyl acetate=95:5→50:50 (V/V)), and fractions containing the desired compound were concentrated under reduced pressure to afford the title compound (1.28 g) as a white foam. (Yield: 95%)

$^1$H-NMR spectrum (CDCl$_3$, δppm): 8.95 (dd, J=2.4, 0.9 Hz, 1H), 8.71 (dd, J=4.9, 1.6 Hz, 1H), 7.90-7.85 (m, 3H), 7.87 (d, J=3.2 Hz, 1H), 7.71 (d, J=8.4 Hz, 1H), 7.51 (dd, J=8.4, 7.4 Hz, 1H), 7.34-7.30 (m, 3H), 7.34 (d, J=3.2 Hz, 1H), 6.85 (d, J=7.4 Hz, 1H), 4.63 (s, 2H), 4.40 (s, 2H), 4.35 (s, 2H), 1.52 (s, 9H), 1.42 (s, 9H).

2-(b) (6-{(Pyridin-3-ylsulfonyl)[4-(thiazol-2-yl)benzyl]aminomethyl}pyridin-2-ylamino)acetic acid hydrochloride To a solution of tert-butyl[tert-butoxycarbonyl(6-{(pyridin-3-ylsulfonyl)[4-(thiazol-2-yl)benzyl]aminomethyl}pyridin-2-yl)amino]acetate (1.28 g, 1.96 mmol) obtained in Example 2-(a) in 1,4-dioxane (30 ml) was added a 4N hydrogen chloride/-1,4-dioxane solution (20 ml), followed by stirring at room temperature for 14 hours. After completion of the reaction, the reaction solution was concentrated under reduced pressure, and methylene chloride was added to the resulting residue, followed by sonication. A precipitated solid was collected by filtration, and the resulting solid was washed with methylene chloride, followed by drying under reduced pressure at 60° C. to afford a crude product (1.66 g) containing the title compound substantially quantitatively as a white solid.

$^1$H-NMR spectrum (CD$_3$OD, δppm): 9.31 (d, J=2.0 Hz, 1H), 9.03 (dd, J=5.3, 1.5 Hz, 1H), 8.75 (ddd, J=8.2, 2.0, 1.5 Hz, 1H), 8.04 (d, J=3.5 Hz, 1H), 8.04-8.00 (m, 1H), 7.85-7.82 (m, 2H), 7.83 (d, J=3.5 Hz, 1H), 7.73 (dd, J=9.0, 7.4 Hz, 1H), 7.48-7.44 (m, 2H), 6.82 (d, J=9.0 Hz, 1H), 6.78 (d, J=7.4 Hz, 1H), 4.69 (s, 2H), 4.64 (s, 2H), 4.08 (s, 2H).

2-(c) (6-{(Pyridin-3-ylsulfonyl)[4-(thiazol-2-yl)benzyl]aminomethyl}pyridin-2-ylamino)acetic acid A solution of (6-{(pyridin-3-ylsulfonyl)[4-(thiazol-2-yl)benzyl]aminomethyl}-pyridin-2-ylamino)acetic acid hydrochloride (1.61 g) (containing 1.90 mmol of the title compound of a pure content) obtained in Example 2-(b) in tetrahydrofuran (10 ml) was homogeneously dissolved with a 1N aqueous sodium hydroxide solution (12 ml). Water (40 ml) was then added, followed by adjustment to pH 6.4 with 1N hydrochloric acid, and a precipitated solid was collected by filtration. The resulting solid was washed with water, and then dried under reduced pressure at 60° C. to afford the title compound (854 mg) as a white solid. (Yield: 91%)

Rf value: 0.55 (n-butanol:acetic acid:water-3:1:1).

Mass spectrum (FAB, m/z): 496 (M$^+$+1).

$^1$H-NMR spectrum (DMSO-d$_6$, δppm): 12.42 (brs, 0.6H), 8.84 (dd, J=2.4, 0.6 Hz, 1H), 8.72 (dd, J=4.8, 1.6 Hz, 1H), 8.04 (ddd, J=8.1, 2.4, 1.6 Hz, 1H), 7.93 (d, J=3.2 Hz, 1H), 7.93-7.89 (m, 2H), 7.79 (d, J=3.2 Hz, 1H), 7.48 (ddd, J=8.1, 4.8, 0.6 Hz, 1H), 7.43-7.39 (m, 2H), 7.23 (dd, J=8.3, 7.2 Hz, 1H), 6.76 (t, J=5.6 Hz, 0.9H), 6.36 (d, J=8.3 Hz, 1H), 6.33 (d, J=7.2 Hz, 1H), 4.71 (s, 2H), 4.21 (s, 2H), 3.71 (d, J=5.6 Hz, 2H).

Example 3

(6-{(Pyridin-2-ylsulfonyl)[4-(thiazol-2-yl)benzyl]aminomethyl}pyridin-2-ylamino)-acetic acid (Exemplified Compound No. 977)

3-(a) tert-Butyl[tert-butoxycarbonyl(6-{(pyridin-2-ylsulfonyl)[4-(thiazol-2-yl)benzyl]-aminomethyl}pyridin-2-yl)amino]acetate Reaction and post-treatment were carried out in the same manner as in Example 2-(a) except for using tert-butyl[tert-butoxycarbonyl(6-hydroxymethylpyridin-2-yl)amino]acetate (279 mg, 0.824 mmol) obtained in Reference Example 3-(b), and using N-[4-(thiazol-2-yl)benzyl]pyridin-2-ylsulfonamide (275 mg, 0.830 mmol) obtained in Reference Example 5 in place of N-[4-(thiazol-2-yl)benzyl]pyridin-3-ylsulfonamide to afford the title compound (496 mg) as a white foam. (Yield: 92%)

Mass spectrum (FAB, m/z): 652 (M$^+$+1).

$^1$H-NMR spectrum (CDCl$_3$, δppm): 8.60 (ddd, J=4.7, 1.7, 0.9 Hz, 1H), 7.85 (d, J=3.1 Hz, 1H), 7.85-7.81 (m, 3H), 7.77 (ddd, J=7.7, 7.6, 1.7 Hz, 1H), 7.65 (d, J=8.3 Hz, 1H), 7.45 (dd, J=8.3, 7.3 Hz, 1H), 7.39 (ddd, J=7.6, 4.7, 1.3 Hz, 1H), 7.34-7.30 (m, 2H), 7.32 (d, J=3.1 Hz, 1H), 6.91 (dd, J=7.3, 0.4 Hz, 1H), 4.75 (s, 2H), 4.49 (s, 2H), 4.45 (s, 2H), 1.52 (s, 9H), 1.42 (s, 9H).

3-(b) (6-{(Pyridin-2-ylsulfonyl)[4-(thiazol-2-yl)benzyl]aminomethyl}pyridin-2-ylamino)acetic acid Reaction was carried out in the same manner as in Example 1-(c) except for using tert-butyl[tert-butoxycarbonyl(6-{(pyridin-2-ylsulfonyl)[4-(thiazol-2-yl)-benzyl]aminomethyl}pyridin-2-yl)amino]acetate (490 mg, 0.752 mmol) obtained in Example 3-(a) in place of tert-butyl(tert-butoxycarbonyl{6-[(6-phenylpyridazin-3-ylmethyl)(pyridin-3-ylsulfonyl)aminomethyl]pyridin-2-yl}amino)acetate. After completion of the reaction, the reaction solution was concentrated under reduced pressure, and tetrahydrofuran (10 ml), water (20 ml) and a 1N aqueous sodium hydroxide solution were added to the residue, followed by adjustment to pH 12.0, and subsequently insolubles were filtered off. 1N Hydrochloric acid was added to the filtrate to adjust the pH to 4.5, and a precipitated solid was collected by filtration. The resulting solid was washed with water, and dried under reduced pressure at 50° C. to afford the title compound (147 mg) as a white solid. (Yield: 39%)

Rf value: 0.53 (n-butanol:acetic acid:water=3:1:1).
Mass spectrum (FAB, m/z): 496 ($M^+$+1).
$^1$H-NMR spectrum (DMSO-$d_6$, δppm): 12.40 (brs, 0.7H), 8.65 (ddd, J=4.6, 1.7, 0.9 Hz, 1H), 7.96 (ddd, J=7.8, 7.7, 1.7 Hz, 1H), 7.92 (d, J=3.2 Hz, 1H), 7.88-7.84 (m, 2H), 7.81 (ddd, J=7.8, 1.0, 0.9 Hz, 1H), 7.78 (d, J=3.2 Hz, 1H), 7.58 (ddd, J=7.7, 4.6, 1.0 Hz, 1H), 7.39-7.36 (m, 2H), 7.19 (dd, J=8.2, 7.1 Hz, 1H), 6.75 (t, J=5.6 Hz, 0.9H), 6.34 (d, J=8.2 Hz, 1H), 6.29 (d, J=7.1 Hz, 1H), 4.75 (s, 2H), 4.25 (s, 2H), 3.82 (d, J=5.6 Hz, 2H).

Example 4

(6-{(4-Fluorobenzenesulfonyl)[4-(thiazol-2-yl)benzyl]amino methyl}pyridin-2-ylamino)acetic acid (Exemplified Compound No. 936)

4-(a) tert-Butyl[tert-butoxycarbonyl(6-{(4-fluorobenzenesulfonyl)[4-(thiazol-2-yl)-benzyl]aminomethyl}pyridin-2-yl)amino]acetate Reaction and post-treatment were carried out in the same manner as in Example 2-(a) except for using tert-butyl([tert-butoxycarbonyl(6-hydroxymethylpyridin-2-yl)amino]acetate (101 mg, 0.298 mmol) obtained in Reference Example 3-(b), and using 4-fluoro-N-[4-(thiazol-2-yl)benzyl]benzenesulfonamide (105 mg, 0.301 mmol) obtained in Reference Example 6 in place of N-[4-(thiazol-2-yl)benzyl]pyridin-3-ylsulfonamide to afford the title compound (181 mg) as a white foam. (Yield: 91%)

Mass spectrum (FAB, m/z): 669 ($M^+$+1).
$^1$H-NMR spectrum (CDCl$_3$, δppm): 7.88-7.85 (m, 3H), 7.73-7.68 (m, 3H), 7.50 (dd, J=8.3, 7.4 Hz, 1H), 7.33 (d, J=3.3 Hz, 1H), 7.31-7.27 (m, 2H), 712-7.07 (m, 2H), 6.85 (d, J=7.4 Hz, 1H), 4.56 (s, 2H), 4.38 (s, 2H), 4.36 (s, 2H), 1.52 (s, 9H), 1.41 (s, 9H).

4-(b) (6-{(4-Fluorobenzenesulfonyl)[4-(thiazol-2-yl)benzyl]aminomethyl}pyridin-2-ylamino)acetic acid hydrochloride Reaction and post-treatment were carried out in the same manner as in Example 1-(c) except for using tert-butyl[tert-butoxycarbonyl(6-{(4-fluorobenzenesulfonyl)[4-(thiazol-2-yl)benzyl]aminomethyl}pyridin-2-yl)amino]acetate (175 mg, 0.261 mmol) obtained in Example 4-(a) in place of tert-butyl(tert-butoxycarbonyl {6-[(6-phenylpyridazin-3-ylmethyl)(pyridin-3-ylsulfonyl)aminomethyl]pyridin-2-yl}amino)acetate to afford the title compound (151 mg) substantially quantitatively as a white solid.

$^1$H-NMR spectrum (CD$_3$OD, δppm): 8.07-8.02 (m, 2H), 7.95 (d, J=3.5 Hz, 1H), 7.81-7.77 (m, 2H), 7.72 (d, J=3.5 Hz, 1H), 7.69 (dd, J=7.4 Hz, 1H), 7.45-7.40 (m, 2H), 7.40-7.36 (m, 2H), 6.79 (d, J=8.9 Hz, 1H), 6.69 (d, J=7.4 Hz, 1H), 4.51 (s, 2H), 4.48 (s, 2H), 4.04 (s, 2H).

4-(c) (6-{(4-Fluorobenzenesulfonyl)[4-(thiazol-2-yl)benzyl]aminomethyl}pyridin-2-ylamino)acetic acid Reaction and post-treatment were carried out in the same manner as in Example 2-(c) except for using (6-{(4-fluorobenzenesulfonyl)[4-(thiazol-2-yl)benzyl]-aminomethyl}pyridin-2-ylamino)acetic acid hydrochloride (148 mg, 0.248 mmol) obtained in Example 4-(b) in place of (6-{(pyridin-3-ylsulfonyl)[4-(thiazol-2-yl)-benzyl]aminomethyl}pyridin-2-ylamino)acetic acid hydrochloride to afford the title compound (122 mg) as a pale brown solid. (Yield: 95%)

Rf value: 0.66 (n-butanol:acetic acid:water=3:1:1).
Mass spectrum (FAB, m/z): 513 ($M^+$+1).
$^1$H-NMR spectrum (DMSO-$d_6$, δppm): 7.92 (d, J=3.3 Hz, 1H), 7.91-7.88 (m, 2H), 7.79-7.74 (m, 2H), 7.79 (d, J=3.3 Hz, 1H), 7.40-7.37 (m, 2H), 7.32-7.26 (m, 2H), 7.23 (dd, J=8.3, 7.2 Hz, 1H), 6.77 (t, J=5.5 Hz, 0.9H), 6.37 (d, J=8.3 Hz, 1H), 6.30 (d, J=7.2 Hz, 1H), 4.64 (s, 2H), 4.16 (s, 2H), 3.75 (d, J=5.5 Hz, 2H).

Example 5

(6-{[4-(4,5-Dihydrothiazol-2-yl)benzyl](4-fluorobenzenesulfonyl)aminomethyl}-pyridin-2-ylamino)acetic acid (Exemplified Compound No. 1326)

5-(a) tert-Butyl[tert-butoxycarbonyl(6-{[4-(4,5-dihydrothiazol-2-yl)benzyl](4-fluorobenzenesulfonyl)aminomethyl}pyridin-2-yl)amino]acetate Reaction and post-treatment were carried out in the same manner as in Example 2-(a) except for using tert-butyl[tert-butoxycarbonyl(6-hydroxymethylpyridin-2-yl)amino]acetate (217 mg, 0.641 mmol) obtained in Reference Example 3-(b), and using N-[4-(4,5-dihydrothiazol-2-yl)benzyl]-4-fluorobenzenesulfonamide (225 mg, 0.641 mmol) obtained in Reference Example 7-(b) in place of N-[4-(thiazol-2-yl)-benzyl]pyridin-3-ylsulfonamide to afford the title compound (404 mg) as a colorless oil. (Yield: 94%)

Mass spectrum (FAB, m/z): 671 ($M^+$+1).
$^1$H-NMR spectrum (CDCl$_3$, δppm): 7.75-7.66 (m, 5H), 7.50 (dd, J=8.3, 7.4 Hz, 1H), 7.27-7.23 (m, 2H), 7.12-7.06 (m, 2H), 6.83 (d, J=7.4 Hz, 1H), 4.55 (s, 2H), 4.45 (t, J=8.3 Hz, 2H), 4.37 (s, 2H), 4.33 (s, 2H), 3.42 (t, J=8.3 Hz, 2H), 1.52 (s, 9H), 1.41 (s, 9H).

5-(b) (6-{[4-(4,5-Dihydrothiazol-2-yl)benzyl](4-fluorobenzenesulfonyl)aminomethyl}-pyridin-2-ylamino)acetic acid Reaction and post-treatment were carried out in the same manner as in with Example 3-(b) except for using tert-butyl

[tert-butoxycarbonyl(6-{[4-(4,5-dihydrothiazol-2-yl)benzyl](4-fluorobenzenesulfonyl)aminomethyl}pyridin-2-yl)amino]acetate (202 mg, 0.301 mmol) obtained in Example 5-(a) in place of tert-butyl(tert-butoxycarbonyl{6-[(pyridin-2-ylsulfonyl)(4-thiazol-2-yl)benzyl]aminomethyl}pyridin-2-ylamino)acetate to afford the title compound (138 mg) as a white solid. (Yield: 89%)

Rf value: 0.54 (n-butanol:acetic acid:water=3:1:1).

Mass spectrum (FAB, m/z): 515 ($M^+$+1).

$^1$H-NMR spectrum (DMSO-$d_6$, δppm): 12.41 (brs, 0.4H), 7.78-7.73 (m, 2H), 7.73-7.70 (m, 2H), 7.37-7.34 (m, 2H), 7.31-7.26 (m, 2H), 7.22 (dd, J=8.4, 7.1 Hz, 1H), 6.78 (t, J=5.8 Hz, 0.9H), 6.37 (dd, J=8.4, 0.6 Hz, 1H), 6.29 (dd, J=7.1, 0.6 Hz, 1H), 4.64 (s, 2H), 4.39 (t, J=8.3 Hz, 2H), 4.14 (s, 2H), 3.75 (d, J=5.8 Hz, 2H), 3.44 (t, J=8.3 Hz, 2H).

Example 6

{6-[(Biphenyl-4-ylmethyl)(pyridin-3-ylsulfonyl)aminomethyl]pyridin-2-ylamino}acetic acid hydrochloride (Exemplified Compound No. 546)

6-(a) tert-Butyl({6-[(biphenyl-4-ylmethyl)(pyridin-3-ylsulfonyl)aminomethyl]pyridin-2-yl}tert-butoxycarbonylamino)acetate Reaction and post-treatment were carried out in the same manner as in Example 2-(a) except for using tert-butyl[tert-butoxycarbonyl(6-hydroxymethylpyridin-2-yl)amino]acetate (523 mg, 1.55 mmol) obtained in Reference Example 3-(b), and using N-(biphenyl-4-ylmethyl)pyridin-3-ylsulfonamide (501 mg, 1.54 mmol) obtained in Reference Example 8 in place of N-[4-(thiazol-2-yl)benzyl]pyridin-3-ylsulfonamide to afford the title compound (934 mg) as a white foam. (Yield: 94%)

Mass spectrum (FAB, m/z): 645 ($M^+$+1).

$^1$H-NMR spectrum (CDCl$_3$, δppm): 8.96 (dd, J=2.3, 0.7 Hz, 1H), 8.71 (dd, J=4.9, 1.7 Hz, 1H), 7.87 (ddd, J=8.0, 2.3, 1.7 Hz, 11-1), 7.71 (d, J=8.4 Hz, 1H), 7.57-7.54 (m, 2H), 7.52 (dd, J=8.4, 7.4 Hz, 1H), 7.51-7.48 (m, 2H), 7.46-7.41 (m, 2H), 7.37-7.33 (m, 1H), 7.33-7.28 (m, 3H), 6.87 (d, J=7.4 Hz, 1H), 4.62 (s, 2H), 4.42 (s, 2H), 4.38 (s, 2H), 1.52 (s, 9H), 1.42 (s, 9H).

6-(b) {6-[(Biphenyl-4-ylmethyl)(pyridin-3-ylsulfonyl)aminomethyl]pyridin-2-ylamino}acetic acid hydrochloride To a solution of tert-butyl({6-[(biphenyl-4-ylmethyl)(pyridin-3-ylsulfonyl)-aminomethyl]pyridin-2-yl}tert-butoxycarbonylamino)acetate (931 mg, 1.44 mmol) obtained in Example 6-(a) in methylene chloride (14.4 ml) was added a 4N hydrogen chloride/1,4-dioxane solution (7.2 ml), and the mixture was left at room temperature for 16 hours. Further, it was stirred at 50° C. for 2 hours. After completion of the reaction, the reaction solution was concentrated under reduced pressure, followed by addition of methylene chloride to the residue, and a precipitated solid was collected by filtration. The resulting solid was dried under reduced pressure at room temperature to afford the title compound (760 mg) as a white solid. (Yield: 94%)

Rf value: 0.62 (n-butanol:acetic acid:water=3:1:1).

Mass spectrum (FAB, m/z): 489 ($M^+$+1).

$^1$H-NMR spectrum (CD$_3$OD, δppm): 9.26 (dd, J=2.3, 0.8 Hz, 1H), 8.99 (dd, J=5.2, 1.5 Hz, 1H), 8.65 (ddd, J=8.1, 2.3, 1.5 Hz, 1H), 7.94 (ddd, J=8.1, 5.2, 0.8 Hz, 1H), 7.72 (dd, J=8.9, 7.3 Hz, 1H), 7.54-7.51 (m, 2H), 7.48-7.40 (m, 4H), 7.36-7.29 (m, 3H), 6.80 (d, J=8.9 Hz, 1H), 6.74 (d, J=7.3 Hz, 1H), 4.63 (s, 2H), 4.56 (s, 2H), 3.99 (s, 2H).

Example 7

(6-{[4-(Pyrazol-1-yl)benzyl](pyridin-3-ylsulfonyl)aminomethyl}pyridin-2-ylamino)-acetic acid hydrochloride (Exemplified Compound No. 880)

7-(a) tert-Butyl[tert-butoxycarbonyl(6-{[4-(pyrazol-1-yl)benzyl](pyridin-3-ylsulfonyl)-aminomethyl}pyridin-2-yl)amino]acetate Reaction and post-treatment were carried out in the same manner as in Example 2-(a) except for using tert-butyl[tert-butoxycarbonyl(6-hydroxymethylpyridin-2-yl)amino]acetate (143 mg, 0.423 mmol) obtained in Reference Example 3-(b), and using N-[4-(pyrazol-1-yl)benzyl]pyridin-3-ylsulfonamide (133 mg, 0.423 mmol) obtained in Reference Example 9-(b) in place of N-[4-(thiazol-2-yl)benzyl]pyridin-3-ylsulfonamide to afford the title compound (247 mg) as a white foam. (Yield: 92%)

Mass spectrum (FAB, m/z): 635 ($M^+$+1).

$^1$H-NMR spectrum (CDCl$_3$, δppm): 8.95 (dd, J=2.3, 0.7 Hz, 1H), 8.71 (dd, J=4.9, 1.6 Hz, 1H), 7.91 (dd, J=2.5, 0.6 Hz, 1H), 7.87 (ddd, J=8.0, 2.3, 1.6 Hz, 1H), 7.72 (dd, J=1.8, 0.6 Hz, 1H), 7.71 (d, J=8.4 Hz, 1H), 7.63-7.60 (m, 2H), 7.51 (dd, J=8.4, 7.3 Hz, 1H), 7.35-7.30 (m, 3H), 6.85 (d, J=7.3 Hz, 1H), 6.47 (dd, J=2.5, 1.8 Hz, 1H), 4.61 (s, 2H), 4.39 (s, 2H), 4.35 (s, 2H), 1.53 (s, 9H), 1.42 (s, 9H).

7-(b) (6-{[4-(Pyrazol-1-yl)benzyl](pyridin-3-ylsulfonyl)aminomethyl}pyridin-2-ylamino)acetic acid hydrochloride Reaction and post-treatment were carried out in the same manner as in Example 2-(b) except for using tert-butyl[tert-butoxycarbonyl(6-{[4-(pyrazol-1-yl)-benzyl](pyridin-3-ylsulfonyl)aminomethyl}pyridin-2-yl)-amino]acetate (240 mg, 0.378 mmol) obtained in Example 7-(a) in place of tert-butyl[tert-butoxycarbonyl(6-{(pyridin-3-ylsulfonyl)[4-(thiazol-2-yl)benzyl]aminomethyl}pyridin-2-yl)amino]acetate to afford the title compound (161 mg) as a white solid. (Yield: 72%)

Rf value: 0.52 (n-butanol:acetic acid:water=3:1:1).

Mass spectrum (FAB, m/z): 479 ($M^+$+1).

$^1$H-NMR spectrum (CD$_3$OD, δppm): 9.29 (d, J=2.1 Hz, 1H), 9.01 (dd, J=5.3, 1.5 Hz, 1H), 8.70 (ddd, J=8.2, 2.1, 1.5 Hz, 1H), 8.17 (d, J=2.5 Hz, 1H), 7.98 (ddd, J=8.2, 5.3, 0.6 Hz, 1H), 7.75-7.70 (m, 2H), 7.61-7.57 (m, 2H), 7.39-7.36 (m, 2H), 6.80 (d, J=9.0 Hz, 1H), 6.75 (d, J=7.2 Hz, 1H), 6.52 (dd, J=2.5, 1.8 Hz, 1H), 4.65 (s, 2H), 4.57 (s, 2H), 4.03 (s, 2H).

Example 8

{6-[(Benzofuran-2-ylmethyl)(pyridin-3-ylsulfonyl)aminomethyl]pyridin-2-ylamino}-acetic acid hydrochloride (Exemplified Compound No. 28)

8-(a) tert-Butyl({6-[benzofuran-2-ylmethyl)(pyridin-3-ylsulfonyl)aminomethyl]-pyridin-2-yl}tert-butoxycarbonylamino)acetate Reaction and post-treatment were carried out in the same manner as in Example 2-(a) except for using tert-butyl[tert-butoxycarbonyl(6-hydroxymethylpyridin-2-yl)amino]acetate (252 mg, 0.745 mmol) obtained in Reference Example 3-(b), and using N-(benzofuran-2-ylmethyl)pyridin-3-ylsulfonamide (215 mg, 0.747 mmol) obtained in Reference Example 10-(c) in place of N-[4-(thiazol-2-yl)benzyl]pyridin-3-ylsulfonamide to afford the title compound (397 mg) as a white foam. (Yield: 88%)

Mass spectrum (FAB, m/z): 609 (M$^+$+1).

$^1$H-NMR spectrum (CDCl$_3$, δppm): 9.04 (d, J=2.0 Hz, 1H), 8.66 (dd, J=4.9, 1.7 Hz, 1H), 7.96 (ddd, J=8.1, 2.0, 1.7 Hz, 1H), 7.79 (d, J=8.3 Hz, 1H), 7.62 (dd, J=8.3, 7.4 Hz, 1H), 7.48-7.44 (m, 1H), 7.26-7.16 (m, 4H), 7.09 (d, J=7.4 Hz, 1H), 6.55 (s, 1H), 4.69 (s, 2H), 4.51 (s, 2H), 4.50 (s, 2H), 1.53 (s, 9H), 1.42 (s, 9H).

8-(b) {6-[(Benzofuran-2-ylmethyl)(pyridin-3-ylsulfonyl)aminomethyl]pyridin-2-yl-amino}acetic acid hydrochloride Reaction and post-treatment were carried out in the same manner as in Example 2-(b) except for using tert-butyl({6-[(benzofuran-2-ylmethyl)(pyridin-3-ylsulfonyl)aminomethyl]pyridin-2-yl}tert-butoxycarbonylamino)acetate (201 mg, 0.330 mmol) obtained in Example 8-(a) in place of tert-butyl[tert-butoxycarbonyl(6-{(pyridin-3-ylsulfonyl)[4-(thiazol-2-yl)benzyl]aminomethyl}pyridin-2-yl)amino]acetate to afford the title compound (134 mg) as a white solid. (Yield: 77%)

Rf value: 0.59 (n-butanol:acetic acid:water=3:1:1).

Mass spectrum (FAB, m/z): 453 (M$^+$+1).

$^1$H-NMR spectrum (CD$_3$OD, δppm): 9.28 (dd, J=2.3, 0.5 Hz, 1H), 8.89 (dd, J=5.3, 1.4 Hz, 1H), 8.70 (ddd, J=8.2, 2.3, 1.4 Hz, 1H), 7.90 (ddd, J=8.2, 5.3, 0.5 Hz, 1H), 7.78 (dd, J=9.0, 7.2 Hz, 1H), 7.47-7.44 (m, 1H), 7.27-7.22 (m, 2H), 7.21-7.15 (m, 1H), 6.88 (d, J=7.2 Hz, 1H), 6.82 (d, J=9.0 Hz, 1H), 6.73 (s, 1H), 4.77 (s, 2H), 4.76 (s, 2H), 4.12 (s, 2H).

Example 9

{6-[(4'-Fluorobiphenyl-4-ylmethyl)(pyridin-3-ylsulfonyl)aminomethyl]pyridin-2-ylamino}acetic acid hydrochloride (Exemplified Compound No. 605)

9-(a) tert-Butyl({6-[(4-bromobenzyl)(pyridin-3-ylsulfonyl)aminomethyl]pyridin-2-yl}tert-butoxycarbonylamino acetate Reaction and post-treatment were carried out in the same manner as in Example 2-(a) except for using tert-butyl[tert-butoxycarbonyl(6-hydroxymethylpyridin-2-yl)amino]acetate (428 mg, 1.26 mmol) obtained in Reference Example 3-(b), and using N-(4-bromobenzyl)pyridin-3-ylsulfonamide (414 mg, 1.26 mmol) obtained in Reference Example 11 in place of N-[4-(thiazol-2-yl)benzyl]pyridin-3-ylsulfonamide to afford the title compound (797 mg) as a white solid. (Yield: 98%)

$^1$H-NMR spectrum (CDCl$_3$, δppm): 8.93 (dd, J=2.4, 0.8 Hz, 1H), 8.71 (dd, J=4.8, 1.6 Hz, 1H), 7.85 (ddd, J=8.0, 2.4, 1.6 Hz, 1H), 7.71 (d, J=8.3 Hz, 1H), 7.51 (dd, J=8.3, 7.3 Hz, 1H), 7.42-7.39 (m, 2H), 7.31 (ddd, J=8.0, 4.8, 0.8 Hz, 1H), 7.14-7.10 (m, 2H), 6.82 (dd, J=7.3, 0.4 Hz, 1H), 4.53 (s, 2H), 4.35 (s, 2H), 4.33 (s, 2H), 1.53 (s, 9H), 1.42 (s, 9H).

9-(b) tert-Butyl(tert-butoxycarbonyl{6-[(4'-fluorobiphenyl-4-ylmethyl)(pyridin-3-ylsulfonyl)aminomethyl]pyridin-2-yl}amino)acetate To a solution of tert-butyl({6-[(4-bromobenzyl)(pyridin-3-ylsulfonyl)aminomethyl]pyridin-2-yl}tert-butoxycarbonylamino)acetate (185 mg, 0.285 mmol) obtained in Example 9-(a) in toluene (2 ml) were added 4-fluorophenylboronic acid (61.3 mg, 0.438 mmol), palladium acetate (4.9 mg, 0.044 mmol), tripotassium phosphate (202 mg, 0.953 mmol) and water (0.2 ml), followed by being subjected to argon atmosphere. Then a solution of tricyclohexylphosphine in 20% toluene (130 μl, 0.088 mmol) was added to the mixture, and it was stirred at 100° C. for 2.5 hours under argon atmosphere. After completion of the reaction, a saturated aqueous sodium chloride solution was added to the reaction solution, followed by extraction with ethyl acetate. The separated organic layer was dried over anhydrous magnesium sulfate, and then concentrated under reduced pressure. The resulting residue was subjected to silica gel column chromatography (eluent; hexane:ethyl acetate=9:1→7:3 (V/V)), and fractions containing the desired compound were concentrated under reduced pressure to afford the title compound (178 mg) as a white foam. (Yield: 94%)

$^1$H-NMR spectrum. (CDCl$_3$, δppm): 8.96 (dd, J=2.4, 0.8 Hz, 1H), 8.71 (dd, J=4.8, 1.7 Hz, 1H), 7.88 (ddd, J=8.1, 2.4, 1.7 Hz, 1H), 7.71 (d, J=8.1 Hz, 1H), 7.53-7.49 (m, 3H), 7.46-7.43 (m, 2H), 7.31 (ddd, J=8.1, 4.8, 0.8 Hz, 1H), 7.31-7.28 (m, 2H), 7.15-7.10 (m, 2H), 6.86 (dd, J=7.3, 0.6 Hz, 1H), 4.62 (s, 2H), 4.41 (s, 2H), 4.37 (s, 2H), 1.52 (s, 9H), 1.42 (s, 9H).

9-(c) {6-[(4'-Fluorobiphenyl-4-ylmethyl)(pyridin-3-ylsulfonyl)aminomethyl]pyridin-2-ylamino}acetic acid hydrochloride Reaction and post-treatment were carried out in the same manner as in Example 2-(b) except for using tert-butyl(tert-butoxycarbonyl{6-[(4'-fluorobiphenyl-4-ylmethyl)(pyridin-3-ylsulfonyl)aminomethyl]pyridin-2-yl}amino)acetate (173 mg, 0.261 mmol) obtained in Example 9-(b) in place of tert-butyl[tert-butoxycarbonyl(6-{(pyridin-3-ylsulfonyl)[4-(thiazol-2-yl)benzyl]aminomethyl}pyridin-2-yl)amino]acetate to afford the title compound (134 mg) as a white solid. (Yield: 89%)

Rf value: 0.62 (n-butanol:acetic acid:water=3:1:1).

Mass spectrum (FAB, m/z): 507 (M$^+$+1).

$^1$H-NMR spectrum (CD$_3$OD, δppm): 9.29 (dd, J=2.2, 0.7 Hz, 1H), 9.01 (dd, J=5.3, 1.5 Hz, 1H), 8.69 (ddd, J=8.2, 2.2, 1.5 Hz, 1H), 7.98 (ddd, J=8.2, 5.3, 0.7 Hz, 1H), 7.72 (dd, J=9.0, 7.3 Hz, 1H), 7.57-7.53 (m, 2H), 7.46-7.42 (m, 2H), 7.33-7.30 (m, 2H), 7.18-7.13 (m, 2H), 6.82 (d, J=9.0 Hz, 1H), 6.74 (d, J=7.3 Hz, 1H), 4.65 (s, 2H), 4.57 (s, 2H), 4.03 (s, 2H).

Example 10

{6-[(4'-Chlorobiphenyl-4-ylmethyl)(pyridin-3-ylsulfonyl)aminomethyl]pyridin-2-ylamino}acetic acid hydrochloride (Exemplified Compound No. 681)

10-(a) tert-Butyl(tert-butoxycarbonyl{6-[(4'-chlorobiphenyl-4-ylmethyl)(pyridin-3-ylsulfonyl)aminomethyl]pyridin-2-yl}amino)acetate Reaction and post-treatment were carried out in the same manner as in Example 9-(b) except for using tert-butyl({6-[(4-bromobenzyl)(pyridin-3-ylsulfonyl)-aminomethyl]pyridin-2-yl}tert-butoxycarbonylamino)acetate (187 mg, 0.289 mmol) obtained in Example 9-(a), and using 4-chlorophenylboronic acid (70.6 mg, 0.452 mmol) in place of 4-fluorophenylboronic acid to afford the title compound (166 mg) as a colorless oil. (Yield: 84%)

¹H-NMR spectrum (CDCl₃, δppm): 8.96 (dd, J=2.4, 0.8 Hz, 1H), 8.71 (dd, J=4.8, 1.6 Hz, 1H), 7.88 (ddd, J=8.0, 2.4, 1.6 Hz, 1H), 7.71 (d, J=8.4 Hz, 1H), 7.51 (dd, J=8.4, 7.3 Hz, 1H), 7.50-7.44 (m, 4H), 7.42-7.39 (m, 2H), 7.32-7.28 (m, 2H), 7.31 (ddd, J=8.0, 4.8, 0.8 Hz, 1H), 6.86 (dd, J=7.3, 0.6 Hz, 1H), 4.62 (s, 2H), 4.41 (s, 2H), 4.36 (s, 2H), 1.52 (s, 9H), 1.42 (s, 9H).

10-(b) {6-[(4'-Chlorobiphenyl-4-ylmethyl)(pyridin-3-ylsulfonyl)aminomethyl]pyridin-2-ylamino}acetic acid hydrochloride Reaction and post-treatment were carried out in the same manner as in Example 2-(b) except for using tert-butyl(tert-butoxycarbonyl{6-[(4'-chlorobiphenyl-4-ylmethyl)(pyridin-3-ylsulfonyl)aminomethyl]pyridin-2-yl}amino)acetate (163 mg, 0.240 mmol) obtained in Example 10-(a) in place of tert-butyl[tert-butoxycarbonyl(6-{(pyridin-3-ylsulfonyl)[4-(thiazol-2-yl)benzyl]aminomethyl}pyridin-2-yl)amino]acetate to afford the title compound (133 mg) as a white solid. (Yield: 93%)
Rf value: 0.64 (n-butanol:acetic acid:water=3:1:1).
Mass spectrum (FAB, m/z): 523 (M⁺+1).
¹H-NMR spectrum (CD₃OD, 3 ppm): 9.31 (dd, J=2.2, 0.6 Hz, 1H), 9.02 (dd, J=5.3, 1.4 Hz, 1H), 8.74 (ddd, J=8.1, 2.2, 1.4 Hz, 1H), 8.02 (ddd, J=8.1, 5.3, 0.6 Hz, 1H), 7.72 (dd, J=9.0, 7.3 Hz, 1H), 7.55-7.51 (m, 2H), 7.48-7.41 (m, 4H), 7.35-7.32 (m, 2H), 6.81 (d, J=9.0 Hz, 1H), 6.74 (d, J=7.3 Hz, 1H), 4.66 (s, 2H), 4.58 (s, 2H), 4.03 (s, 2H).

Example 11

(6-{(Pyridin-3-ylsulfonyl) [4-(thiazol-2-yl)benzyl]aminomethyl}pyridin-2-ylamino)-acetic acid trifluoroacetate (Exemplified Compound No. 985)

11-(a) tert-Butyl[tert-butoxycarbonyl(6-{(pyridin-3-ylsulfonyl)[4-(thiazol-2-yl)benzyl]-aminomethyl}pyridin-2-yl)amino]acetate Reaction and post-treatment were carried out in the same manner as in Example 2-(a) except for using tert-butyl(tert-butoxycarbonyl{6-[(pyridin-3-ylsulfonyl)aminomethyl]pyridin-2-yl}amino)acetate (126 mg, 0.263 mmol) obtained in Reference Example 12-(d) in place of N-[4-(thiazol-2-yl)benzyl]pyridin-3-ylsulfonamide, and using 4-(thiazol-2-yl)benzyl alcohol (49.7 mg, 0.260 mmol) obtained in Reference Example 4-(a) in place of text-butyl[tert-butoxycarbonyl(6-hydroxymethylpyridin-2-yl)amino]acetate to afford the title compound (145 mg) as a white foam. (Yield: 85%)
This compound showed the same ¹H-NMR spectrum as that of tert-butyl[tert-butoxycarbonyl(6-{(pyridin-3-ylsulfonyl) [4-(thiazol-2-yl)benzyl]aminomethyl}pyridin-2-yl)amino]acetate obtained in Example 2-(a).

11-(b) (6-{(Pyridin-3-ylsulfonyl)[4-(thiazol-2-yl)benzyl]aminomethyl}pyridin-2-ylamino)acetic acid trifluoroacetate To a solution of tert-butyl[tert-butoxycarbonyl(6-{(pyridin-3-ylsulfonyl)[4-(thiazol-2-yl)benzyl]aminomethyl}pyridin-2-yl)amino]acetate (135 mg, 0.207 mmol) obtained in Example 11-(a) in methylene chloride (1.23 ml) was added a 4N hydrogen chloride/1,4-dioxane solution (1.02 ml), followed by stirring at room temperature for 16 hours. After completion of the reaction, the reaction solution was concentrated under reduced pressure. The resulting residue was subjected to reversed phase column chromatography (column; Megabond Elut™ C18 (manufactured by Varian, Inc.), eluent; a 1.0% aqueous triethylamine solution→acetonitrile:a 0.5% aqueous trifluoroacetic acid solution=1:1 (V/V)), and fractions containing the desired compound were concentrated under reduced pressure to afford the title compound (35 mg) as a pale yellow solid. (Yield: 24%)
Rf value: 0.52 (n-butanol:acetic acid:water=3:1:1).
Mass spectrum (FAB, m/z): 496 (M⁺+1).
¹H-NMR spectrum (CD₃OD, δppm): 9.04 (d, J=1.9 Hz, 1H), 8.83 (dd, J=4.9, 1.6 Hz, 1H), 8.30 (ddd, J=8.0, 1.9, 1.6 Hz, 1H), 7.86 (d, J=3.3 Hz, 1H), 7.82-7.77 (m, 2H), 7.66 (ddd, J=8.0, 4.9, 0.4 Hz, 1H), 7.61 (d, J=3.3 Hz, 1H), 7.60 (dd, J=8.8, 7.2 Hz, 1H), 7.39-7.35 (m, 2H), 6.68 (d, J=8.8 Hz, 1H), 6.65 (d, J=7.2 Hz, 1H), 4.59 (s, 2H), 4.51 (s, 2H), 3.95 (s, 2H).

Example 12

{6-[(6-Chlorobenzo[b]thiophen-2-ylmethyl)(pyridin-3-ylsulfonyl)aminomethyl]pyridin-2-ylamino}acetic acid hydrochloride (Exemplified Compound No. 186)

12-(a) tert-Butyl(tert-butoxycarbonyl{6-[(6-chlorobenzo[b]thiophen-2-ylmethyl)-(pyridin-3-ylsulfonyl)aminomethyl]pyridin-2-yl}amino)acetate Reaction and post-treatment were carried out in the same manner as in Example 2-(a) except for using tert-butyl(tert-butoxycarbonyl{6-[(pyridin-3-ylsulfonyl)aminomethyl]pyridin-2-yl}amino)acetate (100 mg, 0.209 mmol) obtained in Reference Example 12-(d) in place of N-[4-(thiazol-2-yl)benzyl]pyridin-3-ylsulfonamide, and using (6-chlorobenzo[b]thiophen-2-yl)methanol (see WO 99/37304A, 41.5 mg, 0.209 mmol) in place of tert-butyl[tert-butoxycarbonyl(6-hydroxymethylpyridin-2-yl)amino]acetate to afford the title compound (144 mg) substantially quantitatively as a slightly yellow liquid.
Mass spectrum (FAB, m/z): 659 (M⁺+1).
¹H-NMR spectrum (CDCl₃, δppm): 8.98 (dd, J=2.4, 0.7 Hz, 1H), 8.71 (dd, J=4.8, 1.7 Hz, 1H), 7.91 (ddd, J=8.1, 2.4, 1.7 Hz, 1H), 7.75 (d, J=8.4 Hz, 1H), 7.72-7.70 (m, 1H), 7.58 (d, J=8.8 Hz, 1H), 7.56 (dd, J=8.4, 7.4 Hz, 1H), 7.32-7.28 (m, 2H), 7.09 (d, J=0.7 Hz, 1H), 6.94 (d, J=7.4 Hz, 1H), 4.82 (s, 2H), 4.49 (s, 2H), 4.42 (s, 2H), 1.53 (s, 9H), 1.42 (s, 9H).

12-(b) {6-[(6-Chlorobenzo[b]thiophen-2-ylmethyl)(pyridin-3-ylsulfonyl)aminomethyl]-pyridin-2-ylamino}acetic acid hydrochloride Reaction and post-treatment were carried out in the same manner as in Example 1-(c) except for using tert-butyl(tert-butoxycarbonyl{6-[(6-chlorobenzo[b]-thiophen-2-ylmethyl)(pyridin-3-ylsulfonyl)aminomethyl]pyridin-2-yl}amino)acetate (144 mg, 0.218 mmol) obtained in Example 12-(a) in place of tert-butyl(tert-butoxycarbonyl {6-[(6-phenylpyridazin-3-ylmethyl)(pyridin-3-ylsulfonyl)aminomethyl]-pyridin-2-yl}amino)acetate to afford the title compound (110 mg) as a white solid. (Yield: 88%)
Rf value: 0.64 (n-butanol:acetic acid:water=3:1:1).
Mass spectrum (FAB, m/z): 503 (M⁺+1).
¹H-NMR spectrum (CD₃OD, δppm): 9.22 (dd, J=2.2, 0.6 Hz, 1H), 8.93 (dd, J=5.2, 1.6 Hz, 1H), 8.58 (ddd, J=8.2, 2.2, 1.6 Hz, 1H), 7.85 (ddd, J=8.2, 5.2, 0.6 Hz, 1H), 7.79 (d, J=2.0 Hz, 1H), 7.73 (dd, J=9.0, 7.3 Hz, 1H), 7.63 (d, J=8.5 Hz, 1H), 7.31 (dd, J=8.5, 2.0 Hz, 1H), 7.17 (s, 1H), 6.83 (dd, J=7.3, 0.5 Hz, 1H), 6.79 (d, J=9.0 Hz, 1H), 4.85 (s, 2H), 4.69 (s, 2H), 4.05 (s, 2H).

Example 13

{6-[(Benzo[b]thiophen-2-ylmethyl)(pyridin-3-ylsulfonyl)aminomethyl]pyridin-2-ylamino}acetic acid hydrochloride (Exemplified Compound No. 132)

13-(a) tert-Butyl({6-[(benzo[b]thiophen-2-ylmethyl)(pyridin-3-ylsulfonyl)aminomethyl]pyridin-2-yl}tert-butoxycarbonylamino)acetate Reaction and post-treatment were carried out in the same manner as in Example 2-(a) except for using tert-butyl(tert-butoxycarbonyl{6-[(pyridin-3-ylsulfonyl)aminomethyl]pyridin-2-yl}amino)acetate (126 mg, 0.263 mmol) obtained in Reference Example 12-(d) in place of N-[4-(thiazol-2-yl)benzyl]pyridin-3-ylsulfonamide, and using benzo[b]thiophen-2-ylmethanol (43.2 mg, 0.263 mmol) in place of tert-butyl[tert-butoxycarbonyl(6-hydroxymethylpyridin-2-yl)amino]acetate to afford the title compound (153 mg) as a slightly yellow liquid. (Yield: 93%)

$^1$H-NMR spectrum (CDCl$_3$, δppm): 8.99 (dd, J=2.3, 0.9 Hz, 1H), 8.69 (dd, J=4.8, 1.6 Hz, 1H), 7.91 (ddd, J=8.1, 2.3, 1.6 Hz, 1H), 7.76 (d, J=8.4 Hz, 1H), 7.74-7.66 (m, 2H), 7.57 (dd, J=8.4, 7.4 Hz, 1H), 7.35-7.28 (m, 2H), 7.28 (ddd, J=8.1, 4.8, 0.9 Hz, 1H), 7.12 (d, J=0.7 Hz, 1H), 6.96 (dd, J=7.4, 0.6 Hz, 1H), 4.84 (s, 2H), 4.50 (s, 2H), 4.44 (s, 2H), 1.53 (s, 9H), 1.42 (s, 9H).

13-(b) {6-[(Benzo[b]thiophen-2-ylmethyl)(pyridin-3-ylsulfonyl)aminomethyl]pyridin-2-ylamino}acetic acid hydrochloride Reaction and post-treatment were carried out in the same manner as in Example 2-(b) except for using tert-butyl({6-[(benzo[b]thiophen-2-ylmethyl)(pyridin-3-ylsulfonyl)aminomethyl]pyridin-2-yl}tert-butoxycarbonylamino)acetate (150 mg, 0.240 mmol) obtained in Example 13-(a) in place of tert-butyl[tert-butoxycarbonyl(6-{(pyridin-3-ylsulfonyl)[4-(thiazol-2-yl)benzyl]aminomethyl}pyridin-2-yl)amino]acetate to afford the title compound (96.1 mg) as a white solid. (Yield: 74%)

Rf value: 0.60 (n-butanol:acetic acid:water=3:1:1).
Mass spectrum (FAB, m/z): 469 (M$^+$+1).
$^1$H-NMR spectrum (CD$_3$OD, δppm): 9.27 (dd, J=2.3, 0.7 Hz, 1H), 8.94 (dd, J=5.2, 1.5 Hz, HA 8.66 (ddd, J=8.1, 2.3, 1.5 Hz, 1H), 7.89 (ddd, J=8.1, 5.2, 0.7 Hz, 1H), 7.75-7.64 (m, 3H), 7.34-7.28 (m, 2H), 7.17 (s, 1H), 6.85 (dd, J=7.3, 0.7 Hz, 1H), 6.76 (d, J=9.0 Hz, 1H), 4.87 (s, 2H), 4.72 (s, 2H), 4.00 (s, 2H).

Example 14

(6-{[4-(Pyridazin-4-yl)benzyl](pyridin-3-ylsulfonyl)aminomethyl}pyridin-2-ylamino)-acetic acid hydrochloride (Exemplified Compound No. 1203)

14-(a) tert-Butyl[tert-butoxycarbonyl(6-{[4-(pyridazin-4-yl)benzyl](pyridin-3-ylsulfonyl)aminomethyl}pyridin-2-yl)amino]acetate Reaction and post-treatment were carried out in the same manner as in Example 2-(a) except for using tert-butyl(tert-butoxycarbonyl{6-[(pyridin-3-ylsulfonyl)aminomethyl]pyridin-2-yl}amino)acetate (158 mg, 0.330 mmol) obtained in Reference Example 12-(d) in place of N-[4-(thiazol-2-yl)benzyl]pyridin-3-ylsulfonamide, and using 4-(pyridazin-4-yl)benzyl alcohol (60.2 mg, 0.323 mmol) obtained in Reference Example 13 in place of tert-butyl[tert-butoxycarbonyl(6-hydroxymethylpyridin-2-yl)amino]acetate to afford the title compound (152 mg) as a white foam. (Yield: 73%)

Mass spectrum (FAB, m/z): 647 (M$^+$+1).
$^1$H-NMR spectrum (CDCl$_3$, δppm): 9.44 (dd, J=2.5, 1.2 Hz, 1H), 9.23 (dd, J=5.4, 1.2 Hz, 1H), 8.96 (dd, J=2.4, 0.8 Hz, 1H), 8.73 (dd, J=4.8, 1.7 Hz, 1H), 7.91 (ddd, J=8.0, 2.4, 1.7 Hz, 1H), 7.71 (d, J=8.4 Hz, 1H), 7.63 (dd, J=5.4, 2.5 Hz, 1H), 7.61-7.58 (m, 2H), 7.49 (dd, J=8.4, 7.3 Hz, 1H), 7.45-7.42 (m, 2H), 7.34 (ddd, J=8.0, 4.8, 0.8 Hz, 1H), 6.84 (dd, J=7.3, 0.6 Hz, 1H), 4.65 (s, 2H), 4.41 (s, 2H), 4.34 (s, 2H), 1.53 (s, 9H), 1.42 (s, 9H).

14-(b) (6-{[4-(Pyridazin-4-yl)benzyl](pyridin-3-ylsulfonyl)aminomethyl}pyridin-2-ylamino)acetic acid hydrochloride Reaction was carried out in the same manner as in Example 1-(c) except for using tert-butyl[tert-butoxycarbonyl(6-{[4-(pyridazin-4-yl)benzyl](pyridin-3-ylsulfonyl)aminomethyl}pyridin-2-yl)amino]acetate (150 mg, 0.232 mmol) obtained in Example 14-(a) in place of tert-butyl(tert-butoxycarbonyl {6-[(6-phenylpyridazin-3-ylmethyl)(pyridin-3-ylsulfonyl)aminomethyl]pyridin-2-yl}amino)acetate. After completion of the reaction, the reaction solution was concentrated under reduced pressure. Water and acetone were added to the resulting residue, followed by concentration again under reduced pressure to afford the title compound (137 mg) as a slightly yellow solid. (Yield: 98%)

Rf value: 0.38 (n-butanol:acetic acid:water=3:1:1).
Mass spectrum (FAB, m/z): 491 (M$^+$+1).
$^1$H-NMR spectrum (CD$_3$OD, δppm): 9.91 (dd, J=2.4, 0.9 Hz, 1H), 9.58 (dd, J=6.0, 0.9 Hz, 1H), 9.23 (d, J=2.0 Hz, 1H), 8.98 (dd, J=5.2, 1.5 Hz, 1H), 8.77 (dd, J=6.0, 2.4 Hz, 1H), 8.63 (ddd, J=8.2, 2.0, 1.5 Hz, 1H), 7.99-7.95 (m, 2H), 7.92 (ddd, J=8.2, 5.2, 0.5 Hz, 1H), 7.71 (dd, J=8.9, 7.3 Hz, 1H), 7.61-7.57 (m, 2H), 6.83 (d, J=8.9 Hz, 1H), 6.76 (d, J=7.3 Hz, 1H), 4.69 (s, 2H), 4.69 (s, 2H), 4.17 (s, 2H).

Example 15

{6-[(6-Methoxybenzo[b]thiophen-2-ylmethyl)(pyridin-3-ylsulfonyl)aminomethyl]-pyridin-2-ylamino}acetic acid hydrochloride (Exemplified Compound No. 361)

15-(a) tert-Butyl(tert-butoxycarbonyl{6-[(6-methoxybenzo[b]thiophen-2-ylmethyl)-(pyridin-3-ylsulfonyl)aminomethyl]pyridin-2-yl}amino)acetate Reaction was carried out in the same manner as in Example 2-(a) except for using tert-butyl(tert-butoxycarbonyl{6-[(pyridin-3-ylsulfonyl)aminomethyl]pyridin-2-yl}amino)acetate (69.4 mg, 0.145 mmol) obtained in Reference Example 12-(d) in place of N-[4-(thiazol-2-yl)benzyl]pyridin-3-ylsulfonamide, and using (6-methoxybenzo[b]-thiophen-2-yl)methanol (see WO 2006/106711A, 33.9 mg, 0.175 mmol) in place of tert-butyl [tert-butoxycarbonyl(6-hydroxymethylpyridin-2-yl)amino]acetate. After completion of the reaction, the reaction solution was concentrated under reduced pressure, and water was added to the residue, followed by extraction with toluene. The separated organic layer was dried over anhydrous magnesium sulfate, and concentrated under reduced pressure. The resulting residue was subjected to silica gel column chromatography (eluent; hexane:ethyl acetate=3:1→1:1 (V/V)) and then to reversed phase column chromatography (column; Megabond Elut™ C18 (manufactured by Varian, Inc.), eluent; acetonitrile:water=1:1→1:0 (V/V)), and fractions containing the desired compound were concentrated under reduced pressure to afford the title compound (73.8 mg) as a white foam. (Yield: 78%)

Mass spectrum (FAB, m/z): 655 (M$^+$+1).

$^1$H-NMR spectrum (CDCl$_3$, δppm): 8.99 (dd, J=2.3, 0.8 Hz, 1H), 8.69 (dd, J=4.8, 1.6 Hz, 1H), 7.91 (ddd, J=8.0, 2.3, 1.6 Hz, 1H), 7.76 (d, J=8.4 Hz, 1H), 7.57 (dd, J=8.4, 7.3 Hz, 1H), 7.54 (d, J=8.7 Hz, 1H), 7.28 (ddd, J=8.0, 4.8, 0.8 Hz, 1H), 7.20 (d, J=2.4 Hz, 1H), 7.01 (d, 0.7 Hz, 1H), 6.96 (dd, J=7.3, 0.6 Hz, 1H), 6.95 (dd, J=8.7, 2.4 Hz, 1H), 4.79 (s, 2H), 4.49 (s, 2H), 4.45 (s, 2H), 3.85 (s, 3H), 1.53 (s, 9H), 1.42 (s, 9H).

15-(b) {6-[(6-Methoxybenzo[b]thiophen-2-ylmethyl) (pyridin-3-ylsulfonyl)aminomethyl]pyridin-2-ylamino}acetic acid hydrochloride Reaction and post-treatment were carried out in the same manner as in Example 1-(c) except for using tent-butyl(tert-butoxycarbonyl {6-[(6-methoxybenzo[b]-thiophen-2-ylmethyl)(pyridin-3-ylsulfonyl)aminomethyl]pyridin-2-yl}amino)acetate (72.6 mg, 0.111 mmol) obtained in Example 15-(a) in place of tert-butyl(tert-butoxycarbonyl {6-[(6-phenylpyridazin-3-ylmethyl)(pyridin-3-ylsulfonyl)aminomethyl]-pyridin-2-yl}amino)acetate to afford the title compound (63.1 mg) as a white solid. (Yield: 99%)

Rf value: 0.59 (n-butanol:acetic acid:water=3:1:1).

Mass spectrum (FAB, m/z): 499 (M$^+$+1).

$^1$H-NMR spectrum (CD$_3$OD, δppm): 9.18 (dd, J=2.4, 0.8 Hz, 1H), 8.90 (dd, J=5.1, 1.5 Hz, 1H), 8.51 (ddd, J=8.1, 2.4, 1.5 Hz, 1H), 7.78 (ddd, J=8.1, 5.1, 0.8 Hz, 1H), 7.73 (dd, J=9.1, 7.3 Hz, 1H), 7.51 (d, J=8.7 Hz, 1H), 7.26 (d, J=2.3 Hz, 1H), 7.02 (s, 1H), 6.92 (dd, J=8.7, 2.3 Hz, 1H), 6.82 (dd, J=7.3, 0.8 Hz, 1H), 6.76 (d, J=9.1 Hz, 1H), 4.78 (s, 2H), 4.66 (s, 2H), 4.00 (s, 2H), 3.82 (s, 3H).

Example 16

(6-{(Pyridin-2-ylsulfonyl)[4-(thiazol-4-yl)benzyl] aminomethyl}pyridin-2-ylamino)-acetic acid (Exemplified Compound No. 1090)

16-(a) tert-Butyl[tert-butoxycarbonyl(6-{(pyridin-2-ylsulfonyl)[4-(thiazol-4-yl)benzyl]-aminomethyl}pyridin-2-yl)amino]acetate Reaction and post-treatment were carried out in the same manner as in Example 2-(a) except for using tert-butyl(tert-butoxycarbonyl{6-[(pyridin-2-ylsulfonyl)aminomethyl]pyridin-2-yl}amino)acetate (200 mg, 0.418 mmol) obtained in Reference Example 14 in place of N-[4-(thiazol-2-yl)benzyl]pyridine-3-ylsulfonamide, and using 4-(thiazol-4-yl)benzyl alcohol (79.9 mg, 0.418 mmol) obtained in Reference Example 15-(b) in place of tert-butyl[tert-butoxycarbonyl(6-hydroxymethylpyridin-2-yl)amino]acetate to afford the title compound (240 mg) as a white foam. (Yield: 88%)

Mass spectrum (FAB, m/z): 652 (M$^+$+1).

$^1$H-NMR spectrum (CDCl$_3$, δppm): 8.87 (d, J=2.0 Hz, 1H), 8.60 (ddd, J=4.7, 1.7, 0.9 Hz, 1H), 7.82 (ddd, J=7.7, 1.1, 0.9 Hz, 1H), 7.81-7.78 (m, 2H), 7.77 (ddd, J=7.7, 7.6, 1.7 Hz, 1H), 7.65 (d, J=8.4 Hz, 1H), 7.51 (d, J=2.0 Hz, 1H), 7.45 (dd, J=8.4, 7.3 Hz, 1H), 7.38 (ddd, J=7.6, 4.7, 1.1 Hz, 1H), 7.32-7.29 (m, 2H), 6.91 (d, J=7.3 Hz, 1H), 4.74 (s, 2H), 4.49 (s, 2H), 4.45 (s, 2H), 1.52 (s, 9H), L42 (s, 9H).

16-(b) (6-{(Pyridin-2-ylsulfonyl)[4-(thiazol-4-yl) benzyl]aminomethyl}pyridin-2-ylamino)acetic acid Reaction and post-treatment were carried out in the same manner as in Example 3-(b) except for using tert-butyl[tert-butoxycarbonyl(6-{(pyridin-2-ylsulfonyl)[4-(thiazol-4-yl) benzyl]aminomethyl}pyridin-2-yl)amino]acetate (230 mg, 0.353 mmol) obtained in Example 16-(a) in place of tert-butyl [tert-butoxycarbonyl(6-{(pyridin-2-ylsulfonyl)[4-(thiazol-2-yl)benzyl]aminomethyl}pyridin-2-yl)amino]acetate to afford the title compound (93.5 mg) as a white solid. (Yield: 53%)

Rf value: 0.50 (n-butanol:acetic acid:water=3:1:1).

Mass spectrum. (FAB, m/z): 496 (M$^+$+1).

$^1$H-NMR spectrum (DMSO-d$_6$, δppm): 12.42 (brs, 0.6H), 9.19 (d, J=1.8 Hz, 1H), 8.65 (ddd, J=4.7, 1.7, 0.8 Hz, 1H), 8.14 (d, J=1.8 Hz, 1H), 7.95 (ddd, J=7.8, 7.7, 1.7 Hz, 1H), 7.91-7.88 (m, 2H), 7.81 (ddd, J=7.8, 0.9, 0.8 Hz, 1H), 7.58 (ddd, J=7.7, 4.7, 0.9 Hz, 1H), 7.33-7.30 (m, 2H), 7.20 (dd, J=8.3, 7.2 Hz, 1H), 6.75 (t, J=5.6 Hz, 0.9H), 6.34 (d, J=8.3 Hz, 1H), 6.29 (d, J=7.2 Hz, 1H), 4.73 (s, 2H), 4.24 (s, 2H), 3.83 (d, J=5.6 Hz, 2H).

Example 17

{6-[(Biphenyl-4-ylmethyl)(pyridin-2-ylsulfonyl) aminomethyl]pyridin-2-ylamino}acetic acid hydrochloride (Exemplified Compound No. 538)

17-(a) tert-Butyl({6-[(biphenyl-4-ylmethyl)(pyridin-2-ylsulfonyl)aminomethyl]pyridin-2-yl}tert-butoxycarbonylamino)acetate Reaction and post-treatment were carried out in the same manner as in Example 2-(a) except for using tert-butyl(tert-butoxycarbonyl{6-[(pyridin-2-ylsulfonyl)aminomethyl]pyridin-2-yl}amino)acetate (100 mg, 0.209 mmol) obtained in Reference Example 14 in place of N-[4-(thiazol-2-yl)benzyl] pyridin-3-ylsulfonamide, and using 4-biphenylmethanol (38.8 mg, 0.211 mmol) in place of tert-butyl[tert-butoxycarbonyl(6-hydroxymethylpyridin-2-yl)amino]acetate to afford the title compound (116 mg) as a white foam. (Yield: 86%)

Mass spectrum (FAB, m/z): 645 (M$^+$+1).

$^1$H-NMR spectrum (CDCl$_3$, δppm): 8.60 (ddd, J=4.7, 1.7, 1.0 Hz, 1H), 7.82 (ddd, J=7.8, 1.2, 1.0 Hz, 1H), 7.77 (ddd, J=7.8, 7.6, 1.7 Hz, 1H), 7.65 (d, J=7.5 Hz, 1H), 7.56-7.52 (m, 2H), 7.47-7.41 (m, 5H), 7.39 (ddd, J=7.6, 4.7, 1.2 Hz, 1H), 7.36-7.32 (m, 1H), 7.31-7.28 (m, 2H), 6.92 (d, J=7.3 Hz, 1H), 4.74 (s, 2H), 4.52 (s, 2H), 4.46 (s, 2H), 1.52 (s, 9H), 1.42 (s, 9H).

17-(b) {6-[(Biphenyl-4-ylmethyl)(pyridin-2-ylsulfonyl)aminomethyl]pyridin-2-ylamino}acetic acid hydrochloride Reaction and post-treatment were carried out in the same manner as in Example 14-(b) except for using tert-butyl({6-[(biphenyl-4-ylmethyl)(pyridin-2-ylsulfonyl)aminomethyl] pyridin-2-yl}tert-butoxycarbonylamino)acetate (113 mg, 0.175 mmol) obtained in Example 17-(a) in place of tert-butyl [tert-butoxycarbonyl(6-{[(4-pyridazin-4-yl)benzyl](pyridin-3-ylsulfonyl)aminomethyl}pyridin-2-yl)amino]acetate to afford the title compound (93.9 mg) substantially quantitatively as a white solid.

Rf value: 0.62 (n-butanol:acetic acid:water=3:1:1).
Mass spectrum (FAB, m/z): 489 (M⁺+1).
¹H-NMR spectrum (CD₃OD, δppm): 8.76 (ddd, J=4.8, 1.7, 1.1 Hz, 1H), 8.10 (ddd, J=7.6, 7.6, 1.7 Hz, 1H), 8.06 (ddd, J=7.6, 1.2, 1.1 Hz, 1H), 7.71-7.66 (m, 2H), 7.54-7.50 (m, 2H), 7.46-7.39 (m, 4H), 7.35-7.31 (m, 1H), 7.31-7.28 (m, 2H), 6.76 (d, J=8.8 Hz, 1H), 6.73 (d, J=7.2 Hz, 1H), 4.74 (s, 2H), 4.56 (s, 2H), 4.00 (s, 21-1).

Example 18

(6-{(Pyridin-2-ylsulfonyl)[4-(pyrimidin-2-yl)benzyl]aminomethyl}pyridin-2-ylamino)-acetic acid hydrochloride (Exemplified Compound No. 1266)

18-(a) tert-Butyl[tert-butoxycarbonyl(6-{(pyridin-2-ylsulfonyl)[4-(pyrimidin-2-yl)-benzyl]aminomethyl}pyridin-2-yl)amino]acetate Reaction and post-treatment were carried out in the same manner as in Example 2-(a) except for using tert-butyl(tert-butoxycarbonyl{6-[(pyridin-2-ylsulfonyl)aminomethyl]pyridin-2-yl}amino)acetate (157 mg, 0.328 mmol) obtained in Reference Example 14 in place of N-[4-(thiazol-2-yl)benzyl]pyridin-3-ylsulfonamide, and using 4-(pyrimidin-2-yl)benzyl alcohol (60.8 mg, 0.327 mmol) obtained in Reference Example 16 in place of tert-butyl[tert-butoxycarbonyl(6-hydroxymethylpyridin-2-yl)amino]acetate to afford the title compound (144 mg) as a white foam. (Yield: 68%)
Mass spectrum (FAB, m/z): 647 (M⁺+1).
¹H-NMR spectrum (CDCl₃, δppm): 8.79 (d, J=4.8 Hz, 2H), 8.60 (ddd, J=4.7, 1.6, 0.9 Hz, 1H), 8.33-8.30 (m, 2H), 7.82 (ddd, J=7.7, 1.1, 0.9 Hz, 1H), 7.76 (ddd, J=7.7, 7.6, 1.6 Hz, 1H), 7.65 (d, J=8.3 Hz, 1H), 7.46 (dd, J=8.3, 7.4 Hz, 1H), 7.38 (ddd, J=7.6, 4.7, 1.1 Hz, 1H), 7.37-7.34 (m, 2H), 7.18 (t, J=4.8 Hz, 1H), 6.92 (d, J=7.4 Hz, 1H), 4.79 (s, 2H), 4.50 (s, 2H), 4.46 (s, 2H), 1.52 (s, 9H), 1.42 (s, 9H).

18-(b) (6-{(Pyridin-2-ylsulfonyl)[4-(pyrimidin-2-yl)benzyl]aminomethyl}pyridin-2-ylamino)acetic acid hydrochloride Reaction and post-treatment were carried out in the same manner as in Example 14-(b) except for using tert-butyl[tert-butoxycarbonyl(6-{(pyridin-2-ylsulfonyl)[4-(pyrimidin-2-yl)benzyl]aminomethyl}pyridin-2-yl)-amino]acetate (142 mg, 0.220 mmol) obtained in Example 18-(a) in place of tert-butyl[tert-butoxycarbonyl(6-{[(4-pyridazin-4-yl)benzyl](pyridin-3-ylsulfonyl)aminomethyl}pyridin-2-yl)amino]-acetate to afford the title compound (136 mg) substantially quantitatively as a slightly yellow solid.
Rf value: 0.45 (n-butanol:acetic acid:water=3:1:1).
Mass spectrum (FAB, m/z): 491 (M⁺+1).
¹H-NMR spectrum (CD₃OD, δppm): 8.86 (d, J=5.0 Hz, 2H), 8.78 (ddd, J=4.7, 1.6, 1.0 Hz, 1H), 8.21-8.18 (m, 2H), 8.14-8.07 (m, 2H), 7.72 (dd, J=9.1, 7.4 Hz, 1H), 7.70 (ddd, J=7.1, 4.7, 1.8 Hz, 1H), 7.42 (t, J=5.0 Hz, 1H), 7.40-7.36 (m, 2H), 6.79 (d, J=7.4 Hz, 1H), 637 (d, J=9.1 Hz, 1H), 4.79 (s, 2H), 4.59 (s, 2H), 4.00 (s, 2H).

Example 19

(6-{[4-(Pyridin-2-yl)benzyl](pyridin-3-ylsulfonyl)aminomethyl}pyridin-2-ylamino)-acetic acid (Exemplified Compound No. 1158)

19-(a) tert-Butyl[tert-butoxycarbonyl(6-{[4-(pyridin-2-yl)benzyl](pyridin-3-ylsulfonyl)aminomethyl}pyridin-2-yl)amino]acetate Reaction and post-treatment were carried out in the same manner as in Example 2-(a) except for using tert-butyl(tert-butoxycarbonyl{6-[(pyridin-3-ylsulfonyl)aminomethyl]pyridin-2-yl}amino)acetate (934 mg, 1.95 mmol) obtained in Reference Example 12-(d) in place of N-[4-(thiazol-2-yl)benzyl]pyridin-3-ylsulfonamide, and using 4-(pyridin-2-yl)benzyl alcohol (397 mg, 2.14 mmol) in place of tert-butyl[tert-butoxycarbonyl(6-hydroxymethylpyridin-2-yl)amino]acetate to afford the title compound (1.76 g) (pure content 1.26 g) substantially quantitatively as a yellow oil.
Mass spectrum (FAB, m/z): 646 (M⁺+1).
¹H-NMR spectrum (CDCl₃, δppm): 8.96 (dd, J=2.3, 0.9 Hz, 1H), 8.73-8.66 (m, 2H), 7.94-7.89 (m, 2H), 7.87 (ddd, J=8.1, 2.3, 1.7 Hz, 1H), 7.80-7.67 (m, 2H), 7.71 (d, J=8.4 Hz, 1H), 7.51 (dd, J=8.4, 7.4 Hz, 1H), 7.38-7.32 (m, 2H), 7.31 (ddd, J=8.1, 4.9, 0.9 Hz, 1H), 7.24 (ddd, J=7.1, 4.8, 1.5 Hz, 1H), 6.86 (dd, J=7.4, 0.6 Hz, 1H), 4.65 (s, 2H), 4.41 (s, 2H), 4.37 (s, 2H), 1.52 (s, 9H), 1.42 (s, 9H).

19-(b) (6-{[4-(Pyridin-2-yl)benzyl](pyridin-3-ylsulfonyl)aminomethyl}pyridin-2-ylamino)acetic acid To a solution of tert-butyl[tert-butoxycarbonyl(6-{[4-(pyridin-2-yl)benzyl]-(pyridin-3-ylsulfonyl)aminomethyl}pyridin-2-yl)amino]acetate (1.76 g) (containing 1.95 mmol of a pure content) obtained in Example 19-(a) in tetrahydrofuran (5.6 ml) were added water (5.6 ml) and concentrated hydrochloric acid (2.3 ml), followed by stirring at 65° C. for 4.5 hours. After completion of the reaction, the reaction solution was concentrated under reduced pressure. After the concentrate was adjusted to pH 10.9 with a 1N aqueous sodium hydroxide solution, the insolubles were filtered off. The filtrate was then adjusted to pH 5.6 with 1N hydrochloric acid, followed by addition of ethyl acetate. A precipitated solid was collected by filtration, and then dried under reduced pressure to afford the title compound (553 mg) as a white solid. (Yield: 58%)
Rf value: 0.35 (n-butanol:acetic acid:water=3:1:1).
Mass spectrum (FAB, m/z): 490 (M⁺+1).
¹H-NMR spectrum (CDCl₃, δppm): 9.11 (dd, J=2.2, 0.5 Hz, 1H), 8.79 (dd, J=4.8, 1.6 Hz, 1H), 8.67 (ddd, J=4.9, 1.6, 0.9 Hz, 1H), 8.08 (ddd, J=8.1, 2.2, 1.6 Hz, 1H), 7.81 (ddd, J=7.9, 7.8, 1.6 Hz, 1H), 7.75-7.69 (m, 2H), 7.64 (ddd, J=7.9, 1.0, 0.9 Hz, 1H), 7.43 (ddd, J=8.1, 4.8, 0.5 Hz, 1H), 7.34-7.27 (m, 2H), 7.23-7.17 (m, 2H), 6.58 (d, J=7.1 Hz, 1H), 6.29 (d, J=8.3 Hz, 1H), 4.58 (s, 2H), 4.28 (s, 2H), 3.86 (s, 2H).

Example 20

(6-{(Pyridin-3-ylsulfonyl)[4-(1,2,4-triazol-1-yl)benzyl]aminomethyl}pyridin-2-ylamino)acetic acid (Exemplified Compound No. 1461)

20-(a) tert-Butyl[tert-butoxycarbonyl(6-{(pyridin-3-ylsulfonyl)[4-(1,2,4-triazol-1-yl)-benzyl]aminomethyl}pyridin-2-yl)-amino]acetate Reaction and post-treatment were carried out in the same manner as in Example 2-(a) except for using tert-butyl(tert-butoxycarbonyl{6-[(pyridin-3-ylsulfonyl)aminomethyl]pyridin-2-yl}amino)acetate (840 mg, 1.76 mmol) obtained in Reference Example 12-(d) in place of N-[4-(thiazol-2-yl)benzyl]pyridin-3-ylsulfonamide, and using 4-(triazol-1-yl)benzyl alcohol (342 mg, 1.95 mmol) in place of tert-butyl

[tert-butoxycarbonyl(6-hydroxymethylpyridin-2-yl)amino]acetate to afford the title compound (938 mg) as a white foam. (Yield: 84%)

Mass spectrum (FAB, m/z): 636 (M$^+$+1).

$^1$H-NMR spectrum (CDCl$_3$, δppm): 8.96 (dd, J=2.3, 0.7 Hz, 1H), 8.73 (dd, J=4.9, 1.7 Hz, 1H), 8.56 (s, 1H), 8.10 (s, 1H), 7.90 (ddd, J=8.0, 2.3, 1.7 Hz, 1H), 7.70 (d, J=8.3 Hz, 1H), 7.62-7.57 (m, 2H), 7.49 (dd, J=8.3, 7.4 Hz, 1H), 7.42-7.38 (m, 2H), 7.34 (ddd, J=8.0, 4.9, 0.7 Hz, 1H), 6.83 (d, J=7.4 Hz, 1H), 4.63 (s, 2H), 4.39 (s, 2H), 4.33 (s, 2H), 1.53 (s, 9H), 1.42 (s, 9H).

20-(b) (6-{(Pyridin-3-ylsulfonyl)[4-(1,2,4-triazol-1-yl)benzyl]aminomethyl}pyridin-2-ylamino)acetic acid Reaction was carried out in the same manner as in Example 19-(b) except for using tert-butyl[tert-butoxycarbonyl(6-{(pyridin-3-ylsulfonyl)[4-(1,2,4-triazol-1-yl)benzyl]aminomethyl}pyridin-2-yl)amino]acetate (936 mg, 1.47 mmol) obtained in Example 20-(a) in place of tert-butyl[tert-butoxycarbonyl(6-{[4-(pyridin-2-yl)benzyl]-(pyridin-3-ylsulfonyl)aminomethyl}pyridin-2-yl)amino]acetate. After completion of the reaction, the reaction solution was concentrated under reduced pressure. The concentrate was adjusted to pH 4.5 with a 6N aqueous sodium hydroxide solution, and a precipitated solid was collected by filtration. Acetone (1.3 ml) was added to the crude product, followed by stirring at 50° C. for 1 hour, and then at room temperature for 1 hour. A precipitated solid was collected by filtration, and then dried under reduced pressure to afford the title compound (618 mg) as a white solid. (Yield: 88%)

Rf value: 0.36 (n-butanol:acetic acid:water=3:1:1).

Mass spectrum (FAB, m/z): 480 (M$^+$+1).

$^1$H-NMR spectrum (DMSO-d$_6$, δppm): 9.27 (s, 1H), 8.85 (dd, J=2.4, 0.8 Hz, 1H), 8.73 (dd, J=4.8, 1.7 Hz, 1H), 8.24 (s, 1H), 8.05 (ddd, J=8.1, 2.4, 1.7 Hz, 1H), 7.84-7.79 (m, 2H), 7.49 (ddd, J=8.1, 4.8, 0.8 Hz, 1H), 7.47-7.43 (m, 2H), 7.24 (dd, J=8.3, 7.1 Hz, 1H), 6.75 (t, J=5.6 Hz, 1H), 6.36 (d, J=8.3 Hz, 1H), 6.33 (d, J=7.1 Hz, 1H), 4.71 (s, 2H), 4.21 (s, 2H), 3.69 (d, J=5.6 Hz, 2H).

Example 21

(6-{[4-(Pyrazol-1-yl)benzyl](pyridin-2-ylsulfonyl) aminomethyl}pyridin-2-ylamino)-acetic acid (Exemplified Compound No. 876)

21-(a) tert-Butyl[tert-butoxycarbonyl(6-{[4-(pyrazol-1-yl)benzyl](pyridin-2-ylsulfonyl) aminomethyl}pyridin-2-yl)amino]acetate Reaction and post-treatment were carried out in the same manner as in Example 2-(a) except for using tert-butyl(tert-butoxycarbonyl{6-[(pyridin-2-ylsulfonyl)aminomethyl]pyridin-2-yl}amino)acetate (622 mg, 1.30 mmol) obtained in Reference Example 14 in place of N-[4-(thiazol-2-yl)benzyl]pyridin-3-ylsulfonamide, and using 4-(pyrazol-1-yl)benzyl alcohol (225 mg, 1.29 mmol) in place of tert-butyl [tert-butoxycarbonyl(6-hydroxymethylpyridin-2-yl)amino]acetate to afford the title compound (757 mg) as a white foam. (Yield: 92%)

Mass spectrum (FAB, m/z): 635 (M$^+$+1).

$^1$H-NMR spectrum (CDCl$_3$, δppm): 8.61 (ddd, J=4.7, 1.7, 0.9 Hz, 1H), 7.90 (dd, J=2.4, 0.5 Hz, 1H), 7.83 (ddd, J=7.8, 1.6, 0.9 Hz, 1H), 7.78 (ddd, J=7.8, 7.4, 1.7 Hz, 1H), 7.71 (dd, J=1.8, 0.5 Hz, 1H), 7.65 (d, J=8.4 Hz, 1H), 7.60-7.53 (m, 2H), 7.44 (dd, J=8.4, 7.3 Hz, 1H), 7.39 (ddd, J=7.4, 4.7, 1.6 Hz, 1H), 7.36-7.30 (m, 2H), 6.90 (d, J=7.3 Hz, 1H), 6.46 (dd, J=2.4, 1.8 Hz, 1H), 4.74 (s, 2H), 4.48 (s, 2H), 4.45 (s, 2H), 1.52 (s, 9H), 1.42 (s, 9H).

21-(b) (6-{[4-(Pyrazol-1-yl)benzyl](pyridin-2-ylsulfonyl)aminomethyl}pyridin-2-ylamino)acetic acid Reaction was carried out in the same manner as in Example 19-(b) except for using tert-butyl[tert-butoxycarbonyl(6-{[4-(pyrazol-1-yl)benzyl](pyridin-2-ylsulfonyl) aminomethyl}pyridin-2-yl)amino]acetate (440 mg, 0.611 mmol) obtained in Example 21-(a) in place of tert-butyl[tert-butoxycarbonyl(6-{[4-(pyridin-2-yl)benzyl]-(pyridin-3-ylsulfonyl)aminomethyl}pyridin-2-yl)amino]acetate. After completion of the reaction, the reaction solution was adjusted to pH 4.5 with a 2N aqueous sodium hydroxide solution, followed by extraction with ethyl acetate. The separated organic layer was dried over anhydrous magnesium sulfate, and then concentrated under reduced pressure. To the resulting residue were added ethyl acetate (4 ml) and diisopropyl ether (16 ml), followed by sonication at 40° C. for 15 minutes. The solvent was distilled off under reduced pressure, and then dried under reduced pressure to afford the title compound (542 mg) as a white foam. (Yield: 97%)

Rf value: 0.48 (n-butanol:acetic acid:water=3:1:1).

Mass spectrum (FAB, m/z): 479 (M$^+$+1).

$^1$H-NMR spectrum (DMSO-d$_6$, δ ppm): 12.41 (brs, 0.8H), 8.65 (ddd, J=4.7, 1.7, 0.9 Hz, 1H), 8.45 (dd, J=2.5, 0.5 Hz, 1H), 7.96 (ddd, J=7.8, 7.7, 1.7 Hz, 1H), 7.82 (ddd, J=7.8, 1.1, 0.9 Hz, 1H), 7.76-7.72 (m, 3H), 7.58 (ddd, J=7.7, 4.7, 1.1 Hz, 1H), 7.37-7.33 (m, 2H), 7.20 (dd, J=8.2, 7.1 Hz, 1H), 6.76 (t, J=5.8 Hz, 1H), 6.54 (dd, J=2.5, 1.8 Hz, 1H), 6.34 (d, J=8.2 Hz, 1H), 6.29 (d, J=7.1 Hz, 1H), 4.72 (s, 2H), 4.24 (s, 2H), 3.83 (d, J=5.8 Hz, 2H).

Example 22

(6-{[4-(5-Methylthiazol-2-yl)benzyl](pyridin-2-ylsulfonyl)aminomethyl}pyridin-2-ylamino)acetic acid (Exemplified Compound No. 1446)

22-(a) tert-Butyl({6-[(4-bromobenzyl)(pyridin-2-ylsulfonyl)aminomethyl]pyridin-2-yl}tert-butoxycarbonylamino)acetate Reaction and post-treatment were carried out in the same manner as in Example 2-(a) except for using tert-butyl(tert-butoxycarbonyl{6-[(pyridin-2-ylsulfonyl)aminomethyl]pyridin-2-yl}amino)acetate (3.00 g, 6.27 mmol) obtained in Reference Example 14 in place of N-[4-(thiazol-2-yl)benzyl]pyridin-3-ylsulfonamide, and using 4-bromobenzyl alcohol (1.29 g, 6.90 mmol) in place of tert-butyl[tert-butoxycarbonyl (6-hydroxymethylpyridin-2-yl)amino]acetate to afford the title compound (4.16 g) substantially quantitatively as a pale yellow oil.

Mass spectrum (CI, m/z): 647 (M$^+$+1).

$^1$H-NMR spectrum (CDCl$_3$, δppm): 8.59 (ddd, J=4.6, 1.6, 1.0 Hz, 1H), 7.83-7.74 (m, 2H), 7.68-7.62 (m, 1H), 7.48-7.32 (m, 4H), 7.15-7.10 (m, 2H), 6.87 (d, J=7.8 Hz, 1H), 4.66 (s, 2H), 4.44 (s, 2H), 4.43 (s, 2H), 1.52 (s, 9H), 1.42 (s, 9H).

22-(b) tert-Butyl[tert-butoxycarbonyl(6-{(pyridin-2-ylsulfonyl)[4-(4,4,5,5-tetramethyl-[1,3,2]dioxaborolan-2-yl)benzyl]aminomethyl}pyridin-2-yl)amino] acetate To a solution of tert-butyl({6-[(4-bromobenzyl)(pyridin-2-ylsulfonyl)aminomethyl]pyridin-2-yl}tert-butoxycarbonylamino)acetate (4.15 g, 6.41 mmol) obtained in Example 22-(a) in 1,4-dioxane (42 ml) were added bis(pinacolato)diboron (2.28 g, 8.98 mmol), 1,1'-bis(diphenylphosphino)ferrocenepalladium chloride.methylene chloride complex (105 mg, 0.129 mmol) and potassium acetate (1.88 g, 19.2 mmol), followed by stirring at 85° C. for 31 hours. After completion of the reaction, water was added to the reaction solution, followed by extraction with ethyl acetate. The separated organic layer was washed with a saturated aqueous sodium chloride solution, dried over anhydrous magnesium sulfate, and then concentrated under reduced pressure. The resulting residue was subjected to silica gel column chromatography (eluent; hexane:ethyl acetate=1:0→7:3 (V/V)), and fractions containing the desired compound were concentrated under reduced pressure to afford the title compound (3.76 g) as a white foam. (Yield: 84%)

Mass spectrum (CI, m/z): 695 ($M^+$+1).

$^1$H-NMR spectrum (CDCl$_3$, δppm): 8.59 (ddd, J=4.7, 1.7, 0.9 Hz, 1H), 7.80 (ddd, J=7.7, 1.6, 0.9 Hz, 1H), 7.75 (ddd, J=7.7, 7.3, 1.7 Hz, 1H), 7.71-7.61 (m, 3H), 7.45 (dd, J=8.4, 7.4 Hz, 1H), 7.37 (ddd, J=7.3, 4.7, 1.6 Hz, 1H), 7.25-7.20 (m, 2H), 6.89 (dd, J=7.4, 0.6 Hz, 1H), 4.73 (s, 2H), 4.44 (s, 2H), 4.44 (s, 2H), 1.52 (s, 9H), 1.42 (s, 9H), 1.33 (s, 12H).

22-(c) tert-Butyl[tert-butoxycarbonyl(6-{[4-(5-methylthiazol-2-yl)benzyl](pyridin-2-ylsulfonyl)aminomethyl}pyridin-2-yl)amino]acetate To tert-butyl[tert-butoxycarbonyl(6-{(pyridin-2-ylsulfonyl)[4-(4,4,5,5-tetramethyl-[1,3,2]dioxaborolan-2-yl)benzyl]aminomethyl}pyridin-2-yl)amino]acetate (404 mg) (containing 0.577 mmol of a pure content) obtained in Example 22-(b) were added 2-bromo-5-methylthiazole (212 mg, 1.19 mmol), a mixed solvent (toluene:ethanol=7:3 (V/V), 11.5 ml) and a 2M aqueous sodium carbonate solution (0.58 ml), which was deaerated under reduced pressure, followed by argon substitution. Tetrakis(triphenylphosphine)palladium (66.6 mg, 0.0576 mmol) was then added, followed by stirring at 90° C. for 24 hours under argon atmosphere. After completion of the reaction, water was added to the reaction solution, followed by extraction with toluene. The separated organic layer was washed with a saturated aqueous sodium chloride solution, dried over anhydrous magnesium sulfate, and then concentrated under reduced pressure. The resulting residue was subjected to silica gel column chromatography (eluent; hexane:ethyl acetate=1:0→3:2 (V/V)), and fractions containing the desired compound were concentrated under reduced pressure to afford the title compound (291 mg) as a yellow oil. (Yield: 76%)

Mass spectrum (CI, m/z): 666 ($M^+$+1).

$^1$H-NMR spectrum (CDCl$_3$, δppm): 8.59 (ddd, J=4.7, 1.7, 1.0 Hz, 1H), 7.81 (ddd, J=7.9, 1.6, 1.0 Hz, 1H), 7.80-7.72 (m, 3H), 7.65 (d, J=7.8 Hz, 1H), 7.51-7.42 (m, 2H), 7.38 (ddd, J=7.2, 4.7, 1.6 Hz, 1H), 7.32-7.26 (m, 2H), 6.91 (dd, J=7.3, 0.7 Hz, 1H), 4.74 (s, 2H), 4.49 (s, 2H), 4.45 (s, 2H), 2.51 (d, J=1.2 Hz, 3H), 1.52 (s, 9H), 1.42 (s, 9H).

22-(d) (6-{[4-(5-Methylthiazol-2-yl)benzyl](pyridin-2-ylsulfonyl)aminomethyl}pyridin-2-ylamino)acetic acid Reaction was carried out in the same manner as in Example 19-(b) except for using tert-butyl[tert-butoxycarbonyl(6-{[4-(5-methylthiazol-2-yl)benzyl](pyridin-2-ylsulfonyl)aminomethyl}pyridin-2-yl)amino]acetate (269 mg, 0.404 mmol) obtained in Example 22-(c) in place of tert-butyl[tert-butoxycarbonyl(6-{[4-(pyridin-2-yl)benzyl]-(pyridin-3-ylsulfonyl)aminomethyl}pyridin-2-yl)amino]acetate. After completion of the reaction, water (20 ml) was added to the reaction solution, then it was adjusted to pH 10.9 with a 1N aqueous sodium hydroxide solution, and subsequently insolubles were filtered off. The filtrate was adjusted to pH 5.6 with 1N hydrochloric acid, followed by extraction with ethyl acetate. The separated organic layer was dried over anhydrous magnesium sulfate, and then concentrated under reduced pressure. To the resulting residue were added tert-butyl methylether (1 ml) and diisopropyl ether (10 ml), followed by sonication. A precipitated solid was collected by filtration, and then dried under reduced pressure to afford the title compound (113 mg) as a white solid. (Yield: 55%)

Rf value: 0.51 (n-butanol:acetic acid:water=3:1:1).

Mass spectrum (FAB, m/z): 510 ($M^+$+1).

$^1$H-NMR spectrum (DMSO-d$_6$, δppm): 8.64 (d, J=3.9 Hz, 1H), 7.95 (ddd, J=7.7, 7.7, 1.6 Hz, 1H), 7.83-7.74 (m, 3H), 7.61-7.54 (m, 2H), 7.38-7.32 (m, 2H), 7.18 (dd, J=8.2, 7.2 Hz, 1H), 6.72 (t, J=5.4 Hz, 0.9H), 6.33 (d, J=8.2 Hz, 1H), 6.28 (d, J=7.2 Hz, 1H), 4.74 (s, 2H), 4.24 (s, 2H), 3.81 (d, J=5.4 Hz, 2H), 2.49 (s, 3H).

Example 23

(6-{[4-(4,5-Dimethylthiazol-2-yl)benzyl](pyridin-2-ylsulfonyl)aminomethyl}pyridin-2-ylamino)acetic acid (Exemplified Compound No. 1453)

23-(a) tert-Butyl[tert-butoxycarbonyl(6-{[4-(4,5-dimethylthiazol-2-yl)benzyl](pyridin-2-ylsulfonyl)aminomethyl}pyridin-2-yl)amino]acetate Reaction and post-treatment were carried out in the same manner as in Example 22-(c) except for using tert-butyl[tert-butoxycarbonyl(6-{(pyridin-2-ylsulfonyl)[4-(4,4,5,5-tetramethyl-[1,3,2]dioxaborolan-2-yl)benzyl]aminomethyl}pyridin-2-yl)amino]acetate (490 mg, containing 0.700 mmol of a pure content) obtained in Example 22-(b), and using 2-bromo-4,5-dimethylthiazole (282 mg, 1.47 mmol) in place of 2-bromo-5-methylthiazole to afford the title compound (392 mg) as a white foam. (Yield: 82%)

Mass spectrum (FAB, m/z): 678 ($M^-$–1).

$^1$H-NMR spectrum (CDCl$_3$, δppm): 8.59 (ddd, J=4.7, 1.7, 0.9 Hz, 1H), 7.81 (ddd, J=7.9, 1.6, 0.9 Hz, 1H), 7.80-7.69 (m, 3H), 7.65 (d, J=8.4 Hz, 1H), 7.45 (dd, J=8.4, 7.4 Hz, 1H), 7.38 (ddd, J=7.1, 4.7, 1.6 Hz, 1H), 7.28-7.23 (m, 2H), 6.91 (dd, J=7.4, 0.5 Hz, 1H), 4.72 (s, 2H), 4.48 (s, 2H), 4.45 (s, 2H), 2.41-2.36 (m, 6H), 1.52 (s, 9H), 1.42 (s, 9H).

23-(b) (6-{[4-(4,5-Dimethylthiazol-2-yl)benzyl](pyridin-2-ylsulfonyl)aminomethyl}-pyridin-2-ylamino)acetic acid Reaction and post-treatment were carried out in the same manner as in Example 21-(h) except for using tert-butyl[tert-butoxycarbonyl(6-{[4-(4,5-dimethylthiazol-2-yl)benzyl](pyridin-2-ylsulfonyl)aminomethyl}pyridin-2-yl)amino]acetate (385 mg, 0.566 mmol) obtained in Example 23-(a) in place of tert-butyl[tert-butoxycarbonyl-yl(6-{[4-(pyrazol-1-yl)benzyl](pyridin-2-ylsulfonyl)aminomethyl}pyridin-2-yl)amino]-acetate to afford the title compound (266 mg) as a white solid. (Yield: 90%)

Rf value: 0.51 (n-butanol:acetic acid:water=3:1:1).

Mass spectrum (FAB, m/z): 522 ($M^-$–1).

$^1$H-NMR spectrum (DMSO-d$_6$, δppm): 8.64 (ddd, J=4.7, 1.7, 0.9 Hz, 1H), 7.95 (ddd, J=7.8, 7.7, 1.7 Hz, 1H), 7.80 (ddd, J=7.8, 1.1, 0.9 Hz, 1H), 7.77-7.71 (m, 2H), 7.58 (ddd, J=7.7, 4.7, 1.1 Hz, 1H), 7.36-7.30 (m, 2H), 7.18 (dd, J=8.3, 7.0 Hz, 1H), 6.72 (t, J=5.4 Hz, 0.9H), 6.33 (d, J=8.3 Hz, 1H), 6.27 (d, J=7.0 Hz, 1H), 4.73 (s, 2H), 4.23 (s, 2H), 3.80 (d, J=5.4 Hz, 2H), 2.38 (d, J=0.7 Hz, 3H), 2.31 (d, J=0.7 Hz, 3H).

Example 24

(6-{[4-(5-Chlorothiazol-2-yl)benzyl](pyridin-2-ylsulfonyl)aminomethyl}pyridin-2-ylamino)acetic acid (Exemplified Compound No. 1439)

24-(a) tert-Butyl[tert-butoxycarbonyl(6-{[4-(5-chlorothiazol-2-yl)benzyl](pyridin-2-ylsulfonyl)aminomethyl}pyridin-2-yl)amino]acetate Reaction and post-treatment were carried out in the same manner as in Example 22-(c) except for using tert-butyl[tert-butoxycarbonyl(6-{(pyridin-2-ylsulfonyl)[4-(4,4,5,5-tetramethyl-[1,3,2]dioxaborolan-2-yl)benzyl]aminomethyl}pyridin-2-yl)amino]acetate (404 mg, containing 0.577 mmol of a pure content) obtained in Example 22-(b), and using 2-bromo-5-chlorothiazole (see US2007/300939A) (230 mg, 1.16 mmol) in place of 2-bromo-5-methylthiazole to afford the title compound (277 mg) as an orange foam. (Yield: 70%)

Mass spectrum (CI, m/z): 686 ($M^+$+1).

$^1$H-NMR spectrum (CDCl$_3$, δppm): 8.61-8.58 (m, 1H), 7.84-7.62 (m, 6H), 7.47-7.30 (m, 4H), 6.89 (d, J=7.8 Hz, 1H), 4.75 (s, 2H), 4.48 (s, 2H), 4.44 (s, 2H), 1.52 (s, 9H), 1.42 (s, 9H).

24-(b) (6-{[4-(5-Chlorothiazol-2-yl)benzyl] (pyridin-2-ylsulfonyl)aminomethyl}pyridin-2-ylamino)acetic acid Reaction and post-treatment were carried out in the same manner as in Example 22-(d) except for using tert-butyl[tert-butoxycarbonyl(6-{[4-(5-chlorothiazol-2-yl)benzyl](pyridin-2-ylsulfonyl)aminomethyl}pyridin-2-yl)amino]acetate (265 mg, 0.386 mmol) obtained in Example 24-(a) in place of tert-butyl[tert-butoxycarbonyl(6-{[4-(5-methylthiazol-2-yl)benzyl] (pyridin-2-ylsulfonyl)aminomethyl}pyridin-2-yl)-amino]acetate to afford the title compound (135 mg) as a slightly brown solid. (Yield: 66%)

Rf value: 0.55 (n-butanol:acetic acid:water=3:1:1).

Mass spectrum (FAB, m/z): 530 ($M^+$+1).

$^1$H-NMR spectrum (DMSO-d$_6$, δppm): 8.64 (ddd, J=4.7, 1.7, 0.9 Hz, 1H), 7.96 (ddd, J=7.8, 7.7, 1.7 Hz, 1H), 7.95 (s, 1H), 7.83-7.78 (m, 3H), 7.59 (ddd, J=7.7, 4.7, 1.1 Hz, 1H), 7.41-7.37 (m, 2H), 7.18 (dd, J=8.3, 7.0 Hz, 1H), 6.70 (brs, 0.8H), 6.33 (d, J=8.3 Hz, 1H), 6.27 (d, J=7.0 Hz, 1H), 4.75 (s, 2H), 4.24 (s, 2H), 3.79 (d, J=5.3 Hz, 2H).

Example 25

(6-{(Pyridin-2-ylsulfonyl)[4-(4-trifluoromethylthiazol-2-yl)benzyl]aminomethyl}-pyridin-2-ylamino)acetic acid (Exemplified Compound No. 1024)

25-(a) tert-Butyl[tert-butoxycarbonyl(6-{(pyridin-2-ylsulfonyl)[4-(4-trifluoromethylthiazol-2-yl)benzyl]aminomethyl}pyridin-2-yl)amino]acetate Reaction and post-treatment were carried out in the same manner as in Example 22-(c) except for using tert-butyl[tert-butoxycarbonyl(6-{(pyridin-2-ylsulfonyl)[4-(4,4,5,5-tetramethyl-[1,3,2]dioxaborolan-2-yl)benzyl]aminomethyl}pyridin-2-yl)amino]acetate (490 mg, containing 0.700 mmol of a pure content) obtained in Example 22-(b), and using 2-bromo-4-trifluoromethylthiazole (see WO 2005/077912A) (341 mg, 1.47 mmol) in place of 2-bromo-5-methylthiazole to afford the title compound (454 mg) as a white foam. (Yield: 90%)

Mass spectrum (FAB, m/z): 718 ($M^-$−1).

$^1$H-NMR spectrum (CDCl$_3$, δppm): 8.63-8.60 (m, 1H), 7.87-7.82 (m, 3H), 7.79 (ddd, J=7.7, 7.7, 1.8 Hz, 1H), 7.74-7.72 (m, 1H), 7.65 (d, J=7.8 Hz, 1H), 7.47-7.38 (m, 2H), 7.37-7.32 (m, 2H), 6.90 (d, J=7.3 Hz, 1H), 4.76 (s, 2H), 4.47 (s, 2H), 4.44 (s, 2H), 1.52 (s, 9H), 1.42 (s, 9H).

25-(b) (6-{(Pyridin-2-ylsulfonyl)[4-(4-trifluoromethylthiazol-2-yl)benzyl]aminomethyl}pyridin-2-ylamino)acetic acid Reaction and post-treatment were carried out in the same manner as in Example 21-(b) except for using tert-butyl[tert-butoxycarbonyl(6-{(pyridin-2-ylsulfonyl)[4-(4-trifluoromethylthiazol-2-yl)benzyl]aminomethyl}pyridin-2-yl)amino]acetate (440 mg, 0.611 mmol) obtained in Example 25-(a) in place of tert-butyl[tert-butoxycarbonyl(6-{[4-(pyrazol-1-yl)benzyl](pyridin-2-ylsulfonyl)aminomethyl}pyridin-2-yl)amino]acetate to afford the title compound (293 mg) as a white solid. (Yield: 85%)

Rf value: 0.58 (n-butanol:acetic acid:water=3:1:1).

Mass spectrum (FAB, m/z): 562 ($M^-$−1).

$^1$H-NMR spectrum (DMSO-d$_6$, δppm): 8.65 (ddd, J=4.6, 1.6, 0.9 Hz, 1H), 8.57-8.54 (m, 1H), 7.96 (ddd, J=7.8, 7.7, 1.6 Hz, 1H), 7.93-7.87 (m, 2H), 7.82 (ddd, J=7.8, 1.0, 0.9 Hz, 1H), 7.59 (ddd, J=7.7, 4.6, 1.0 Hz, 1H), 7.46-7.38 (m, 2H), 7.18 (dd, J=8.2, 7.2 Hz, 1H), 6.74 (t, J=5.4 Hz, 0.9H), 6.33 (d, J=8.2 Hz, 1H), 6.28 (d, J=7.2 Hz, 1H), 4.77 (s, 2H), 4.24 (s, 2H), 3.81 (d, J=5.4 Hz, 2H).

Example 26

(6-{(4-Fluorobenzenesulfonyl)[4-(pyrazol-1-yl)benzyl]aminomethyl}pyridin-2-ylamino)acetic acid (Exemplified Compound No. 856)

26-(a) tert-Butyl[tert-butoxycarbonyl(6-{(4-fluorobenzenesulfonyl)[4-(pyrazol-1-yl)-benzyl]aminomethyl}pyridin-2-yl)amino]acetate Reaction and post-treatment were carried out in the same manner as in Example 2-(a) except for using tert-butyl(tert-butoxycarbonyl{6-[(4-fluorobenzenesulfonyl)aminomethyl]pyridin-2-yl}amino)acetate (644 mg, 1.30 mmol) obtained in Reference Example 17 in place of N-[4-(thiazol-2-yl)benzyl]pyridin-3-ylsulfonamide, and using 4-(pyrazol-1-yl)benzyl alcohol (226 mg, 1.30 mmol) in place of tert-butyl [tert-butoxycarbonyl(6-hydroxymethylpyridin-2-yl)amino]acetate to afford the title compound (806 mg) as a white foam. (Yield: 95%)

Mass spectrum (FAB, m/z): 652 ($M^+$+1).

$^1$H-NMR spectrum (CDCl$_3$, δppm): 7.91 (dd, J=2.4, 0.7 Hz, 1H), 7.75-7.66 (m, 4H), 7.63-7.56 (m, 2H), 7.49 (dd, J=8.4, 7.5 Hz, 1H), 7.33-7.27 (m, 2H), 7.15-7.05 (m, 2H), 6.83 (d, J=7.5 Hz, 1H), 6.47 (dd, J=2.4, 1.7 Hz, 1H), 4.54 (s, 2H), 4.37 (s, 2H), 4.35 (s, 2H), 1.52 (s, 9H), 1.42 (s, 9H).

26-(b) (6-{(4-Fluorobenzenesulfonyl)[4-(pyrazol-1-yl)benzyl]aminomethyl}pyridin-2-ylamino)acetic acid Reaction and post-treatment were carried out in the same manner as in Example 21-(b) except for using tert-butyl[tert-butoxycarbonyl(6-{(4-fluorobenzenesulfonyl)[4-(pyrazol-1-yl)benzyl]aminomethyl}pyridin-2-yl)amino]acetate (794 mg, 1.22 mmol) obtained in Example 26-(a) in place of tert-butyl[tert-butoxycarbonyl(6-{[4-(pyrazol-1-yl)benzyl](pyridin-2-ylsulfonyl)aminomethyl}pyridin-2-yl)amino]-acetate to afford the title compound (517 mg) as a white solid. (Yield: 86%)

Rf value: 0.61 (n-butanol:acetic acid:water=3:1:1).

Mass spectrum (FAB, m/z): 496 (M$^+$+1).

$^1$H-NMR spectrum (DMSO-d$_6$, δppm): 12.43 (brs, 0.7H), 8.47 (dd, J=2.5, 0.5 Hz, 1H), 7.80-7.73 (m, 5H), 7.38-7.34 (m, 2H), 7.33-7.26 (m, 2H), 7.24 (dd, J=8.3, 7.2 Hz, 1H), 6.80 (t, J=5.8 Hz, 0.9H), 6.54 (dd, J=2.5, 1.8 Hz, 1H), 6.38 (d, J=8.3 Hz, 1H), 6.30 (d, J=7.2 Hz, 1H), 4.62 (s, 2H), 4.15 (s, 2H), 3.76 (d, J=5.8 Hz, 2H).

Example 27

Ethyl(6-{(pyridin-2-ylsulfonyl)[4-(thiazol-2-yl)benzyl]aminomethyl}pyridin-2-ylamino)acetate (Exemplified Compound No. 920)

To tert-butyl[tert-butoxycarbonyl(6-{(pyridin-2-ylsulfonyl)[4-(thiazol-2-yl)-benzyl]aminomethyl}pyridin-2-yl)amino]acetate (120 mg, 0.184 mmol) obtained in Example 3-(a) was added a 6M hydrogen chloride/ethanol solution (1 ml), and the mixture was left at room temperature for 16 hours. After completion of the reaction, the reaction solution was concentrated under reduced pressure, and a saturated aqueous sodium hydrogencarbonate solution was added to the residue, followed by extraction with ethyl acetate. The separated organic layer was dried over anhydrous magnesium sulfate, and then concentrated under reduced pressure. The resulting residue was subjected to silica gel column chromatography (eluent; hexane:ethyl acetate=2:1 (V/V)), and fractions containing the desired compound were concentrated under reduced pressure to afford the title compound (81.0 mg) as a colorless oil. (Yield: 84%)

Rf value: 0.58 (ethyl acetate).

Mass spectrum (FAB, m/z): 524 (M$^+$+1).

$^1$H-NMR spectrum (CDCl$_3$, δppm): 8.62 (ddd, J=4.8, 1.7, 0.9 Hz, 1H), 7.87-7.82 (m, 4H), 7.77 (ddd, J=7.7, 7.7, 1.7 Hz, 1H), 7.39 (ddd, J=7.7, 4.8, 1.2 Hz, 1H), 7.39-7.35 (m, 2H), 7.33 (d, J=3.3 Hz, 1H), 7.23 (dd, J=8.3, 7.2 Hz, 1H), 6.50 (d, J=7.2 Hz, 1H), 6.23 (d, J=8.3 Hz, 1H), 4.80 (s, 2H), 4.70 (t, J=5.5 Hz, 1H), 4.40 (s, 2H), 4.23 (q, J=7.2 Hz, 2H), 3.95 (d, J=5.5 Hz, 2H), 1.29 (t, J=7.2 Hz, 3H).

Example 28

Isopropyl(6-{(pyridin-2-ylsulfonyl)[4-(thiazol-2-yl)benzyl]aminomethyl}pyridin-2-ylamino)acetate (Exemplified Compound No. 914)

To a solution of tert-butyl[tert-butoxycarbonyl(6-{(pyridin-2-ylsulfonyl)[4-(thiazol-2-yl)benzyl]aminomethyl}pyridin-2-yl)amino]acetate (200 mg, 0.307 mmol) obtained in Example 3-(a) in isopropanol (1.5 ml) was added a 4N hydrogen chloride/-1,4-dioxane solution (1.5 ml), followed by stirring at 40° C. for 9 hours. After completion of the reaction, a saturated aqueous sodium hydrogencarbonate solution was added to the reaction solution, followed by extraction with ethyl acetate. The separated organic layer was dried over anhydrous magnesium sulfate, and then concentrated under reduced pressure. The resulting residue was subjected to silica gel column chromatography (eluent; hexane:ethyl acetate=1:2 (V/V)), and fractions containing the desired compound were concentrated under reduced pressure to afford the title compound (132 mg) (pure content: 118 mg) as a colorless oil. (Yield: 80%)

Rf value: 0.62 (ethyl acetate).

Mass spectrum (FAB, m/z): 538 (M$^+$+1).

$^1$H-NMR spectrum (CDCl$_3$, δppm): 8.62 (ddd, J=4.7, 1.8, 0.9 Hz, 1H), 7.87-7.82 (m, 4H), 7.77 (ddd, J=7.7, 7.7, 1.8 Hz, 1H), 7.39 (ddd, J=7.7, 4.7, 1.2 Hz, 1H), 7.39-7.35 (m, 2H), 7.33 (d, J=3.1 Hz, 1H), 7.23 (dd, J=8.2, 7.2 Hz, 1H), 6.49 (d, J=7.2 Hz, 1H), 6.22 (d, J=8.2 Hz, 1H), 5.09 (heptet, J=6.3 Hz, 1H), 4.80 (s, 2H), 4.70 (t, J=5.3 Hz, 1H), 4.40 (s, 2H), 3.91 (d, J=5.3 Hz, 2H), 1.26 (d, J=6.3 Hz, 6H).

Example 29

Hexyl(6-{(pyridin-2-ylsulfonyl)[4-(thiazol-2-yl)benzyl]aminomethyl}pyridin-2-ylamino)acetate (Exemplified Compound No. 1433)

To a solution of (6-{(pyridin-2-ylsulfonyl)[4-(thiazol-2-yl)benzyl]aminomethyl}pyridin-2-ylamino)acetic acid (110 mg, 0.222 mmol) obtained in Example 3-(b) in 1-hexanol (0.83 ml) was added a 4N hydrogen chloride/1,4-dioxane solution (0.83 ml), followed by stirring at room temperature for 16 hours. After completion of the reaction, the reaction solution was concentrated under reduced pressure, and a saturated aqueous sodium hydrogencarbonate solution was added to the residue, followed by extraction with ethyl acetate. The separated organic layer was dried over anhydrous magnesium sulfate, and then concentrated under reduced pressure. The resulting residue was subjected to silica gel column chromatography (eluent; hexane:ethyl acetate=2:1→1:1 (V/V)), and fractions containing the desired compound were concentrated under reduced pressure to afford the title compound (119 mg) as a colorless oil. (Yield: 92%)

Mass spectrum (FAB, m/z): 580 (M$^+$+1).

Rf value: 0.67 (ethyl acetate).

$^1$H-NMR spectrum (CDCl$_3$, δppm): 8.62 (ddd, J=4.7, 1.7, 0.8 Hz, 1H), 7.87-7.82 (m, 4H), 7.77 (ddd, J=7.7, 7.7, 1.7 Hz, 1H), 7.39 (ddd, J=7.7, 4.7, 1.2 Hz, 1H), 7.38-7.34 (m, 2H), 7.33 (d, J=3.3 Hz, 1H), 7.23 (dd, J=8.2, 7.2 Hz, 1H), 6.50 (d, J=7.2 Hz, 1H), 6.22 (d, J=8.2 Hz, 1H), 4.80 (s, 2H), 4.70 (t, J=5.4 Hz, 1H), 4.40 (s, 2H), 4.15 (t, J=6.8 Hz, 2H), 3.95 (d, J=5.4 Hz, 2H), 1.68-1.57 (m, 2H), 1.36-1.23 (m, 6H), 0.87 (t, J=7.0 Hz, 3H).

Example 30

Ethyl(6-{[4-(pyrazol-1-yl)benzyl](pyridin-3-ylsulfonyl)aminomethyl}pyridin-2-ylamino)acetate (Exemplified Compound No. 1467)

Reaction was carried out in the same manner as in Example 27 except for using (6-{[4-(pyrazol-1-yl)benzyl](pyridin-3-ylsulfonyl)aminomethyl}pyridin-2-ylamino)acetic acid hydrochloride (21.6 mg, 0.0367 mmol) obtained in Example 7-(b) in place of tert-butyl[tert-butoxycarbonyl(6-{(pyridin-2-ylsulfonyl)[4-(thiazol-2-yl)benzyl]aminomethyl}pyridin-2-yl)amino]acetate. After completion of the reaction, the reaction solution was concentrated under reduced pressure, and a saturated aqueous sodium hydrogencarbonate solution was added to the residue, followed by extraction with ethyl acetate. The separated organic layer was dried over anhydrous magnesium sulfate, and then concentrated under reduced pressure to afford the title compound (17.6 mg) as a colorless oil. (Yield: 95%)

Rf value: 0.32 (ethyl acetate).

Mass spectrum (FAB, m/z): 507 ($M^+ +1$).

$^1$H-NMR spectrum (CDCl$_3$, δ ppm): 8.98 (d, J=1.8 Hz, 1H), 8.71 (dd, J=5.0, 1.1 Hz, 1H), 7.97-7.91 (m, 1H), 7.92 (dd, J=2.5, 0.5 Hz, 1H), 7.72 (dd, J=1.8, 0.5 Hz, 1H), 7.66-7.62 (m, 2H), 7.42-7.38 (m, 2H), 7.35-7.26 (m, 2H), 6.47 (dd, J=2.5, 1.8 Hz, 1H), 6.45 (d, J=6.8 Hz, 1H), 6.28 (d, J=8.1 Hz, 1H), 4.78 (brs, 0.8H), 4.64 (s, 2H), 4.32 (s, 2H), 4.22 (q, J=7.1 Hz, 2H), 3.86 (d, J=5.3 Hz, 2H), 1.29 (t, J=7.1 Hz, 3H).

Example 31

Isopropyl(6-{[4-(pyrazol-1-yl)benzyl](pyridin-3-ylsulfonyl)aminomethyl}pyridin-2-ylamino)acetate (Exemplified Compound No. 1473)

Reaction was carried out in the same manner as in Example 29 except for using (6-{[4-(pyrazol-1-yl)benzyl](pyridin-3-ylsulfonyl)aminomethyl}pyridin-2-ylamino)-acetic acid hydrochloride (25.8 mg, 0.0439 mmol) obtained in Example 7-(b) in place of (6-{(pyridin-2-ylsulfonyl) [4-(thiazol-2-yl)benzyl]aminomethyl}pyridin-2-ylamino)-acetic acid, and using isopropanol (0.20 ml) in place of 1-hexanol. After completion of the reaction, the reaction solution was concentrated under reduced pressure, and a saturated aqueous sodium hydrogencarbonate solution was added to the residue, followed by extraction with ethyl acetate. The separated organic layer was dried over anhydrous magnesium sulfate, and then concentrated under reduced pressure to afford the title compound (20.6 mg) as a colorless oil. (Yield: 90%)

Rf value: 0.39 (ethyl acetate).

Mass spectrum (FAB, m/z): 521 ($M^+ +1$).

$^1$H-NMR spectrum (CDCl$_3$, δ ppm): 8.98 (dd, J=2.3, 0.8 Hz, 1H), 8.71 (dd, J=4.9, 1.6 Hz, 1H), 7.95 (ddd, J=8.0, 2.3, 1.6 Hz, 1H), 7.92 (dd, J=2.5, 0.6 Hz, 1H), 7.72 (dd, J=1.8, 0.6 Hz, 1H), 7.66-7.62 (m, 2H), 7.42-7.38 (m, 2H), 7.32 (ddd, J=8.0, 4.9, 0.8 Hz, 1H), 7.28 (dd, J=8.1, 7.0 Hz, 1H), 6.47 (dd, J=2.5, 1.8 Hz, 1H), 6.43 (d, J=7.0 Hz, 1H), 6.27 (d, J=8.1 Hz, 1H), 5.09 (heptet, J=6.3 Hz, 1H), 4.74 (t, J=5.3 Hz, 1H), 4.64 (s, 2H), 4.32 (s, 2H), 3.82 (d, J=5.3 Hz, 2H), 1.26 (d, J=6.3 Hz, 61-1).

Compounds used for Examples were synthesized as follows.

Reference Example 1 tert-Butyl[(5-bromo-6-bromomethylpyridin-2-yl)tert-butoxycarbonylamino]acetate 1-(a) tert-Butyl[tert-butoxycarbonyl(6-methylpyridin-2-yl)amino]acetate To a solution of 2-(tert-butoxycarbonylamino)-6-methylpyridine (723 mg, 3.47 mmol) in N,N-dimethylformamide (11.5 ml) was added sodium hydride (mineral oil 55% dispersion) (0.18 g, 4.2 mmol) in portions under ice cooling. After stirring at room temperature for 30 minutes, tert-butyl bromoacetate (0.62 ml, 4.2 mmol) was added dropwise under ice cooling, followed by stirring at room temperature for 2 hours. After completion of the reaction, water was added to the reaction solution, followed by extraction with ethyl acetate. The separated organic layer was washed with a saturated aqueous sodium chloride solution, dried over anhydrous sodium sulfate, and then concentrated under reduced pressure. The resulting residue was subjected to silica gel column chromatography (eluent; hexane:ethyl acetate-10:1→5:1 (V/V)), and fractions containing the desired compound were concentrated under reduced pressure to afford the title compound (1.14 g) substantially quantitatively as a colorless liquid.

Mass spectrum (EI, m/z): 322 ($M^+$).

$^1$H-NMR spectrum (CDCl$_3$, δ ppm): 7.58 (d, J=8.2 Hz, 1H), 7.51 (dd, J=8.2, 7.1 Hz, 1H), 6.86-6.81 (m, 1H), 4.56 (s, 2H), 2.43 (s, 3H), 1.51 (s, 9H), 1.45 (s, 9H).

1-(b) tert-Butyl[(5-bromo-6-methylpyridin-2-yl)tert-butoxycarbonylamino]acetate

To a solution of tert-butyl[tert-butoxycarbonyl(6-methylpyridin-2-yl)amino]-acetate (477 mg, 1.48 mmol) obtained in Reference Example 1-(a) in acetonitrile (3 ml) was added NBS (398 mg, 2.24 mmol), followed by stirring at 40° C. for 3 hours. After completion of the reaction, the reaction solution was concentrated under reduced pressure. The resulting residue was subjected to silica gel column chromatography (eluent; hexane:ethyl acetate=20:1→5:1 (V/V)), and fractions containing the desired compound were concentrated under reduced pressure to afford the title compound (565 mg) as a white solid. (Yield: 95%)

Mass spectrum (EI, m/z): 400 ($M^+$).

$^1$H-NMR spectrum (CDCl$_3$, δ ppm): 7.69 (d, J=8.9 Hz, 1H), 7.56 (d, J=8.9 Hz, 1H), 4.54 (s, 2H), 2.52 (s, 3H), 1.52 (s, 9H), 1.45 (s, 9H).

1-(c) tert-Butyl[(5-bromo-6-bromomethylpyridin-2-yl)tert-butoxycarbonylamino]-acetate To a solution of tert-butyl[(5-bromo-6-methylpyridin-2-yl)tert-butoxycarbonylamino]acetate (560 mg, 1.40 mmol) obtained in Reference Example 1-(b) in 1,2-dichloroethane (4.7 ml) were added NBS (373 mg, 2.10 mmol) and 2,2'-azobis(2-methylbutyronitrile) (10 mg, 0.052 mmol), followed by stirring at 90° C. for 1 hour. After completion of the reaction, the reaction solution was concentrated under reduced pressure. The resulting residue was subjected to silica gel column chromatography (eluent; hexane:ethyl acetate=20:1→10:1 (V/V)), and fractions containing the desired compound were concentrated under reduced pressure to afford a mixture (355 mg) containing the title compound as a slightly yellow oil. (Yield: 38%)

Mass spectrum (EI, m/z): 478 ($M^+$).

$^1$H-NMR spectrum (CDCl$_3$, δ ppm): 7.75 (s, 2H), 4.58 (s, 2H), 4.56 (s, 2H), 1.52 (s, 9H), 1.47 (s, 9H).

Reference Example 2

N-(6-Phenylpyridazin-3-ylmethyl)pyridin-3-ylsulfonamide 2-(a) 3-Bromomethyl-6-phenylpyridazine To a solution of 3-methyl-6-phenylpyridazine (925 mg, 5.43 mmol) in 1,2-dichloroethane (28 ml) were added NBS (1.07 g, 6.01 mmol) and 2,2'-azobis(2,4-dimethylvaleronitrile) (67.3 mg, 0.271 mmol), followed by stirring at 80° C. for 1 hour. During the reaction, 2,2'-azobis(2,4-dimethylvaleronitrile)(134 mg, 0.540 mmol) was additionally added in two portions. After completion of the reaction, the reaction solution was concentrated under reduced pressure. The resulting residue was subjected to silica gel column chromatography (eluent; hexane:ethyl acetate=5:1→0:1 (V/V)), and fractions containing the desired compound were concentrated under reduced pressure to afford the title compound (449 mg) as a slightly brown solid. (Yield: 33%)

Mass spectrum (CI, m/z): 249 ($M^+$+1).

$^1$H-NMR spectrum (CDCl$_3$, δppm): 8.13-8.07 (m, 2H), 7.89 (d, J=8.9 Hz, 1H), 7.72 (d, J=8.9 Hz, 1H), 7.56-7.50 (m, 3H), 4.80 (s, 2H).

2-(b) 3-[Bis(tert-butoxycarbony)aminomethyl]-6-phenylpyridazine

To a solution of 3-bromomethyl-6-phenylpyridazine (120 mg, 0.482 mmol) obtained in Reference Example 2-(a) in N,N-dimethylformamide (1.57 ml) were added di-tert-butyl iminodicarboxylate (127 mg, 0.585 mmol) and potassium carbonate (134 mg, 0.970 mmol), followed by stirring at 50° C. for 2 hours. After completion of the reaction, water was added to the reaction solution, followed by extraction with ethyl acetate. The separated organic layer was dried over anhydrous sodium sulfate, and then concentrated under reduced pressure. The resulting residue was subjected to silica gel column chromatography (eluent; hexane:ethyl acetate=2:1→1:1 (UV)), and fractions containing the desired compound were concentrated under reduced pressure to afford the title compound (180 mg) as a slightly yellow solid. (Yield: 97%)

Mass spectrum (FAB, m/z): 386 ($M^+$+1).

$^1$H-NMR spectrum (CDCl$_3$, δppm): 8.10-8.07 (m, 2H), 7.83 (d, J=8.8 Hz, 1H), 7.56-7.49 (m, 3H), 7.44 (d, J=8.8 Hz, 1H), 5.19 (s, 2H), 1.47 (s, 9H), 1.47 (s, 9H).

2-(c) (6-Phenylpyridazin-3-ylmethyl)amine hydrochloride

To a solution of 3-[bis(tert-butoxycarbony)aminomethyl]-6-phenylpyridazine (178 mg, 0.462 mmol) obtained in Reference Example 2-(b) in methylene chloride (2.33 ml) was added a 4N hydrogen chloride/1,4-dioxane solution (2.33 ml, 9.32 mmol), followed by stirring at 30° C. for 1 hour. After completion of the reaction, the reaction solution was concentrated under reduced pressure to afford the title compound (122 mg) substantially quantitatively as a slightly brown solid.

Mass spectrum (CI, m/z): 186 ($M^+$+1).

$^1$H-NMR spectrum (CD$_3$OD, δppm): 8.35 (d, J=8.9 Hz, 1H), 8.12-8.07 (m, 2H), 7.96 (d, J=8.9 Hz, 1H), 7.63-7.59 (m, 3H), 4.57 (s, 2H).

2-(d) N-(6-phenylpyridazin-3-ylmethyl)pyridin-3-ylsulfonamide

To a solution of (6-phenylpyridazin-3-ylmethyl)amine hydrochloride (121 mg) (containing 0.458 mmol of a pure content) obtained in Reference Example 2-(c) in methylene chloride (1 ml) were added triethylamine (0.26 ml, 1.8 mmol) and 3-pyridylsulfonyl chloride (see The Journal of Organic Chemistry, 54, 389 (1989)) (83.2 mg, 0.468 mmol), followed by stirring at room temperature for 17 hours. After completion of the reaction, the reaction solution was concentrated under reduced pressure, and water was added to the residue, followed by extraction with ethyl acetate. The separated organic layer was washed with a saturated aqueous sodium chloride solution, dried over anhydrous sodium sulfate, and then concentrated under reduced pressure. The resulting residue was subjected to silica gel column chromatography (eluent; ethyl acetate:acetonitrile=1:0→0:1 (V/V), then chloroform), and fractions containing the desired compound were concentrated under reduced pressure to afford the title compound (130 mg) as a slightly brown solid. (Yield: 87%)

Mass spectrum (CI, m/z): 327 ($M^+$+1).

$^1$H-NMR spectrum (CDCl$_3$, δppm): 9.11 (dd, J=2.4, 0.9 Hz, 1H), 8.75 (dd, J=4.8, 1.6 Hz, 1H), 8.19 (ddd, J=8.1, 2.4, 1.6 Hz, 1H), 8.05-8.00 (m, 2H), 7.82 (d, J=8.8 Hz, 1H), 7.56-7.49 (m, 4H), 7.42 (ddd, J=8.1, 4.8, 0.9 Hz, 1H), 6.30 (brs, 1H), 4.57 (s, 2H).

Reference Example 3 tert-Butyl[tert-butoxycarbonyl(6-hydroxymethylpyridin-2-yl)amino]acetate 3-(a) tert-Butyl[tert-butoxycarbonyl(6-ethoxycarbonypyridin-2-yl)amino]acetate To a solution of sodium hydride (mineral oil 55% dispersion) (15.7 g, 0.360 mol) in N,N-dimethylformamide (362 ml) was added dropwise a solution of ethyl 6-tert-butoxycarbonylaminopyridin-2-carboxylate (see WO 2006/074884A) (81.2 g, 0.305 mol) in N,N-dimethylformamide (300 ml) over 20 minutes under ice cooling in an argon atmosphere, followed by stirring at room temperature for 1 hour. tert-Butyl bromoacetate (54.0 ml, 0.366 mol) was then added dropwise over 10 minutes under ice cooling, followed by further stirring at room temperature for 1 hour. After completion of the reaction, to the reaction solution was added an aqueous solution in which ammonium chloride (1.77 g, 33.0 mmol) was dissolved in water (300 ml), followed by extraction with toluene. The separated organic layer was washed with a saturated aqueous sodium chloride solution, dried over anhydrous magnesium sulfate, and then concentrated under reduced pressure. The resulting residue was subjected to silica gel column chromatography (eluent; hexane:ethyl acetate=9:1→4:1 (V/V)), and fractions containing the desired compound were concentrated under reduced pressure to afford the title compound (108 g) as a pale yellow liquid. (Yield: 93%)

Mass spectrum (CI, m/z): 381 ($M^+$+1).

$^1$H-NMR spectrum (CDCl$_3$, δppm): 8.04 (d, J=7.8 Hz, 1H), 7.81 (dd, J=7.6, 1.5 Hz, 1H), 7.76 (dd, J=7.8, 7.6 Hz, 1H), 4.67 (s, 2H), 4.40 (q, J=7.1 Hz, 2H), 1.52 (s, 9H), 1.45 (s, 9H), 1.40 (t, J=7.1 Hz, 3H).

3-(b) tert-Butyl[tert-butoxycarbonyl(6-hydroxymethylpyridin-2-yl)amino]acetate

To a solution of tert-butyl[tert-butoxycarbonyl(6-ethoxycarbonypyridin-2-yl)amino]acetate (98.8 g, 0.260 mol) obtained in Reference Example 3-(a) in ethanol (195 ml), was added dropwise a solution of calcium chloride (34.6 g, 0.312 mol) in ethanol (195 ml) over 20 minutes under ice cooling. A 3M sodium borohydride/-tetraethylene glycol dimethyl ether solution (105 ml, 0.315 mol) was then added dropwise over 20 minutes at 35° C. or lower, followed by further stirring at room temperature for 15 minutes. After completion of the reaction, the reaction solution was added dropwise to an aqueous solution of acetic acid (17.8 ml) in water (195 ml) over 10 minutes under ice cooling, followed by stirring at room temperature for 1 hour. Water (315 ml) was then added, followed by extraction with toluene. The separated organic layer was washed with a saturated aqueous sodium hydrogencarbonate solution, water and then a saturated aqueous sodium chloride solution, followed by concentration under reduced pressure. The resulting residue was subjected to silica gel column chromatography (eluent; hexane:ethyl acetate=4:1→3:2 (V/V)), and fractions containing the desired compound were concentrated under reduced pressure to afford the title compound (81.1 g) as a pale yellow liquid. (Yield: 92%)

Mass spectrum (CI, m/z): 339 (M$^+$+1).

$^1$H-NMR spectrum (CDCl$_3$, δppm): 7.74 (d, J=8.2 Hz, 1H), 7.63 (dd, J=8.2, 7.4 Hz, 1H), 6.93-6.98 (m, 1H), 4.68-4.65 (m, 2H), 4.54 (s, 2H), 3.39 (t, J=5.3 Hz, 1H), 1.54 (s, 9H), 1.46 (s, 9H).

Reference Example 4

N-[4-(Thiazol-2-yl)benzyl]pyridin-3-ylsulfonamide 4-(a) 4-(Thiazol-2-yl)benzyl alcohol To 4-(thiazol-2-yl)benzaldehyde (see JP 2001-519414A) (1.57 g, 8.30 mmol) were added ethanol (20 ml), tetrahydrofuran (0.46 ml), and then sodium borohydride (157 mg, 4.15 mmol), followed by stirring at room temperature for 1.5 hours. After completion of the reaction, water was added to the reaction solution, followed by extraction with ethyl acetate. The separated organic layer was dried over anhydrous sodium sulfate, and then concentrated under reduced pressure. The resulting residue was subjected to silica gel column chromatography (eluent; hexane:ethyl acetate=2: 1→1:1 (V/V)), and fractions containing the desired compound were concentrated under reduced pressure to afford the title compound (1.49 g) as a white solid. (Yield: 94%)

Mass spectrum (CI, m/z): 192 (M$^+$+1).

$^1$H-NMR spectrum (CDCl$_3$, δppm): 7.94-7.89 (m, 2H), 7.84 (d, J=3.2 Hz, 1H), 7.44-7.38 (m, 2H), 7.32 (d, J=3.2 Hz, 1H), 4.72 (d, J=5.9 Hz, 2H), 2.41 (t, J=5.9 Hz, 1H).

4-(b) 4-(Thiazol-2-yl)benzyl bromide

To a solution of 4-(thiazol-2-yl)benzyl alcohol (1.31 g, 6.85 mmol) obtained in 4-(a) in tetrahydrofuran (55.8 ml) were added triphenylphosphine (1.80 g, 8.90 mmol) and NBS (1.59 g, 8.93 mmol), followed by stirring at room temperature for 1.5 hours. After completion of the reaction, a saturated aqueous sodium hydrogencarbonate solution was added to the reaction solution, followed by extraction with ethyl acetate. The separated organic layer was washed with a saturated aqueous sodium chloride solution, dried over anhydrous sodium sulfate, and then concentrated under reduced pressure. The resulting residue was subjected to silica gel column chromatography (eluent; hexane:ethyl acetate=2:1 (V/V)), and fractions containing the desired compound were concentrated under reduced pressure to afford the title compound (1.26 g) as a slightly yellow solid. (Yield: 72%)

Mass spectrum (CI, m/z): 254 (M$^+$+1).

$^1$H-NMR spectrum (CDCl$_3$, δppm): 7.98-7.92 (m, 2H), 7.88 (d, J=3.3 Hz, 1H), 7.50-7.45 (m, 2H), 7.35 (d, J=3.3 Hz, 1H), 4.52 (s, 2H).

4-(c) 2-{4-[Bis(tert-butoxycarbony)aminomethyl] phenyl}thiazole

To a solution of 4-(thiazol-2-yl)benzyl bromide (1.25 g, 4.92 mmol) obtained in Reference Example 4-(b) in N,N-dimethylformamide (16 ml) were added di-tert-butyl iminodicarboxylate (1.28 g, 5.89 mmol) and potassium carbonate (1.35 g, 9.76 mmol), followed by stirring at room temperature for 3 hours. After completion of the reaction, water was added to the reaction solution, followed by extraction with ethyl acetate. The separated organic layer was washed with a saturated aqueous sodium chloride solution, dried over anhydrous sodium sulfate, and then concentrated under reduced pressure. The resulting residue was subjected to silica gel column chromatography (eluent; hexane:ethyl acetate=2:1 (V/V)), and fractions containing the desired compound were concentrated under reduced pressure to afford the title compound (2.05 g) substantially quantitatively as a colorless oil.

$^1$H-NMR spectrum (CDCl$_3$, δppm): 7.95-7.89 (m, 2H), 7.85 (d, J=3.4 Hz, 1H), 7.39-7.34 (m, 2H), 7.32 (d, J=3.4 Hz, 1H), 4.81 (s, 2H), 1.46 (s, 9H), 1.46 (s, 9H).

4-(d) 4-(Thiazol-2-yl)benzylamine hydrochloride

Reaction and post-treatment were carried out in the same manner as in Reference Example 2-(c) except for using 2-{4-[bis(tert-butoxycarbony)aminomethyl]-phenyl}thiazole (1.91 g, 4.89 mmol) obtained in Reference Example 4-(c) in place of 3-[bis(tert-butoxycarbony)aminomethyl]-6-phenylpyridazine to afford a crude product (1.37 g) containing the title compound substantially quantitatively as a white solid.

$^1$H-NMR spectrum (DMSO-d$_6$, δppm): 8.56 (brs, 2H), 8.03-7.97 (m, 2H), 7.95 (d, J=3.2 Hz, 1H), 7.83 (d, J=3.2 Hz, 1H), 7.67-7.60 (m, 2H), 4.12-4.03 (m, 2H).

4-(e) N-[4-(Thiazol-2-yl)benzyl]pyridin-3-ylsulfonamide

Reaction and post-treatment were carried out in the same manner as in Reference Example 2-(d) except for using 3-pyridylsulfonyl chloride (495 mg, 2.79 mmol), and using 4-(thiazol-2-yl)benzylamine hydrochloride (687 mg, 2.61 mmol) obtained in Reference Example 4-(d) in place of (6-phenylpyridazin-3-ylmethyl)amine hydrochloride to afford the title compound (689 mg) as a white solid. (Yield: 80%)

Mass spectrum (CI, m/z): 332 (M$^+$+1).

$^1$H-NMR spectrum (DMSO-d$_6$, δppm): 8.92 (d, J=2.4 Hz, 1H), 8.77 (dd, J=4.9, 1.5 Hz, 1H), 8.17-8.12 (m, 1H), 7.91 (d, J=3.1 Hz, 1H), 7.87-7.82 (m, 2H), 7.77 (d, J=3.1 Hz, 1H), 7.61-7.55 (m, 1H), 7.39-7.32 (m, 2H), 4.13 (s, 2H).

Reference Example 5

N-[4-Thiazol-2-1 benzyl]pyridin-2-ylsulfonamide

Reaction and post-treatment were carried out in the same manner as in Reference Example 2-(d) except for using 2-pyridylsulfonyl chloride (see Heterocycles, 28, 1115 (1989)) (220 mg, 1.24 mmol) in place of 3-pyridylsulfonyl chloride, and using 4-(thiazol-2-yl)benzylamine hydrochloride (300 mg, 1.14 mmol) obtained in Reference Example 4-(d) in place of (6-phenylpyridazin-3-ylmethyl)amine hydrochloride to afford the title compound (284 mg) as a white solid. (Yield: 75%)

Mass spectrum (CI, m/z): 332 (M$^+$+1).

$^1$H-NMR spectrum (CDCl$_3$, δppm): 8.66 (ddd, J=4.6, 1.7, 1.0 Hz, 1H), 7.98 (ddd, J=7.9, 1.2, 1.0 Hz, 1H), 7.91-7.82 (m, 4H), 7.47 (ddd, J=7.6, 4.6, 1.2 Hz, 1H), 7.35-7.30 (m, 3H), 5.59 (t, J=6.5 Hz, 1H), 4.32 (d, J=6.5 Hz, 2H).

Reference Example 6

4-Fluoro-N-[4-(thiazol-2-yl)benzyl]benzenesulfonamide

Reaction and post-treatment were carried out in the same manner as in Reference Example 2-(d) except for using 4-fluorobenzenesulfonyl chloride (278 mg, 1.42 mmol) in place of 3-pyridylsulfonyl chloride, and using 4-(thiazol-2-yl)benzylamine hydrochloride (364 mg, 1.38 mmol) obtained in Reference Example 4-(d) in place of (6-phenylpyridazin-3-ylmethyl)amine hydrochloride to afford the title compound (411 mg) as a slightly yellow solid. (Yield: 85%)

Mass spectrum (CI, m/z): 349 ($M^+$+1).
$^1$H-NMR spectrum (DMSO-$d_6$, δppm): 8.29 (brs, 0.8H), 7.91 (d, J=3.2 Hz, 1H), 7.89-7.81 (m, 4H), 7.77 (d, J=3.2 Hz, 1H), 7.45-7.32 (m, 4H), 4.06 (s, 2H).

Reference Example 7

N-[4-(4,5-Dihydrothiazol-2-yl)benzyl]-4-fluorobenzenesulfonamide 7-(a)
N-(4-Cyanobenzyl)-4-fluorobenzenesulfonamide Reaction was carried out in the same manner as in a Reference Example 2-(d) except for using 4-fluorobenzenesulfonyl chloride (1.18 g, 6.06 mmol) in place of 3-pyridylsulfonyl chloride, and using 4-cyanobenzylamine hydrochloride (1.00 g, 5.93 mmol) in place of (6-phenylpyridazin-3-ylmethyl)amine hydrochloride. After completion of the reaction, a saturated aqueous sodium chloride solution was added to the reaction solution, followed by extraction with ethyl acetate. The separated organic layer was dried over anhydrous magnesium sulfate, and then concentrated under reduced pressure. To the resulting residue dissolved in a small amount of methylene chloride was added hexane, and a precipitated solid was collected by filtration. The resulting solid was dried under reduced pressure at 60° C. to afford the title compound (1.54 g) as a slightly brown solid. (Yield: 89%)

Mass spectrum (CI, m/z): 291 ($M^+$+1).
$^1$H-NMR spectrum (CDCl$_3$, δppm): 7.92-7.83 (m, 2H), 7.62-7.55 (m, 2H), 7.40-7.33 (m, 2H), 7.24-7.15 (m, 2H), 5.07 (t, J=6.5 Hz, 1H), 4.22 (d, J=6.5 Hz, 2H).

7-(b) N-[4-(4,5-Dihydrothiazol-2-yl)benzyl]-4-fluorobenzenesulfonamide

To a solution of N-(4-cyanobenzyl)-4-fluorobenzenesulfonamide (1.23 g, 4.24 mmol) obtained in Reference Example 7-(a) in ethanol (5 ml) was added 2-aminoethanethiol (0.426 g, 5.52 mmol), which was deaerated under reduced pressure, followed by argon substitution. This reaction mixture was then heated to reflux for 6 hours. After completion of the reaction, a saturated aqueous sodium chloride solution was added to the reaction solution, followed by extraction with ethyl acetate. The separated organic layer was dried over anhydrous magnesium sulfate, and then concentrated under reduced pressure. The resulting residue was subjected to silica gel column chromatography (eluent; chloroform:ethyl acetate=7:3 (VAT)), and fractions containing the desired compound were concentrated under reduced pressure to afford the title compound (1.32 g) as a white solid. (Yield: 89%)

Mass spectrum (CI, m/z): 351 ($M^4$+1).
$^1$H-NMR spectrum (CDCl$_3$, δppm): 7.91-7.83 (m, 2H), 7.77-7.71 (m, 2H), 7.25-7.13 (m, 4H), 4.82 (t, J=6.2 Hz, 1H), 4.45 (t, J=8.4 Hz, 2H), 4.20 (d, J=6.2 Hz, 2H), 3.42 (t, J=8.4 Hz, 2H).

Reference Example 8

N-(Biphenyl-4-ylmethyl)pyridin-3-ylsulfonamide

Reaction was carried out in the same manner as in Reference Example 2-(d) except for using 3-pyridylsulfonyl chloride (890 mg, 5.01 mmol), and using (biphenyl-4-ylmethyl)amine (1.01 g, 5.51 mmol) in place of (6-phenylpyridazin-3-ylmethyl)amine hydrochloride. After completion of the reaction, water was added to the reaction solution, followed by extraction with ethyl acetate. The separated organic layer was washed with a saturated aqueous sodium chloride solution, dried over anhydrous sodium sulfate, and then concentrated under reduced pressure. The resulting residue was subjected to silica gel column chromatography (eluent; hexane:ethyl acetate=1:1 (V/V)→chloroform:ethyl acetate=1:1 (V/V)→ethyl acetate), and fractions containing the desired compound were concentrated under reduced pressure. To the resulting crude product were added methylene chloride (5 ml) and diisopropyl ether (10 ml), followed by being left for 1 hour. A precipitated solid was collected by filtration, and dried under reduced pressure at 35° C. to afford the title compound (1.49 g) as a white solid. (Yield: 92%)

Mass spectrum (CI, m/z): 325 ($M^+$+1).
$^1$H-NMR spectrum (CDCl$_3$, δppm): 9.09 (dd, J=2.3, 0.7 Hz, 1H), 8.78 (dd, J=4.9, 1.7 Hz, 1H), 8.10 (ddd, J=8.1, 2.3, 1.7 Hz, 1H), 7.57-7.31 (m, 8H), 7.29-7.23 (m, 2H), 4.96 (t, J=5.9 Hz, 1H), 4.27 (d, J=5.9 Hz, 2H).

Reference Example 9

N-[4-(Pyrazol-1-yl)benzyl]pyridin-3-ylsulfonamide 9-(a) 4-(Pyrazol-1-yl)benzylamine To 4-(pyrazol-1-yl)benzonitrile (see WO 2005/095343A) (1.46 g, 8.63 mmol) was added a solution of 1M borane.tetrahydrofuran complex in tetrahydrofuran (93 ml, 93 mmol), followed by heating to reflux for 16 hours. After completion of the reaction, methanol (14 ml) was added to the reaction solution, followed by concentration under reduced pressure. 6N Hydrochloric acid (265 ml) was added to the residue, followed by further heating to reflux for 3 hours. After this solution was concentrated under reduced pressure, a small amount of water was added. The resulting solution was adjusted to pH 11 with a 30% aqueous sodium hydroxide solution under ice cooling, followed by extraction with methylene chloride. The separated organic layer was dried over anhydrous sodium sulfate, and then concentrated under reduced pressure. The resulting residue was subjected to silica gel column chromatography (eluent; chloroform:methanol:28% aqueous ammonia=90:10:1 (V/V/V)), and fractions containing the desired compound were concentrated under reduced pressure to afford the title compound (1.24 g) as a pale yellow solid. (Yield: 83%)

Mass spectrum (CI, m/z): 174 ($M^+$+1).
$^1$H-NMR spectrum (CDCl$_3$, δ ppm): 7.91 (dd, J=2.5, 0.5 Hz, 1H), 7.72 (d, J=1.6 Hz, 1H), 7.69-7.63 (m, 2H), 7.44-7.37 (m, 2H), 6.46 (dd, J=2.5, 1.6 Hz, 1H), 3.91 (s, 2H).

9-(b) N-[4-(Pyrazol-1-yl)benzyl]pyridin-3-ylsulfonamide

Reaction and post-treatment were carried out in the same manner as in Reference Example 2-(d) except for using 3-pyridylsulfonyl chloride (150 mg, 0.845 mmol), and using 4-(pyrazol-1-yl)benzylamine (133 mg, 0.767 mmol) obtained in Reference Example 9-(a) in place of (6-phenylpyridazin-3-ylmethyl)amine hydrochloride to afford the title compound (186 mg) as a white solid. (Yield: 77%)

Mass spectrum (CI, m/z): 315 ($M^+$+1).
$^1$H-NMR spectrum (CDCl$_3$, δppm): 8.98 (dd, J=2.4, 0.9 Hz, 1H), 8.78 (dd, J=4.9, 1.7 Hz, 1H), 8.10 (ddd, J=8.0, 2.4, 1.7 Hz, 1H), 7.88 (dd, J=2.5, 0.5 Hz, 1H), 7.70 (dd, J=1.8, 0.5 Hz, 1H), 7.61-7.55 (m, 2H), 7.42 (1H, ddd, J=8.0, 4.9, 0.9 Hz, 1H), 7.30-7.24 (m, 2H), 6.46 (dd, J=2.5, 1.8 Hz, 1H), 5.72 (t, J=6.0 Hz, 1H), 4.23 (d, J=6.0 Hz, 2H).

Reference Example 10

N-(Benzofuran-2-ylmethyl)pyridin-3-ylsulfonamide 10-(a) 2-Benzofuran carbaldehyde oxime To a solution of 2-benzofuran carbaldehyde (1.00 g, 6.85 mmol) in methanol (20 ml) were added hydroxylammonium chloride (530 mg, 7.63 mmol) and pyridine (2.8 ml), followed by stirring at room temperature for 6.5 hours. After completion of the reaction, the reaction solution was concentrated under reduced pressure. Ethyl acetate was added to the resulting residue, followed by washing sequentially with a 5% aqueous potassium hydrogensulfate solution, a saturated aqueous sodium hydrogen carbonate solution and then a saturated aqueous sodium chloride solution. The resulting organic layer was dried over anhydrous magnesium sulfate, and then concentrated under reduced pressure to afford the title compound (1.07 g) as a white solid. (Yield: 97%)

$^1$H-NMR spectrum (CDCl$_3$, δppm): 8.47 & 7.81 (brs, total 1H), 8.14 & 7.67 (s, total 1H), 7.69 & 6.96 (d, J=0.9 Hz, total 1H), 7.67 & 7.60 (ddd, J=7.7, 1.2, 0.9 Hz, total 1H), 7.55-7.49 (m, 1H), 7.43-7.22 (m, 2H).

10-(b) (Benzofuran-2-ylmethyl)amine

To a solution of 2-benzofuran carbaldehyde oxime (1.07 g, 6.64 mmol) obtained in Reference Example 10-(a) in ethanol (30 ml) was added 10% palladium-active carbon (50% hydrate) (0.75 g), followed by stirring at room temperature for 4.5 hours under hydrogen atmosphere at 1 atm. After completion of the reaction, insolubles were filtered off, and the filtrate was concentrated under reduced pressure. The resulting residue was subjected to silica gel column chromatography (eluent; chloroform:methanol:28% aqueous ammonia=190:10:1 (V/V/V)), and fractions containing the desired compound were concentrated under reduced pressure to afford the title compound (0.21 g) as a pale yellow oil. (Yield: 21%)

Mass spectrum (CI, m/z): 147 (M$^+$).

$^1$H-NMR spectrum (CDCl$_3$, δppm): 7.54-7.49 (m, 1H), 7.46-7.41 (m, 1H), 7.28-7.16 (m, 2H), 6.54-6.51 (m, 1H), 3.98 (d, J=0.8 Hz, 2H).

10-(c) N-(Benzofuran-2-ylmethyl)pyridin-3-ylsulfonamide

Reaction and post-treatment were carried out in the same manner as in Reference Example 2-(d) except for using 3-pyridylsulfonyl chloride (154 mg, 0.867 mmol), and using (benzofuran-2-ylmethyl)amine (128 mg, 0.870 mmol) obtained in Reference Example 10-(b) in place of (6-phenylpyridazin-3-ylmethyl)amine hydrochloride to afford the title compound (239 mg) as a white solid. (Yield: 96%)

$^1$H-NMR spectrum (DMSO-d$_6$, δppm): 8.92 (d, J=1.8 Hz, 1H), 8.67 (dd, J=5.1, 1.7 Hz, 1H), 8.13 (ddd, J=8.0, 1.8, 1.7 Hz, 1H), 7.56-7.45 (m, 2H), 7.35 (d, J=8.0 Hz, 1H), 7.29-7.14 (m, 2H), 6.67 (s, 1H), 4.30 (s, 2H).

Reference Example 11

N-(4-Bromobenzyl)pyridin-3-ylsulfonamide

Reaction and post-treatment were carried out in the same manner as in Reference Example 2-(d) except for using 3-pyridylsulfonyl chloride (300 mg, 1.69 mmol), and using 4-bromobenzylamine hydrochloride (342 mg, 1.54 mmol) in place of (6-phenylpyridazin-3-ylmethyl)amine hydrochloride to afford the title compound (422 mg) as a white solid. (Yield: 84%)

Mass spectrum (CI, m/z): 327 (M$^+$+1).

$^1$H-NMR spectrum (CDCl$_3$, δppm): 9.05 (dd, J=2.3, 0.7 Hz, 1H), 8.79 (dd, J=4.9, 1.7 Hz, 1H), 8.07 (ddd, J=8.0, 2.3, 1.7 Hz, 1H), 7.46-7.37 (m, 3H), 7.11-7.05 (m, 2H), 5.09 (t, J=5.9 Hz, 1H), 4.18 (d, J=5.9 Hz, 2H).

Reference Example 12 tert-Butyl(tert-butoxycarbonyl {6-[(pyridin-3-ylsulfonyl)aminomethyl]pyridin-2-yl}-amino)acetate 12-(a) tert-Butyl[tert-butoxycarbonyl(6-formylpyridin-2-yl)amino]acetate To a solution of Dess-martin reagent (12.9 g, 30.4 mmol) in methylene chloride (130 ml) was added dropwise a solution of tert-butyl[tert-butoxycarbonyl(6-hydroxymethylpyridin-2-yl)amino]acetate (10.0 g, 29.6 mmol) obtained in Reference Example 3-(b) in methylene chloride (50 ml) over 20 minutes under ice cooling in argon atmosphere. After completion of the dropwise addition, the mixture was stirred at room temperature for 2 hours. After completion of the reaction, a 0.1% aqueous sodium thiosulfate solution (305 ml) was added to the reaction solution, followed by extraction with methylene chloride. The separated organic layer was washed sequentially with a 0.5N aqueous sodium hydroxide solution and a saturated aqueous sodium chloride solution, dried over anhydrous magnesium sulfate, and then concentrated under reduced pressure to afford the title compound (9.61 g) substantially quantitatively as a slightly yellow oil.

Mass spectrum (CI, m/z): 336 (M$^+$).

$^1$H-NMR spectrum (DMSO-d$_6$, δppm): 9.82 (s, 1H), 8.11-7.99 (m, 2H), 7.68 (dd, J=6.6, 1.5 Hz, 1H), 4.58 (s, 2H), 1.48 (s, 9H), 1.42 (s, 9H).

12-(b) tert-Butyl[tert-butoxycarbonyl(6-hydroxyiminomethylpyridin-2-yl)amino]-acetate To a solution of tert-butyl[tert-butoxycarbonyl(6-formylpyridin-2-yl)amino]-acetate (2.88 g, 8.56 mmol) obtained in Reference Example 12-(a) in methanol (28.5 ml) were added hydroxylammonium chloride (0.650 g, 9.35 mmol) and pyridine (3.5 ml), followed by stirring at room temperature for 1 hour. After completion of the reaction, the reaction solution was concentrated under reduced pressure. Ethyl acetate was added to the concentrate, which was washed sequentially with a 5% aqueous potassium hydrogensulfate solution, a saturated aqueous sodium hydrogencarbonate solution and a saturated aqueous sodium chloride solution, then dried over anhydrous magnesium sulfate, and subsequently concentrated under reduced pressure. The resulting residue was subjected to silica gel column chromatography (eluent; hexane:ethyl acetate=3:2 (V/V)), and fractions containing the desired compound were concentrated under reduced pressure to afford the title compound (2.76 g) as a colorless oil. (Yield: 92%)

Mass spectrum (EI, m/z): 351 (M$^+$).

$^1$H-NMR spectrum (CDCl$_3$, δppm): 8.06 (s, 1H), 7.91 (s, 1H), 7.85 (d, J=8.2 Hz, 1H), 7.65 (dd, J=8.2, 7.6 Hz, 1H), 7.47 (dd, J=7.6, 0.7 Hz, 1H), 4.59 (s, 2H), 1.53 (s, 9H), 1.45 (s, 9H).

12-(c) tert-Butyl[(6-aminomethylpyridin-2-yl)tert-butoxycarbonylamino]acetate To a solution of tert-butyl[tert-butoxycarbonyl(6-hydroxyiminomethylpyridin-2-yl)amino]acetate (2.75 g, 7.83 mmol) obtained in Reference Example 12-(b) in ethanol (49 ml) was added 10% palladium-active carbon (50% hydrate) (0.98 g), followed by stirring at room temperature for 1 hour under hydrogen atmosphere at 1 atm. After completion of the reaction, insolubles were filtered off; and the filtrate was concentrated under reduced pressure to afford the title compound (2.48 g) as a colorless oil. (Yield: 94%)

Mass spectrum (CI, m/z): 338 ($M^+$+1).

$^1$H-NMR spectrum (CDCl$_3$, δppm): 7.68 (d, J=8.3 Hz, 1H), 7.58 (dd, J=8.3, 7.4 Hz, 1H), 6.91 (d, J=7.4 Hz, 1H), 4.57 (s, 2H), 3.85 (s, 2H), 1.53 (s, 9H), 1.46 (s, 9H).

12-(d) tert-Butyl(tert-butoxycarbonyl{6-[(pyridin-3-ylsulfonyl)aminomethyl]pyridin-2-yl}amino)acetate To a solution of 3-pyridylsulfonyl chloride (640 mg, 3.60 mmol) in methylene chloride (14 ml) were added tert-butyl [(6-aminomethylpyridin-2-yl)tert-butoxycarbonylamino]acetate (1.20 g, 3.56 mmol) obtained in Reference Example 12-(c) and triethylamine (2.24 ml, 16.2 mmol), followed by stirring at room temperature for 1 hour. After completion of the reaction, a 5% aqueous potassium hydrogensulfate solution was added to the reaction solution, followed by extraction with chloroform. The separated organic layer was washed sequentially with a saturated aqueous sodium hydrogencarbonate solution and a saturated aqueous sodium chloride solution, dried over anhydrous magnesium sulfate, and then concentrated under reduced pressure. The resulting residue was subjected to silica gel column chromatography (eluent; hexane:ethyl acetate=1:1→1:2 (V/V)), and fractions containing the desired compound were concentrated under reduced pressure to afford the title compound (1.45 g) as a colorless oil. (Yield: 85%)

Mass spectrum (CI, m/z): 479 ($M^+$+1).

$^1$H-NMR spectrum (CDCl$_3$, δppm): 9.06 (d, J=2.2 Hz, 1H), 8.71 (dd, J=4.6, 1.5 Hz, 1H), 8.13-8.08 (m, 1H), 7.68 (d, J=8.2 Hz, 1H), 7.52 (dd, J=8.2, 7.4 Hz, 1H), 7.38-7.32 (m, 1H), 6.77 (d, J=7.4 Hz, 1H), 5.80 (t, J=5.1 Hz, 1H), 4.40 (s, 2H), 4.24 (d, J=5.1 Hz, 2H), 1.53 (s, 9H), 1.46 (s, 9H).

Reference Example 13

4-(Pyridazin-4-yl)benzyl alcohol

To a solution of 4-bromopyridazine (131 mg, 0.824 mmol) in 1,2-dimethoxyethane (16.4 ml) were added 4-hydroxymethylphenylboronic acid (189 mg, 1.24 mmol), potassium carbonate (517 mg, 3.74 mmol) and water (8.2 ml), which was deaerated under reduced pressure, followed by argon substitution. Tetrakis(triphenylphosphine)-palladium (73.5 mg, 0.0636 mmol) was then added, followed by heating to reflux for 5 hours under argon atmosphere. After completion of the reaction, the reaction solution was concentrated under reduced pressure. The resulting residue was subjected to reversed phase column chromatography (column; Megabond Elut™ C18 (manufactured by Varian, Inc.), eluent; acetonitrile:water=0:1→1:4 (VAT), then methanol), and fractions containing the desired compound were concentrated under reduced pressure to afford the title compound (97.7 mg) as a slightly brown solid. (Yield: 64%)

Mass spectrum (CI, m/z): 187 ($M^+$+1).

$^1$H-NMR spectrum (CD$_3$OD, δppm): 9.55 (dd, J=2.4, 1.2 Hz, 1H), 9.19 (dd, J=5.5, 1.2 Hz, 1H), 8.01 (dd, J=5.5, 2.4 Hz, 1H), 7.88-7.83 (m, 2H), 7.60-7.54 (m, 2H), 4.70 (s, 2H).

Reference Example 14 tert-Butyl(tert-butoxycarbonyl{6-[(pyridin-2-ylsulfonyl)aminomethyl]pyridin-2-yl}-amino)acetate Reaction and post-treatment were carried out in the same manner as in Reference Example 12-(d) except for using tert-butyl[(6-aminomethylpyridin-2-yl)tert-butoxycarbonylamino]acetate (1.20 g, 3.56 mmol) obtained in Reference Example 12-(c), and using 2-pyridylsulfonyl chloride (640 mg, 3.60 mmol) in place of 3-pyridylsulfonyl chloride to afford the title compound (1.46 g) as a white solid. (Yield: 86%)

Mass spectrum (APCI, m/z): 479 ($M^+$+1).

$^1$H-NMR spectrum (CDCl$_3$, δppm): 8.56 (ddd, J=4.7, 1.7, 0.9 Hz, 1H), 7.97 (ddd, J=7.8, 1.1, 0.9 Hz, 1H), 7.84 (ddd, J=7.8, 7.7, 1.7 Hz, 1H), 7.68 (d, J=8.4 Hz, 1H), 7.52 (dd, J=8.4, 7.4 Hz, 1H), 7.40 (ddd, J=7.7, 4.7, 1.1 Hz, 1H), 6.84 (dd, J=7.4, 0.5 Hz, 1H), 5.86 (t, J=5.6 Hz, 1H), 4.48 (s, 2H), 4.36 (d, J=5.6 Hz, 2H), 1.53 (s, 9H), 1.45 (s, 9H).

Reference Example 15

4-(Thiazol-4-yl)benzyl alcohol

15-(a) 4-(Thiazol-4-yl)benzaldehyde

To a solution of 4-bromothiazole (see The Journal of Organic Chemistry, 71, 3754 (2006)) (1.31 g, 7.98 mmol) in 1,2-dimethoxyethane (38.0 ml) were added 4-formylphenylboronic acid (1.45 g, 9.67 mmol), sodium hydrogencarbonate (2.00 g, 23.8 mmol) and water (19 ml), which was deaerated under reduced pressure, followed by argon substitution. Tetrakis(triphenylphosphine)palladium (270 mg, 0.234 mmol) was then added, followed by heating to reflux for 16 hours under argon atmosphere. After completion of the reaction, a saturated aqueous sodium chloride solution was added to the reaction solution, followed by extraction with chloroform. The separated organic layer was dried over anhydrous magnesium sulfate, and then concentrated under reduced pressure. The resulting residue was subjected to silica gel column chromatography (eluent; hexane:ethyl acetate=4:1 (V/V)), and fractions containing the desired compound were concentrated under reduced pressure to afford the title compound (1.29 g) as a slightly yellow solid. (Yield: 85%)

Mass spectrum (CI, ink): 190 ($M^+$+1).

$^1$H-NMR spectrum (CDCl$_3$, δppm): 10.05 (s, 1H), 8.93 (d, J=2.0 Hz, 1H), 8.14-8.10 (m, 2H), 7.99-7.94 (m, 2H), 7.73 (d, J=2.0 Hz, 1H).

15-(b) 4-(Thiazol-4-yl)benzyl alcohol

Reaction and post-treatment were carried out in the same manner as in Reference Example 4-(a) except for using 4-(thiazol-4-yl)benzaldehyde (1.28 g, 6.76 mmol) obtained in Reference Example 15-(a) in place of 4-(thiazol-2-yl)benzaldehyde to afford the title compound (1.07 g) as a white solid. (Yield: 83%)

Mass spectrum (CI, m/z): 192 (M$^+$+1).

$^1$H-NMR spectrum (CDCl$_3$, δppm): 8.88 (d, J=2.0 Hz, 1H), 7.95-7.90 (m, 2H), 7.54 (d, J=2.0 Hz, 1H), 7.46-7.41 (m, 2H), 4.74 (d, J=5.9 Hz, 2H), 1.85 (t, J=5.9 Hz, 1H).

Reference Example 16

4-(Pyrimidin-2-yl)benzyl alcohol

Reaction and post-treatment were carried out in the same manner as in Reference Example 13 except for using 4-hydroxymethylphenylboronic acid (144 mg, 0.948 mmol), and using 2-bromopyrimidine (101 mg, 0.635 mmol) in place of 4-bromopyridazine to afford the title compound (119 mg) substantially quantitatively as a slightly yellow solid.

Mass spectrum (CI, m/z): 187 (M$^+$+1).

$^1$H-NMR spectrum (CDCl$_3$, δppm): 8.81 (d, J=4.7 Hz, 2H), 8.47-8.42 (m, 2H), 7.52-7.47 (m, 2H), 7.19 (t, J=4.7 Hz, 1H), 4.79 (d, 0.1-6.0 Hz, 2H), 1.75 (t, J=6.0 Hz, 1H).

Reference Example 17 tert-Butyl(tert-butoxycarbonyl{6-[(4-fluorobenzenesulfonyl)aminomethyl]pyridin-2-yl}amino)acetate Reaction and post-treatment were carried out in the same manner as in Reference Example 12-(d) except for using tert-butyl[(6-aminomethylpyridin-2-yl)tert-butoxycarbonylamino]acetate (7.00 g, 20.7 mmol) obtained in Reference Example 12-(c), and using 4-fluorobenzenesulfonyl chloride (4.00 g, 20.6 mmol) in place of 3-pyridylsulfonyl chloride to afford the title compound (4.91 g) as a white solid. (Yield: 48%)

Mass spectrum (FAB, m/z): 496 (M$^+$+1).

$^1$H-NMR spectrum (CDCl$_3$, δppm): 7.90-7.81 (m, 2H), 7.69 (d, J=8.3 Hz, 1H), 7.52 (dd, J=8.3, 7.4 Hz, 1H), 7.14-7.05 (m, 2H), 6.76 (dd, J=7.4, 0.6 Hz, 1H), 5.60 (t, J=5.3 Hz, 0.9H), 4.42 (s, 2H), 4.18 (d, J=5.3 Hz, 2H), 1.53 (s, 9H), 1.46 (s, 9H).

Test Example 1

Measurement of EP2 Receptor Binding Action

Measurement of EP2 receptor binding action was carried out in compliance with the method of Abramovitz et al. (Biochimica et Biophysica Acta, 1483, 285 (2000)). A test compound dissolved in dimethylsulfoxide and [$^3$H]prostaglandin E$_2$ (NET-428, PerkinFlmer) (final concentration: 10 nM) were added to a buffer solution (10 mM MES-KOH (pH 6.0), 10 mM MgCl$_2$, 1 mM EDTA) in which was suspended 10 μg of a membrane fraction of HEK293 cells expressing human EP2 receptor followed by incubating for 60 minutes at 30° C. The membrane fraction was recovered on glass fiber filter paper (GF/B, Whatmann) using a cell harvester (M30R, Brandel), and after washing with buffer solution (10 mM MES-KOH (pH 6.0), 10 mM MgCl$_2$), radioactivity was measured with a liquid scintillation analyzer (2000CA, Packard). The concentration of test compound required to replace 50% of the [$^3$H]prostaglandin E$_2$ bound to the receptor (IC$_{50}$ value) was calculated using EXSAS (Ver. 7.1.6, Arm Systex), and the inhibition constant (Ki value) was determined using the formula indicated below. The dissociation constant (Kd) was calculated by Scatchard analysis.

$Ki=IC_{50}/(1+([^3H]\text{prostaglandin } E_2 \text{ concentration}/Kd))$

The test results are shown in Table 2. Furthermore, a Compound A shown in the table is a sodium salt of {3-[(4-tert-butylbenzyl)(pyridin-3-ylsulfonyl)aminomethyl]-phenoxy}acetic acid (CP-533,536), which is the compound of Example 14e of WO 99/19300A, and is a control compound having EP2 receptor binding action.

TABLE 2

| Test Compound Example No. | Ki Value of EP2 Receptor Binding Action (nM) |
|---|---|
| Example 3 | 1.9 |
| Example 4 | 2.8 |
| Example 5 | 7.0 |
| Example 6 | 3.8 |
| Example 9 | 4.4 |
| Example 11 | 3.8 |
| Example 12 | 1.1 |
| Example 13 | 13 |
| Example 15 | 9.4 |
| Example 16 | 3.1 |
| Example 17 | 1.5 |
| Example 18 | 9.2 |
| Compound A | 16 |

In this test, compounds of the present invention demonstrated superior EP2 receptor binding action in comparison with the control compound.

Text Example 2

Measurement of EP2 Agonist Activity

Measurement of EP2 agonist activity was carried out in compliance with the method of Wilson et al. (European Journal of Pharmacology, 501, 49 (2004)). HEK293 cells (ES-562-C, Euroscreen) were cultured in MEM medium containing 10% FBS and seeded at 2×10$^4$ cells per well of a 96-well plate. On the following day, the medium was replaced with serum-free MEM medium containing 3-isobutyl-1-methylxanthine (final concentration: 500 μM) and after culturing for 30 minutes, a test compound dissolved in dimethylsulfoxide was added followed by allowing to stand undisturbed in a carbon dioxide incubator. After 30 minutes, the amount of cAMP in the cells was measured with a cAMP Biotrak EIA System kit (GE Healthcare Sciences). The concentration of test compound required to increase the amount of cAMP to 50% of the maximum increase (EC$_{50}$ value) was calculated by non-linear regression of the test compound concentration and amount of cAMP using EXSAS.

The test results are shown in Table 3.

TABLE 3

| Test Compound Example No. | EC$_{50}$ Value of EP2 Agonist Activity (nM) |
|---|---|
| Example 3 | 0.45 |
| Example 4 | 0.29 |
| Example 5 | 1.8 |
| Example 6 | 2.0 |
| Example 7 | 2.8 |
| Example 8 | 5.6 |
| Example 11 | 0.42 |
| Example 12 | 0.49 |
| Example 13 | 3.4 |
| Example 15 | 0.96 |
| Example 16 | 0.62 |
| Example 17 | 1.8 |
| Example 18 | 5.0 |
| Example 19 | 2.0 |

TABLE 3-continued

| Test Compound Example No. | EC$_{50}$ Value of EP2 Agonist Activity (nM) |
|---|---|
| Example 21 | 1.1 |
| Example 25 | 7.9 |
| Example 26 | 0.78 |
| Compound A | 17 |

In this test, compounds of the present invention demonstrated superior EP2 agonist activity in comparison with the control compound.

Test Example 3

Isolated Guinea Pig Trachea Relaxation Test

The tracheas were isolated from guinea pigs (Hartley, male, age 7 to 9 weeks, supplier: Nippon SLC) followed by cutting as rings containing cartilage. Trachea specimens were prepared by cutting the side opposite from the smooth muscle from the rings. The trachea specimens were suspended in Krebs solution containing 3 μM indomethacin while applying a load of 0.5 g, and changes in tension were measured through an FD pickup (TB-611T, Nippon Kohden). The trachea specimens were then warmed to 37° C. and perfused with a mixed gas consisting of 95% oxygen and 5% carbon dioxide. Next, after causing the trachea specimen to contract by adding 0.1 μM carbachol, a test compound dissolved in dimethylsulfoxide was cumulatively added starting at a low concentration to cause the trachea specimen to relax. The concentration of test compound required to cause 50% relaxation of the carbachol-induced contraction (EC$_{50}$ value) was calculated using EXSAS.

The test results are shown in Table 4.

TABLE 4

| Test Compound Example No. | IC$_{50}$ Value of Trachea Relaxation Activity (nM) |
|---|---|
| Example 2 | 5.7 |
| Example 4 | 4.5 |
| Example 15 | 2.6 |
| Example 16 | 2.6 |
| Example 17 | 2.6 |
| Compound A | 86 |

In this test, compounds of the present invention demonstrated superior trachea relaxation activity in comparison with the control compound.

PREPARATION EXAMPLES

Preparation Example 1

Hard Capsule Preparation 50 mg of powdered compound of Example 6, 128.7 mg of lactose, 70 mg of cellulose and 1.3 mg of magnesium stearate were mixed and passed through a 60 mesh sieve followed by placing 250 mg of the powder in a No. 3 gelatin capsule to obtain a capsule preparation.

Preparation Example 2

Tablet Preparation 50 mg of powdered compound of Example 6, 124 mg of lactose, 25 mg of cellulose and 1 mg of magnesium stearate were mixed and formed into a tablet with a tablet-making machine to obtain a tablet preparation weighing 200 mg of the mixture per tablet. This tablet preparation can be provided with a sugar coating as necessary.

INDUSTRIAL APPLICABILITY

Since the pyridylaminoacetic acid compound represented by the formula (1) of the present invention, or a pharmacologically acceptable salt thereof, demonstrates superior bronchodilatory action based on potent EP2 agonistic action, while also having superior properties as a pharmaceutical composition in terms of tissue distribution, bioavailability (BA), fast-acting pharmacological effect, sustained pharmacological effect, solubility, physical stability, drug interaction, toxicity and the like, it is preferably useful as a pharmaceutical for treatment or prevention of respiratory diseases (such as asthma, COPD, bronchitis, emphysema, pulmonary fibrosis, acute respiratory distress syndrome (ARDS), cystic fibrosis or pulmonary hypertension), and moreover, is also useful as a pharmaceutical for treatment and/or prevention of diseases for which EP2 agonistic action is thought to be useful (such as dysmenorrhea, premature labor, ischemic organ diseases (including arteriosclerosis obliterans, Berger's disease, Raynaud's disease, myocardial infarction, angina pectoris, cerebral infarction and diabetic neuropathy), bone diseases, gastric ulcer, hypertension or glaucoma).

The invention claimed is:

1. A pyridylaminoacetic acid compound represented by the formula (1):

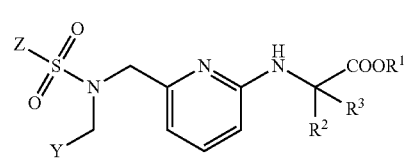

(1)

wherein,

R$^1$, R$^2$ and R$^3$ respectively and independently represent a hydrogen atom or a C$_1$-C$_6$ alkyl group, Y represents a -Q$^1$-Q$^2$ group, wherein Q$^1$ represents an arylene group and Q$^2$ represents a pyrazolyl group which may be substituted with a group(s) selected from the group consisting of a halogen atom, a hydroxy group, a C$_1$-C$_6$ alkyl group, a halogeno-C$_1$-C$_6$ alkyl group, a C$_1$-C$_6$ alkoxy group and a halogeno-C$_1$-C$_6$ alkoxy group, and Z represents a pyridyl group which may be substituted with a group(s) selected from the group consisting of a halogen atom, a C$_1$-C$_6$ alkyl group, a halogeno-C$_1$-C$_6$ alkyl group, a C$_1$-C$_6$ alkoxy group and a halogeno-C$_1$-C$_6$ alkoxy group, or a pharmacologically acceptable salt thereof.

2. The pyridylaminoacetic acid compound or pharmacologically acceptable salt thereof according to claim 1, wherein R$^2$ and R$^3$ respectively and independently represent a hydrogen atom or a C$_1$-C$_4$ alkyl group.

3. The pyridylaminoacetic acid compound or pharmacologically acceptable salt thereof according to claim 1, wherein Q$^2$ may be substituted with a group(s) selected from the group consisting of a halogen atom, a hydroxy group, a C$_1$-C$_4$ alkyl group, a halogeno-C$_1$-C$_4$ alkyl group, a C$_1$-C$_4$ alkoxy group and a halogeno-C$_1$-C$_4$ alkoxy group.

4. The pyridylaminoacetic acid compound or pharmacologically acceptable salt thereof according to claim 1, wherein Z may be substituted with a group(s) selected from the group consisting of a halogen atom, a $C_1$-$C_4$ alkyl group, a halogeno-$C_1$-$C_4$ alkyl group, a $C_1$-$C_4$ alkoxy group and a halogeno-$C_1$-$C_4$ alkoxy group.

5. The pyridylaminoacetic acid compound or pharmacologically acceptable salt thereof according to claim 1, wherein Y a -$Q^1$-$Q^2$ group, wherein $Q^1$ represents a phenylene group and $Q^2$ represents a pyrazolyl group which may be substituted with a group(s) selected from the group consisting of a halogen atom, a hydroxy group, a $C_1$-$C_4$ alkyl group, a halogeno-$C_1$-$C_4$ alkyl group, a $C_1$-$C_4$ alkoxy group and a halogeno-$C_1$-$C_4$ alkoxy group.

6. The pyridylaminoacetic acid compound or pharmacologically acceptable salt thereof according to claim 5, wherein Y represents a -$Q^1$-$Q^2$ group, wherein $Q^1$ represents a phenylene group and $Q^2$ represents a pyrazolyl group, which may be substituted with a group(s) selected from the group consisting of a fluorine atom, a chlorine atom, a bromine atom, a hydroxy group, a methyl group, an ethyl group, a propyl group, an isopropyl group, a tert-butyl group, a trifluoromethyl group, a difluoromethyl group, a trichloromethyl group, a dichloromethyl group, a 2,2,2-trifluoroethyl group, a 2,2,2-trichloroethyl group, a methoxy group, an ethoxy group, a propoxy group, an isopropoxy group, a tert-butoxy group, a trifluoromethoxy group, a difluoromethoxy group, a trichloromethoxy group and a dichloromethoxy group.

7. The pyridylaminoacetic acid compound or pharmacologically acceptable salt thereof according to claim 1, wherein Z represents a pyridyl group which may be substituted with a group(s) selected from the group consisting of a fluorine atom, a chlorine atom, a bromine atom, a methyl group, an ethyl group, a propyl group, an isopropyl group, a tert-butyl group, a trifluoromethyl group, a difluoromethyl group, a trichloromethyl group, a dichloromethyl group, a 2,2,2-trifluoroethyl group, a 2,2,2-trichloroethyl group, a methoxy group, an ethoxy group, a propoxy group, an isopropoxy group, a tert-butoxy group, a trifluoromethoxy group, a difluoromethoxy group, a trichloromethoxy group and a dichloromethoxy group.

8. The pyridylaminoacetic acid compound or pharmacologically acceptable salt thereof according to claim 1, wherein $R^2$ and $R^3$ respectively and independently represent a hydrogen atom or a methyl group.

9. The pyridylaminoacetic acid compound or pharmacologically acceptable salt thereof according to claim 1, wherein Z represents a pyridyl group which may be substituted with a group(s) selected from the group consisting of a halogen atom and a $C_1$-$C_4$ alkoxy group.

10. The pyridylaminoacetic acid compound or pharmacologically acceptable salt thereof according to claim 1, wherein $R^1$ represents a hydrogen atom, a methyl group, an ethyl group, a propyl group, an isopropyl group, a butyl group, an isobutyl group, a sec-butyl group, a tert-butyl group, a pentyl group or a hexyl group,
$R^2$ and $R^3$ respectively and independently represent a hydrogen atom or a methyl group,
Y represents a 4-(pyrazol-1-yl)phenyl
Z represents a a pyridin-2-yl group, a 5-fluoropyridin-2-yl group, a 5-chloropyridin-2-yl group, a 5-methylpyridin-2-yl group, a 5-ethylpyridin-2-yl group, a 5-trifluoromethylpyridin-2-yl group, a 5-methoxypyridin-2-yl group, a 5-difluoromethoxypyridin-2-yl group, a pyridin-3-yl group, a 6-fluoropyridin-3-yl group, a 6-chloropyridin-3-yl group, a 6-methylpyridin-3-yl group, a 6-ethylpyridin-3-yl group, a 6-trifluoromethylpyridin-3-yl group, a 6-methoxypyridin-3-yl group, a 6-difluoromethoxypyridin-3-yl group, or a pyridin-4-yl group.

11. The pyridylaminoacetic acid compound or pharmacologically acceptable salt thereof according to claim 1, wherein $R^1$ represents a hydrogen atom, a methyl group, an ethyl group, a propyl group, an isopropyl group, a tert-butyl group or a hexyl group,
$R^2$ and $R^3$ respectively and independently represent a hydrogen atom or a methyl group,
Y represents a 4-(pyrazol-1-yl)phenyl group and
Z represents a pyridin-2-yl group, a 5-fluoropyridin-2-yl group, a 5-chloropyridin-2-yl group, a 5-methoxypyridin-2-yl group, a pyridin-3-yl group, a 6-fluoropyridin-3-yl group, a 6-chloropyridin-3-yl group, a 6-methoxypyridin-3-yl group or a pyridin-4-yl group.

12. The pyridylaminoacetic acid compound or pharmacologically acceptable salt thereof according to claim 1, wherein $R^1$ represents a hydrogen atom, a methyl group, an ethyl group, an isopropyl group or a hexyl group,
$R^2$ and $R^3$ both represent hydrogen atoms,
Y represents a 4 (pyrazol-1-yl)phenyl group, and
Z represents a pyridin-2-yl group or a pyridin-3-yl group.

13. The pyridylaminoacetic acid compound or pharmacologically acceptable salt thereof according to claim 1, wherein $R^1$ represents a hydrogen atom, a methyl group, an ethyl group, an isopropyl group or a hexyl group,
$R^2$ and $R^3$ both represent hydrogen atoms,
Y represents a 4 (pyrazol-1-yl)phenyl group, and
Z represents a pyridin-2-yl group or a pyridin-3-yl group.

14. The pyridylaminoacetic acid compound or pharmacologically acceptable salt thereof according to claim 1, wherein the pyridylaminoacetic acid compound is:
(6-{[4-(pyrazol-1-yl)benzyl](pyridin-2-ylsulfonyl)aminomethyl}pyridin-2-ylamino)acetic acid,
(6-{[4-(pyrazol-1-yl)benzyl](pyridin-3-ylsulfonyl)aminomethyl}pyridin-2-ylamino)acetic acid,
ethyl (6-{[4-(pyrazol-1-yl)benzyl](pyridin-3-ylsulfonyl)aminomethyl}pyridin-2-ylamino)acetate, or
isopropyl (6-{[4-(pyrazol-1-yl)benzyl](pyridin-3-ylsulfonyl)aminomethyl}pyridin-2-ylamino)acetate.

15. A pharmaceutical composition comprising the pyridylaminoacetic acid compound according to claim 1, or a pharmacologically acceptable salt thereof as an active ingredient; and
one or more additive selected from the group consisting of vehicles, lubricants, binders, disintegrators, emulsifiers, stabilizers, corrigents and diluents.

* * * * *

UNITED STATES PATENT AND TRADEMARK OFFICE
CERTIFICATE OF CORRECTION

| | | |
|---|---|---|
| PATENT NO. | : 8,648,097 B2 | Page 1 of 1 |
| APPLICATION NO. | : 12/922028 | |
| DATED | : February 11, 2014 | |
| INVENTOR(S) | : Iwamura et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 215 days.

Signed and Sealed this
Eighth Day of March, 2016

Michelle K. Lee
*Director of the United States Patent and Trademark Office*